(12) United States Patent
Boroughs et al.

(10) Patent No.: US 12,257,304 B2
(45) Date of Patent: Mar. 25, 2025

(54) SYSTEMS TARGETING PSMA AND CA9

(71) Applicant: Arsenal Biosciences, Inc., South San Francisco, CA (US)

(72) Inventors: Angela Boroughs, San Mateo, CA (US); Levi Gray-Rupp, Philadelphia, PA (US); Samuel A. Williams, Burlingame, CA (US); Zhen Jian Zhou, San Francisco, CA (US); Matthew Drever, Concord, CA (US); Duy Nguyen, San Diego, CA (US); Amy-Jo Casbon, San Francisco, CA (US); Anzhi Yao, San Francisco, CA (US); Thomas Gardner, San Francisco, CA (US)

(73) Assignee: Arsenal Biosciences, Inc., South San Francisco, CA (US)

( * ) Notice: Subject to any disclaimer, the term of this patent is extended or adjusted under 35 U.S.C. 154(b) by 0 days.

(21) Appl. No.: 18/593,711

(22) Filed: Mar. 1, 2024

(65) Prior Publication Data
US 2024/0342284 A1    Oct. 17, 2024

Related U.S. Application Data

(60) Provisional application No. 63/618,233, filed on Jan. 5, 2024, provisional application No. 63/613,712, filed on Dec. 21, 2023, provisional application No. 63/601,617, filed on Nov. 21, 2023, provisional application No. 63/578,854, filed on Aug. 25, 2023, provisional application No. 63/495,869, filed on Apr. 13, 2023, provisional application No. 63/489,837, filed on Mar. 13, 2023, provisional application No. 63/488,386, filed on Mar. 3, 2023.

(51) Int. Cl.
| | | |
|---|---|---|
| A61P 35/00 | (2006.01) |
| A61K 35/17 | (2015.01) |
| A61K 39/00 | (2006.01) |
| C07K 14/725 | (2006.01) |
| C07K 16/30 | (2006.01) |
| C07K 16/40 | (2006.01) |
| C12N 5/10 | (2006.01) |
| C12N 9/22 | (2006.01) |
| C12N 15/00 | (2006.01) |
| C12N 15/11 | (2006.01) |
| C12N 15/12 | (2006.01) |
| C12N 15/62 | (2006.01) |
| C12N 15/79 | (2006.01) |
| C12N 15/90 | (2006.01) |
| C12N 5/078 | (2010.01) |
| C12N 15/63 | (2006.01) |

(52) U.S. Cl.
CPC .. *A61K 39/464495* (2023.05); *A61K 39/4631* (2023.05); *A61K 39/464454* (2023.05); *A61P 35/00* (2018.01); *C07K 14/7051* (2013.01); *C07K 16/3069* (2013.01); *C07K 16/40* (2013.01); *C12N 9/22* (2013.01); *C12N 15/11* (2013.01); *C12N 15/907* (2013.01); *A61K 35/17* (2013.01); *C07K 2317/31* (2013.01); *C07K 2319/00* (2013.01); *C12N 5/0634* (2013.01); *C12N 5/10* (2013.01); *C12N 15/00* (2013.01); *C12N 15/62* (2013.01); *C12N 15/63* (2013.01); *C12N 2310/20* (2017.05)

(58) Field of Classification Search
CPC .......... C07K 2317/31; C07K 2317/622; A61K 39/4611; A61K 39/464495; A61K 35/17; C12N 5/10; C12N 15/00; C12N 15/12; C12N 15/62; C12N 15/79
See application file for complete search history.

(56) References Cited

U.S. PATENT DOCUMENTS

| | | |
|---|---|---|
| 5,955,075 A | 9/1999 | Zavada et al. |
| 5,981,711 A | 11/1999 | Zavada et al. |
| 6,107,090 A | 8/2000 | Bander |
| 6,150,508 A | 11/2000 | Murphy et al. |
| 6,485,974 B1 | 11/2002 | Popoff |
| 7,446,190 B2 | 11/2008 | Sadelain et al. |
| 7,476,513 B2 | 1/2009 | Murphy et al. |
| 7,514,078 B2 | 4/2009 | Bander et al. |
| 7,666,425 B1 | 2/2010 | Bander |
| 7,875,278 B2 | 1/2011 | Cardarelli et al. |
| 8,022,045 B1 | 9/2011 | Bogdahn et al. |
| RE43,586 E | 8/2012 | Israeli et al. |

(Continued)

FOREIGN PATENT DOCUMENTS

| | | |
|---|---|---|
| EP | 1851250 B1 | 6/2012 |
| EP | 2508596 A2 | 10/2012 |

(Continued)

OTHER PUBLICATIONS

Thomas, J., "High-throughput Arrayed Screening of Logic-gated CARs Enables the Selection of Candidates for ccRCC with Optimal Potency and Fidelity Traits," ASGCT May 17, 2023, ArsenalBio, Poster #1218.

(Continued)

*Primary Examiner* — Hong Sang
(74) *Attorney, Agent, or Firm* — Goodwin Procter LLP

(57) ABSTRACT

Provided herein are antibodies and chimeric priming receptors that bind PSMA and antibodies and chimeric antigen receptors that bind CA9. Also provided are systems of chimeric priming receptors that bind PSMA and chimeric antigen receptors that bind CA9, cells expressing such systems, and methods of use thereof.

61 Claims, 36 Drawing Sheets
Specification includes a Sequence Listing.

(56) References Cited

U.S. PATENT DOCUMENTS

| | | |
|---|---|---|
| 8,461,308 B2 | 6/2013 | Cardarelli et al. |
| 8,703,918 B2 | 4/2014 | Colombatti et al. |
| 8,772,459 B2 | 7/2014 | Ho et al. |
| 9,238,694 B2 | 1/2016 | Elsässer-Beile et al. |
| 9,855,298 B2 | 1/2018 | Bot et al. |
| 9,987,308 B2 | 6/2018 | Riddell et al. |
| 10,100,126 B2 | 10/2018 | Gros et al. |
| 10,202,601 B2 | 2/2019 | Saetrom |
| 10,266,592 B2 | 4/2019 | Jensen |
| 10,548,921 B2 | 2/2020 | Leen et al. |
| 10,654,928 B2 | 5/2020 | Kloss et al. |
| 10,780,120 B2 | 9/2020 | Zhao et al. |
| 10,800,854 B2 | 10/2020 | Pule et al. |
| 10,870,705 B2 | 12/2020 | Marasco |
| 10,876,120 B2 | 12/2020 | Wucherpfennig et al. |
| 10,934,550 B2 | 3/2021 | Wolfson et al. |
| 11,008,548 B2 | 5/2021 | Martin et al. |
| 11,033,584 B2 | 6/2021 | Roth et al. |
| 11,059,903 B2 | 7/2021 | Holgate et al. |
| 11,065,278 B2 | 7/2021 | Riddell et al. |
| 11,072,644 B2 | 7/2021 | Rajpal et al. |
| 11,083,753 B1 | 8/2021 | Roth et al. |
| 11,130,820 B2 | 9/2021 | Abbot et al. |
| 11,155,616 B2 | 10/2021 | Jensen |
| 11,155,633 B2 | 10/2021 | Kirshner et al. |
| 11,161,907 B2 | 11/2021 | June et al. |
| 11,186,822 B2 | 11/2021 | Martin et al. |
| 11,202,801 B2 | 12/2021 | Roybal et al. |
| 11,203,758 B2 | 12/2021 | Zhao et al. |
| 11,208,661 B2 | 12/2021 | Zhao et al. |
| 11,213,541 B2 | 1/2022 | Hossbach et al. |
| 11,326,167 B2 | 5/2022 | Simons et al. |
| 11,331,346 B2 | 5/2022 | Roth et al. |
| 11,332,744 B1 | 5/2022 | Zheng et al. |
| 11,365,262 B2 | 6/2022 | Pulé et al. |
| 11,384,335 B2 | 7/2022 | Martin et al. |
| 11,414,497 B2 | 8/2022 | Zhao et al. |
| 11,453,861 B2 | 9/2022 | Martin et al. |
| 11,466,291 B2 | 10/2022 | Cabaniols et al. |
| 11,485,792 B2 | 11/2022 | Jones et al. |
| 11,572,560 B2 | 2/2023 | Burge et al. |
| 11,590,171 B2 | 2/2023 | Roth et al. |
| 11,597,934 B2 | 3/2023 | Wucherpfennig et al. |
| 11,612,646 B2 | 3/2023 | Salih et al. |
| 11,617,766 B2 | 4/2023 | Roybal et al. |
| 11,649,455 B2 | 5/2023 | Krause et al. |
| 11,746,157 B2 | 9/2023 | Anderson et al. |
| 11,761,004 B2 | 9/2023 | Zheng et al. |
| 11,766,453 B2 | 9/2023 | Zhao |
| 11,814,624 B2 | 11/2023 | Roth et al. |
| 12,024,567 B2 | 7/2024 | Marasco |
| 12,037,407 B2 | 7/2024 | Williams et al. |
| 2002/0004490 A1 | 1/2002 | Dean et al. |
| 2003/0064944 A1 | 4/2003 | Murray et al. |
| 2003/0165892 A1 | 9/2003 | Park et al. |
| 2004/0121353 A1 | 6/2004 | Lewis et al. |
| 2004/0136998 A1 | 7/2004 | Bander |
| 2005/0227936 A1 | 10/2005 | McSwiggen et al. |
| 2007/0031438 A1 | 2/2007 | Junghans |
| 2010/0105134 A1 | 4/2010 | Quay et al. |
| 2017/0175128 A1 | 6/2017 | Welstead et al. |
| 2017/0224731 A1 | 8/2017 | Tiganis et al. |
| 2017/0335331 A1 | 11/2017 | Zhao et al. |
| 2018/0171298 A1 | 6/2018 | Duchateau et al. |
| 2019/0136230 A1 | 5/2019 | Sather et al. |
| 2019/0183936 A1 | 6/2019 | Shum, Shum et al. |
| 2019/0194282 A1 | 6/2019 | Levitzki et al. |
| 2019/0292533 A1 | 9/2019 | Nager et al. |
| 2020/0002402 A1 | 1/2020 | Emtage et al. |
| 2020/0140815 A1 | 5/2020 | Terrett et al. |
| 2020/0197437 A1 | 6/2020 | Leen et al. |
| 2020/0206248 A1 | 7/2020 | Ivachtchenko et al. |
| 2020/0216514 A1 | 7/2020 | Fussenegger et al. |
| 2020/0283729 A1 | 9/2020 | Loew et al. |
| 2020/0330515 A1 | 10/2020 | Maus et al. |
| 2020/0347386 A1 | 11/2020 | Benson et al. |
| 2020/0392204 A1 | 12/2020 | Leung |
| 2020/0407728 A1 | 12/2020 | Zhao et al. |
| 2021/0015940 A1 | 1/2021 | Bhowmik et al. |
| 2021/0052648 A1 | 2/2021 | Tiganis et al. |
| 2021/0163574 A1 | 6/2021 | Schneider et al. |
| 2021/0221906 A1 | 7/2021 | Marasco |
| 2021/0238258 A1 | 8/2021 | Garcia et al. |
| 2021/0371491 A1 | 12/2021 | Cathomen et al. |
| 2021/0388362 A1 | 12/2021 | Roth et al. |
| 2022/0008464 A1 | 1/2022 | Wang et al. |
| 2022/0081691 A1 | 3/2022 | Haining et al. |
| 2022/0089750 A1 | 3/2022 | June et al. |
| 2022/0127373 A1 | 4/2022 | Lim et al. |
| 2022/0185858 A1 | 6/2022 | Li et al. |
| 2022/0185910 A1 | 6/2022 | Liu et al. |
| 2022/0202863 A1 | 6/2022 | Bornschein et al. |
| 2022/0204930 A1 | 6/2022 | Drever et al. |
| 2022/0235380 A1 | 7/2022 | Williams et al. |
| 2022/0348928 A1 | 11/2022 | Kim et al. |
| 2022/0372479 A1 | 11/2022 | Jaschinski et al. |
| 2022/0378739 A1 | 12/2022 | Rezvani et al. |
| 2022/0409663 A1 | 12/2022 | Fix et al. |
| 2022/0411530 A1 | 12/2022 | Wang et al. |
| 2023/0009232 A1 | 1/2023 | Shu et al. |
| 2023/0039030 A1 | 2/2023 | Cathomen et al. |
| 2023/0061455 A1 | 3/2023 | Burleigh et al. |
| 2023/0117089 A1 | 4/2023 | Rigo et al. |
| 2023/0131727 A1 | 4/2023 | Goldberg et al. |
| 2023/0159928 A1 | 5/2023 | Steklov et al. |
| 2023/0183709 A1 | 6/2023 | Roybal et al. |
| 2023/0242612 A1 | 8/2023 | June et al. |
| 2023/0250189 A1 | 8/2023 | Hechler et al. |
| 2023/0374150 A1 | 11/2023 | Cheung et al. |
| 2023/0381316 A1 | 11/2023 | He |
| 2023/0416747 A1 | 12/2023 | Zheng et al. |
| 2024/0002530 A1 | 1/2024 | Liu |
| 2024/0240164 A1 | 7/2024 | Cooper et al. |

FOREIGN PATENT DOCUMENTS

| | | |
|---|---|---|
| EP | 2506876 B1 | 10/2016 |
| EP | 3445847 A1 | 2/2019 |
| EP | 3504223 A1 | 7/2019 |
| EP | 3693396 A2 | 8/2020 |
| EP | 3737765 B1 | 12/2021 |
| EP | 4063387 A1 | 9/2022 |
| EP | 3119423 B1 | 12/2022 |
| EP | 4183805 A1 | 5/2023 |
| EP | 3305890 B1 | 8/2023 |
| EP | 4282434 A2 | 11/2023 |
| EP | 4284838 A2 | 12/2023 |
| WO | 1999/043710 A1 | 9/1999 |
| WO | 2000/014257 A1 | 3/2000 |
| WO | 2002098897 A2 | 12/2002 |
| WO | 2005/070456 A2 | 8/2005 |
| WO | 2007065027 A2 | 6/2007 |
| WO | 2008/109532 A2 | 9/2008 |
| WO | 2008/109546 A2 | 9/2008 |
| WO | 2014/055668 A1 | 4/2014 |
| WO | 2014/128258 A1 | 8/2014 |
| WO | 2014/164554 A1 | 10/2014 |
| WO | 2015/157391 A1 | 10/2015 |
| WO | 201606132 A1 | 1/2016 |
| WO | 2016/069282 A1 | 5/2016 |
| WO | 2016069283 A1 | 5/2016 |
| WO | 2016/145139 A1 | 9/2016 |
| WO | 2017/029512 A1 | 2/2017 |
| WO | 2017/180713 A1 | 10/2017 |
| WO | 2017/212250 A1 | 12/2017 |
| WO | 2018/033749 A1 | 2/2018 |
| WO | 2018/042411 A1 | 3/2018 |
| WO | 2018098354 A1 | 5/2018 |
| WO | 2018/208067 A1 | 11/2018 |
| WO | 2019/089884 A2 | 5/2019 |
| WO | 2019/173324 A1 | 9/2019 |
| WO | 2019/178422 A1 | 9/2019 |
| WO | 2019/191728 A1 | 10/2019 |
| WO | 2019/204939 A1 | 10/2019 |

(56) References Cited

FOREIGN PATENT DOCUMENTS

| | | |
|---|---|---|
| WO | 2019186274 A2 | 10/2019 |
| WO | 2019/224718 A2 | 11/2019 |
| WO | 2019/245991 A1 | 12/2019 |
| WO | 2020/002015 A1 | 1/2020 |
| WO | 2020/025564 A1 | 2/2020 |
| WO | 2020/046766 A1 | 3/2020 |
| WO | 2020/057486 A1 | 3/2020 |
| WO | 2020088631 A1 | 5/2020 |
| WO | 2020/113000 A1 | 6/2020 |
| WO | 2020/113029 A2 | 6/2020 |
| WO | 2020/113224 A2 | 6/2020 |
| WO | 2020/150534 A2 | 7/2020 |
| WO | 2020/163365 A2 | 8/2020 |
| WO | 2020180694 A1 | 9/2020 |
| WO | 2020/200325 A1 | 10/2020 |
| WO | 2020/206248 A1 | 10/2020 |
| WO | 2020/219682 A2 | 10/2020 |
| WO | 2020/221939 A1 | 11/2020 |
| WO | 2020/226612 A1 | 11/2020 |
| WO | 2020221873 A1 | 11/2020 |
| WO | 2021/009701 A1 | 1/2021 |
| WO | 2021/016174 A1 | 1/2021 |
| WO | 2021/050752 A1 | 3/2021 |
| WO | 2021/050862 A1 | 3/2021 |
| WO | 2021/060926 A1 | 4/2021 |
| WO | 2021/062227 A2 | 4/2021 |
| WO | 2021/068068 A1 | 4/2021 |
| WO | 2021/097521 A1 | 5/2021 |
| WO | 2021/108650 A1 | 6/2021 |
| WO | 2021/108665 A1 | 6/2021 |
| WO | 2021/108671 A1 | 6/2021 |
| WO | 2021/123810 A1 | 6/2021 |
| WO | 2021108619 A1 | 6/2021 |
| WO | 2021/130042 A1 | 7/2021 |
| WO | 2021/162521 A1 | 8/2021 |
| WO | 2021/170666 A1 | 9/2021 |
| WO | 2021/211948 A1 | 10/2021 |
| WO | 2021224278 A1 | 11/2021 |
| WO | 2022/047237 A1 | 3/2022 |
| WO | WO-2022093846 A1 | 5/2022 |
| WO | 2022/140159 A1 | 6/2022 |
| WO | 2022/162247 A1 | 8/2022 |
| WO | 2022/165111 A1 | 8/2022 |
| WO | 2022/183074 A2 | 9/2022 |
| WO | WO-2022/221467 A1 | 10/2022 |
| WO | WO-2023/064928 A2 | 4/2023 |
| WO | 2023/086336 A2 | 5/2023 |
| WO | 2023/092020 A2 | 5/2023 |
| WO | 2023/114918 A1 | 6/2023 |
| WO | 2023192948 A1 | 10/2023 |
| WO | WO-2023225059 A2 * | 11/2023 |
| WO | 2022/162518 A2 | 12/2023 |
| WO | 2023/225059 A3 | 1/2024 |
| WO | WO-2024059618 A2 | 3/2024 |
| WO | WO-2024192100 A1 | 9/2024 |

OTHER PUBLICATIONS

Boroughs, A. "A Neovasculature-inducible CA9 CAR Resistant to FASL and TGFβ Mediated Suppression for the Treatment of ccRCC," AACR Apr. 18, 2023, ArsenalBio, Poster #4088.

Mohanty, S., "AB-2100, A PSMA-Inducible CA9-Specific Car T Cell Product for the Treatment of ccRCC Provides Long-Term Tumor Responses in Preclinical Mouse Model," AACR Apr. 7, 2024, ArsenalBio, Abstract #38.

Scarfo, I. "Development of AB-2100, An Autologous Integrated Circuit T (ICT) Cell Therapy Targeting CA9 Intended for the Treatment of ccRcc," ArsenalBio, Jan. 27, 2024, Poster #472.

Attanasio, N. "Identification of Target Antigens for Logic-Gated CAR T Therapeutics for the Treatment of ccRCC: An Opportunity to Prime with PSMA and Kill with CA9," AACR Apr. 17, 2023, ArsenalBio, Poster #LBO92.

Gardner, T. et al. "Discovery of Synthetic Signaling Pathway Receptors that Increase the Potency of CAR-T Cells through Optimized STAT Activity," SITC Nov. 3, 2023, ArsenalBio, Poster #259.

Landon, M. et al. "Development of AB-2100, A PSMA-inducible Anti-CA9 CAR T Cell Therapy Intended for the Treatment of ccRCC," ASGCT May 8, 2024, ArsenalBio, Poster #811.

Millare, B. et al. "Tunable STAT Activation By Synthetic Pathway Activators (SPAs) Increase Engineered T Cell Potency and Persistence," AACR 2023, ArsenalBio, Poster #4073.

Yao, A. et al. "Synthetic Pathway Activators (SPAs) Increase Engineered T-Cell Potency and Persistence Through Tunable STAT Activation," ArsenalBio, May 19, 2023, Abstract.

Duong et al. "Enhancing the specificity of T-cell cultures for adoptive immunotherapy of cancer," Immunotherapy, 2011, 3(1):33-48.

Fedorov et al. "PD-1- and CTLA-4-Based Inhibitory Chimeri Antigen Receptors (iCARs) Divert Off-Target Immunotherapy Responses," Immunotherapy, 2013, 5(215):1-32.

Hegde et al. "Combinatorional Targeting Offsets Antigen Escape and Enhances Effector Functions of Adoptively Transferred T Cells in Glioblastoma," Molecular Therapy, 2013, 21(11):2087-2101.

Kunkele et al. "Functional Tuning of CARs Reveals Signaling Threshold above Which CD8+ CTL Antitumor Potency Is Attenuated due to Cell Fas-FasL-Dependent AICD," Cancer Immunol Res, 2015, 3(4):368-379.

Kuespert, Sabrina et al. Antisense Oligonucleotide in LNA-Gapmer Design Targeting TGFBR2-A Key Single Gene Target for Safe and Effective fInhibition of TGFβ Signaling, International Journal of Molecular Sciences, 2020, 21, 1952, doi:10.3390/ijms21061952.

Tarfiei, Ghorban Ali et al. "GDF15 Induced Apoptosis and Cytotoxicity in A549 Cells on TFGBR2 Expression," John Wiley & Sons, Ltd. Cell Biochem Funct. 2019;37:320-330.

Wang, Yang et al., "MiR-130a-3p Attenuates Activation and Induces Apoptosis of Hepatic Stellate Cells in Nonalcoholic Fibrosing Steatohepatitis by Directly Targeting TGFBR1 and TGFBR2," Cell Death Disease (2017) 8, e2792; doi: 10.1038/cddis.2017.10, Official Journal of the Cell Death Differntiation Association.

Zhang, Lan et al., "Network-based Transcriptom-wide Expression Study for Postmenopausal Osteoporosis," J Clin Endocrinol Metab, Aug. 2020, 105(8):2678-2691, doi:10.1210/clinem/dgaa319.

Gardner, T. et al., "Abstract 1768: Multiplexed shRNA Cassettes Targeting Orthogonal Pathways (FAS/PTPN2/TGFBR) Enhance the Potency of Integrated Circuit T Cells (ICTs) in Multiple Solid Tumor Models," Cancer Res (2023) 83 (7_Supplement):1768.

Bleumer, I. et al., "A Phase II Trial of Chimeric Monoclonal Antibody G250 for Advanced Renal Cell Carcinoma Patients," British Journal of Cancer (2004) 90(5), 985-990.

Lamers, Cor H. J. et al. "Chimeric Antigen Receptor Therapy in Haematology and Oncology: Current Successes and Challenges. Treatment of Metastatic Renal Cell Carcinoma (mRCC) with CAIX CAR-Engineered T-cells—A Completed Study Overview" Biochemical Society. Trans. (2016) 44, part 3, 951-959, doi: 10.1042/BST20160037.

Watanabe, C. et al., (2016) "Quantitative Evaluation of First, Second, and Third Generation Hairpin Systems Reveals the Limit of Mammalian Vector-Based RNAi," RNA Biology, 13:1, 25-33, DOI:10.1080/15476286.2015.1128062.

Xu, C. et al., (2010) "Unique Biological Properties of Catalytic Domain Directed Human Anti-CAIX Antibodies Discovered through Phage-Display Technology," PLoS ONE, 5(3):e9625. doi:10.1371/journal.pone.0009625.

Fellman, C. et al., "An Optimized MicroRNA Backbone for Effective Single-Copy RNAi," Cell Reports 5, 1704-1713, Dec. 26, 2013.

Narayan et al., "PSMA-Targeting TGFβ-insensitive Armored CAR T-cells in Metastatic Castration Resistant Prostate Cancer: A Phase 1 Trial" Nature Medicine, vol. 28, Apr. 2022, pp. 724-734, https://doi.org/10.1038%2Fs41591-022-01726-1.

Kloss et al., "Dominant-Negative TGF-β Receptor Enhances PSMA-Targeted Human CAR T-cell Proliferation and Augments Prostate Cancer Eradication," Molecular Therapy, American Society of Gene & Cell Therapy, vol. 26, No. 7, Jul. 2018, pp. 1855-1866, https://doi.org/10.1016/j.ymthe.2018.05.003.

(56) References Cited

OTHER PUBLICATIONS

Cooper, A. "AB-1015, A Novel Integrated Circuit T cell (ICT cell) containing an ALPG/MSLN Logic Gate and FAS/PTPN2 shRNA-miR," ArsenalBio, CAR-TCR Summit, Sep. 19, 2022.
Gray-Rupp, "AB-2100: A Novel Investigation Cell Therapy for Clear Cell Renal Cell Carcinoma," KCRS24 Kidney Cancer Research Summit, Jul. 12, 2024.
Drever, M. Utilizing Synthetic Biology to Engineer Safter and more durable Integrated Circuit T Cell (ICT) Therapies, ArsenalBio, Synthetic Biology-Based Therapies Summit, Dec. 14, 2022.
Gray-Rupp, L. "Integrated Circuit T Cells (ICTs) for Solid Tumors," World Oncology Cell Therapy Congress, ArsenalBio, Apr. 25, 2023.
Boroughs, A. et al. "Selections Of A Multi-Feature Logic-Gated CAR T Cell Candidate," PEGs Europe 2023, ArsenalBio, Nov. 13, 2023.
Ahmed et al. "Immunotherapy for Osteosarcoma: Genetic Modification of T cells Overcomes Low Levels of Tumor Antigen Expression," Molecular Therapy, 17(10):1779-1787, 2009.
Rahbarizadeh et al. "Nanobody; an Old Concept and New Vehicle for Immunotargeting," Immunological Investigations, 2011, 40:299-338.
Pirooznia et al. "The Construction of Chimeric T-Cell Receptor with Spacer Base of Modeling Study of VHH and MUC1 Interaction," Journal of Biomedicine and Biotechnology, 2011, 11 pages.
Maher et al. "Human T-lymphocyte cytotoxicity and proliferation directed by a single chimeric TCRz/CD28 receptor," Nature Biotechnology, 2002, 20:71-75.
Sharifzadeh et al. "Genetically engineered T cells bearing chimeric nanoconstructed receptors harboring TAG-72-specific camelid single domain antibodies as targeting agents," Cancer Letters, 2013, 334:237-244.
Jamnani et al. "T cells expressing VHH-directed oligoclonal chimeric HER2 antigen receptors: Towards tumor-directed oligoclonal T cell therapy," Biochimica et Biophysica Acta, 2014, 378-386.
Rahbarizadeh et al. "Nanobody, New Agent for Combating Against Breast Cancer Cells," Breat Cancer—Current and Alternative Therapeutic Modalities, 2011, 347-370.
Kershaw et al. "Gene-engineered T cells for cancer therapy," Nature Reviews, 2013, 13:525-541.
Kakarla et al. "CAR T cells for solid tumors: armed and ready to go?" Cancer J., 2014, 20(2):151-155.
Mao et al. "Immunological research using RNA interference technology," Immunology, 2007, 121:295-307.
Dotti et al. "Design and development of therapies using chimeric antigen receptor-expressing T cells," Immunological Reviews, 2013, 257(1):107-126.
Dotti et al. "Human cytotoxic T lymphocytes with reduced sensitivity to Fas-induced apoptosis," Blood, 205, 105 (2):4677-4684.
International Search Report and Written Opinion for PCT/US2023/022501, received Nov. 30, 2023, 18 pages.
Bertran E et al., Overactivation of the TGF-β Pathway Confers a Mesenchymal-like Phenotype and CXCR4-dependent Migratory Properties to Liver Tumor Cells, Hepatology, vol. 58, No. 6, 2013.
Westbrook TF et al., A Genetic Screen for Candidate Tumor Suppressors Identifies REST, Cell, vol. 121, 837-848, Jun. 17, 2005.
Mahmoud, A. M., "Antibody-Based Therapeutics for the Treatment of Renal Cell Carcinoma: Challenges and Opportunies," The Oncologist, vol. 28, No. 4, Feb. 6, 2023, (Feb. 6, 2023). pp. 297-308 XP093169698, ISSN: 1083-7159, DOI: 10.1093/oncolo/oyac263.
Roybal Kole T. et al., "Precision Tumor Recognition by T Cells with Combinatorial Antigen-Sensing Circuits," Cell, Elsevier, Amsterdam NL, vol. 164, No. 4, Jan. 28, 2016 (Jan. 28, 2016), pp. 770-779, XP029416808, ISSN: 0092-8674, DOI: 10.1016/J.CELL.2016.01.011.
Abbott, Rebecca C. et al. "To go or not to go? Biological Logic Gating Engineered T Cells," J. Immunother Cancer, vol. 10, No. e004185, Apr. 4, 2022 (Apr. 4, 2022), pp. 1-10, XP093170041, DOI: 10.1136/jitc-2021-004185.
Rafiq Sarwish: "Recent advances and discoveries in the mechanisms and functions of CAR T Cells," Nature Reviews Clinical Oncology Volume, Dec. 17, 2019 (Dec. 17, 2019), XP093046951.
Loberg, R. D. et al., "Detection and Isolation of Circulating Tumor Cells in Urologic Cancers: A Review," Neoplasia, vol. 6, No. 4, Jul. 1, 2004 (Jul. 1, 2004), pp. 302-309, XP055325119, US, ISSN: 1476-5586, DOI: 10.1593/neo.03484.
De La Taille, A. et al. "Biomarkers of Renal Cell Carcinoma Past and Future Considerations," Urologic Oncology, vol. 5, No. 4, Jul. 1, 2000 (Jul. 1, 2000), pp. 139-148. XP093171469, DOI: 10.1016/S1078-1439(00)00064-8.
Scarfo, I. et al., "301 Preclinical Development of AB-2100, a PSMA Neovasculature-inducible CA9 Car resistant fo FASL and TGFb Mediated Suppression for the Treatment of ccRCC," Regular And Young Investigaror Award Abstracts, Nov. 1, 2023 (Nov. 1, 2023) pp. A344-A344, XP093169748, DOI: 10.1136/jitc-2023-SITC2023.0301.
U.S. Appl. No. 18/311,856, Immune cells having co-expressed shRNAs and logic gate systems, filed May 3, 2023, Allowed.
U.S. Appl. No. 17/689,837, Immune cells having co-expressed shRNAs and logic gate systems, filed Mar. 8, 2022, Abandoned.

\* cited by examiner

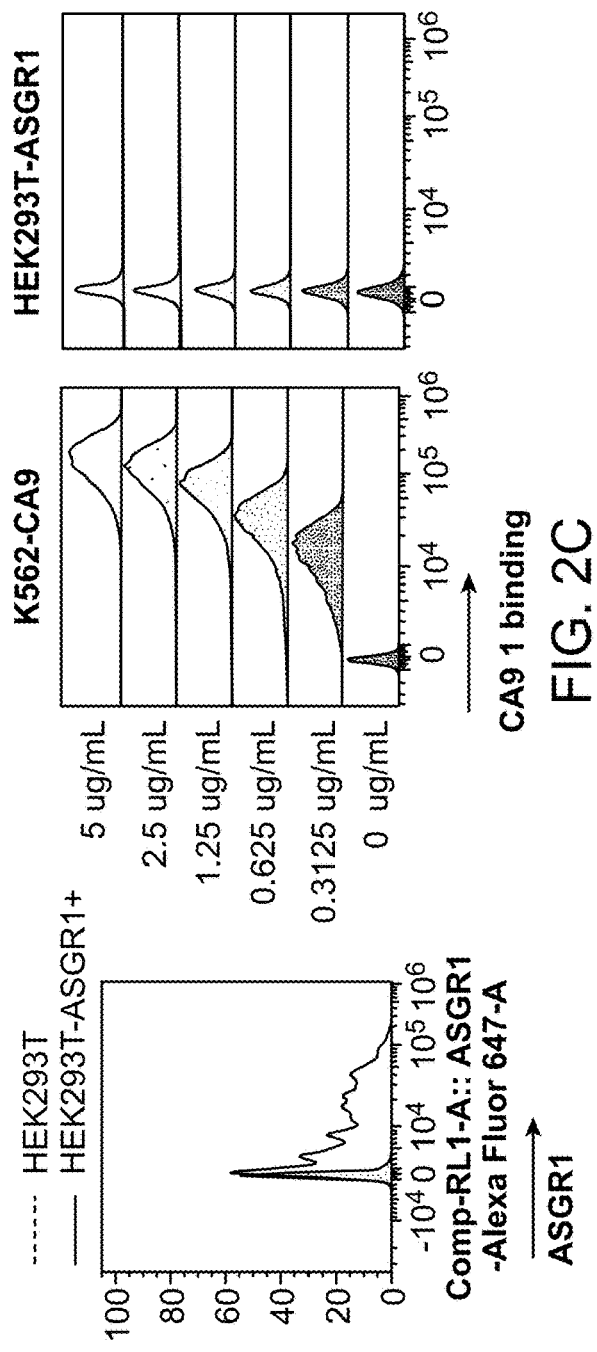
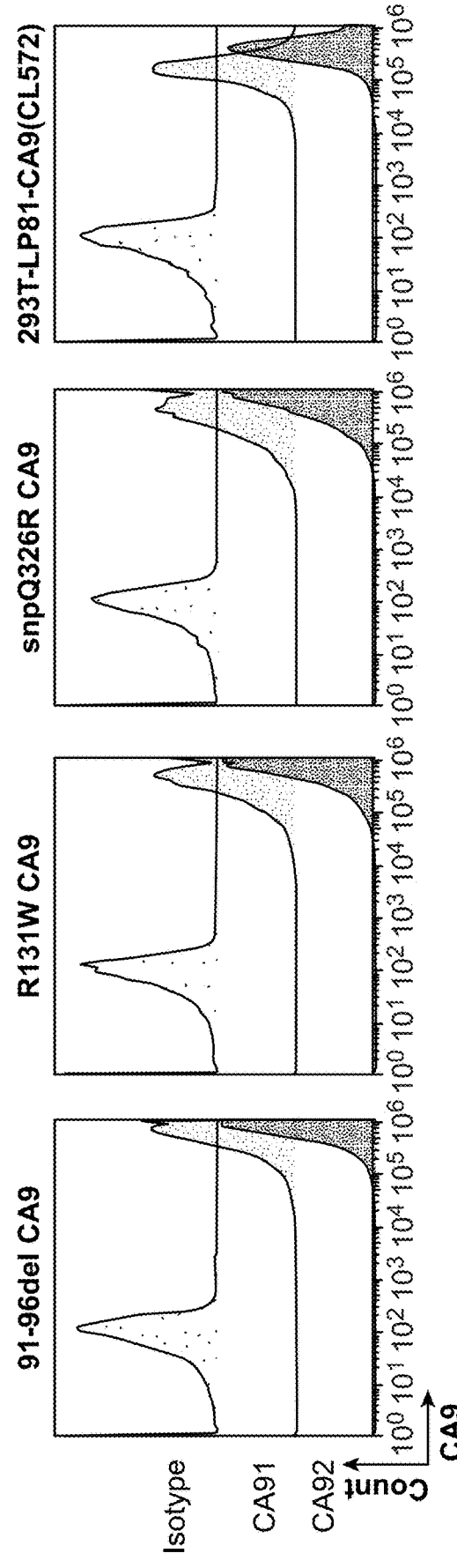
FIG. 2C
FIG. 2D

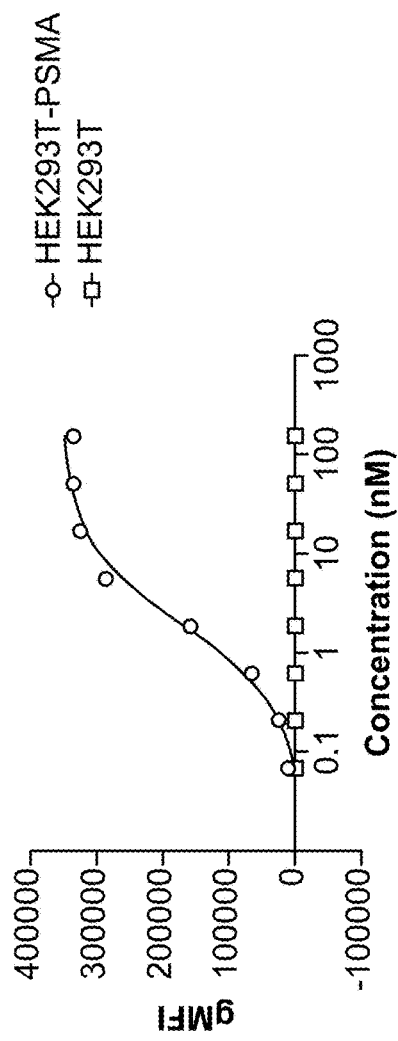
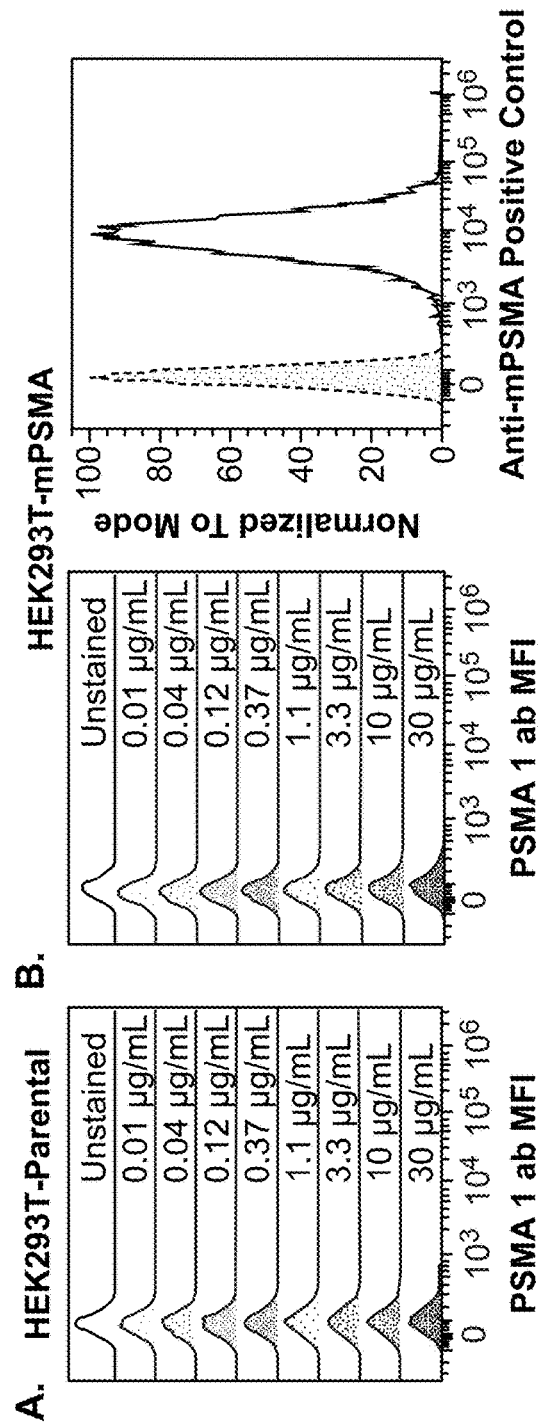
FIG. 3A
FIG. 3B

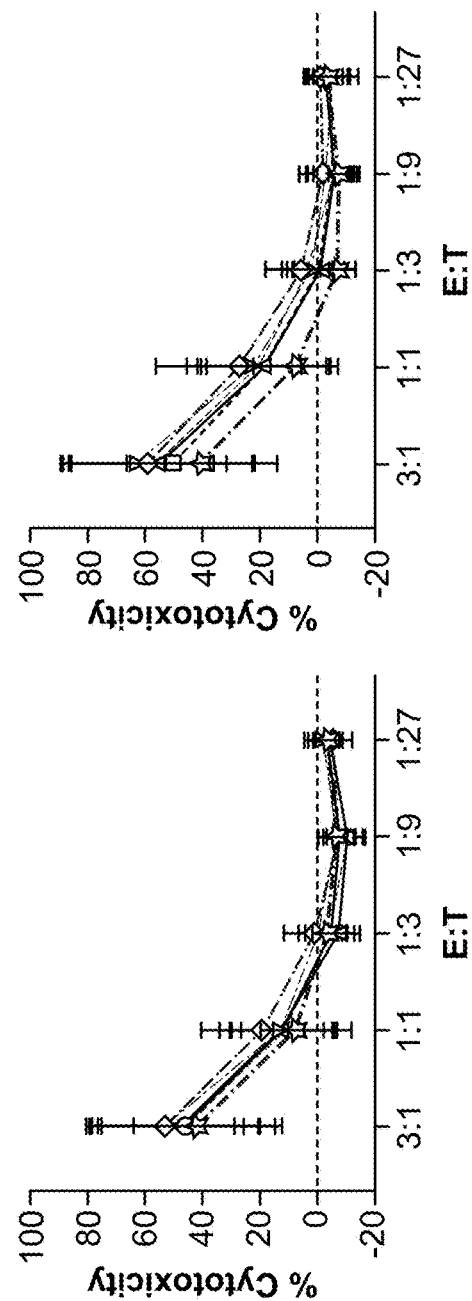
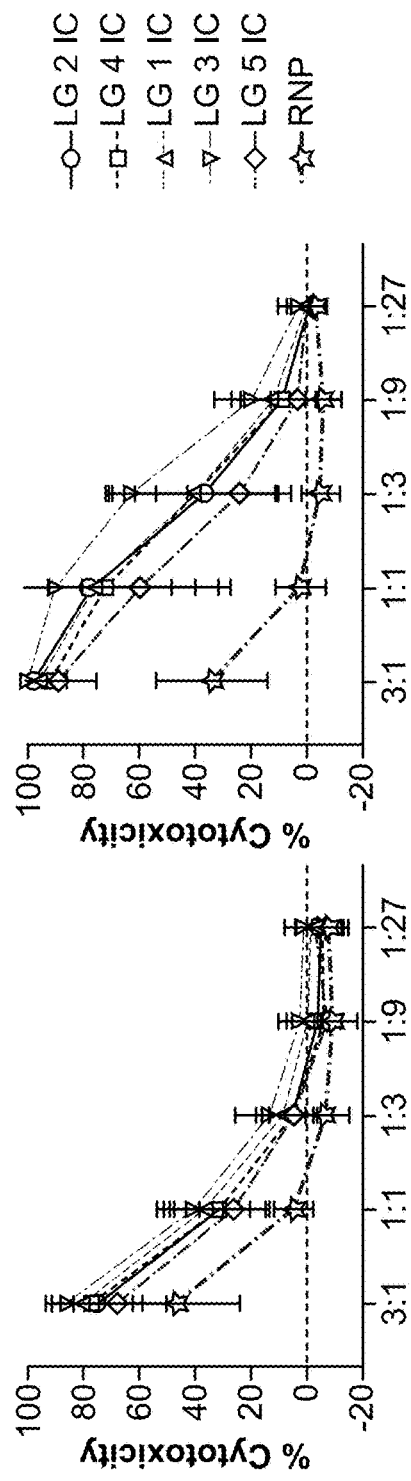
FIG. 7A
FIG. 7B
FIG. 7C
FIG. 7D

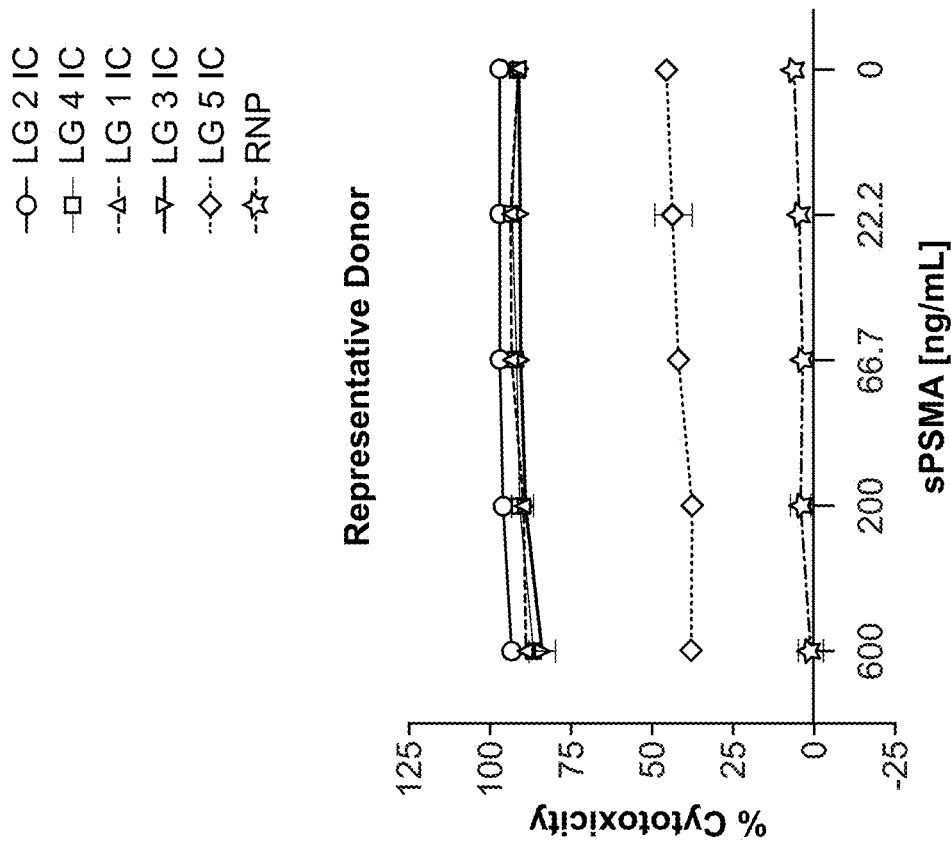
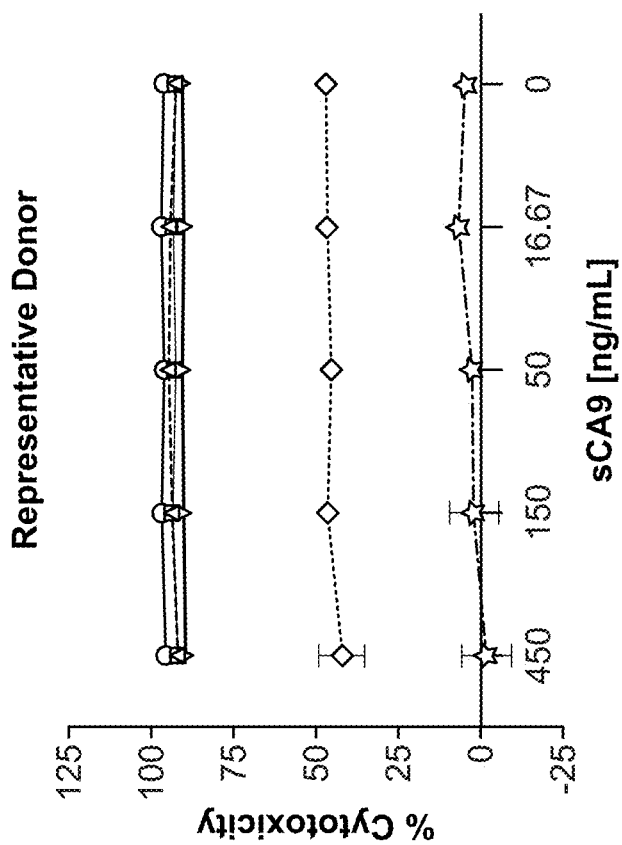
FIG. 11A
FIG. 11B

```
                            SEQUENCE LISTING

Sequence total quantity: 389
SEQ ID NO: 1            moltype = AA   length = 459
FEATURE                 Location/Qualifiers
source                  1..459
                        mol_type = protein
                        organism = Homo sapiens
SEQUENCE: 1
MAPLCPSPWL  PLLIPAPAPG  LTVQLLLSLL  LLVPVHPQRL  PRMQEDSPLG  GGSSGEDDPL    60
GEEDLPSEED  SPREEDPPGE  EDLPGEEDLP  GEEDLPEVKP  KSEEEGSLKL  EDLPTVEAPG   120
DPQEPQNNAH  RDKEGDDQSH  WRYGGDPPWP  RVSPACAGRF  QSPVDIRPQL  AAFCPALRPL   180
ELLGFQLPPL  PELRLRNNGH  SVQLTLPPGL  EMALGPGREY  RALQLHLHWG  AAGRPGSEHT   240
VEGHRFPAEI  HVVHLSTAFA  RVDEALGRPG  GLAVLAAFLE  EGPEENSAYE  QLLSRLEEIA   300
EEGSETQVPG  LDISALLPSD  FSRYFQYEGS  LTTPPCAQGV  IWTVFNQTVM  LSAKQLHTLS   360
DTLWGPGDSR  LQLNFRATQP  LNGRVIEASF  PAGVDSSPRA  AEPVQLNSCL  AAGDILALVF   420
GLLFAVTSVA  FLVQMRRQHR  RGTKGGVSYR  PAEVAETGA                            459

SEQ ID NO: 2            moltype = AA   length = 750
FEATURE                 Location/Qualifiers
source                  1..750
                        mol_type = protein
                        organism = Homo sapiens
SEQUENCE: 2
MWNLLHETDS  AVATARRPRW  LCAGALVLAG  GFFLLGFLFG  WFIKSSNEAT  NITPKHNMKA    60
FLDELKAENI  KKFLYNFTQI  PHLAGTEQNF  QLAKQIQSQW  KEFGLDSVEL  AHYDVLLSYP   120
NKTHPNYISI  INEDGNEIFN  TSLFEPPPPG  YENVSDIVPP  FSAFSPQGMP  EGDLVYVNYA   180
RTEDFFKLER  DMKINCSGKI  VIARYGKVFR  GNKVKNAQLA  GAKGVILYSD  PADYFAPGVK   240
SYPDGWNLPG  GGVQRGNILN  LNGAGDPLTP  GYPANEYAYR  RGIAEAVGLP  SIPVHPIGYY   300
DAQKLLEKMG  GSAPPDSSWR  GSLKVPYNVG  PGFTGNFSTQ  KVKMHIHSTN  EVTRIYNVIG   360
TLRGAVEPDR  YVILGGHRDS  WVFGGIDPQS  GAAVVHEIVR  SFGTLKKEGW  RPRRTILFAS   420
WDAEEFGLLG  STEWAEENSR  LLQERGVAYI  NADSSIEGNY  TLRVDCTPLM  YSLVHNLTKE   480
LKSPDEGFEG  KSLYESWTKK  SPSPEFSGMP  RISKLGSGND  FEVFFQRLGI  ASGRARYTKN   540
WETNKFSGYP  LYHSVYETYE  LVEKFYDPMF  KYHLTVAQVR  GGMVFELANS  IVLPFDCRDY   600
AVVLRKYADK  IYSISMKHPQ  EMKTYSVSFD  SLFSAVKNFT  EIASKFSERL  QDFDKSNPIV   660
LRMMNDQLMF  LERAFIDPLG  LPDRPFYRHV  IYAPSSHNKY  AGESFPGIYD  ALFDIESKVD   720
PSKAWGEVKR  QIYVAAFTVQ  AAAETLSEVA                                      750

SEQ ID NO: 3            moltype = RNA   length = 3696
FEATURE                 Location/Qualifiers
source                  1..3696
                        mol_type = mRNA
                        organism = Homo sapiens
SEQUENCE: 3
ctcttctccc gcgggttggt ggacccgctc agtacggagt tggggaagct ctttcacttc         60
ggaggattgc tcaacaacca tgctgggcat ctggaccctc ctacctctgg ttcttacgtc        120
tgttgctaga ttatcgtcca aaagtgttaa tgcccaagtg actgacatca actccaaggg        180
attggaattg aggaagactg ttactacagt tgagactcag aacttggaag gcctgcatca        240
tgatggccaa ttctgccata agccctgtcc tccaggtgaa aggaaagcta gggactgcac        300
agtcaatggg gatgaaccag actgcgtgcc ctgccaagaa gggaaggagt acacagacaa        360
agcccatttt tcttccaaat gcagaagatg tagattgtgt gatgaaggac atggcttaga        420
agtggaaata aactgcaccc ggacccagaa taccaagtgc agatgtaaac caaactttt         480
ttgtaactct actgtatgtg aacactgtga cccttgcacc aaatgtgaac atggaatcat        540
caaggaatgc acactcacca gcaacaccaa gtgcaaagag aaggatcca gatctaactt        600
ggggtggctt tgtcttcttc ttttgccaat tccactaatt gtttgggtga agagaaagga      660
agtacagaaa acatgcagaa agcacagaaa ggaaaaccaa ggttctcatg aatctccaac        720
tttaaatcct gaaacagtgg caataaattt atctgatgtt gacttgagta aatatatcac        780
cactattgct ggagtcatga cactaagtca agttaaaggc tttgttcgaa agaatggtgt        840
caatgaagcc aaaatagatg agatcaagaa tgcaatgtc caagcacag cagaacagaa        900
agttcaactg cttcgtaatt ggcatcaact tcatggaaag aaagaagcgt atgacacatt        960
gattaaagat ctcaaaaaag ccaatctttg tactcttgca gagaaaattc agactatcat       1020
cctcaaggac attactagtg actcagaaaa ttcaaacttc agaaatgaaa tccaaagctt       1080
ggtctagagt gaaaaacaac aaattcagtt ctgagtatat gcaattagtg tttgaaaaga       1140
ttcttaatag ctggctgtaa atactgcttg gtttttttact gggtacattt tatcatttat       1200
tagcgctgaa gagccaacat atttgtagat ttttaaatatc tcatgattct gcctccaagg       1260
atgtttaaaa tctagttggg aaaacaaact tcatcaagag taaatgcagt ggcatgctaa       1320
gtacccaaat aggagtgtat gcagaggatg aaagattaag attatgctct ggcatctaac       1380
atatgattct gtagtatgaa tgtaatcagt gtatgttagt acaaatgtct atccacaggc       1440
taaccccact ctatgaatca atagaagaag ctatgacctt tgctgaaat atcagttact       1500
gaacaggcag gccactttgc ctctaaatta cctctgataa ttctagagat tttaccatat       1560
```

```
ttctaaactt tgtttataac tctgagaaga tcatatttat gtaaagtata tgtatttgag 1620
tgcagaattt aaataaggct ctacctcaaa gacctttgca cagttttattg gtgtcatatt 1680
atacaatatt tcaattgtga attcacatag aaaacattaa attataatgt ttgactatta 1740
tatatgtgta tgcattttac tggctcaaaa ctacctactt ctttctcagg catcaaaagc 1800
attttgagca ggagagtatt actagagctt tgccacctct ccattttttgc cttggtgctc 1860
atcttaatgg cctaatgcac ccccaaacat ggaaatatca ccaaaaaata cttaatagtc 1920
caccaaaagg caagactgcc cttagaaatt ctagcctggt ttggagatac taactgctct 1980
cagagaaagt agctttgtga catgtcatga acccatgttt gcaatcaaag atgataaaat 2040
agattcttat ttttcccca cccccgaaaa tgttcaataa tgtcccatgt aaaacctgct 2100
acaaatggca gcttatacat agcaatggta aaatcatcat ctggatttag gaattgctct 2160
tgtcataccc ccaagtttct aagatttaag attctcctta ctactatcct acgtttaaat 2220
atctttgaaa gtttgtatta aatgtgaatt ttaagaaata atatttatat ttctgtaaat 2280
gtaaactgtg aagatagtta taaactgaag cagatacctg gaaccaccta aagaacttcc 2340
atttatggag gattttttg ccccttgtgt ttggaattat aaaatatagg taaaagtacg 2400
taattaaata atgtttttgg tatttctggt tttctcttt ttggtagggg cttgcttttt 2460
ggttttgtct tccttttctc taactgatgc taaatataac ttgtctttaa tgcttcttgg 2520
atcccttaga aggtacttcc tttttaacct taacccttttt agtagttaaa taattatttc 2580
cataggttgc tattgccaag aagacctctt ccaaacagca catgattatt cgtcaaacag 2640
tttcgtattc cagatactgg aatgtggata agaaagtata catttcaagg ggtaggtttt 2700
attattaaga aagccaaatg aggattttga aatattcttt cctgcatatt atccattcta 2760
gctacatgct ggccagtggg ccacctttct tttctgcaat ttaatgctag taatatattc 2820
tatttaaccc atgagtccca aagtattagc atttcaacat gtaagcatgt cggtaagata 2880
gttgtgcttt gcttagggtt ccctcctgtg ttatggtctg gaaagtgtct ttaggcagaa 2940
agtctgagtg atcacagggt tcactcatta atttctcttt tctgagccat catagtctgt 3000
gctgtctgct ctccagtttt ctatttctag acagaagtag ggcaagttag gtactagtta 3060
ttcttcatgg ccagaagtgc aagttctact ttgcaagaca agattaagtt agagaacacg 3120
ctattccact ttggtgaact cagagcaaga actttgagtt cctttgggag gaagacagtg 3180
gagaagtctt tgtacttggt gatgtggttt ttttcctcat ggcttcacct agtggcccca 3240
agcatgactt ctcccatgtc aatgagcaca gccacattcc cgagttgagg tgaccccacg 3300
gtccagaatc atcctcattc tggtgaacct ggttctcttt gtggtgggca tactgggtag 3360
gagaatcacc caaaggtcac ccatgagctg cagaaaaaaa ggctatttgc agaaggagct 3420
cacagatcac attgaaagca ttgcatattc aaacatcttg gtcttcttta ttggcatgcc 3480
cacagggtct tctgacctct gattagatca gacacttttt agatattgaa tcatcagttt 3540
ctgtacaact atctgaataa ggtatataat caatgaaatt tagaattttt ttctatgctt 3600
actcctgatt ggtaatttgt ttgggtttag aattctatac aaggccattt gtaattttcc 3660
tcagcacttt aaaaatatta aaccatgttt tcttaa 3696

SEQ ID NO: 4         moltype = DNA   length = 4530
FEATURE              Location/Qualifiers
source               1..4530
                     mol_type = genomic DNA
                     organism = Homo sapiens
SEQUENCE: 4
actcgcgcgc acggagcgac gacaccccg cgcgtgcacc cgctcgggac aggagccgga 60
ctcctgtgca gcttccctcg gccgcggggg gcctcccgc gcctcgcgg cctccaggcc 120
ccctcctggc tggcgagcgg gcgccacatc tggcccgcac atctgcgctg ccggcccggc 180
gcggggtccg gagagggcgc ggcgcggagg cgcagccagg ggtccgggaa ggccgcgtcc 240
gctgcgctgg gggctcggtc tatgacgagc agcggggtct gccatgggtc gggggctgct 300
caggggcctg tggccgctgc acatcgtcct gtggacgcgt atcgcagca cgatcccacc 360
gcacgttcag aagtcggtta ataacgacat gatagtcact gacaacaacg gtgcagtcaa 420
gtttccacaa ctgtgtaaat tttgtgatgt gagattttcc acctgtgaca accagaaatc 480
ctgcatgagc aactgcagca tcacctccat ctgtgagaag ccacaggaag tctgtgtggc 540
tgtatggaga aagaatgacg agaacataac actagagaca gtttgccatg accccaagct 600
cccctaccat gactttattc tggaagatgc tgcttctcca aagtgcatta tgaaggaaaa 660
aaaaaagcct ggtgagactt tcttcatgtg ttcctgtagt ctgatgagt gcaatgacaa 720
catcatcttc tcagaagaat ataacaccag caatcctgac ttgttgctag tcatatttca 780
agtgacaggc atcagcctcc tgccaccact gggagttgcc atatctgtca tcatcatctt 840
ctactgctac cgcgttaacc ggcagcagaa gctgagttca acctgggaaa ccggcaagac 900
gcggaagctc atggagttca gcgagcactg tgccatcatc ctggaagatg accgctctga 960
catcagctcc acgtgtgcca acacatcca ccacaacaga gagctgctgc ccattgagct 1020
ggacacctg tgtgggaaag gtcgctttgc tgaggtctat aaggccaagc tgaagcagaa 1080
cacttcagag cagtttgaga cagtggcagt caagatcttt ccctatgagg agtatgcctc 1140
ttggaagaca gagaaggaca tcttctcaga catcaatctg aagcatgaga acatactcca 1200
gttcctgacg gctgaggagc ggaagacgga gttgggaaca caatactggc tgatcaccgc 1260
cttcacgcc aagggcaacc tacaggagta cctgacgcgg catgtcatca gctgggagga 1320
cctgcgcaag ctgggcagct ccctcgcccg gggattgct cacctccaca gtgatcacac 1380
tccatgtggg aggcccaaga tgccatcgt gcacagggac ctcaagagct ccaatatcct 1440
cgtgaagaac gacctaacct gctgcctgtg tgactttggg ctttcccctgc gtctggaccc 1500
tactctgtct gtggatgacc tggctaacag tgggcaggtg ggaactgcaa gatacatggc 1560
tccagaagtc ctagaatcca ggatgaattt ggagaatgtt gagtccttca agcagaccga 1620
tgtctactcc atggctctgg tgctctggga aatgacatct cgctgtaatg cagtgggaga 1680
agtaaaagat tatgagcctc catttggttc caaggtgcgg gagcacccct gtgtcgaaag 1740
catgaaggac aacgtgttga gagatcgagg cgaccagaa attcccagct tctggctcaa 1800
ccaccagggc atccagatgg tgtgtgagac gttgactgga tgctgggaca agaccccaga 1860
ggccccgtct acagcccagt gtgtggcaga acgcttcagt gagctggagc atctggacag 1920
gctctcgggg aggagctgct cggaggagaa gattcctgaa gacggctccc taaacactac 1980
caaatagctc ttctggggca ggctgggcca tgtccaaaga ggctgcccct ctcaccaaag 2040
aacagaggca gcaggaagct gccctgaac tgatgcttcc tggaaaacca ggggtcac 2100
tccctccct gtaagctgtg gggataagca gaaacaacag cagcagggag tgggtgacat 2160
```

```
agagcattct atgcctttga cattgtcata ggataagctg tgttagcact tcctcaggaa    2220
atgagattga tttttacaat agccaataac atttgcactt tattaatgcc tgtatataaa    2280
tatgaatagc tatgttttat atatatatat atatatctat atatgtctat agctctatat    2340
atatagccta accttgaaaa gagacaagga aaaacatcaa atattcccag gaaattggtt    2400
ttattggaga actccagaac caagcagaga aggaaggcac ccatgacagc attagcattt    2460
gacaatcaca catgcagtgg ttctctgact gtaaaacagt gaactttgca tgaggaaaga    2520
ggctccatgt ctcacagcca gctatgacca cattgcactt gcttttgcaa ataatcatt    2580
ccctgcctag cacttctctt ctggccatgg aactaagtac agtggcactg tttgaggacc    2640
agtgttcccg gggttcctgt gtgccctttat ttctcctgga cttttcattt aagctccaag    2700
ccccaaatct ggggggctag tttagaaact ctccctcaac ctagtttaga aactctaccc    2760
catctttaat accttgaatg ttttgaaccc cacttttac cttcatgggt tgcagaaaaa    2820
tcagaacaga tgtccccatc catgcgattg ccccaccatc tactaatgaa aaattgttct    2880
ttttttcatc tttcccctgc acttatgtta ctattctctg ctcccagcct tcatcctttt    2940
ctaaaaagga gcaaattctc actctaggct ttatcgtgtt tactttttca ttacacttga    3000
cttgattttc tagttttcta tacaaacacc aatgggttcc atcttctggg gctcctgatt    3060
gctcaagcac agtttggcct gatgaagagg atttcaacta cacaatacta tcattgtcag    3120
gactatgacc tcaggcactc taaacatatg tttttgtttgg tcagcacagc gtttcaaaaa    3180
gtgaagccac tttataaata tttgaagatt ttgcaggaaa atctgatcc ccaggtaagg    3240
atagcagatg gttttcagtt atctccagtc cacgttcaca aaatgtgaag gtgtggagac    3300
acttacaaag ctgcctcact tctcactgta aacattagct ctttccactg cctacctgga    3360
ccccagtcta ggaattaaat ctgcacctaa ccaaggtccc ttgtaagaaa tgtccattca    3420
agcagtcatt ctctgggtat ataatatgat tttgactacc ttctcgtgtg ttaagatttg    3480
aagttggcct tttattggac taaagggaa ctcctttaag ggtctcagtt agcccaagtt    3540
tcttttgctt atatgttaat agttttaccc tctgcattgg agagaggagt gctttactcc    3600
aagaagcttt cctcatggtt accgttctct ccatcatgcc agccttctca acctttgcag    3660
aaattactag agaggatttg aatgtgggac acaaaggtcc catttgcagt tagaaaattt    3720
gtgtccacaa ggacaagaac aaagtatgag ctttaaaact ccataggaaa cttgttaatc    3780
aacaaagaag tgttaatgct gcaagtaatc tctttttta aacttttga agctacttat    3840
tttcagccaa ataggaatat tagagaggga ctggtagtga gaatatcagc tctgtttgga    3900
tggtggaagg tctcattta ttgagatttt taagatacat gcaaaggttt ggaaatagaa    3960
cctctaggca ccctcctcag tgtgggtggg ctgagagtta aagacagtgt ggctgcagta    4020
gcatagaggc gcctagaaat tccacttgca ccgtagggca tgctgatacc atcccaatag    4080
ctgttgccca ttgacctcta gtggtgagtt tctagaatac tggtccattc atgagatatt    4140
caagattcaa gagtattctc acttctgggt tatcagcata actggaatg tagtgtcaga    4200
ggatactgtg gcttgttttg tttatgtttt tttttcttat tcaagaaaaa agaccaagga    4260
ataacattct gtagttccta aaaatactga ctttttcac tactatacat aaagggaaag    4320
ttttattctt ttatgaaaca cttcagctgt actcatgtat taaaataga atgtgaatgc    4380
tatatactct ttttatatca aaagtctcaa gcacttattt ttattctatg cattgtttgt    4440
cttttacata aataaaatgt ttattagatt gaataaagca aaatactcag gtgagcatcc    4500
tgcctcctgt tcccattcct agtagctaaa                                     4530
SEQ ID NO: 5           moltype = RNA   length = 3470
FEATURE                Location/Qualifiers
source                 1..3470
                       mol_type = mRNA
                       organism = Homo sapiens
SEQUENCE: 5
gcatgcgccg cagcgccagc gctctccccg gatcgtgcgg ggcctgagcc tctccgccgg      60
cgcaggctct gctcgcgcca gctcgctccc gcagccatgc ccaccaccat cgagcgggag     120
ttcgaagagt tggatactca gcgtcgctgg cagccgctgt acttggaaat tcgaaatgag     180
tcccatgact atcctcatag agtggccaag ttttcagaaa acagaaatcg aaacagatac     240
agagatgtaa gcccatatga tcacagtcgt gttaaactgc aaaatgctga gaatgattat     300
attaatgcca gtttagttga catagaagag cacaaagga gttacatctt aacacagggt     360
ccacttccta cacacatgctg ccatttctgg cttatggttt ggcagcagaa gaccaaagca     420
gttgtcatgc tgaaccgcat tgtgggagaa gaatcggtta aatgtgcaca gtactggcca     480
acagatgacc aagagatgct gtttaaagaa acaggattca gtgtgaagac cttgtcagaa     540
gatgtgaagt cgtattata agtacatcta ctacaattag aaaatatcaa tagtggtgaa     600
accagaacaa tatctcactt tcattatact acctggccag attttggagt ccctgaatca     660
ccagcttcat ttctcaattt cttgtttaaa gtgagagaat ctggctcctt gaaccctgac     720
catgggcctg cggtgatcca ctgtagtgca ggcattgggc gctctggcac cttctctctg     780
gtagacactt gtcttgtttt gatggaaaaa ggagatgata ttaacataaa acaagtgtta     840
ctgaacatga gaaataccg aatgggtctt ttcagaccc cagatcaact gagattctca     900
tacatggcta ataaggaagg agcaaaatgt ataaggaag attctagtat acagaaacga     960
tggaaagaac tttctaagga agacttatct cctgcctttg atcattccac aaacaaaata    1020
atgactgaaa aatacaatgg gaacagaata ggtctagaaa aagaaaaact gacaggtgac    1080
cgatgtacag gactttcctc taaaatgcaa gatacaatgg aggagaacag tgagagtgct    1140
ctacggaaac gtattcgaga ggacagaaag gccaccacag ctcagaaggt gcagcagatg    1200
aaacagaggc taaatgagaa tgaacgaaaa agaaaaaggt ggtatattg gcaacctatt    1260
ctcactaaga tggggttat gtcagtcatt ttggttgcg cttttgttgg ctggacactg    1320
tttttttcagc aaaatgccct ataaacaatt aattttgccc agcaagcttc tgcactagta    1380
actgacagtg ctacattaat cataggggtt tgtctgcagc aaacgcctca tatcccaaaa    1440
acggtgcagt agaatagaca tcaaccagat aagtgatatt tacagtcaca gcccaacat    1500
ctcaggactc ttgactgcag gttcctctga acccaaact gtaaatggct gtctaaaata    1560
aagacattca tgtttgttaa aaactgtaa atttgcaac tgtattcata catgtcaaaac    1620
acagtatttc acctgaccaa cattgagata tcctttatca caggatttgt ttttggagc    1680
tatctggatt ttaacctgca cttgataaa gcaataaata ttgtggtttt atctacgtta    1740
ttggaaagaa aatgacattt aaataatgtg tgtaatgtat aatgtactat tgacatgggc    1800
atcaacactt ttattcttaa gcatttcagg gtaaatatat tttataagta tctatttaat    1860
cttttgtagt taactgtact ttttaagagc tcaatttgaa aaatctgtta ctaaaaaaat    1920
```

```
aaattgtatg tcgattgaat tgtactggat acattttcca tttttctaaa gagaagtttg    1980
atatgagcag ttagaagttg gaataagcaa tttctactat atattgcatt tcttttatgt    2040
tttacagttt tccccatttt aaaaagaaaa gcaaacaaag aaacaaaagt ttttcctaaa    2100
aatatctttg aaggaaaatt ctccttactg ggatagtcag gtaaacagtt ggtcaagact    2160
ttgtaaagaa attggtttct gtaaatccca ttattgatat gtttatttt  catgaaaatt    2220
tcaatgtagt tggggtagat tatgatttag gaagcaaaag taagaagcag cattttatga    2280
ttcataattt cagtttacta gactgaagtt ttgaagtaaa cacttttcag tttcttttcta   2340
cttcaataaa tagtatgatt atatgcaaac cttacattgt cattttaact taatgaatat    2400
ttttaaagc aaactgttta atgaatttaa ctgctcattt gaatgctagc tttcctcaga     2460
tttcaacatt ccattcagtg tttaatttgt cttacttaaa cttgaaattg ttgttacaaa    2520
tttaattgct aggaggcatg gatagcatac attattatgg atagcatacc ttatttcagt    2580
ggttttcaaa ctatgctcat tggatgtcca ggtgggtcaa gaggttactt tcaaccacag    2640
catctctgcc ttgtctcttt atatgccaca taagattct gcataaggct taagtatttt    2700
aaaggggca gttatcattt aaaaacagtt tggtcgggcg cggtggctca tgcctgtaat    2760
cccagcactt tgggaggctg aagtgggcag atcacctgag gtcaggagtt caagaccagc    2820
ctggccaacg tggtgaaaca ccatctctac taaaaatgca aaaattagct gggcatggtg    2880
gagggcacct gtaatctcag ctactcagga ggctgaggta ggagaattgc ttgaacccag    2940
gagatggagg ttgcagtgag ctgagatcac gtcactgcac tccagccagg gcgacagagc    3000
gagactccat ctcaaaagaa acaaacaaaa aaaacagttt gggccgggtg tggtggctca    3060
cgcttgtaat cccagcactt cggaaggcca aggcgggcgg atcacgaggt caagagatgg    3120
agactgtcct ggccaacatg gtgaaatccc ttctttacta aaaatacaaa aattatctgg    3180
gcgtggtggt gcatgcctgt agtcccagct ccttgggagg ctaaggcagg agaatcactt    3240
gaacccggga ggcagaggtt gcagtgagcc gagattgcac cactgcactc cagcctggca    3300
acagagcaag acttcgtctc aaaaaaaaaa aaaaaaaag tttgaaaacc attggtatag    3360
atagatattt tgaattgatt tgcatagtct ccttgaatgt gttaaattat gttgaaagta    3420
tgaaagcagg atgtaggtgg tactacatat taaataagat ttatataaca              3470

SEQ ID NO: 6             moltype = RNA   length = 22
FEATURE                  Location/Qualifiers
source                   1..22
                         mol_type = other RNA
                         organism = synthetic construct
SEQUENCE: 6
tagattttaa acatccttgg ag                                             22

SEQ ID NO: 7             moltype = RNA   length = 22
FEATURE                  Location/Qualifiers
source                   1..22
                         mol_type = other RNA
                         organism = synthetic construct
SEQUENCE: 7
tagattttaa acatccttgg ag                                             22

SEQ ID NO: 8             moltype = RNA   length = 22
FEATURE                  Location/Qualifiers
source                   1..22
                         mol_type = other RNA
                         organism = synthetic construct
SEQUENCE: 8
ttactcttga tgaagtttgt tt                                             22

SEQ ID NO: 9             moltype = RNA   length = 22
FEATURE                  Location/Qualifiers
source                   1..22
                         mol_type = other RNA
                         organism = synthetic construct
SEQUENCE: 9
ttgaactttc tgttctgctg tg                                             22

SEQ ID NO: 10            moltype = RNA   length = 22
FEATURE                  Location/Qualifiers
source                   1..22
                         mol_type = other RNA
                         organism = synthetic construct
SEQUENCE: 10
ttgtctgtgt actccttccc tt                                             22

SEQ ID NO: 11            moltype = RNA   length = 22
FEATURE                  Location/Qualifiers
source                   1..22
                         mol_type = other RNA
                         organism = synthetic construct
SEQUENCE: 11
tctttgattg caaacatggg tt                                             22

SEQ ID NO: 12            moltype = RNA   length = 22
FEATURE                  Location/Qualifiers
source                   1..22
                         mol_type = other RNA
```

```
                        organism = synthetic construct
SEQUENCE: 12
ttgatctcat ctattttggc tt                                                    22

SEQ ID NO: 13           moltype = RNA   length = 22
FEATURE                 Location/Qualifiers
source                  1..22
                        mol_type = other RNA
                        organism = synthetic construct
SEQUENCE: 13
ttaagaatct tttcaaacac ta                                                    22

SEQ ID NO: 14           moltype = RNA   length = 22
FEATURE                 Location/Qualifiers
source                  1..22
                        mol_type = other RNA
                        organism = synthetic construct
SEQUENCE: 14
ttctattgat tcatagagtg gg                                                    22

SEQ ID NO: 15           moltype = RNA   length = 22
FEATURE                 Location/Qualifiers
source                  1..22
                        mol_type = other RNA
                        organism = synthetic construct
SEQUENCE: 15
taatcttaat ctttcatcct ct                                                    22

SEQ ID NO: 16           moltype = RNA   length = 22
FEATURE                 Location/Qualifiers
source                  1..22
                        mol_type = other RNA
                        organism = synthetic construct
SEQUENCE: 16
ttaacttgac ttagtgtcat ga                                                    22

SEQ ID NO: 17           moltype = RNA   length = 22
FEATURE                 Location/Qualifiers
source                  1..22
                        mol_type = other RNA
                        organism = synthetic construct
SEQUENCE: 17
ttacataaat atgatcttct ca                                                    22

SEQ ID NO: 18           moltype = RNA   length = 22
FEATURE                 Location/Qualifiers
source                  1..22
                        mol_type = other RNA
                        organism = synthetic construct
SEQUENCE: 18
tacataaata tgatcttctc ag                                                    22

SEQ ID NO: 19           moltype = RNA   length = 22
FEATURE                 Location/Qualifiers
source                  1..22
                        mol_type = other RNA
                        organism = synthetic construct
SEQUENCE: 19
taaaaatcta caaatatgtt gg                                                    22

SEQ ID NO: 20           moltype = RNA   length = 22
FEATURE                 Location/Qualifiers
source                  1..22
                        mol_type = other RNA
                        organism = synthetic construct
SEQUENCE: 20
tttggtttac atctgcactt gg                                                    22

SEQ ID NO: 21           moltype = RNA   length = 22
FEATURE                 Location/Qualifiers
source                  1..22
                        mol_type = other RNA
                        organism = synthetic construct
SEQUENCE: 21
tataatacga cttcacatct tc                                                    22

SEQ ID NO: 22           moltype = RNA   length = 22
FEATURE                 Location/Qualifiers
source                  1..22
```

```
                        mol_type = other RNA
                        organism = synthetic construct
SEQUENCE: 22
tagaaagttc tttccatcgt tt                                               22

SEQ ID NO: 23           moltype = RNA   length = 22
FEATURE                 Location/Qualifiers
source                  1..22
                        mol_type = other RNA
                        organism = synthetic construct
SEQUENCE: 23
ttctatgtca actaaactgg ca                                               22

SEQ ID NO: 24           moltype = RNA   length = 22
FEATURE                 Location/Qualifiers
source                  1..22
                        mol_type = other RNA
                        organism = synthetic construct
SEQUENCE: 24
ttaaacagca tctcttggtc at                                               22

SEQ ID NO: 25           moltype = RNA   length = 22
FEATURE                 Location/Qualifiers
source                  1..22
                        mol_type = other RNA
                        organism = synthetic construct
SEQUENCE: 25
tcgaatttcc aagtacagcg gc                                               22

SEQ ID NO: 26           moltype = RNA   length = 22
FEATURE                 Location/Qualifiers
source                  1..22
                        mol_type = other RNA
                        organism = synthetic construct
SEQUENCE: 26
ttagaaagtt ctttccatcg tt                                               22

SEQ ID NO: 27           moltype = RNA   length = 22
FEATURE                 Location/Qualifiers
source                  1..22
                        mol_type = other RNA
                        organism = synthetic construct
SEQUENCE: 27
tagatgtact gtataatacg ac                                               22

SEQ ID NO: 28           moltype = RNA   length = 22
FEATURE                 Location/Qualifiers
source                  1..22
                        mol_type = other RNA
                        organism = synthetic construct
SEQUENCE: 28
tctgtatact agaatctccc tt                                               22

SEQ ID NO: 29           moltype = RNA   length = 22
FEATURE                 Location/Qualifiers
source                  1..22
                        mol_type = other RNA
                        organism = synthetic construct
SEQUENCE: 29
ttttatgtta atatcatctc ct                                               22

SEQ ID NO: 30           moltype = RNA   length = 22
FEATURE                 Location/Qualifiers
source                  1..22
                        mol_type = other RNA
                        organism = synthetic construct
SEQUENCE: 30
tgagaatctc agttgatctg gg                                               22

SEQ ID NO: 31           moltype = RNA   length = 22
FEATURE                 Location/Qualifiers
source                  1..22
                        mol_type = other RNA
                        organism = synthetic construct
SEQUENCE: 31
tctgacaaga gcttcacact ga                                               22

SEQ ID NO: 32           moltype = RNA   length = 22
FEATURE                 Location/Qualifiers
```

```
source                        1..22
                              mol_type = other RNA
                              organism = synthetic construct
SEQUENCE: 32
ttctattata gccatgtatg ag                                                    22

SEQ ID NO: 33            moltype = RNA  length = 22
FEATURE                  Location/Qualifiers
source                   1..22
                         mol_type = other RNA
                         organism = synthetic construct
SEQUENCE: 33
tgatattttc taattgtagt ag                                                    22

SEQ ID NO: 34            moltype = RNA  length = 22
FEATURE                  Location/Qualifiers
source                   1..22
                         mol_type = other RNA
                         organism = synthetic construct
SEQUENCE: 34
tttcttacaa gggaccttgg tt                                                    22

SEQ ID NO: 35            moltype = RNA  length = 22
FEATURE                  Location/Qualifiers
source                   1..22
                         mol_type = other RNA
                         organism = synthetic construct
SEQUENCE: 35
tataagcaaa agaaacttgg gc                                                    22

SEQ ID NO: 36            moltype = RNA  length = 22
FEATURE                  Location/Qualifiers
source                   1..22
                         mol_type = other RNA
                         organism = synthetic construct
SEQUENCE: 36
tttctggttg tcacaggtgg aa                                                    22

SEQ ID NO: 37            moltype = RNA  length = 22
FEATURE                  Location/Qualifiers
source                   1..22
                         mol_type = other RNA
                         organism = synthetic construct
SEQUENCE: 37
ttgttgatta acaagtttcc ta                                                    22

SEQ ID NO: 38            moltype = RNA  length = 22
FEATURE                  Location/Qualifiers
source                   1..22
                         mol_type = other RNA
                         organism = synthetic construct
SEQUENCE: 38
tagagtgaga atttgctcct tt                                                    22

SEQ ID NO: 39            moltype = RNA  length = 22
FEATURE                  Location/Qualifiers
source                   1..22
                         mol_type = other RNA
                         organism = synthetic construct
SEQUENCE: 39
ttcaggaatc ttctcctccg ag                                                    22

SEQ ID NO: 40            moltype = RNA  length = 22
FEATURE                  Location/Qualifiers
source                   1..22
                         mol_type = other RNA
                         organism = synthetic construct
SEQUENCE: 40
tttaatacat gagtacagct ga                                                    22

SEQ ID NO: 41            moltype = RNA  length = 22
FEATURE                  Location/Qualifiers
source                   1..22
                         mol_type = other RNA
                         organism = synthetic construct
SEQUENCE: 41
tttctaaact aggttgaggg ag                                                    22

SEQ ID NO: 42            moltype = RNA  length = 22
```

```
FEATURE              Location/Qualifiers
source               1..22
                     mol_type = other RNA
                     organism = synthetic construct
SEQUENCE: 42
ttgtcagtga ctatcatgtc gt                                              22

SEQ ID NO: 43        moltype = RNA   length = 22
FEATURE              Location/Qualifiers
source               1..22
                     mol_type = other RNA
                     organism = synthetic construct
SEQUENCE: 43
tattttaata catgagtaca gc                                              22

SEQ ID NO: 44        moltype = RNA   length = 22
FEATURE              Location/Qualifiers
source               1..22
                     mol_type = other RNA
                     organism = synthetic construct
SEQUENCE: 44
taagcaaaag aaacttgggc ta                                              22

SEQ ID NO: 45        moltype = RNA   length = 22
FEATURE              Location/Qualifiers
source               1..22
                     mol_type = other RNA
                     organism = synthetic construct
SEQUENCE: 45
ttttaataca tgagtacagc tg                                              22

SEQ ID NO: 46        moltype = RNA   length = 22
FEATURE              Location/Qualifiers
source               1..22
                     mol_type = other RNA
                     organism = synthetic construct
SEQUENCE: 46
ttaaaaaaga gattacttgc ag                                              22

SEQ ID NO: 47        moltype = RNA   length = 22
FEATURE              Location/Qualifiers
source               1..22
                     mol_type = other RNA
                     organism = synthetic construct
SEQUENCE: 47
tattcatatt tatatacagg ca                                              22

SEQ ID NO: 48        moltype = RNA   length = 22
FEATURE              Location/Qualifiers
source               1..22
                     mol_type = other RNA
                     organism = synthetic construct
SEQUENCE: 48
ttttaaaaaa gagattactt gc                                              22

SEQ ID NO: 49        moltype = RNA   length = 22
FEATURE              Location/Qualifiers
source               1..22
                     mol_type = other RNA
                     organism = synthetic construct
SEQUENCE: 49
ttatgtaaaa gacaaacaat gc                                              22

SEQ ID NO: 50        moltype = RNA   length = 22
FEATURE              Location/Qualifiers
source               1..22
                     mol_type = other RNA
                     organism = synthetic construct
SEQUENCE: 50
ttaaatgaaa agtccaggag aa                                              22

SEQ ID NO: 51        moltype = RNA   length = 22
FEATURE              Location/Qualifiers
source               1..22
                     mol_type = other RNA
                     organism = synthetic construct
SEQUENCE: 51
ttgattaaca agtttcctat gg                                              22
```

```
SEQ ID NO: 52          moltype = RNA  length = 22
FEATURE                Location/Qualifiers
source                 1..22
                       mol_type = other RNA
                       organism = synthetic construct
SEQUENCE: 52
tttaattcct agactggggt cc                                               22

SEQ ID NO: 53          moltype = RNA  length = 22
FEATURE                Location/Qualifiers
source                 1..22
                       mol_type = other RNA
                       organism = synthetic construct
SEQUENCE: 53
tcaaaatcat attatatacc ca                                               22

SEQ ID NO: 54          moltype = RNA  length = 22
FEATURE                Location/Qualifiers
source                 1..22
                       mol_type = other RNA
                       organism = synthetic construct
SEQUENCE: 54
tatatataga gctatagaca ta                                               22

SEQ ID NO: 55          moltype = RNA  length = 22
FEATURE                Location/Qualifiers
source                 1..22
                       mol_type = other RNA
                       organism = synthetic construct
SEQUENCE: 55
tgtaatgaaa aagtaaacac ga                                               22

SEQ ID NO: 56          moltype = RNA  length = 22
FEATURE                Location/Qualifiers
source                 1..22
                       mol_type = other RNA
                       organism = synthetic construct
SEQUENCE: 56
ttctaaacta ggttgaggga ga                                               22

SEQ ID NO: 57          moltype = RNA  length = 22
FEATURE                Location/Qualifiers
source                 1..22
                       mol_type = other RNA
                       organism = synthetic construct
SEQUENCE: 57
tattctagaa actcaccact ag                                               22

SEQ ID NO: 58          moltype = RNA  length = 22
FEATURE                Location/Qualifiers
source                 1..22
                       mol_type = other RNA
                       organism = synthetic construct
SEQUENCE: 58
ttgaaatcct cttcatcagg cc                                               22

SEQ ID NO: 59          moltype = RNA  length = 22
FEATURE                Location/Qualifiers
source                 1..22
                       mol_type = other RNA
                       organism = synthetic construct
SEQUENCE: 59
tgagaatact cttgaatctt ga                                               22

SEQ ID NO: 60          moltype = RNA  length = 22
FEATURE                Location/Qualifiers
source                 1..22
                       mol_type = other RNA
                       organism = synthetic construct
SEQUENCE: 60
ttgaatatct catgaatgga cc                                               22

SEQ ID NO: 61          moltype = RNA  length = 22
FEATURE                Location/Qualifiers
source                 1..22
                       mol_type = other RNA
                       organism = synthetic construct
SEQUENCE: 61
tttaaaaaag agattacttg ca                                               22
```

| | | |
|---|---|---|
| SEQ ID NO: 62 | moltype = RNA length = 22 | |
| FEATURE | Location/Qualifiers | |
| source | 1..22 | |
| | mol_type = other RNA | |
| | organism = synthetic construct | |
| SEQUENCE: 62 | | |
| ttcacttttt gaaacgctgt gc | | 22 |
| SEQ ID NO: 63 | moltype = RNA length = 22 | |
| FEATURE | Location/Qualifiers | |
| source | 1..22 | |
| | mol_type = other RNA | |
| | organism = synthetic construct | |
| SEQUENCE: 63 | | |
| taatctttta cttctcccac tg | | 22 |
| SEQ ID NO: 64 | moltype = RNA length = 22 | |
| FEATURE | Location/Qualifiers | |
| source | 1..22 | |
| | mol_type = other RNA | |
| | organism = synthetic construct | |
| SEQUENCE: 64 | | |
| tatatataaa acatagctat tc | | 22 |
| SEQ ID NO: 65 | moltype = RNA length = 22 | |
| FEATURE | Location/Qualifiers | |
| source | 1..22 | |
| | mol_type = other RNA | |
| | organism = synthetic construct | |
| SEQUENCE: 65 | | |
| tatatatata aaacatagct at | | 22 |
| SEQ ID NO: 66 | moltype = RNA length = 22 | |
| FEATURE | Location/Qualifiers | |
| source | 1..22 | |
| | mol_type = other RNA | |
| | organism = synthetic construct | |
| SEQUENCE: 66 | | |
| ttgtggttga tgttgttggc ac | | 22 |
| SEQ ID NO: 67 | moltype = RNA length = 22 | |
| FEATURE | Location/Qualifiers | |
| source | 1..22 | |
| | mol_type = other RNA | |
| | organism = synthetic construct | |
| SEQUENCE: 67 | | |
| tagaataaaa ataagtgctt ga | | 22 |
| SEQ ID NO: 68 | moltype = RNA length = 22 | |
| FEATURE | Location/Qualifiers | |
| source | 1..22 | |
| | mol_type = other RNA | |
| | organism = synthetic construct | |
| SEQUENCE: 68 | | |
| taatgtttac agtgagaagt ga | | 22 |
| SEQ ID NO: 69 | moltype = RNA length = 22 | |
| FEATURE | Location/Qualifiers | |
| source | 1..22 | |
| | mol_type = other RNA | |
| | organism = synthetic construct | |
| SEQUENCE: 69 | | |
| tagggaaaga tcttgactgc ca | | 22 |
| SEQ ID NO: 70 | moltype = RNA length = 22 | |
| FEATURE | Location/Qualifiers | |
| source | 1..22 | |
| | mol_type = other RNA | |
| | organism = synthetic construct | |
| SEQUENCE: 70 | | |
| tagagtttct aaactaggtt ga | | 22 |
| SEQ ID NO: 71 | moltype = RNA length = 22 | |
| FEATURE | Location/Qualifiers | |
| source | 1..22 | |
| | mol_type = other RNA | |
| | organism = synthetic construct | |
| SEQUENCE: 71 | | |

```
ttttagaaaa ggatgaaggc tg                                              22

SEQ ID NO: 72          moltype = RNA   length = 22
FEATURE                Location/Qualifiers
source                 1..22
                       mol_type = other RNA
                       organism = synthetic construct
SEQUENCE: 72
tttagaaaag gatgaaggct gg                                              22

SEQ ID NO: 73          moltype = RNA   length = 22
FEATURE                Location/Qualifiers
source                 1..22
                       mol_type = other RNA
                       organism = synthetic construct
SEQUENCE: 73
atagaataaa aataagtgct tg                                              22

SEQ ID NO: 74          moltype = RNA   length = 22
FEATURE                Location/Qualifiers
source                 1..22
                       mol_type = other RNA
                       organism = synthetic construct
SEQUENCE: 74
tcttgaatct tgaatatctc at                                              22

SEQ ID NO: 75          moltype = RNA   length = 22
FEATURE                Location/Qualifiers
source                 1..22
                       mol_type = other RNA
                       organism = synthetic construct
SEQUENCE: 75
tttcattagt agatggtggg gc                                              22

SEQ ID NO: 76          moltype = RNA   length = 22
FEATURE                Location/Qualifiers
source                 1..22
                       mol_type = other RNA
                       organism = synthetic construct
SEQUENCE: 76
ttagaaaagg atgaaggctg gg                                              22

SEQ ID NO: 77          moltype = RNA   length = 22
FEATURE                Location/Qualifiers
source                 1..22
                       mol_type = other RNA
                       organism = synthetic construct
SEQUENCE: 77
atatatatat aaaacatagc ta                                              22

SEQ ID NO: 78          moltype = RNA   length = 22
FEATURE                Location/Qualifiers
source                 1..22
                       mol_type = other RNA
                       organism = synthetic construct
SEQUENCE: 78
ttatattctt ctgagaagat ga                                              22

SEQ ID NO: 79          moltype = RNA   length = 22
FEATURE                Location/Qualifiers
source                 1..22
                       mol_type = other RNA
                       organism = synthetic construct
SEQUENCE: 79
taaaaatcaa tctcatttcc tg                                              22

SEQ ID NO: 80          moltype = RNA   length = 22
FEATURE                Location/Qualifiers
source                 1..22
                       mol_type = other RNA
                       organism = synthetic construct
SEQUENCE: 80
taataaacat tttatttatg ta                                              22

SEQ ID NO: 81          moltype = RNA   length = 22
FEATURE                Location/Qualifiers
source                 1..22
                       mol_type = other RNA
                       organism = synthetic construct
```

```
SEQUENCE: 81
tgattaacaa gtttcctatg ga                                              22

SEQ ID NO: 82           moltype = RNA   length = 22
FEATURE                 Location/Qualifiers
source                  1..22
                        mol_type = other RNA
                        organism = synthetic construct
SEQUENCE: 82
ttaaaaatct caataaaatg ag                                              22

SEQ ID NO: 83           moltype = RNA   length = 638
FEATURE                 Location/Qualifiers
source                  1..638
                        mol_type = other RNA
                        organism = synthetic construct
SEQUENCE: 83
gtaagtcgac tcgttggatc cccactaccc ggatcaacgc cctaggttta tgtttggatg      60
aactgacata cgcgtatccg tcttaagaat cttttcaaac actagtagtg aaatatatat     120
taaactagtg tttgaaaaga ttcttattac ggtaacgcgg aattcgcaac tatttttatca    180
attttttgcg tcgacgacgg tgacttagga gtatgccgga tcaacgccct aggtttatgt    240
tggatgaac tgacatacgc gtatccgtct aaaaatcaat ctcatttcct ggtagtgaaa     300
tatatattaa accaggaaat gagattgatt ttttacggt aacgcggaat tcgcaactat     360
tttatcaatt ttttgcgtcg acgactgtga cagcagagta tgccggatca acgccctagg    420
tttatgtttg gatgaactga catacgcgta tccgtcttat gtaaaagaca aacaatgcgt    480
agtgaaatat atattaaacg cattgtttgt cttttacata ttacggtaac gcggaattcg    540
caactatttt atcaattttt tgcgtcgacc ggaactatct tgaagagtag tagtggacta    600
gtgtgacgct gctgacccct ttctttccct tctacaga                            638

SEQ ID NO: 84           moltype = RNA   length = 995
FEATURE                 Location/Qualifiers
source                  1..995
                        mol_type = other RNA
                        organism = synthetic construct
SEQUENCE: 84
gtaagtcgac tcgttggatc cccactaccc ggatcaacgc cctaggttta tgtttggatg      60
aactgacata cgcgtatccg tcttaagaat cttttcaaac actagtagtg aaatatatat     120
taaactagtg tttgaaaaga ttcttattac ggtaacgcgg aattcgcaac tatttttatca    180
attttttgcg tcgacacttc aaggggcttg cggccgcaac catctccatg gctgtttgaa    240
tgaggcttca gtactttaca gaatcgttgc ctgcacatct tggaaacact tgctgggatt    300
acttcgactt cttaacccaa cagaaggctc gagaaggtat attgctgttg acagtgagcg    360
ccagtgtgaa gctcttgtca gatagtgaag ccacagatgt atctgacaag agcttcacac    420
tgatgcctac tgcctcggac ttcaaggggc tagaattgca caattatct tgtttactaa     480
aactgaatac cttgctatct ctttgataca tttttacaaa gctgaattaa atggtataa     540
attaaatcac tttgacggtg acttaggagt atgccggatc aacgccctag gtttatgttt    600
ggatgaactg acatacgcgt atccgtctaa aaatcaatct catttcctgg tagtgaaata    660
tatattaaac caggaaatga gattgatttt tttacggtaa cgcggaattc gcaactattt    720
tatcaatttt ttgcgtcgac gactgtgaca gcagagtatg ccggatcaac gccctaggtt    780
tatgtttgga tgaactgaca tacgcgtatc cgtcttatgt aaaagacaaa caatgcgtag    840
tgaaatatat attaaacgca ttgtttgtct tttacatatt acggtaacgc ggaattcgca    900
actattttat caattttttg cgtcgaccgg aactatcttg aagagtagta gtggactagt    960
gtgacgctgc tgaccccttt ctttcccttc tacag                               995

SEQ ID NO: 85           moltype = AA    length = 27
FEATURE                 Location/Qualifiers
source                  1..27
                        mol_type = protein
                        organism = synthetic construct
SEQUENCE: 85
TTTPAPRPPT PAPTIASQPL SLRPEAC                                         27

SEQ ID NO: 86           moltype = AA    length = 22
FEATURE                 Location/Qualifiers
source                  1..22
                        mol_type = protein
                        organism = synthetic construct
SEQUENCE: 86
FMYVAAAAFV LLFFVGCGVL LS                                              22

SEQ ID NO: 87           moltype = AA    length = 43
FEATURE                 Location/Qualifiers
source                  1..43
                        mol_type = protein
                        organism = synthetic construct
SEQUENCE: 87
RKRRRQHGQL WFPEGFKVSE ASKKKRREPL GEDSVGLKPL KNA                       43

SEQ ID NO: 88           moltype = AA    length = 283
FEATURE                 Location/Qualifiers
```

```
source                        1..283
                              mol_type = protein
                              organism = synthetic construct
SEQUENCE: 88
MVSKLSQLQT ELLAALLESG LSKEALLQAL GEPGPYLLAG EGPLDKGESC GGGRGELAEL    60
PNGLGETRGS EDETDDDGED FTPPILKELE NLSPEEAAHQ KAVVETLLQE DPWRVAKMVK   120
SYLQQHNIPQ REVVDTTGLN QSHLSQHLNK GTPMKTQKRA ALYTWYVRKQ REVAQQFTHA   180
GQGGLIEEPT GDELPTKKGR RNRFKWGPAS QQILFQAYER QKNPSKEERE TLVEECNRAE   240
CIQRGVSPSQ AQGLGSNLVT EVRVYNWFAN RRKEEAFRHK LAM                     283

SEQ ID NO: 89                 moltype = AA  length = 191
FEATURE                       Location/Qualifiers
source                        1..191
                              mol_type = protein
                              organism = synthetic construct
SEQUENCE: 89
DEFPTMVFPS GQISQASALA PAPPQVLPQA PAPAPAPAMV SALAQAPAPV PVLAPGPPQA    60
VAPPAPKPTQ AGEGTLSEAL LQLQFDDEDL GALLGNSTDP AVFTDLASVD NSEFQQLLNQ   120
GIPVAPHTTE PMLMEYPEAI TRLVTGAQRP PDPAPAPLGA PGLPNGLLSG DEDFSSIADM   180
DFSALLSQIS S                                                        191

SEQ ID NO: 90                 moltype = AA  length = 477
FEATURE                       Location/Qualifiers
source                        1..477
                              mol_type = protein
                              organism = synthetic construct
SEQUENCE: 90
MVSKLSQLQT ELLAALLESG LSKEALLQAL GEPGPYLLAG EGPLDKGESC GGGRGELAEL    60
PNGLGETRGS EDETDDDGED FTPPILKELE NLSPEEAAHQ KAVVETLLQE DPWRVAKMVK   120
SYLQQHNIPQ REVVDTTGLN QSHLSQHLNK GTPMKTQKRA ALYTWYVRKQ REVAQQFTHA   180
GQGGLIEEPT GDELPTKKGR RNRFKWGPAS QQILFQAYER QKNPSKEERE TLVEECNRAE   240
CIQRGVSPSQ AQGLGSNLVT EVRVYNWFAN RRKEEAFRHK LAMTCRDEFP TMVFPSGQIS   300
QASALAPAPP QVLPQAPAPA PAPAMVSALA QAPAPVPVLA PGPPQAVAPP APKPTQAGEG   360
TLSEALLQLQ FDDEDLGALL GNSTDPAVFT DLASVDNSEF QQLLNQGIPV APHTTEPMLM   420
EYPEAITRLV TGAQRPPDPA PAPLGAPGLP NGLLSGDEDF SSIADMDFSA LLSQISS      477

SEQ ID NO: 91                 moltype = AA  length = 21
FEATURE                       Location/Qualifiers
source                        1..21
                              mol_type = protein
                              organism = synthetic construct
SEQUENCE: 91
MALPVTALLL PLALLLHAAR P                                              21

SEQ ID NO: 92                 moltype = AA  length = 45
FEATURE                       Location/Qualifiers
source                        1..45
                              mol_type = protein
                              organism = synthetic construct
SEQUENCE: 92
TTTPAPRPPT PAPTIASQPL SLRPEACRPA AGGAVHTRGL DFACD                    45

SEQ ID NO: 93                 moltype = AA  length = 24
FEATURE                       Location/Qualifiers
source                        1..24
                              mol_type = protein
                              organism = synthetic construct
SEQUENCE: 93
IYIWAPLAGT CGVLLLSLVI TLYC                                           24

SEQ ID NO: 94                 moltype = AA  length = 39
FEATURE                       Location/Qualifiers
source                        1..39
                              mol_type = protein
                              organism = synthetic construct
SEQUENCE: 94
IEVMYPPPYL DNEKSNGTII HVKGKHLCPS PLFPGPSKP                           39

SEQ ID NO: 95                 moltype = AA  length = 27
FEATURE                       Location/Qualifiers
source                        1..27
                              mol_type = protein
                              organism = synthetic construct
SEQUENCE: 95
FWVLVVVGGV LACYSLLVTV AFIIFWV                                        27

SEQ ID NO: 96                 moltype = AA  length = 42
FEATURE                       Location/Qualifiers
source                        1..42
```

```
                            mol_type = protein
                            organism = synthetic construct
SEQUENCE: 96
KRGRKKLLYI FKQPFMRPVQ TTQEEDGCSC RFPEEEEGGC EL                      42

SEQ ID NO: 97               moltype = AA   length = 112
FEATURE                     Location/Qualifiers
source                      1..112
                            mol_type = protein
                            organism = synthetic construct
SEQUENCE: 97
RVKFSRSADA PAYQQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 98               moltype = AA   length = 240
FEATURE                     Location/Qualifiers
source                      1..240
                            mol_type = protein
                            organism = synthetic construct
SEQUENCE: 98
QVQLVQSGAE VKKPGASVKV SCKASGYTFT SYYMHWVRQA PGQGLEWMGI INPSRGSASY    60
AQKFQGRVTM ARDTSTSTVY MELSSLRSED TAVYYCARDR NYYYYMDVWG KGTTVTVSSG   120
GGGSGGGGSG GGGSEIVMTQ SPATLSVSPG ERATLSCRAS QNISSNLAWY QQKPGQAPRL   180
LIYGASTRAT DIPARFSGSG SGTEFTLTIS SLQSEDFAVY YCQQYITWYT FGQGTKLEIK   240

SEQ ID NO: 99               moltype = AA   length = 119
FEATURE                     Location/Qualifiers
source                      1..119
                            mol_type = protein
                            organism = synthetic construct
SEQUENCE: 99
QVQLVQSGAE VKKPGASVKV SCKASGYTFT SYYMHWVRQA PGQGLEWMGI INPSRGSASY    60
AQKFQGRVTM ARDTSTSTVY MELSSLRSED TAVYYCARDR NYYYYMDVWG KGTTVTVSS    119

SEQ ID NO: 100              moltype = AA   length = 106
FEATURE                     Location/Qualifiers
source                      1..106
                            mol_type = protein
                            organism = synthetic construct
SEQUENCE: 100
EIVMTQSPAT LSVSPGERAT LSCRASQNIS SNLAWYQQKP GQAPRLLIYG ASTRATDIPA    60
RFSGSGSGTE FTLTISSLQS EDFAVYYCQQ YITWYTFGQG TKLEIK                  106

SEQ ID NO: 101              moltype = AA   length = 7
FEATURE                     Location/Qualifiers
source                      1..7
                            mol_type = protein
                            organism = synthetic construct
SEQUENCE: 101
GYTFTSY                                                               7

SEQ ID NO: 102              moltype = AA   length = 6
FEATURE                     Location/Qualifiers
source                      1..6
                            mol_type = protein
                            organism = synthetic construct
SEQUENCE: 102
NPSRGS                                                                6

SEQ ID NO: 103              moltype = AA   length = 10
FEATURE                     Location/Qualifiers
source                      1..10
                            mol_type = protein
                            organism = synthetic construct
SEQUENCE: 103
DRNYYYYMDV                                                           10

SEQ ID NO: 104              moltype = AA   length = 11
FEATURE                     Location/Qualifiers
source                      1..11
                            mol_type = protein
                            organism = synthetic construct
SEQUENCE: 104
RASQNISSNL A                                                         11

SEQ ID NO: 105              moltype = AA   length = 7
FEATURE                     Location/Qualifiers
source                      1..7
                            mol_type = protein
```

```
                        organism = synthetic construct
SEQUENCE: 105
GASTRAT                                                                  7

SEQ ID NO: 106          moltype = AA    length = 8
FEATURE                 Location/Qualifiers
source                  1..8
                        mol_type = protein
                        organism = synthetic construct
SEQUENCE: 106
QQYITWYT                                                                 8

SEQ ID NO: 107          moltype = DNA   length = 720
FEATURE                 Location/Qualifiers
source                  1..720
                        mol_type = other DNA
                        organism = synthetic construct
SEQUENCE: 107
caggtccagc ttgtccagtc cggagcggag gtgaaaaaac cgggcgcgtc cgtgaaagta        60
tcctgcaagg cctccggtta tactttcaca tcctactaca tgcattgggt ccggcaggca       120
cctgggcagg gcctggaatg gatggggatt attaatccct ctcgcggttc tgcatcatat       180
gctcagaagt tcaagggag agtgacaatg gccagagca cacgaccctc aaccgtttac         240
atggaactca gctcgctaag gagcgaggac acagccgtct actattgtgc tcgtgatcgc       300
aactactatt actacatgga tgtgtgggc aaagggacta ccgttacagt ttcatctggc        360
ggcggcggaa gcgtggagg cggttctggc ggaggaggaa gtgaaattgt gatgacccag        420
tctccccgcta cactcagtgt gtcgcctgga gagcgagcta ccctgagttg cagggcctct      480
caaaacatct caagtaatct ggcctggtat cagcaaaagc ccgggcaggc accaaggctg       540
ctgatatacg gagccagcac tagagctacc gatataccag cacggttttc cggcagcggt       600
tcagggaccg agtttacgtt gacgatcagt agcttacaat ccgaggactt cgccgtgtac       660
tattgtcaac agtatatcac ctggtacact ttcggccaag gacaaagtt ggaaatcaag        720

SEQ ID NO: 108          moltype = AA    length = 484
FEATURE                 Location/Qualifiers
source                  1..484
                        mol_type = protein
                        organism = synthetic construct
SEQUENCE: 108
MALPVTALLL PLALLLHAAR PQVQLVQSGA EVKKPGASVK VSCKASGYTF TSYYMHWVRQ        60
APGQGLEWMG IINPSRGSAS YAQKFQGRVT MARDTSTSTV YMELSSLRSE DTAVYYCARD       120
RNYYYYMDVW GKGTTVTVSS GGGGSGGGGS GGGGSEIVMT QSPATLSVSP GERATLSCRA       180
SQNISSNLAW YQQKPGQAPR LLIYGASTRA TDIPARFSGS GSGTEFTLTI SSLQSEDFAV       240
YYCQQYITWY TFGQGTKLEI KAAAIEVMYP PPYLDNEKSN GTIIHVKGKH LCPSPLFPGP       300
SKPFWVLVVV GGVLACYSLL VTVAFIIFWV KRGRKKLLYI FKQPFMRPVQ TTQEEDGCSC       360
RFPEEEEGGC ELRVKFSRSA DAPAYQQGQN QLYNELNLGR REEYDVLDKR RGRDPEMGGK       420
PRRKNPQEGL YNELQKDKMA EAYSEIGMKG ERRRGKGHDG LYQGLSTATK DTYDALHMQA       480
LPPR                                                                   484

SEQ ID NO: 109          moltype = DNA   length = 1455
FEATURE                 Location/Qualifiers
source                  1..1455
                        mol_type = other DNA
                        organism = synthetic construct
SEQUENCE: 109
atggccctgc cagtaacggc tctgctgctg ccacttgctc tgctcctcca tgcagccagg        60
cctcaggtcc agcttgtcca gtccggagcg gaggtgaaaa aaccgggcgc gtccgtgaaa       120
gtatcctgca aggcctccgg ttatactttc acatcctact acatgcattg ggtccggcag       180
gcacctgggc agggcctgga atggatgggg attattaatc cctctcgcgg ttctgcatca       240
tatgctcaga gtttcaagg gagagtgaca atggccagag acactagcac ctcaaccgtt        300
tacatggaac tcagctcgct aaggagcgag gacacagccg tctactattg tgctcgtgat       360
cgcaactact attactacat ggatgtgtgg ggcaaaggga ctaccgttac agtttcatct       420
ggcggcggcg gaagcggtgg aggcggttct ggcggaggag gaagtgaaat tgtgatgacc       480
cagtctcccg ctacactcag tgtgtcgcct ggagagcgag ctaccctgag ttgcagggcc       540
tctcaaaaca tctcaagtaa tctggcctgg tatcagcaaa agcccgggca ggcaccaagg       600
ctgctgatat acggagccag cactagagct accgatatac cagcacggtt ttccggcagc       660
ggttcaggga ccgagtttac gttgacgatc agtagcttac aatccgagga cttcgccgtg       720
tactattgtc aacagtatat cacctggtac actttcggcc aagggacaaa gttggaaatc       780
aaggcggcag caattgaagt atgtaccct ccaccttacc tcgacaatga aaagcaat         840
ggaaccatta tccatgtgaa agggaaacac ctttgtccaa gtccctatt tcccggacct       900
tctaagccct tttgggtgct ggtggtggtt gtgggagtcc tggcttgcta tagcttgcta      960
gtaacagtgg cctttattat tttctgggtt aaacggggca gaaagaaact cctgtatata      1020
ttcaaacaac catttatgag accagtacaa actactcaag aagaggacgg ctgtagctgc      1080
cgatttccag aagaagaaga aggaggatgt gaactgagag tgaagttcag caggagcgca      1140
gacgcccccg cgtaccagca gggccagaac cagctctata acgagctcaa tctaggacga      1200
agagaggagt acgatgtttt ggacaagagg cgtggccgcg accctgagat ggggggaaag      1260
ccgagaagga gaaaccctca ggaaggcctg tacaatgaac ttcagaaaga taagatggcg      1320
gaggcctaca gtgagattgg gatgaaaggc gagcgccgga ggggcaaggg cacgatggc      1380
ctttaccagg gtctcagtac agccaccaag gacacctacg atgccttgca catgcaagcc      1440
ctgcccctc gctaa                                                        1455
```

```
SEQ ID NO: 110           moltype = AA  length = 127
FEATURE                  Location/Qualifiers
source                   1..127
                         mol_type = protein
                         organism = synthetic construct
SEQUENCE: 110
EVQLVESGGG LVQPGGSLRL SCAASGFSFS DYSGMSWVRQ APGKEELVS AISPGGGDTY    60
YADSVKGRFT ISRDNSKNTL YLQMNSLRAE DTAVYYCARR WWYYSNHSGD YDYFDYRGQG   120
TLVTVSS                                                            127

SEQ ID NO: 111           moltype = AA  length = 8
FEATURE                  Location/Qualifiers
source                   1..8
                         mol_type = protein
                         organism = synthetic construct
SEQUENCE: 111
GFSFSDYS                                                             8

SEQ ID NO: 112           moltype = AA  length = 6
FEATURE                  Location/Qualifiers
source                   1..6
                         mol_type = protein
                         organism = synthetic construct
SEQUENCE: 112
SPGGGD                                                               6

SEQ ID NO: 113           moltype = AA  length = 17
FEATURE                  Location/Qualifiers
source                   1..17
                         mol_type = protein
                         organism = synthetic construct
SEQUENCE: 113
RWWYYSNHSG DYDYFDY                                                  17

SEQ ID NO: 114           moltype = DNA  length = 381
FEATURE                  Location/Qualifiers
source                   1..381
                         mol_type = other DNA
                         organism = synthetic construct
SEQUENCE: 114
gaggtccagc tcgtcgagag cggcggtggg ctggttcagc ctggaggaag tctccggctg    60
agctgtgctg caagtggatt ctcatttca gattactccg gatgtcctg ggtgcgtcag    120
gcgccaggga aaggcgaaga attagtgtct gccatttcg ccggtggtgg ggatacttat   180
tatgcagaca gcgtaaaggg ccgattcaca atctcaaggg acaattccaa gaatacgctg   240
tacttgcaga tgaacagcct aagggctgag gataccgccg tgtactattg cgccagaaga   300
tggtggtatt actctaacca ttcaggcgac tacgactatt ttgattaccg cggccaagga   360
acacttgtta ccgtgtctag t                                             381

SEQ ID NO: 115           moltype = AA  length = 374
FEATURE                  Location/Qualifiers
source                   1..374
                         mol_type = protein
                         organism = synthetic construct
SEQUENCE: 115
MALPVTALLL PLALLLHAAR PEVQLVESGG GLVQPGGSLR LSCAASGFSF SDYGMSWVR     60
QAPGKEELV SAISPGGGDT YYADSVKGRF TISRDNSKNT LYLQMNSLRA EDTAVYYCAR    120
RWWYYSNHSG DYDYFDYRGQ GTLVTVSSAA ATTTPAPRPP TPAPTIASQP LSLRPEACRP   180
AAGGAVHTRG LDFACDIYIW APLAGTCGVL LLSLVITLYC KRGRKKLLYI FKQPFMRPVQ   240
TTQEEDGCSC RFPEEEEGGC ELRVKFSRSA DAPAYQQGQN QLYNELNLGR REEYDVLDKR   300
RGRDPEMGGK PRRKNPQEGL YNELQKDKMA EAYSEIGMKG ERRRGKGHDG LYQGLSTATK   360
DTYDALHMQA LPPR                                                    374

SEQ ID NO: 116           moltype = DNA  length = 1122
FEATURE                  Location/Qualifiers
source                   1..1122
                         mol_type = other DNA
                         organism = synthetic construct
SEQUENCE: 116
atggccctgc cagtaacggc tctgctgctg ccacttgctc tgctcctcca tgcagccagg    60
cctgaggtcc agctcgtcga gagcggcggt gggctggttc agcctggagg aagtctccgg   120
ctgagctgtg ctgcaagtgg attctcattt tcagattact ccgggatgtc ctgggtgcgt   180
caggcgccag gaaaggcga agaattagtg tctgccattt cgcccggtgg tggggatact   240
tattatgcag acagcgtaaa gggccgattc acaatctcaa gggacaattc aagaatacg   300
ctgtacttgc agatgaacag cctaagggct gaggataccg ccgtgtacta ttgcgccaga   360
agatggtggt attactctaa ccattcaggc gactacgact attttgatta ccgcggccaa   420
ggaacacttg ttaccgtgtc tagtgcggca gcaaccacga cgccagcgcc gcgaccacca   480
acaccggcgc ctaccatcgc gtcgcagcca ctgtcactgc gcccagaagc gtgccggcca   540
gcggcgggtg gcgcagtgca cacgaggggg ctggacttcg cctgtgatat ctacatctgg   600
gcgcccttgg ccgggacttg tgggtccctt ctcctgtcac tggttatcac cctttactgc   660
```

-continued

```
aaacggggca gaaagaaact cctgtatata ttcaaacaac catttatgag accagtacaa    720
actactcaag aagaggacgg ctgtagctgc cgatttccag aagaagaaga aggaggatgt    780
gaactgagag tgaagttcag caggagcgca gacgccccg  cgtaccagca gggccagaac    840
cagctctata acgagctcaa tctaggacga agagaggagt acgatgtttt ggacaagagg    900
cgtggccggg accctgagat gggggaaag  ccgagaagga agaaccctca ggaaggcctg    960
tacaatgaac tgcagaaaga taagatggc  gaggcctaca gtgagattgg gatgaaaggc   1020
gagcgccgga ggggcaaggg gcacgatggc ctttaccagg gtctcagtac agccaccaag   1080
gacacctacg atgccttgca catgcaagcc ctgccccctc gc                      1122
```

SEQ ID NO: 117        moltype = AA  length = 246
FEATURE               Location/Qualifiers
source                1..246
                        mol_type = protein
                        organism = synthetic construct
SEQUENCE: 117
```
EIVLTQSPGT LSLSPGERAT VSCRASQSVS SSYLAWYQQK PGQAPRLLIY GASSRATGIP     60
DRFSGSGSGT DFTLTISRLE PEDFAVYYCQ QYGSSPYTFG QGTKLEIKGG GGSGGGGSGG    120
GGSGVQLVQS GPEVKKPGAS VKVSCKASGY TFTSYGITWV RQAPGQGLEW MGWISEYNGN    180
TNYAQKFQGR VTMTIDTSTT TAYMELRSLR SDDTAVYFCA RGGILPYYFF YYMDVWGKGT    240
TVTVSS                                                              246
```

SEQ ID NO: 118        moltype = AA  length = 123
FEATURE               Location/Qualifiers
source                1..123
                        mol_type = protein
                        organism = synthetic construct
SEQUENCE: 118
```
QVQLVQSGPE VKKPGASVKV SCKASGYTFT SYGITWVRQA PGQGLEWMGW ISEYNGNTNY     60
AQKFQGRVTM TIDTSTTTAY MELRSLRSDD TAVYFCARGG ILPYYFFYYM DVWGKGTTVT    120
VSS                                                                 123
```

SEQ ID NO: 119        moltype = AA  length = 108
FEATURE               Location/Qualifiers
source                1..108
                        mol_type = protein
                        organism = synthetic construct
SEQUENCE: 119
```
EIVLTQSPGT LSLSPGERAT VSCRASQSVS SSYLAWYQQK PGQAPRLLIY GASSRATGIP     60
DRFSGSGSGT DFTLTISRLE PEDFAVYYCQ QYGSSPYTFG QGTKLEIK                 108
```

SEQ ID NO: 120        moltype = AA  length = 7
FEATURE               Location/Qualifiers
source                1..7
                        mol_type = protein
                        organism = synthetic construct
SEQUENCE: 120
GYTFTSY                                                               7

SEQ ID NO: 121        moltype = AA  length = 6
FEATURE               Location/Qualifiers
source                1..6
                        mol_type = protein
                        organism = synthetic construct
SEQUENCE: 121
SEYNGN                                                                6

SEQ ID NO: 122        moltype = AA  length = 14
FEATURE               Location/Qualifiers
source                1..14
                        mol_type = protein
                        organism = synthetic construct
SEQUENCE: 122
GGILPYYFFY YMDV                                                      14

SEQ ID NO: 123        moltype = AA  length = 12
FEATURE               Location/Qualifiers
source                1..12
                        mol_type = protein
                        organism = synthetic construct
SEQUENCE: 123
RASQSVSSSY LA                                                        12

SEQ ID NO: 124        moltype = AA  length = 7
FEATURE               Location/Qualifiers
source                1..7
                        mol_type = protein
                        organism = synthetic construct
SEQUENCE: 124
GASSRAT                                                               7

```
SEQ ID NO: 125          moltype = AA   length = 9
FEATURE                 Location/Qualifiers
source                  1..9
                        mol_type = protein
                        organism = synthetic construct
SEQUENCE: 125
QQYGSSPYT                                                                 9

SEQ ID NO: 126          moltype = DNA   length = 738
FEATURE                 Location/Qualifiers
source                  1..738
                        mol_type = other DNA
                        organism = synthetic construct
SEQUENCE: 126
gagatcgtgc tgacccagtc tcccggcacc ctgtccctgt ctcccggcga aagggctacc    60
gtgagctgta gggcctccca gtccgtgagc agcagctacc tggcctggta tcagcaaaag   120
cccggccagg ctcccaggct gctgatctac ggagccagca gcagggctac aggaataccg   180
gaccggttca gcggcagcgg cagcggcacc gacttcacac tgacaataag ccggctggaa   240
cccgaggact cgccgtgta ctattgtcaa cagtacggca gcagcccta caccttcggc     300
cagggaacca agctcgagat caagggcggc ggaggatctg gcgaggagg atctggagga    360
ggaggcagcc aagtgcaact ggtgcagagc ggccctgaag tgaagaagcc cggcgccagc   420
gtgaaagtgt cctgcaaagc cagcggctac accttcacca gctacggcat cacctgggtg   480
cgacaggctc ccggccaggg actgagtgg atgggctgga tcagcgagta caatggcaac    540
accaactacg cccagaagtt ccaggaagg gtgacaatga ccatcgacac cagcaccacc    600
accgcctaca tggagctgag gagcctcagg agcgacgaca ccgccgtgta cttctgcgcc   660
agaggcggca tcctgcccta ctacttcttc tactacatgg acgtgtgggg caagggcacc   720
accgtgaccg tgtccagc                                                  738

SEQ ID NO: 127          moltype = AA   length = 837
FEATURE                 Location/Qualifiers
source                  1..837
                        mol_type = protein
                        organism = synthetic construct
SEQUENCE: 127
MALPVTALLL PLALLLHAAR PEIVLTQSPG TLSLSPGERA TVSCRASQSV SSSYLAWYQQ     60
KPGQAPRLLI YGASSRATGI PDRFSGSGSG TDFTLTISRL EPEDFAVYYC QQYGSSPYTF    120
GQGTKLEIKG GGGSGGGGSG GGGSQVQLVQ SGPEVKKPGA SVKVSCKASG YTFTSYGITW    180
VRQAPGQGLE WMGWISEYNG NTNYAQKFQG RVTMTIDTST TTAYMELRSL RSDDTAVYFC    240
ARGGILPYYF FYYMDVWGKG TTVTVSSATT TPAPRPPTPA PTIASQPLSL RPEACFMYVA    300
AAAFVLLFFV GCGVLLSRKR RRQHGQLWFP EGFKVSEASK KKRREPLGED SVGLKPLKNA    360
MVSKLSQLQT ELLAALLESG LSKEALLQAL GEPGPYLLAG EPLDKGESC GGGRGELAEL     420
PNGLGETRGS EDETDDDGED FTPPILKELE NLSPEEAAHQ KAVVETLLQE DPWRVAKMVK    480
SYLQQHNIPQ REVVDTTGLN QSHLSQHLNK GTPMKTQKRA ALYTWYVRKQ REVAQQFTHA    540
GQGGLIEEPT GDELPTKKGR RNRFKWGPAS QQILFQAYER QKNPSKEERE TLVEECNRAE    600
CIQRGVSPSQ AQGLGSNLVT EVRVYNWFAN RRKEEAFRHK LAMTCRDEFP TMVFPSGQIS    660
QASALAPAPP QVLPQAPAPA PAPAMVSALA QAPAPVPVLA PGPPQVAPAPP APKPTQAGEG    720
TLSEALLQLQ FDDEDLGALL GNSTDPAVFT DLASVDNSEF QQLLNQGIPV APHTTEPMLM    780
EYPEAITRLV TGAQRPPDPA PAPLGAPGLP NGLLSGDEDF SSIADMDFSA LLSQISS       837

SEQ ID NO: 128          moltype = DNA   length = 738
FEATURE                 Location/Qualifiers
source                  1..738
                        mol_type = other DNA
                        organism = synthetic construct
SEQUENCE: 128
gagatcgtgc tgacccagtc tcccggcacc ctgtccctgt ctcccggcga aagggctacc    60
gtgagctgta gggcctccca gtccgtgagc agcagctacc tggcctggta tcagcaaaag   120
cccggccagg ctcccaggct gctgatctac ggagccagca gcagggctac aggaataccg   180
gaccggttca gcggcagcgg cagcggcacc gacttcacac tgacaataag ccggctggaa   240
cccgaggact cgccgtgta ctattgtcaa cagtacggca gcagcccta caccttcggc     300
cagggaacca agctcgagat caagggcggc ggaggatctg gcgaggagg atctggagga    360
ggaggcagcc aagtgcaact ggtgcagagc ggccctgaag tgaagaagcc cggcgccagc   420
gtgaaagtgt cctgcaaagc cagcggctac accttcacca gctacggcat cacctgggtg   480
cgacaggctc ccggccaggg actgagtgg atgggctgga tcagcgagta caatggcaac    540
accaactacg cccagaagtt ccagggaagg gtgacaatga ccatcgacac cagcaccacc   600
accgcctaca tggagctgag gagcctcagg agcgacgaca ccgccgtgta cttctgcgcc   660
agaggcggca tcctgcccta ctacttcttc tactacatgg acgtgtgggg caagggcacc   720
accgtgaccg tgtccagc                                                  738

SEQ ID NO: 129          moltype = AA   length = 247
FEATURE                 Location/Qualifiers
source                  1..247
                        mol_type = protein
                        organism = synthetic construct
SEQUENCE: 129
EIVLTQSPAT LSLSPGERAT LSCGASQSVS SSYLAWYQQK PGLAPRLLIY DASSRATGIP     60
DRFSGSGSGT DFTLTISRLE PEDFAVYYCQ QYGSSPYTFG QGTKLEIKGG GGSGGGGSG     120
GGSQVQLVQS GAEVKKPGAS VKVSCKASGY TFSSYGVSWV RQAPGQGLEW MGWISKYNGN    180
```

```
TNYAQKFQGR VTMTTDTSTS TAYMELRSLR SDDTAVYFCA RGGIHGDSYY FYYLDVWGKG    240
TTVTVSS                                                             247

SEQ ID NO: 130          moltype = AA  length = 124
FEATURE                 Location/Qualifiers
source                  1..124
                        mol_type = protein
                        organism = synthetic construct
SEQUENCE: 130
QVQLVQSGAE VKKPGASVKV SCKASGYTFS SYGVSWVRQA PGQGLEWMGW ISKYNGNTNY    60
AQKFQGRVTM TTDTSTSTAY MELRSLRSDD TAVYFCARGG IHGDSYYFYY LDVWGKGTTV   120
TVSS                                                                124

SEQ ID NO: 131          moltype = AA  length = 108
FEATURE                 Location/Qualifiers
source                  1..108
                        mol_type = protein
                        organism = synthetic construct
SEQUENCE: 131
EIVLTQSPAT LSLSPGERAT LSCGASQSVS SSYLAWYQQK PGLAPRLLIY DASSRATGIP    60
DRFSGSGSGT DFTLTISRLE PEDFAVYYCQ QYGSSPYTFG QGTKLEIK                108

SEQ ID NO: 132          moltype = AA  length = 7
FEATURE                 Location/Qualifiers
source                  1..7
                        mol_type = protein
                        organism = synthetic construct
SEQUENCE: 132
GYTFSSY                                                             7

SEQ ID NO: 133          moltype = AA  length = 6
FEATURE                 Location/Qualifiers
source                  1..6
                        mol_type = protein
                        organism = synthetic construct
SEQUENCE: 133
SKYNGN                                                              6

SEQ ID NO: 134          moltype = AA  length = 15
FEATURE                 Location/Qualifiers
source                  1..15
                        mol_type = protein
                        organism = synthetic construct
SEQUENCE: 134
GGIHGDSYYF YYLDV                                                    15

SEQ ID NO: 135          moltype = AA  length = 12
FEATURE                 Location/Qualifiers
source                  1..12
                        mol_type = protein
                        organism = synthetic construct
SEQUENCE: 135
GASQSVSSSY LA                                                       12

SEQ ID NO: 136          moltype = AA  length = 7
FEATURE                 Location/Qualifiers
source                  1..7
                        mol_type = protein
                        organism = synthetic construct
SEQUENCE: 136
DASSRAT                                                             7

SEQ ID NO: 137          moltype = AA  length = 9
FEATURE                 Location/Qualifiers
source                  1..9
                        mol_type = protein
                        organism = synthetic construct
SEQUENCE: 137
QQYGSSPYT                                                           9

SEQ ID NO: 138          moltype = AA  length = 837
FEATURE                 Location/Qualifiers
source                  1..837
                        mol_type = protein
                        organism = synthetic construct
SEQUENCE: 138
MALPVTALLL PLALLLHAAR PEIVLTQSPA TLSLSPGERA TLSCGASQSV SSSYLAWYQQ    60
KPGLAPRLLI YDASSRATGI PDRFSGSGSG TDFTLTISRL EPEDFAVYYC QQYGSSPYTF   120
GQGTKLEIKG GGGSGGGGSG GGGSQVQLVQ SGAEVKKPGA SVKVSCKASG YTFSSYGVSW   180
```

| | | | | | |
|---|---|---|---|---|---|
| VRQAPGQGLE | WMGWISKYNG | NTNYAQKFQG | RVTMTTDTST | STAYMELRSL | RSDDTAVYFC | 240 |
| ARGGIHGDSY | YFYYLDVWGK | GTTVTVSSAT | TTPAPRPPTP | APTIASQPLS | LRPEACFMYV | 300 |
| AAAAFVLLFF | VGCGVLLSRK | RRRQHGQLWF | PEGFKVSEAS | KKKRREPLGE | DSVGLKPLKN | 360 |
| AMVSKLSQLQ | TELLAALLES | GLSKEALLQA | LGEPGPYLLA | GEGPLDKGES | CGGGRGELAE | 420 |
| LPNGLGETRG | SEDETDDDGE | DFTPPILKEL | ENLSPEEAAH | QKAVVETLLQ | EDPWRVAKMV | 480 |
| KSYLQQHNIP | QREVVDTTGL | NQSHLSQHLN | KGTPMKTQKR | AALYTWYVRK | QREVAQQFTH | 540 |
| AGQGGLIEEP | TGDELPTKKG | RRNRFKWGPA | SQQILFQAYE | RQKNPSKEER | ETLVEECNRA | 600 |
| ECIQRGVSPS | QAQGLGSNLV | TEVRVYNWFA | NRRKEEAFRH | KLAMTCRDEF | PTMVFPSGQI | 660 |
| SQASALAPAP | PQVLPQAPAP | APAPAMVSAL | AQAPAPVPVL | APGPPQAVAP | PAPKPTQAGE | 720 |
| GTLSEALLQL | QFDDEDLGAL | LGNSTDPAVF | TDLASVDNSE | FQQLLNQGIP | VAPHTTEPML | 780 |
| MEYPEAITRL | VTGAQRPPDP | APAPLGAPGL | PNGLLSGDED | FSSIADMDFS | ALLSQIS | 837 |

```
SEQ ID NO: 139         moltype = DNA  length = 2512
FEATURE                Location/Qualifiers
source                 1..2512
                       mol_type = other DNA
                       organism = synthetic construct
SEQUENCE: 139
atggccttac cagtgaccgc cttgctcctg ccgctggcct tgctgctcca cgccgccagg   60
cctgagatcg tgctgaccca gtctcccgcc accctgtccc tgtctcccgg cgaaagggct  120
accctgtctt gcgcgcctc ccagtccgtg agcagcagct acctggcctg gtatcagcaa  180
aagccggcc tggctcccag gctgctgatc tacgacgca gcagcagggc tacaggaata  240
ccagaccggt tcagcggcag cggcagcggc accgacttca cactgacaat aagccggctg  300
gaacccgagg acttcgccgt gtactattgt caacagtacg gcagcagccc ttacaccttc  360
ggccaggaa ccaagctcga gatcaagggc ggcgaggat ctggcggagg aggatctgga  420
ggaggaggca gccaagtgca actggtgcag agccggccg aagtgaagaa gcccggcgcc  480
agcgtgaaag tgtcctgcaa agccagcgga tacacattca gctcctacgg cgtgagctgg  540
gtgcgacagg ctcccggaca aggcctggag tggatgggct ggatcagcaa gtataacggc  600
aacaccaact acgcccagaa gttccaggga agggtgacaa tgaccaccga caccagcacc  660
agcaccgctc acatggagct gaggagcctc aggagcgacg acaccgcagt gtacttctgc  720
gcacgcggcg gcatccacgg cgacagctac tacttctatt acctggacgt gtggggcaag  780
ggcaccaccg tgaccgtgtc cagcgcaacc acaacacccg ctcccagacc tcccacacca  840
gcaccaacaa tagcaagtca acccttgagc ttgcgccctg aggcctgctt catgtacgtg  900
gccgccgcg ccttcgtgtt gctgttcttc gtgggctgtg gcgtgctgtt gtccagaaag  960
cgccgccgcc agcacggaca gctctgggtt cctgagggct tcaaagtgtc agaggccagc 1020
aagaagaagc ggcgcgaacc tctgggcgag gacagcgtgg gcctgaagcc tctgaaaaac 1080
gctatggtgt caaagctcag ccagctccag acagagctgc tggccgccct gctggaaagc 1140
ggcctgagca aggaggccct gttgcaggct ctgggagagc aggcccctta cctgctggct 1200
ggcgagggac ctttggataa gggcgagagc tgcggaggga gcggaggcga gctgccgaa 1260
ctgcctaatg gcttgggcga gacacgcggc agcgaggacg agacagacga cgacggcgag 1320
gatttcacac ctcccatcct caaggagttg agaatctgt ctcccgagga ggccgccac 1380
cagaaggccg tggtggagac actgctgcaa gaggacctt ggcgcgtggc caagatggtg 1440
aagagctacc tgcaacagca caacatccct cagcgcgagg tggtggatac caccggcctg 1500
aaccagagcc acctgtccca gcacctgaac aagggcacac ccatgaagac ccagaagcgc 1560
gccgccctct acacctggta cgtgcgcaag cagcgcgagg ttgctcaaca gttcacccac 1620
gccggccagg gcggcttgat tgaggaaccc acaggcgacg agctgcccac caagaagggc 1680
cgccgcaacc gcttcaaatg gggacccgcc tcgcagcaga tactgttcca agcctacgag 1740
cgccagaaga atccccagcaa ggaggagcgc gagacactcg tggaggagtg caaccgcgct 1800
gagtgcatcc agaggggcgt gagccctagc caagcccagg gcttgggcag caacctggtg 1860
acagaagtgc gcgtgtataa ctggttcgcc aaccgccgca aggaggaggc cttccgccac 1920
aagctggcca tgacttgccg cgacgagttc cctacaatgg tcttttccag cggccagatc 1980
agccaggcct ctgccctggc accagcacca ccacaagtgt tacctcaagc tcccgctccc 2040
gctcccgctc ctgctatggt gtcggcattg gctcaagctc ctgctcccgt gccggtgttg 2100
gcacctggac cgcctcaagc tgttgctcct cccgctccca gcccacacta agccggcgaa 2160
ggcaccctgt ctgaggccct gctgcaactg caattcgacg acgaggatct gggcgccctg 2220
ctgggcaaca gcaccgatcc cgctgtcttt accgatctgg ccagcgtgga taatagcgag 2280
ttccagcagc tcctgaacca gggtatccct gtggcgccgc acacaacgga gcccatgctg 2340
atggagtacc ctgaggccat caccagactc gtgactggcg cacaacgccc tcctgatcca 2400
gcaccagcgc cgttaggcgc acctggcctg cctaacggct tgctgagcgg cgacgaggat 2460
ttctccagca tcgccgatat ggatttcagc gcactgctga gtcaaatctc ca          2512

SEQ ID NO: 140         moltype = DNA  length = 741
FEATURE                Location/Qualifiers
source                 1..741
                       mol_type = other DNA
                       organism = synthetic construct
SEQUENCE: 140
gagatcgtgc tgacccagtc tcccgccacc ctgtccctgt ctcccggcga aagggctacc   60
ctgtcttgcg cgcctccca gtccgtgagc agcagctacc tggcctggta tcagcaaaag  120
cccggcctgg ctcccaggct gctgatctac gacgccagca gcagggctac aggaatacca  180
gaccggttca gcggcagcgg cagcggcacc gacttcacac tgacaataag ccggctggaa  240
cccgaggact tcgccgtgta ctattgtcaa cagtacggca gcagcccta caccttcggc  300
cagggaacca agctcgagat caagggcggc ggaggatctg gcggaggagg atctggagga  360
ggaggcagcc aagtgcaact ggtgcagagc cggccgaaag tgaagaagcc cggcgccagc  420
gtgaaagtgt cctgcaaagc cagcggatac acattcagct cctacggcgt gagctgggtg  480
cgacaggctc ccggacaagg cctggagtgg atgggctgga tcagcaagta taacggcaac  540
accaactacg cccagaagtt ccagggaagg gtgacaatga ccaccgacac cagcaccagc  600
accgcctaca tggagctgag gagcctcagg agcgacgaca ccgcagtgta cttctgcgca  660
cgcggcggca tccacggcga cagctactac ttctattacc tggacgtgtg gggcaagggc  720
```

```
accaccgtga ccgtgtccag c                                                  741

SEQ ID NO: 141           moltype = AA  length = 341
FEATURE                  Location/Qualifiers
source                   1..341
                         mol_type = protein
                         organism = synthetic construct
SEQUENCE: 141
MALPVTALLL PLALLLHAAR PELPTQGTFS NVSTNVSELC GGAIVVPVCL AFLLTTLLGV         60
LFCFNKRDLI KKHIWPNVPD PSKSHIAQWS PHTPPRHNFN SKDQMYSDGN FTDVSVVEIE        120
ANDKKPFPED LKSLDLFKKE KINTEGHSSG IGGSSCMSSS RPSISSSDEN ESSQNTSSTV        180
QYSTVVHSGY RHQVPSVQVF SRSESTQPLL DSEERPEDLQ LVDHVDGGDG ILPRQQYFKQ        240
NCSQHESSPD ISHFERSKQV SSVNEEDFVR LKQQISDHIS QSCGSGQMKM FQEVSAADAF        300
GPGTEGQVER FETVGMEAAT DEGMPKSYLP QTVRQGGYMP Q                            341

SEQ ID NO: 142           moltype = AA  length = 277
FEATURE                  Location/Qualifiers
source                   1..277
                         mol_type = protein
                         organism = synthetic construct
SEQUENCE: 142
MGAGATGRAM DGPRLLLLLL LGVSLGGAKE ACPTGLYTHS GECCKACNLG EGVAQPCGAN         60
QTVCEPCLDS VTFSDVVSAT EPCKPCTECV GLQSMSAPCV EADDAVCRCA YGYYQDETTG        120
RCEACRVCEA GSGLVFSCQD KQNTVCEECP DGTYSDEANH VDPCLPCTVC EDTERQLREC        180
TRWADAEECE IPGRWITRST PPEGSDSTAP STQEPEAPPE QDLIASTVAG VVTTVMGSSQ        240
PVVTRGTTDN LIPVYCSILA AVVVGLVAYI AFKRWNS                                 277

SEQ ID NO: 143           moltype = RNA  length = 8819
FEATURE                  Location/Qualifiers
source                   1..8819
                         mol_type = other RNA
                         organism = synthetic construct
SEQUENCE: 143
gagccatgct tggcttacga gggcgaccaa cccatcaaac tccccgcccc cagcactttt         60
atttctcctc tttaggaagt acacttcagt atctttggca cagtgcatga gcacgactaa        120
agtaaaacat cgcagaaaac atagctttag tctacccttc gtgtcctaaa aggaaaacca        180
gtagcttccc aggccaccgg aagggcaaca catgtcctct gcagtttctg cacacgggaa        240
ggtaaagaca gagagaggac ctactcctca acacagaaac atttcaaaat ctttcctcgc        300
ctgcaaccca agctgaagtc attctcccca gaaataacaa aagttggaag agaagccgga        360
gacaggatag gtgcaggaag cccacacttt gagggcagca ctcagacacc ctctcctgtg        420
tgcaggacgt gccgaatgtt caggtgcaat gagaatgagc catgcttggc ttataaggta        480
cgactgtgcc ttctagttgc cagccatctg ttgtttgccc ctccccgtg ccttcctgta        540
ccctggaagg tgccactccc actgtccttt cctaataaaa tgatcgcatt                   600
gtctgagtag gtgtcattct attctggggg gtgggtgggg gcaggacagc aagggggagg        660
attgggaaga caatagcagg catgctgggg atgcggtggg ctctatggga taagcttgat        720
atcgaattca tcgatgttaa taattaacat atatgttaat cattaacata tagttaatta        780
ttaaccgcta tgttaatgat taacaacggt taataattaa catatatgtt aatcattaac        840
atataactag tctagagggt atataatggg ggccactagt ctactaccag agttcatcgc        900
tagcgctacc ggatccgcca ccatggccct gccagtaacg gctctgctgc tgccacttgc        960
tctgctcctc catgcagcca ggcctcaggt ccagcttgtc cagtccggag cggaggtgaa       1020
aaaaccgggc gcgtccgtga agtatcctg caaggcctcc ggttatactt tcacatccta       1080
ctacatgcat tgggtccggc aggcacctgg gcagggcctg aatggatggg gattattaa        1140
tccctctcgc ggttctgcat catatgctca gaagttcaa gggagagtga caatggccag       1200
agacactagc acctcaaccg tttacatgga actcagctcg ctaaggagcg aggacacagc       1260
cgtctactat tgtgctcgtg atcgcaacta ctattactac ttatggtgt ggggcaaaagg       1320
gactaccgtt acagtttcat ctggcggcgg cggaagcggt ggaggcggtt ctggcggagg       1380
aggaagtgaa attgtgatga cccagtctcc cgctacactc agtgtgtcgc ctggagagcg       1440
agctacccctg agttgcaggg cctctcaaaa catctcaagt aatctggcct ggtatcagca       1500
aaagcccggg caggccacca aggctgctga tatacggagcc agcactagag ctaccgatat       1560
accagcacgg ttttccggca gcggttcagg gaccgagttt acgttgacga tcagtagctt       1620
acaatccgag gacttcgccg tgtactattg tcaacagtat atcacctggt acactttcgg       1680
ccaagggaca aagttggaaa tcaaggcggc agcaattgaa gttatgtacc ctccacctta       1740
cctcgacaat gagaaaagca atggaaccat tatccatgtg aaagggaaac acctttgtcc       1800
aagtcccta tttccggac cttctaagcc ctttggggtg tcggttggga ttggaatcct       1860
cctggcttgc tatagcttgc tagtaacagt ggccttatt attttctggg ttaaacgggg       1920
cagaaagaaa ctcctgtata tattcaaaca accatttatg gaccagtac aaactactca       1980
agaagaggac ggctgtagct gccgattcc agaagaagaa gaaggagat gtgaactgag       2040
agtgaagttc agcaggagcg cagacgcccc cgcgtaccag cagggccaga accagctca       2100
taacgagctc aatctaggac gaagagga gtacgatgt ttggacaaga ggcgtggccg       2160
ggacccctgag atggggggaa agccgagaag gaagaaccct caggaaggcc tgtacaatga       2220
actcagaaaa gataagatgg cggaggccta cagtgagatt gggatgaaag cgagcgccg       2280
gaggggcaag gggcacgatg gcctttacca gggtctcagt acagccacca aggacaccta       2340
cgatgccttg cacatgcaag ccctgccccc tgctaaaat caacctctgg attacaaaat       2400
ttgtgaaaga ttgactggta ttcttaacta tgttgctcct tttacggcta tgtgatacgc       2460
tgctttaatg cctttgtatc atgctattgc ttcccgtatg gctttcattt tctcctcctt       2520
gtataaatcc tggttgctgt ctctttatga ggagttgtgg cccgttgtca ggcaacgtgg       2580
cgtggtgtgc actgtgtttg ctgacgcaac ccccactggt tggggcattg ccaccacctg       2640
tcagctcctt tccgggactt tcgctttccc ctcccctatt gccacggcgg aactcatcgc       2700
cgcctgcctt gcccgctgct ggacaggggc tcggctgttg ggcactgaca attccgtggt       2760
```

```
gttgtcgggg aaatcatcgt cctttccttg gctgctcgcc tgtgttgcca cctggattct  2820
gcgcgggacg tccttctgct acgtcccttc ggccctcaat ccagcggacc ttccttcccg  2880
cggcctgctg ccggctctgc ggcctcttcc gcgtcttcgc cttcgccctc agacgagtcg  2940
gatctcccct tgggccgcct ccccgcctgg atccttgact tgcggccaac ttgtttattg  3000
cagcttataa tggttacaaa taaagcaata gcatcacaaa tttcacaaat aaagcatttt  3060
tttcactgca ttctagttgt ggtttgtcca aactcatcaa tgtatcttat catgtctgga  3120
atccttgact tgcggccgca actcccacct gcaacatgcg tgactgactg aggccgcgac  3180
tctagagtcg accggatctg cgatcgctcc ggtgcccgtc agtgggcaga gcgcacatcg  3240
cccacagtcc ccgagaagtt gggggagggg tcggcaatt gaacgggtgc ctagagaagg  3300
tggcgcgggg taaactggga aagtgatgtc gtgtactggc tccgcctttt tcccgagggt  3360
gggggagaac cgtatataag tgcagtagtc gccgtgaacg ttcttttcg caacgggttt  3420
gccgccagaa cacagctgaa gcttcgaggg gctcgcatct ctccttcacg cgcccgccgc  3480
cctacctgag gccgccatcc acgccggttg agtcgcgttc tgccgcctcc cgcctgtggt  3540
gcctccctgaa ctgcgtccgc cgtctaggta agtcgactcg ttggatccc actacccga  3600
tcaacgccct aggtttatgt ttggatgaac tgacatacgc gtatccgtct taagaatctt  3660
ttcaaacact agtagtgaaa tatatattaa actagtgttt gaaaagattc ttattacggt  3720
aacgcggaat tcgcaactat tttatcaatt ttttgcgtcg acgacggtga cttaggagta  3780
tgccggatca acgccctagg tttatgtttg gatgaactga catacgcgta tccgtctaaa  3840
aatcaatctc atttcctggt agtgaaatat atattaaacc aggaaatgag attgattttt  3900
ttacggtaac gcggaattcg caactatttt atcaattttt tgcgtcgacg actgtgacag  3960
cagagtatgc cggatcaacg ccctaggttt atgtttggat gaactgacat acgcgtatcc  4020
gtcttatgta aaagacaaac aatgcgtagt gaaatatata ttaaacgcat tgtttgtctt  4080
ttacatatta cggtaacgcg gaattcgcaa ctattttatc aattttttgc gtcgaccgga  4140
actatcttga agagtagtag tggactagtg tgacgctgct gacccctttc tttcccttct  4200
acagatccaa gctgtgaccg gcgcctacac ctgcagccca agcttaccat ggccttacca  4260
gtgaccgcct tgctcctgcc gctgccttg cgtgctccacg ccgccaggcc tgagatccgg  4320
ctgacccagt ctcccggcac cctgtccctg tctcccggcg aaagggctac cgtgagctgt  4380
agggcctccc agtccgtgag cagcagctac ctggcctggt atcagcaaaa gcccggccag  4440
gctcccaggc tgctgatcta cggagccagc agcagggcta caggaatacc agaccggttc  4500
agcggcagcg gcagcggcac cgacttcaca ctgacaataa gccggctgga acccgaggac  4560
ttcgccgtgt actattgtca acagtacggc agcagccctt acaccttcgg ccagggaacc  4620
aagctcgaga tcaagggcgg cggaggatct ggcggaggag gatctggagg aggaggcagc  4680
caagtgcaac tggtgcagag cggccctgaa gtgaagaagc ccggcgccag cgtgaaagtg  4740
tcctgcaaag ccagcggcta caccttcacc agctacggca tcagctgggt gcgacaggcc  4800
cccggccagg gactggagtg gatgggctgg atcagcggat acaatggcaa caccaactac  4860
gcccagaagt tccagggaag ggtgacaatg accatcgaca ccagcaccac caccgcctac  4920
atggagctga ggagcctcag gagcgacgac accgccgtgt acttctgcgc cagaggcggc  4980
atcctgcccct actacttctt ctactacatg gacgtgtggg gcaagggcac caccgtgacc  5040
gtgtccagcg caaccacaac acccgctccc agcctcccca ccagcgcc aacaatagca  5100
agtcaaccct tgagcttgcg ccctgaggcc tgcttcatgt acgtggccgc cgccgccttc  5160
gtgttgctgt tcttcgtggg ctgtggcgtg ctgttgtcca gaaagcgccg ccgccagcac  5220
ggacagctct ggttccctga gggcttcaaa gtgtcagagg ccagcaagaa gaagcggcgc  5280
gaacctctgg gcgaggacga cgtgggccctg aagcctctga aaaacgctat ggtgtcaaag  5340
ctcagccagc tccagacaga gctgctggcc gccctgctgg aaagcggcct gagcaaggag  5400
gccctgttgc aggctctggg agagccaggc ccttacctgc tggctggcga gggaccttg  5460
gataaggcgc agagctgcgg aggcggacgc ggagagctgc ccgaactgcc taatggcttg  5520
ggcgagacac gcggcagcga ggacgagaca gacgacgacg gcgaggattt cacacctccc  5580
atcctcaagg agttggagaa tctgtctccc gaggaggccg cccaccagaa ggccgtggtg  5640
gagacactgc tgcaagagga cccttggcgc gtgccaaga tggtgaagag ctacctgcaa  5700
cagcacaaca tccctcagcg cgaggtggtg gataccaccg gctgaaccag agccacctg  5760
tcccagcacc tgaacaaggg cacacccatg aagaccagca agcgcgcgcc cctctacacc  5820
tggtacgtgc gcaagcagcg cgaggttgct caacagttca cccacgccgg ccagggcggc  5880
ttgattgagg aacccacagg cgacgagctg cccaccaaga agggccgccc caaccgcttc  5940
aaatggggac ccgcctcgca gcagatactg ttccaagcct acgagcgcca gaagaatccc  6000
agcaaggagg agcgcgagac actcgtggag gagtgcaacc agcgctgagtg catccagagg  6060
ggcgtgagcc ctagccaagc ccagggcttg ggcagcaacc tggtgacaga agtgcgcgtg  6120
tataactggt tcgccaaccg ccgcaaggag gaggccttcc gccacaagct ggccatgact  6180
tgccgcgacg agttccctac aatggtcttt cccagcggcc agatcagcca ggcctctgcc  6240
ctggcaccag caccaccaca agtgttacct caagctcccg ctcccgctcc cgctcctcgc  6300
atggtgtcgg cattggctca agctcctgct cccgtgccgg tgttggcacc tggaccgcct  6360
caagctgttg ctcctcccgc tcccaagccc acacaagccg gcgaaggcac cctgtctgag  6420
gccctgctgc aactgcaatt cgacgacgag gatctgggcg ccctgctggg caacagcacc  6480
gatcccgctg tctttaccga tctggccagc gtggataata gcgagttcca gcagctcctg  6540
aaccagggta tccctgtggc gccgcacaca acggagcccg tgctgatgga gtaccctgag  6600
gccatcacca gactcgtgac tggcgcacaa cgccctcctg atccagcacc agcgccgtta  6660
ggcgcacctg gcctgcctaa cggcttgctg agcggcgacg aggatttctc cagcatcgcc  6720
gatatgggatt tcagcgcact gctgagtcaa atctccagcc gggccaagcg gtccggatcc  6780
ggagagggca ggggatctct ccttacttgt ggggacgtcg aggaaaaaacc tggaccaatg  6840
gccctgcccg tgacagccct gctcctgcct ctggccctgc ttctgcatgc agcacggccc  6900
gagctgccca cacaaggcac attcagcaac gtgtccacca acgtgtccga gctgtgcggc  6960
ggcgctatcg tggtgcccgt gtgcttggcc ttcctgctga ccaccctgct gggcgtgctg  7020
ttctgcttca caagcggga cctgattaag aagcacatct ggcccaacgt gcccgaccct  7080
agcaagagcc acatcgccca gtggagccct cacacacctc ccaggcacaa cttcaacagc  7140
aaggaccaga tgtactccga cggcaacttc accgacgtgt ccgtggtggga gatcgaggcc  7200
aacgacaaga gcccttccc tgaggacctg aagtccgtgg acctgttcaa gaaggagaag  7260
atcaacaccg gggacacag cagcggcatc ggcggctcta gctgtatgag cagcagcagg  7320
cccagcatct ccagcagcga cgagaacgag agcagccaga acaccagcag caccgtgcag  7380
tacagcaccg tggtgcacag cggctacagg caccaggtgc catcagtgca agtgttcagc  7440
cgatccgagt ccacccagcc tctgctggac agcgaggaga ggccccgagga cctgcaactg  7500
```

```
gtggaccacg tggacggagg cgacggcatc ctgcctaggc agcaatactt caagcagaat   7560
tgcagccagc acgagagcag ccctgacatc agccacttcg agaggagcaa gcaagtgtcc   7620
agcgtgaacg aggaggactt cgtgaggctg aagcagcaga tcagcgacca catcagccag   7680
agctgcggca gcggccagat gaagatgttc caggaagtgt ccgccgccga cgccttcggc   7740
cctggcacag aaggacaagt ggaggagttc gaaaccgtgg gcatggaggc cgccaccgac   7800
gagggaatgc ccaagagcta cctgcctcag accgtgcggc agggcggcta catgcctcag   7860
taaaggacgg gtggcatccc tgtgacccct cccagtgcc tctcctggcc ctggaagttg   7920
ccactccagt gcccaccagc cttgtcctaa taaaattaag ttgcatcatt ttgtctgact   7980
aggtgtcctt ctataatatt atggggtgga gggggtggt atggagcaag gggcaagttg   8040
ggaagacaac ctgtagggcc tgcggggtct attgggaacc aagctggagt gcagtggcac   8100
aatcttggct cactgcaatc tccgcctcct gggttcaagc gattctcctg cctcagcctc   8160
ccgagttgtt gggattccag gcatgcatga ccaggctcag ctaattttg ttttttggt    8220
agaaacgggg tttcaccata ttggccaggc tggtctccaa ctcctaatct caggtgatct   8280
acccaccttg gcctcccaaa ttgctgggat tacaggcgtg aaccactgct cccttccctg   8340
tccttccgag ggcaatctgg cccatcaagt ggccttcgcc tctgggagta acaaaaatgc   8400
acttcaaaat agcttctgta atcaagctgc atggggtgga tactcccag ctgactccag    8460
gaagttctct atccaaagct attcattagg ccagagctgt gcaaataatt agtcacccac   8520
ttgctccata acccctcatg acagcccagg cattgagtcc aggtgggacc atcaagccat   8580
gctctggtgg ctcatgcatt atcatagaaa tgggaggctt tatttatttt actaaaaaga   8640
acaaaaacaa cagactgctg tcctttagac aataggatca cgtcatctga gccctctgtg   8700
ccccaggtga caagcccagc cccaagttct ctttcctcag cctccccaca catgttctgg   8760
aggagatggg cccagcaggc tgctctgagg cctggccct cgtaagccaa gcatggctc    8819

SEQ ID NO: 144          moltype = RNA  length = 8492
FEATURE                 Location/Qualifiers
source                  1..8492
                        mol_type = other RNA
                        organism = synthetic construct
SEQUENCE: 144
gagccatgct tggcttacga gggcgaccaa cccatcaaac tccccgcccc cagcacttt    60
atttctcctc tttaggaagt acacttcagt atctttggca cagtgcatga gcacgactaa   120
agtaaaacat cgcagaaaac atagctttag tctaccttc gtgtcctaaa aggaaaacca   180
gtagcttccc aggccaccgg aagggcaaca catgtcctct gcagtttctg cacacgggaa   240
ggtaaagaca gagagaggac ctactcctca acacagaaac atttcaaaat ctttcaaat    300
ctgcaaccca agctgaagtc attctcccca gaaataacaa aagttggaag agaagccgga   360
gacaggatag gtgcaggaag cccacacttt gagggcagca ctcagacacc ctctcctgtg   420
tgcaggacgt gccgaatgtt caggtgcaat gagaatgagc catgcttggc ttataaggta   480
cgactgtgcc ttctagttgc cagccatctg ttgtttgccc ctccccgtg ccttccttga    540
ccctgaagg tgccactccc actgtccttt cctaataaaa tgaggaaatt gcatcgcatt    600
gtctgagtag gtgtcattct attctggggg gtgggtggg gcaggacagc aagggggagg   660
attgggaaga caatagcagg catgctgggg atgcggtggg ctctatggga taagcttgat   720
atcgaattca tcgatgttaa taattaacat atatgttaat cattaacata tagttaatta   780
ttaaccgcta tgttaatgat taacaacggt taataattaa catatatgtt aatcattaac   840
atataactag tctagagggt ataatggg ggcactagt ctactaccag agttcatcgc     900
tagcgctacc ggatccgcca ccatggccct gccagtaacg gctctgctgc tgccacttgc   960
tctgctcctc catgcagcca ggcctgaggt ccagctcgtc gagagcggcg gtgggctggt  1020
tcagcctgga ggaagtctcc ggctgagctg tgctgcaagt ggattctcat tttcagatta  1080
ctccgggatg tcctgggtgc gtcaggcgcc agggaaaggc gaagaattag tgtctgccat  1140
ttcgcccggt ggtgggata cttattatgc agacagcgta aagggccgat tcacaatctc    1200
aagggacaat tccaagaata cgctgtactt gcagatgaac agcctaaggg ctgaggatac  1260
cgccgtgtac tattgcgcca gaagatggtg gtattactct aaccattcag gcgactacga  1320
ctattttgat taccgcggcc aaggaacact tgttaccgtg tctagtgcgg cagcaaccac  1380
gacgccagcg ccgcgaccac caacaccggc gcctaccatc gcgtcgcagc cactgtcact  1440
gcgcccagaa gcgtgccggc cagcggcggg tggcgcagtg cacacgaggg ggctggactt  1500
cgcctgtgat atctacatct gggcgccctt ggccgggact tgtggggtcc ttctcctgtc  1560
actggttatc accctttact gcaaacgggg cagaaagaaa ctcctgtata tattcaaaca  1620
accatttatg agaccagtac aaactactca agaagaggac ggctagct gccgatttcc     1680
agaagaagaa gaaggaggat gtgaactgag agtgaagttc agcaggagcg cagacgcccc  1740
cgcgtaccag cagggccaga accagctcta taacgagctc aatctaggac gaagagagga  1800
gtacgatgtt ttggacaaga ggcgtggcgc ggaccctgag atgggggaa agccgagaag   1860
gaagaaccct caggaaggcc tgtacaatga actgcagaaa gataagatgg cggaggccta  1920
cagtgagatt gggatgaaag gcgagcgccg gaggggcaag gggcacgatg cctttacca    1980
gggtctcagt acagccacca aggacaccta cgatgccttg cacatgcaag ccctgcccc    2040
tcgctaaaat caacctctgg attacaaaat ttgtgaaaga ttgactggta ttcttaacta  2100
tgttgctcct tttacgctat gtggatacgc tgctttaatg cctttgtatc atgctattgc  2160
ttcccgtatg gctttcattt tctcctcctt gtataaatcc tggttgctgt ctctttatga  2220
ggagttgtgc ccgttgtca ggcaacgtgg cgtggtgtgc actgtgtttg ctgacgcaac    2280
cccactggt tggggcattg ccaccacctg tcagctcctt tccgggactt tcgctttccc    2340
cctccctatt gccacgcgg aactcatcgc cgcctgcctt gcccgctgct ggacagggc     2400
tcggctgttg ggcactgaca attccgtggt gttgtcgggg aaatcatcgt cctttccttg  2460
gctgctcgcc tgtgttgcca cctggattct gcgcgggacg tccttctgct acgtcccttc  2520
ggccctcaat ccagcggacc ttccttcccg cggcctgctg ccggctctgc ggcctcttcc  2580
gcgtcttcgc cttcgccctc agacgagtcg gatctccctt gggccgcct cccgcctgg    2640
atccttgact tgcggcaac ttgttttattg cagcttataa tggttacaaa taaagcaata   2700
gcatcacaaa tttcacaaat aaagcatttt tttcactgca ttctagttgt ggtttgtcca  2760
aactcatcaa tgtatcttat catgtctggg atccttgact tgcggccgca actcccacct  2820
gcaacatgcg tgactgactg aggccgcgac tctagagtcg accggatctg cgatcgctcc  2880
ggtgcccgtc agtgggcaga gcgcacatcg cccacagtcc ccgagaagtt ggggggaggg  2940
gtcggcaatt gaacgggtgc ctagagaagg tggcgcgggg taaactggga aagtgatgtc  3000
```

```
gtgtactggc tccgcctttt tcccgagggt gggggagaac cgtatataag tgcagtagtc   3060
gccgtgaacg ttcttttttcg caacgggttt gccgccagaa cacagctgaa gcttcgaggg   3120
gctcgcatct ctccttcacg cgccgccgc cctacctgag gccgccatcc acgccggttg   3180
agtcgcgttc tgccgcctcc cgcctgtggt gcctcctgaa ctgcgtccgc cgtctaggta   3240
agtcgactcg ttggatcccc actacccgga tcaacgccct aggtttatgt ttggatgaac   3300
tgacatacgc gtatccgtct taagaatctt ttcaaacact agtagtgaaa tatatattaa   3360
actagtgttt gaaaagattc ttattacggt aacgcggaat tcgcaactat tttatcaatt   3420
ttttgcgtcg acgacggtga cttaggagta tgccggatca acgccctagg tttatgtttg   3480
gatgaactga catacgcgta tccgtctaaa aatcaatctc atttcctggt agtgaaatat   3540
atattaaacc aggaaatgag attgattttt ttacggtaac gcggaattcg caactatttt   3600
atcaattttt tgcgtcgacg actgtgacag cagagtatgc cggatcaacg ccctaggttt   3660
atgtttggat gaactgacat acgcgtatcc gtcttatgta aaagacaaac aatgcgtagt   3720
gaaatatata ttaaacgcat tgtttgtctt ttacatatta cggtaacgcg gaattcgcaa   3780
ctattttatc aattttttgc gtcgaccgga actatcttga agagtagtag tggactagtg   3840
tgacgctgct gacccctttc tttccttct acagatccaa gctgtgaccg gcgcctacac   3900
ctgcagccca agcttaccat ggccttacca gtgaccgcct tgctcctgcc gctggccttg   3960
ctgctccacg ccgccaggcc tgagatcgtg ctgacccagt ctcccgccac cctgtccctg   4020
tctcccggcg aaagggctac cctgtcttgc ggcgcctccc agtccgtgag cagcagctac   4080
ctggcctggt atcagcaaaa gcccggcctg ctcccaggcc tgctgatcta cgacgccagc   4140
agcagggcta caggaatacc agaccggttc agcggcagcg gcagcggcac cgacttcaca   4200
ctgacaataa gccggctgga acccgaggac ttcgccgtgt actattgtca acagtacggc   4260
agcagccctt acaccttcgg ccagggggaaccaa agctcagta caagggcgg cggaggatct   4320
ggcggaggag gatctggagg aggaggcagc caagtgcaac tggtgcagag cggcgccgaa   4380
gtgaagaagc ccggcgccag cgtgaaagtg tcctgcaaag ccagcggata cactttcagc   4440
tcctacgcg tgagctggt gcgacaggct cccgacaag gctggagtg gatgggctgg   4500
atcagcaagt ataacggcaa caccaactac gcccagaagt tccaggggaag ggtgacaatg   4560
accaccgaca ccagcaccag caccgcctac atggagctga ggagcctcag gagcgacgac   4620
accgcagtgt acttctgcgc acgcggcgg atccacggcg acagctacta cttctattac   4680
ctggacgtgt ggggcaaggg caccaccgtg accgtgtcca gcgcaaccac aacacccgct   4740
cccagacctc ccacaccagc accaaccata gcaagtcaac cctgagctt gcgcctgag   4800
gcctgcttca tgtacgtggc cgcgccgcc ttcgtgttgc tgttcttcgt gggctgtgc   4860
gtgctgttgt ccagaaagcg ccgcgccag cacggcagc tctggttccc tgagggcttc   4920
aaagtgtcag aggccagcaa gaagaagcgg cgcgaacctc tgggcgagga cagcgtgggc   4980
ctgaagcctc tgaaaaacgc tatggtgtca aagctccagc agctccgcac agagctgctg   5040
gccgccctgc tggaaagcgg cctgagcaag gaggccctgt tgcaggctct gggagagcca   5100
ggcccttacc tgctggctgg cgagggacct ttggataagg gcgagagctg cggaggcgga   5160
cgcggagagc tggccgaact gcctaatggc ttgggcgaga cacgcggcag cgaggacgag   5220
acagacgacg acggcgagga tttcacacct cccatcctca aggagttgga gaatctgtct   5280
cccgaggagg ccgcccacca gaaggccgtg gtggagcaca tgctgcaaga ggaccctgga   5340
cgcgtggcca agatggtgaa gagctacctg caacagcaca acatccctca gcgcgaggtg   5400
gtggatacca ccggcctgaa ccagagccac ctgtcccagc acctgaacaa gggcacaccc   5460
atgaagaccc agaagcgcgc cgccctctac acctggtacg tgcgcaagca gcgcgaggtt   5520
gctcaacagt tcacccagcg cggccagggc ggcttgattg aggaacccac aggcgacgag   5580
ctgcccacca agaagggccg ccgcaaccgc ttcaaatggg gacccgcctc gcagcagata   5640
ctgttccaag cctacgagcg ccagaagaat cccagcaagg aggagcgcga gacactcgtg   5700
gaggagtgca accgcgctga gtgcatccag aggggcgtga gccctagcca gcccagggc   5760
ttgggcacga acctggtgac agaagtgcgc gtgtataact ggttcgccaa ccgccgcaag   5820
gaggaggcct tccgccacaa gctggccatg acttgccgcg acgagttccc tacaatggtc   5880
tttcccagcg gccagatcag ccaggcctct gccctggcac cagcaccacc acaagtgtta   5940
cctcaagctc ccgctcccgc tcccgctcct gctatggtgt cggcattggc tcaagctcct   6000
gctcccgtgc cggtgttggc acctggaccg cctcaagctg ttgctcctcc cgctcccaag   6060
cccacacaag ccggcgaagg caccctgtct gaggccctgc tgcaactgca attcgacgag   6120
gaggatctgg gcgccctgct gggcaacagc accgatcccg ctgtctttac cgatctggcc   6180
agcgtggata atagcgagtt ccagcagctc ctgaaccagg gtatccctgt ggcgccgcac   6240
acaacggagc ccatgctgat ggagtaccct gaggccatca ccagactgct gactggcgca   6300
caacgccctc ctgatccagc accagcgccg ttaggcgcac ctggcctgcc taacggcttg   6360
ctgagcggcg acgaggattt ctccagcatc gccgatatgg atttcagcgc actgctgagt   6420
caaatctcca gccgggccaa gcggtccgga tccgagaggg caggggatc tctccttact   6480
tgtgggacg tcgaggaaaa ccctggacca atggccctgc ccgtgacgac cctgctcctg   6540
cctctggccc tgttgctgca tgcagcacgg cctgagctgc ccacacaagg cacattcagc   6600
aacgtgtcca ccaacgtgtc cgagctgtgc ggcggcgcta tcgtggtgcc cgtgtgcttg   6660
gccttcctgc tgaccaccct gctgggcgtg ctgttctgct tcaacaagcg ggacctgatt   6720
aagaagcaca tctgggccaa cgtgcccgac cctagcaaga gccacatcgc ccagtggagc   6780
cctcacacac ctcccaggca caacttcaac agcaaggacc agatgtactc cgacgcaa   6840
ttcaccgacg tgtccgtggt ggagatcgag gccaacgaca gaagccctt ccctgaggac   6900
ctgaagtccc tggacctgtt caagaaggag aagatcaaca ccgagggaca cagcagcggc   6960
atcggcggct ctagctgtat gagcagcagc aggcccagca tctccagcag cgacgagaac   7020
gagagcgcc agaacaccag cagcaccgtg cagtacaacc cgtggtgca cagcggctac   7080
aggcaccagg tgcatcagt gcaagtgttc agccgatccg agtccaccca gcctctgctg   7140
gacagcgagg agaggcccga ggacctgcaa ctggtggacc acgtggacgg aggcgacggc   7200
atcctgccta ggcagcaata cttcaagcag aattgcagcc agcacgagag cagccctgac   7260
atcagccact cgagaggag caagcaagtg tccagcgtga acgaggagga cttcgtgagg   7320
ctgaagcagc agatcagcga ccacatcagc cagagctgcg gcagcggcca gatgaagatg   7380
ttccaggaag tgtccgcgc cgaccgcctc ggcctgccc agaaggaca agtggagagg   7440
ttcgaaccgt ggggcatgga ggccgccacc gacgagggaa tgcccaagag ctacctgcct   7500
cagaccgtgc ggcagggcgg ctacatgcct cagtaaagga cggtggcat ccctgtgacc   7560
cctcccagt gcctctcctg gcctggaag ttgccactcc agtgcccacc agccttgtcc   7620
taataaaatt aagttgcatc attttgtctg actaggtgtc cttctataat attatgggt   7680
ggaggggggt ggtatggagc aaggggcaag ttgggaagac aacctgtagg gcctgcgggg   7740
```

```
tctattggga accaagctgg agtgcagtgg cacaatcttg gctcactgca atctccgcct   7800
cctgggttca agcgattctc ctgcctcagc ctcccgagtt gttgggattc caggcatgca   7860
tgaccaggct cagctaattt ttgttttttt ggtagaaacg gggtttcacc atattggcca   7920
ggctggtctc caactcctaa tctcaggtga tctacccacc ttggcctccc aaattgctgg   7980
gattacaggc gtgaaccact gctcccttcc ctgtcctcc  gagggcaatc tggcccatca   8040
agtggccttc gcctctggga gtaacaaaaa tgcacttcaa aatagcttct gtaatcaagc   8100
tgcatgggtg gagtactccc cagctgactc caggaagttc tctatccaaa gctattcatt   8160
aggccagagc tgtgcaaata attagtcacc cacttgctcc ataaccctcc atgacagccc   8220
aggcattgag tccaggtggg accatcaagc catgctctgg tggctcatgc attatcatag   8280
aaatgggagg ctttatttat tttactaaaa agaacaaaaa caacagactg ctgtcctta    8340
gacaatagga tcacgtcatc tgagccctct gtgcccagg  tgacaagccc agccccaagt   8400
tctctttcct cagcctcccc acacatgttc tggaggagat gggcccagca ggctgctctg   8460
aggcctggcc cctcgtaagc caagcatggc tc                                 8492

SEQ ID NO: 145        moltype = RNA  length = 8822
FEATURE               Location/Qualifiers
source                1..8822
                      mol_type = other RNA
                      organism = synthetic construct
SEQUENCE: 145
gagccatgct tggcttacga gggcgaccaa cccatcaaac tccccgcccc cagcactttt    60
atttctcctc tttaggaagt acacttcagt atctttggca cagtgcatga gcacgactaa   120
agtaaaacat cgcagaaaac atagcttag  tctaccttc  gtgtcctaaa aggaaaacca   180
gtagcttccc aggccaccgg aagggcaaca catgtcctct gcagtttctg cacacgggaa   240
ggtaaagaca gagagaggac ctactcctca acacagaaac atttcaaaat cttcctcgc    300
ctgcaaccca agctgaagtc attctcccca gaaataacaa aagttggaag aagaagcgga   360
gacaggatag gtgcaggaag cccacacttt gagggcagca ctcagacacc ctctcctgtg   420
tgcaggacgt gccgaatgtt caggtgcaat gagaatgagc catgcttggc ttataaggta   480
cgactgtgcc ttctagttgc cagccatctg ttgtttgccc ctccccgtg  ccttccttga   540
ccctgaaagg tgccactccc actgtccttt cctaataaaa tggaggaaatt gcatcgcatt  600
gtctgagtag gtgtcattct attctggggg gtgggggtgg gcaggacagc aagggggagg   660
attgggaaga caatagcagg catgctgggg atgcggtggg ctctatggga taagcttgat   720
atcgaattca tcgatgttaa taattaacat atatgttaat cattaacata tagttaatta   780
ttaaccgcta tgttaatgat taacaacggt taataattaa catatatgtt aatcattaac   840
atataactag tctagagggt atataatggg ggccactagt ctactaccag agttcatcgc   900
tagcgctacc ggatccgcca ccatggccct gccagtaacg gctctgctgc tgccacttgc   960
tctgctcctc catgcagcca ggcctcaggt ccagcttgtc cagtccggag cggaggtgaa  1020
aaaaccgggc gcgtccgtga agtatcctg  caaggcctcc ggttatactt tcacatcta   1080
ctacatgcat tgggtccggc aggcacctgg gcaggggctg gaattattaa                1140
tccctctcgc ggttctgcat catatgctca gaagtttcaa gggagagtga caatggccag  1200
agacactagc acctcaaccg tttacatgga actcagctcg ctaaggagcg aggacacagc  1260
cgtctactat tgtgctcgtg atcgcaacta ctattactac atggatgtgt ggggcaaagg  1320
gactaccgtt acagtttcat ctggcggcgg cggaagcggt ggaggcggtt ctggcggagg  1380
aggaagtgaa attgtgatga cccagtctcc cgctacactc agtgtgtcgc ctggagagcg  1440
agctaccctg agttgcaggg cctctcaaaa catctcaagt aatctggcct ggtatcagca  1500
aaaagcccgg caggcaccaa ggctgctgat atacggagcc agcactagag ctaccgatat  1560
accagcacgg ttttccggca gcggttcagg gaccgagttt acgttgacga tcagtagctt  1620
acaatccgag gacttcgccg tgtactattg tcaacagtat atcacctggt acactttcgg  1680
ccaagggaca aagttggaaa tcaaggcggc agcaattgaa gttatgtacc ctccacctta  1740
cctcgacaat gagaaaagca atggaaccat tatccatgtg aaagggaaac acctttgtcc  1800
aagtccccta tttcccggac cttctaagcc cttttgggtc ctggtggtgg ttggtggaag  1860
cctggcttgc tatagcttgc tagtaacagt ggcctttatt attttctggg ttaaacgggg  1920
cagaaagaaa ctcctgtata tattcaaaca accatttatg agaccagtac aaactactca  1980
agaagaggac ggctgtagct gccgatttcc agaagaagaa gaaggaggat gtgaactgag  2040
agtgaagttc agcaggagcg cagacgcccc cgcgtaccag cagggccaga accagctcta  2100
taacgagctc aatctaggac gaagagagga gtacgatgtt ttggacaaga ggcgtggccg  2160
ggaccctgag atgggggga  agccgagaag gaagaaccct caggaaggcc tgtacaatga  2220
actgcagaaa gataagatgg cggaggccta cagtgagatt gggatgaaag gcgagcgccg  2280
gaggggcaag gggcacgatg gcctttacca gggtctcagt acagccacca aggacaccta  2340
cgatgccttg cacatgcaag ccctgccccc tcgctaaaat caacctctgg attacaaaat  2400
ttgtgaaaga ttgactggta ttcttaacta tgttgctcct tttacgctat gtggatacgc  2460
tgctttaatg cctttgtatc atgctattgc ttcccgtatg gctttcattt tctcctcctt  2520
gtataaatcc tggttgctgt ctctttatga ggagttgtgc ccgttgtca  ggcaacgtgg  2580
cgtggtgtgc actgtgtttg ctgacgcaac ccccacctgt tgggcattg  ccaccacctg  2640
tcagctcctt tccgggactt tcgctttccc cctccctatt gccacggcgg aactcatcgc  2700
cgcctgcctt gcccgctgct ggacagggc  tcggctgttg ggcactgaca attccgtggt  2760
gttgtcgggg aaatcatcgt cctttccttg gctgctcgcc tgtgttgcca cctggattct  2820
gcgcgggacg tccttctgct acgtcccttc ggccctcaat ccagcggacc ttccttcccg  2880
cggcctgctg ccggctctgc ggcctcttcc gcgtcttcgc cttcgccctc agacgagtcg  2940
gatctccctt tgggccgcct ccccgcctgg atccttgact gcggccaac  ttgtttattg  3000
cagcttataa tggttacaaa taaagcaata gcatcacaaa tttcacaaat aaagcatttt  3060
tttcactgca ttctagttgt ggtttgtcca aactcatcaa tgtatcttat catgtctggg  3120
atccttgact tgcggccgca actccccacct gcaacatgcg tgactgactg aggccgcgac  3180
tctagagtcg accggatctg cgatcgctcc ggtgcccgtc agtgggcaga gcgcacatcg  3240
cccacagtcc ccgagaagtt ggggggaggg gtcggcaatt gaacgggtgc ctagagaagg  3300
tggcgcgggg taaactggga aagtgatgtc gtgtactggc tccgcctttt tcccgagggt  3360
gggggagaac cgtatataag tgcagtagtc gccgtgaacg ttcttttcg  caacgggttt  3420
gccgccagaa cacagctgaa gcttcgaggg gctcgcatct ctccttcacg cgcccgccgc  3480
cctacctgag gccgccatcc acgccggttg agtcgcgttc tgccgcctcc cgcctgtggt  3540
```

```
gcctcctgaa ctgcgtccgc cgtctaggta agtcgactcg ttggatcccc actacccgga 3600
tcaacgccct aggtttatgt ttggatgaac tgacatacgc gtatccgtct taagaatctt 3660
ttcaaacact agtagtgaaa tatatattaa actagtgttt gaaaagattc ttattacggt 3720
aacgcggaat tcgcaactat tttatcaatt ttttgcgtcg acgacggtga cttaggagta 3780
tgccggatca acgccctagg tttatgtttg gatgaactga catacgcgta tccgtctaaa 3840
aatcaatctc atttcctggt agtgaaatat atattaaacc aggaaatgag attgattttt 3900
ttacggtaac gcggaattcg caactatttt atcaattttt tgcgtcgacg actgtgacag 3960
cagagtatgc cggatcaacg ccctaggttt atgtttggat gaactgacat acgcgtatcc 4020
gtcttatgta aaagacaaac aatgcgtagt gaaatatata ttaaacgcat tgtttgtctt 4080
ttacatatta cggtaacgcg gaattcgcaa ctattttatc aattttttgc gtcgaccgga 4140
actatcttga agagtagtag tggactagtg tgacgctgct gacccctttc tttcccttct 4200
acagatccaa gctgtgaccg cgcctacac ctgcagccca agcttaccat ggccttacca 4260
gtgaccgcct tgctcctgcc gctggccttg ctgctccacg ccgccaggcc tgagatcgtg 4320
ctgacccagt ctcccgccac cctgtccctg tctcccggcg aaagggctac cctgtcttgc 4380
ggcgcctccc agtccgtgag cagcagctac ctggcctggt atcagcaaaa gcccggcctg 4440
gctcccaggc tgctgatcta cgacgccagc agcagggcta caggaatacc agaccggttc 4500
agcggcagcg gcagcggcac cgacttcaca ctgacaataa gccggctgga acccgaggac 4560
ttcgccgtgt actattgtca acagtacggc agcagccctt acaccttcgg ccagggaacc 4620
aagctcgaga tcaagggcgg cggaggatct ggcggaggag gatctggagg aggaggcagc 4680
caagtgcaac tggtgcagag cggcgccgaa gtgaagaagc ccggcgccag cgtgaaagtg 4740
tcctgcaaag ccagcggata cacattcagc tcctacggcg tgagctgggt gcgacaggct 4800
cccggaacag gcctggagtg gatgggctgg atcagcaagt ataacggcaa caccaactac 4860
gcccagaagt tccagggaag ggtgacaatg accaccgaca ccagcaccag caccgcctac 4920
atggagctga ggagcctcag gagcgacgac accgcagtgt actctgcgc acgcggcggc 4980
atccacggcg acagctacta cttctattac ctggacgtgt ggggcaaggg caccaccgtg 5040
accgtgtcca gcgcaaccac aaacacccgct cccagactc ccaccaccag accaaccaata 5100
gcaagtcaac ccttgagctt gcgcctgag gcctgcttca tgtacgtggc cgccgccgcc 5160
ttcgtgttgc tgttcttcgt gggctgtggc gtgctgttgt ccagaaagcg ccgccgccag 5220
cacggacagc tctggttccc tgagggcttc aaagtgtcag aggccagcaa gaagaagcgg 5280
cgcgaacctc tgggcgagga cagcgtggc ctgaagcctc tgaaaaacc tatggtgtca 5340
aagctcagcc agctccagac agagctgctg gccgccctgc tggaaagcgg cctgagcaag 5400
gaggccctgt tgcaggctct gggagagcca ggcccttacc tgctggctgg cgagggacct 5460
ttggataagg gcgagagctg cggaggcgga cgcggagagc tggccgaact gcctaatggc 5520
ttgggcgaga cacgcggcag cgaggacgag acagacgag acggcgagga tttcacacct 5580
cccatcctca aggagttgga gaatctgtct cccgaggagg cgcccacca gaaggccgtg 5640
gtggagacac tgctgcaaga ggaccctggg cgcgtggcca agatggtgaa gagctacctg 5700
caacagcaca acatccctca gcgcgaggtg gtggatacca ccggcctgaa ccagagccac 5760
ctgtcccagc acctgaacaa gggcacaccc atgaagaccc agaagcgcgc cgccctctac 5820
acctggtacg tgcgcaagca gcgcgaggtt gctcaacagt tcacccacgc cggccaggagc 5880
ggcttgattg aggaacccac aggcgacgag ctgcccacca agaagggccg ccgcaaccgc 5940
ttcaaatggg gacccgcctc gcagcagata ctgttccaag cctacgagcg ccagaagaat 6000
cccagcaagg aggagcgcga gacactcgtg gaggagtgca accgcgctga gtgcatccag 6060
aggggcgtga gccctagcca agcccagggc ttgggcacaa acctggtgac gaaagtgcga 6120
gtgtataact ggttcgccaa ccgccgcaag gaggaggcct tccgcacaca gctggccatg 6180
acttgccgcg acgagttccc tacaatggtc tttcccagcg gccagatcag ccaggcctct 6240
gccctggcac cagcaccacc acaagtgtta cctcaagctc ccgctcccgc tcccgctcct 6300
gctatgtgt cggcattggc tcaagctcct gctcccgtgc cggtgttggc acctggaccg 6360
cctcaagctg ttgctcctcc cgctcccaag cccacacaag ccggcgaagg caccctgtct 6420
gaggccctgc tgcaactgca attcgacgac gaggatctgg gcgccctgct gggcaacagc 6480
accgatcccg ctgtctttac cgatctggcc agcgtggata tagcgagtt ccagcagctc 6540
ctgaaccagg gtatccctgt ggcgccgcac acaaccgagc ccatgctgat ggagtaccct 6600
gaggccatca ccagactcgt gactggcgca caacgccctc ctgatccagc accagccgcg 6660
ttaggcgcac ctggcctgcc taacggcttg ctgagcggcg acgaggattt ctccagcatc 6720
gccgatatgg atttcagcgc actgctgagt caaatctcca gccgggccaa gcggtccgga 6780
tccggagagg gcaggggatc tctccttact tgtgggacg tcgaggaaaa ccctggacca 6840
atggccctgc ccgtgacagc cctgctcctg cctctggccc tgttgctgca tgcagcacgg 6900
cctgagctgc ccacacaagg cacattcagc aacgtgtcca caacgtgtc cgagctgtgc 6960
ggcggcgcta tcgtggtgcc cgtgtgcttg gccttcctgc tgaccaccct gctgggcgtg 7020
ctgttctgct tcaacaagcg ggacctgatt aagaagcaca tctggccccaa cgtgcccgac 7080
cctagcaaga gccacatcgc ccagtggagc cctcacacac ctcccaggca caacttcaac 7140
agcaaggacc agatgtactc cgacggcaac ttcaccgacg tgtccgtggt ggagatcgag 7200
gccaacgaca agaagccctt ccctgaggac ctgaagtccc tggacctgtt caagaaggag 7260
aagatcaaca ccgagggaca cagcagcggc atcggcggct tagctgtat gagcagcagc 7320
aggccagca tctccagcag cgacgagac gagagcaccg cagcaccgtg 7380
cagtacagca ccgtggtgca cagcggctac aggcaccagg tgccatcagt gcaagtgttc 7440
agccgatccg agtccaccca gcctctgctg gacagcgagg agaggcccga ggacctgcaa 7500
ctggtggacc acgtggacgg aggcgacggc atcctgccta ggcagcaata cttcaagcag 7560
aattgcaacc agcacgagag cagccctgac atcacgaact tcgagaggag caagcaagtg 7620
tccagcgtga acgaggagga cttcgtggag ctgaagcagc agatcagcga ccacatcgat 7680
cagagctgcg gcagcggcca gatgaagatg ttccaggaag tgtccgcgc cgacgccttc 7740
ggccctggca cagaaggaca agtgagagg ttcgaaaccg tgggcatgga ggccgccacc 7800
gacgaggaa tgcccaagag ctacctgcct cagaccgtgc ggcagggcgg ctacatgcct 7860
cagtaaagga cgggtggcat ccctgtgacc cctccccagt gcctcctg gccctggaag 7920
ttgccactcc agtgcccacc agccttgtcc taataaaatt aagttgcatc attttgtctt 7980
actaggtgtc cttctataat attatggggt ggaggggggt ggtatgagc aagggcaag 8040
ttgggaagac aacctgtagg gcctgcgggg tctattggga accaagctgg agtgcagtgg 8100
cacaatcttg gctcactgca atctccgcct cctgggttca agcgattctc ctgcctcagc 8160
ctcccgagtt gttgggattc caggcatgca tgaccaggct cagctaattt tgttttttt 8220
ggtagaaacg ggtttcacc atattggcca ggctggtctc caactcctaa tctcaggtga 8280
```

```
tctacccacc ttggcctccc aaattgctgg gattacaggc gtgaaccact gctcccttcc   8340
ctgtccttcc gagggcaatc tggcccatca agtggcctte gcctctggga gtaacaaaaa   8400
tgcacttcaa aatagcttct gtaatcaagc tgcatgggtg gagtactccc cagctgactc   8460
caggaagttc tctatccaaa gctattcatt aggccagagc tgtgcaaata attagtcacc   8520
cacttgctcc ataaccctcc atgacagccc aggcattgag tccaggtggg accatcaagc   8580
catgctctgg tggctcatgc attatcatag aaatgggagg ctttatttat tttactaaaa   8640
agaacaaaaa caacagactg ctgtccttta gacaatagga tcacgtcatc tgagccctct   8700
gtgcccagg tgacaagccc agccccaagt tctctttcct cagcctcccc acacatgttc    8760
tggaggagat gggcccagca ggctgctctg aggcctggcc cctcgtaagc caagcatggc   8820
tc                                                                  8822
```

| | | |
|---|---|---|
| SEQ ID NO: 146 | moltype = RNA length = 8490 | |
| FEATURE | Location/Qualifiers | |
| source | 1..8490 | |
| | mol_type = other RNA | |
| | organism = synthetic construct | |

SEQUENCE: 146

```
gagccatgct tggcttacga gggcgaccaa cccatcaaac tccccgcccc cagcactttt   60
atttctcctc tttaggaagt acacttcagt atctttggca cagtgcatga gcacgactaa   120
agtaaaacat cgcagaaaac atagctttag tctacccttc gtgtcctaaa aggaaaacca   180
gtagcttccc aggccaccgg aagggcaaca catgtcctct gcagtttctg cacacggaaa   240
ggtaaagaca gagagaggac ctactcctca acacagaaca atttcaaaat cttccctcgc   300
ctgcaaccca agctgaagtc attctcccca gaaataacaa aagttggaag agaagccgga   360
gacaggatag gtgcaggaag cccacacttt gagggcagca ctcagacacc ctctcctgtg   420
tgcaggacgt gccgaatgtt caggtgcaat gagaatgagc catgcttggc ttataaggta   480
cgactgtgcc ttctagttgc cagccatctg ttgtttgccc ctccccgtg ccttccttga   540
ccctggaagg tgccactccc actgtccttt cctaataaaa tgaggaaatt gcatcgcatt   600
gtctgagtag gtgtcattct attctggggg gtgggtggg gcaggacagc aaggggggagg   660
attgggaaga caatagcagg catgctgggg atgcggtggg ctctatggga taagcttgat   720
atcgaattca tcgatgttaa taattaacat atatgttaat cattaacata tagttaatta   780
ttaaccgcta tgttaatgat taacaacggt taataattaa catatatgtt aatcattaac   840
atataactag tctagagggt atataatggg ggccactagt ctactaccag agttcatcgc   900
tagcgctacc ggatccgcca ccatggccct gccagtaacg gctctgctgc tgccacttgc   960
tctgctcctc catgcagcca ggcctgaggt ccagctcgtc gagagcggcg gtgggctggt   1020
tcagcctgga ggaagtctcc ggctgagctg tgctgcaagt ggattctcat tttcagatta   1080
ctccgggatg tcctgggtgc gtcaggcgcc agggaaaggc gaagaattag tgtctgccat   1140
ttcgcccggt ggtggggata cttattatgc agacagcgta aagggccgat tcacaatctc   1200
aagggacaat tccaagaata cgctgtactt gcagatgaac agcctaaggg ctgaggatac   1260
cgccgtgtac tattgcgcca gaatgtgt gtattactct aaccattcag gcgactacga   1320
ctattttgat taccgcggcc aaggaacact tgttaccgtg tctagtgcgg cagcaaccac   1380
gacgccagcg ccgcgaccac caacaccggc gcctaccatc gcgtcgcagc cactgtcact   1440
gcgcccagaa gcgtgccggc cagcggcggg tggcgcagtg cacacgaggg ggctggactt   1500
cgcctgtgat atctacatct gggcgccctt ggccgggact tgtgggtcc ttctcctgtc   1560
actggttatc ccctttact gcaaacgggg cagaaagaaa ctcctgtata tattcaaaca   1620
accatttatg agaccagtac aaactactca agaagaggac ggctgtagct gccgatttcc   1680
agaagaagaa gaaggaggat gtgaactgag agtgaagttc agcaggagcg cagacgcccc   1740
cgcgtaccag cagggccaga accagctcta taacgactac atgaatctag gaagagagga   1800
gtacgatgtt ttggacaaga gcgtggccg gaccctgag atggggggaa agccgagaag   1860
gaagaaccct caggaaggcc tgtacaatga actcagaaa gataagatgg cggaggccta   1920
cagtgagatt gggatgaaag gcgagcgccg gaggggcaag gggcacgatg gcctttacca   1980
gggtctcagt acagccacca aggacaccta cgatgccttg cacatgcaag cctgccccc   2040
tcgctaaaat caacctctgg attacaaaat ttgtgaaaga ttgactggta ttcttaacta   2100
tgttgctcct tttacgctat gtggatacgc tgctttaatg cctttgtatc atgctattgc   2160
ttcccgtatg gctttcattt tctcctcctt gtataaatcc tggttgctgt ctctttatga   2220
ggagttgtgg cccgttgtca ggcaacgtgg cgtggtgtgc actgtgtttg ctgacgcaac   2280
ccccactggt tggggcattg ccaccacctg tcagctcctt tccgggactt tcgctttccc   2340
cctccctatt gccacggcgg aactcatcgc cgcctgcctt gcccgctgct ggacaggggc   2400
tcggctgttg ggcactgaca attccgtggt gttgtcgggg aaatcatcgt cctttccttg   2460
gctgctcgcc tgtgttgcca cctggattct gcgcgggacg tccttctgct acgtcccttc   2520
ggccctcaat ccagcggacc ttccttcccg cggcctgctg ccggctctgc ggcctcttcc   2580
gcgtcttcgc cttcgccctc agacgagtcg gatctccctt gggccgcct cccgcctgg   2640
atccttgact tgcggccaac ttgtttattg cagcttataa tggttacaaa taagcaata   2700
gcatcacaaa tttcacaaat aaagcatttt tttcactgca ttctagttgt ggtttgtcca   2760
aactcatcaa tgtatcttat catgtctggg atccttgact tgccgccgca actcccacct   2820
gcaacatgcg tgactgactg aggccgcgac tctagagtcg accggatctg cgatcgctcc   2880
ggtgcccgtc agtgggcaga gcgcacatcg cccacagtcc ccgagaagtt ggggggaggg   2940
gtcggcaatt gaacgggtgc ctagagaagg tggcgcgggg taaactggga aagtgatgtc   3000
gtgtactggc tccgccttt tcccgagggt ggggagaac cgtatataag tgcagtagtc   3060
gccgtgaacg ttcttttcg caacgggttt gccgccagaa cacagctgaa gcttcgaggg   3120
gctcgcatct ctccttcacg cgcccgccgc cctacctgag gccgccatcc acgccggttg   3180
agtcgcgttc tgccgcctcc cgcctgtggt gcctcctgaa ctgcgtccgc cgtctaggta   3240
agtcgactcg ttggatcccc actacccgga tcaacgccct aggtttatgt ttggatgaac   3300
tgacatacgc gtatccgtct taagaatctt tcaaacact agtagtgaaa tatatattaa   3360
actagtgttt gaaaagattc ttattacggt aagattcaaa tcgcaactat tttatcaatt   3420
tttttgcgtc acgacggtga cttaggagta tgccggatca acgccctagg tttatgtttg   3480
gatgaactga catacgcgta tccgtctaaa aatcaatctc atttcctggt agtgaaatat   3540
atattaaacc aggaaatgag attgattttt ttacggtaac gcggaattcg caactatttt   3600
atcaattttt tgcgtcgacg actgtgacag cagagtatgc cggatcaacg ccctaggttt   3660
atgtttggat gaactgacat acgcgtatcc gtcttatgta aaagacaaac aatgcgtagt   3720
```

```
gaaatatata ttaaacgcat tgtttgtctt ttacatatta cggtaacgcg gaattcgcaa    3780
ctattttatc aatttttgc gtcgaccgga actatcttga agagtagtag tggactagtg     3840
tgacgctgct gacccctttc tttcccttct acagatccaa gctgtgaccg gcgcctacac    3900
ctgcagccca agcttaccat ggccttacca gtgaccgcct tgctcctgcc gctggccttg    3960
ctgctccacg ccgccaggcc tgagatcgtg ctgacccagt ctccggcac cctgtccctg     4020
tctcccggcg aaagggctac cgtgagctgt agggcctccc agtccgtgag cagcagctac    4080
ctggcctggt atcagcaaaa gcccggccag gctcccaggc tgctgatcta cggagccagc    4140
agcagggcta caggaatacc agaccggttc agcggcagcg gcagcggcac cgacttcaca    4200
ctgacaataa gccggctgga acccgaggac ttcgccgtgt actattgtca acagtacggc    4260
agcagccctt acaccttcgg ccagggaacc aagctcgaga tcaagggcgg cggaggatct    4320
ggcggaggag gatctggagg aggaggcagc caagtgcaac tggtgcagag cggccctgaa    4380
gtgaagaagc ccgcgccag cgtgaaagtg tcctgcaaag ccagcggcta caccttcacc     4440
agctacggca tcacctgggt gcgacaggct cccggccagg gactggagtg gatgggctgg    4500
atcagcgagt acaatggcaa caccaactac gcccagaagt tccagggaag ggtgacaatg    4560
accatcgaca ccagcaccac caccgcctac atggagctga ggagcctcag gagcgacgac    4620
accgccgtgt acttctgcgc cagaggcggc atcctgccct actacttctt ctactacatg    4680
gacgtgtggg gcaagggcac caccgtgacc gtgtccagcg caaccacaac acccgctccc    4740
agacctccca caccagcacc aacaatagca agtcaaccct tgagcttgcg ccctgaggcc    4800
tgcttcatgt acgtgccgc cgccgccttc gtgttgctgt tcttcgtggg ctgtggcgtg    4860
ctgttgtcca gaaagcgccg ccgccagcac ggacagctct ggttccctga gggcttcaaa    4920
gtgtcagagg ccagcaagaa gaagcggcgc gaacctctgg gcgaggacag cgtgggcctg    4980
aagcctctga aaaacgctat ggtgtcaaag ctcagccagc tccagacaga gctgctggcc    5040
gccctgctgg aaagcggcct gagcaaggag gccctgttgc aggctctggg agagccaggc    5100
ccttacctgc tggctggcga gggacctttg gataagggcg agagctgcgg aggcggacgc    5160
ggagagctgg ccgaactgcc taatggcttg gcgagacac gcggcagcga ggacgagaca    5220
gacgacgacg gcgaggattt cacacctccc atcctcaagg agttggagaa tctgtctctg    5280
gaggaggccg cccaccagaa ggccgtggtg gagacactgc tgcaagagga ccctgcgc     5340
gtggccaaga tggtgaagag ctacctgcaa cagcacaaca tccctcagcg cgaggtggtg    5400
gataccaccg gcctgaacca gagccacctg tcccagcacc tgaacaaggg cacacccatg    5460
aagacccaga agcgcgccgc cctctacacc tggtacgtgc caagcagcg cgaggttgct    5520
caacagttca cccacgccgg ccagggcggc ttgattgagg aacccacagg cgacgagctg    5580
cccaccaaga agggccgccg caaccgcttc aaatgggac ccgcctcgca gcagatactg     5640
ttccaagcct acgagcgcca aagaatccc agcaaggagg agcgcgagac actcgtggag    5700
gagtgcaacc gcgctgagtg catccagagg ggcgtgagcc ctagccaagc ccagggcttg    5760
ggcagcaacc tggtgacaga agtgcgcgtg tataactggt tcgccaaccg ccgcaaggag    5820
gaggccttcc gccacaagct ggccatgact tgccgcgacg agttccctac aatggtctt    5880
cccagcggcc agatcagcca ggcctctgcc ctggcaccag caccaccaca agtgttacct    5940
caagctcccg ctcccgctcc cgctcctgct atggtgtcgg cattggctca agctcctgct    6000
cccgtgcctg tgttggcacc tggaccgcct caagctgttg ctcctcccgc tcccaagcca    6060
acacaagccg gcgaaggcac cctgtctgag gccctgctgc aactgcaatt cgacgacgag    6120
gatctgggcg ccctgctggg caacagcacc gatcccgctg tctttaccga tctggccagc    6180
gtggataata gcgagttcca gcagctcctg aaccagggta tccctgtggc gccgcacaca    6240
acggagcca tgctgatgga gtaccctgag gccatcacca gactcgtgac tggcgcacaa    6300
cgccctcctg atccagcacc agcgccgtta ggcgcacctg gcctgcctaa cggcttgctg    6360
agcggcgacg aggatttctc cagcatcgcc gatatggatt tcagcgcact gctgagtcaa    6420
atctccagcc gggccaagcg gtccggatcc ggagagggca ggggatctct ccttacttgt    6480
ggggacgtcg aggaaaaccc tggaccaatg gccctgcccg tgacagccct gctcctgcct    6540
ctggccctgt tgctgcatgc agcacgcct gagctgcca cacaaggcac attcagcaac    6600
gtgtccacca acgtgtccga gctgtgcggc ggcgctatcg tggtgccgt gtgcttggcc     6660
ttcctgctga ccaccctgct gggcgtgctg ttctgcttca caagcggga cctgattaag    6720
aagcacatct ggcccaacgt gcccgaccct agcaagagcc acatcgccca gtggagcctt    6780
cacacacctc caggcacaa cttcaacagc aaggaccaga tgtactccga cggcaacttc    6840
accgacgtgt ccgtggtgga gatcgaggcc aacgacaaga gcccttccc tgaggacctg    6900
aagtccctgg acctgttcaa gaaggagaag atcaacaccg agggacacag cagcggcatc    6960
ggcggctcta gctgtatgag cagcagcagg cccagcatct ccagcagcga cgagaacgag    7020
agcagccaga caccagcag caccgtgcag tacagcaccg tggtgcacag cggctacagg    7080
caccaggtgc catcagtgca agtgttcagc cgatccgagt ccaccagcc tctgctggac    7140
agcgaggaga ggcccgagga cctgcaactg gtggaccacg tggacggagg cgacggcatc    7200
ctgcctaggc agcaatactt caagcagaat tgcagccagc acgagagcac ccctgacatc    7260
agccacttcg agaggagcaa gcaagtgtcc agcgtgaacg aggagacttt cgtcgaggctg    7320
aagcagcaga tcagcgacca catcagccag agctgcggca gcggccagat gaagatgttc    7380
caggaagtgt ccgccgccga cgccttcggc cctggcacag aaggacaagt ggagaggttc    7440
gaaaccgtgg gcatggaggc cgccaccgac gagggaatgc caagagcta cctgcctcag    7500
accgtgcggc agggcggcta catgcctcag taaaggacgg gtggcatcc tgtgaccct     7560
ccccagtgcc tctcctggcc ctggaagttg ccactccagt gcccaccagc cttgtcctaa    7620
taaaattaag ttgcatcatt ttgtctgact aggtgtcctt ctataatatt atgggtggga    7680
gggggtggt atggagcaag gggcaagttg gaagacaac ctgtagggcc tgcgggtct     7740
attgggaacc aagctggagt gcagtggcac aatcttggct cactgcaatc tccgcctcct    7800
gggttcaagc gattctcctg cctcagcctc ccgagttgtt gggattccag gcatcgatga    7860
ccaggctcag ctaattttg tttttttggt agaaacgggg tttcaccata ttggccaggc    7920
tggtctccaa ctcctaatct caggtgatct acccaccttg gcctcccaaa ttgctgggat    7980
tacaggcgtg aaccactgct cccttccctg tccttcgag gcaatctggg cccatcaagt    8040
ggccttcgcc tctgggagta caaaaatgc acttcaaaat agcttctgta atcaagctgc    8100
atgggtggga tactcccag ctgactccag gaagttctct atccaaagct attcattagg    8160
ccagagctgt gcaaataatt agtcaccac ttgctccata accctccatg acagcccagg    8220
cattgagtcc aggtgggacc atcaagccat gctctggtgg ctcatgcatt atcatagaaa    8280
tgggaggctt tatttatttt actaaaaaga acaaaaacaa cagactgctg tcctttagac    8340
aataggatca cgtcatctga gccctctgtg ccccaggtga caagcccagc cccaagttct    8400
cttcctcag cctccccaca catgttctgg aggagatggg cccagcaggc tgctctgagg    8460
```

| | | | | |
|---|---|---|---|---|
| cctggcccct | cgtaagccaa | gcatggctca | | 8490 |

SEQ ID NO: 147        moltype = RNA  length = 8659
FEATURE               Location/Qualifiers
source                1..8659
                        mol_type = other RNA
                        organism = synthetic construct
SEQUENCE: 147

| | | | | |
|---|---|---|---|---|
| gagccatgct | tggcttacga | gggcgaccaa | cccatcaaac tccccgcccc | cagcactttt | 60 |
| atttctcctc | tttaggaagt | acacttcagt | atctttggca | cagtgcatga gcacgactaa | 120 |
| agtaaaacat | cgcagaaaac | atagctttag | tctaccctct | gtgtcctaaa aggaaaacca | 180 |
| gtagcttccc | aggccaccgg | aagggcaaca | catgtcctct | gcagtttctg cacacgggaa | 240 |
| ggtaaagaca | gagagaggac | ctactcctca | acacagaaac | atttcaaaat ctttcctcgc | 300 |
| ctgcaaccca | agctgaagtc | attctcccca | gaaataacaa | aagttggaag agaagccgga | 360 |
| gacaggatag | gtgcaggaag | cccacacttt | gagggcagca | ctcagacacc ctctcctgtg | 420 |
| tgcaggacgt | gccgaatgtt | caggtgcaat | gagaatgagc | catgcttggc ttataaggta | 480 |
| cgactgtgcc | ttctagttgc | cagccatctg | ttgtttgccc | ctccccgtg ccttccttga | 540 |
| ccctgaagg | tgccactccc | actgtccttt | cctaataaaa | tgagggaatt gcatcgcatt | 600 |
| gtctgagtag | gtgtcattct | attctggggg | gtgggtggg | gcaggacagc aaggggagg | 660 |
| attgggaaga | caatagcagg | catgctggg | atgcggtggg | ctctatggga taagcttgat | 720 |
| atcgaattca | tcgatgttaa | taattaacat | atatgttaat | cattaacata tagttaatta | 780 |
| ttaacgcta | tgttaatgat | taacaacggt | taataattaa | catatatgtt aatcattaac | 840 |
| atataactag | tctagagggt | ataatgggg | ggcactagt | ctactaccag agttcatcgc | 900 |
| tagcgctacc | ggatccgcca | ccatggccct | gccagtaacg | gctctgctgc tgccacttgc | 960 |
| tctgctcctc | catgcagcca | ggcctgaggt | ccagctcgtc | gagagcggcg gtgggctggt | 1020 |
| tcagcctgga | ggaagtctcc | ggctgagctg | tgctgcaagt | ggattctcat tttcagatta | 1080 |
| ctccgggatg | tcctgggtgc | gtcaggcgcc | agggaaaggc | gaagaattag tgtctgccat | 1140 |
| ttcgcccggt | ggtggggata | cttattatgc | agacagcgta | aagggccgat tcacaatctc | 1200 |
| aagggacaat | tccaagaata | cgctgtactt | gcagatgaac | agcctaaggg ctgaggatac | 1260 |
| cgccgtgtac | tattgcgcca | gaagatggtg | gtattactct | aaccattcag gcgactacga | 1320 |
| ctatttgat | taccgcggcc | aaggaacact | tgttaccgtg | tctagtcgg cagcaaccac | 1380 |
| gacgccagcg | ccgcgaccac | caacaccggc | gcctaccatc | gcgtcgcagc cactgtcact | 1440 |
| gcgcccagaa | gcgtgccggc | cagcggcggg | tggcgcagtg | cacacgaggg ggctggactt | 1500 |
| cgcctgtgat | atctacatct | gggcgccctt | ggccgggact | tgtggggtcc ttctcctgtc | 1560 |
| actggttatc | acccttact | gcaaacgggg | cagaaagaaa | ctcctgtata tattcaaaca | 1620 |
| accatttatg | agaccagtac | aaactactca | agaagaggac | ggctagct gccgatttcc | 1680 |
| agaagaagaa | gaaggaggat | gtgaactgag | agtgaagttc | agcaggagcg cagacgcccc | 1740 |
| cgcgtaccag | cagggccaga | accagctcta | taacgagctc | aatctaggac gaagagagga | 1800 |
| gtacgatgtt | ttggacaaga | ggcgtggccg | ggaccctgag | atgggggaa agccgagaag | 1860 |
| gaagaaccct | caggaaggcc | tgtacaatga | actgcagaaa | gataagatgg cggaggccta | 1920 |
| cagtgagatt | gggatgaaag | gcgagcgccg | gaggggcaag | gggcacgatg gcctttacca | 1980 |
| gggtctcagt | acagccacca | aggaccccta | cgatgccttg | cacatgcaag ccctgccccc | 2040 |
| tcgctaaaat | caacctctgg | attacaaaat | ttgtgaaaga | ttgactggta ttcttaacta | 2100 |
| tgttgctcct | tttacgctat | gtggatacgc | tgctttaatg | cctttgtatc atgctattgc | 2160 |
| ttcccgtatg | gctttcattt | tctcctcctt | gtataaatcc | tggttgctgt ctctttatga | 2220 |
| ggagttgtg | cccgttgtca | ggcaacgtgg | cgtggtgtgc | actgtgtttg ctgacgcaac | 2280 |
| ccccactggt | tggggcattg | ccaccacctg | tcagctcctt | tccgggactt tcgctttccc | 2340 |
| cctccctatt | gccacggcgg | aactcatcgc | cgcctgcctt | gcccgctgct ggacaggggc | 2400 |
| tcggctgttg | ggcactgaca | attccgtggt | gttgtcgggg | aaatcatcgt cctttccttg | 2460 |
| gctgctcgcc | tgtgttgcca | cctggattct | gcgcgggacg | tccttctgct acgtcccttc | 2520 |
| ggccctcaat | ccagcgacc | ttccttcccg | cggcctgctg | ccggctctgc ggcctcttcc | 2580 |
| gcgtcttcgc | cttcgccctc | agacgagtcg | gatctccctt | gggccgcct cccgcctgtg | 2640 |
| atccttgact | tgcggccaac | ttgttttaatg | cagcttataa | tggttacaaa taaagcaata | 2700 |
| gcatcacaaa | tttcacaaat | aaagcatttt | tttcactgca | ttctagttgt ggtttgtcca | 2760 |
| aactcatcaa | tgtatcttat | catgtctgg | atccttgact | tgcgggccgca actcccacct | 2820 |
| gcaacatgcg | tgactgactg | aggccgcgac | tctagagtcg | accggatctg cgatcgctcc | 2880 |
| ggtgcccgtc | agtgggcaga | gcgcacatcg | cccacagtcc | ccgagaagtt ggggggaggg | 2940 |
| gtcggcaatt | gaacgggtgc | ctagagaagg | tggcgcgggg | taaactggga aagtgatgtc | 3000 |
| gtgtactggc | tccgcctttt | tcccgagggt | ggggagaac | cgtatataag tgcagtagtc | 3060 |
| gccgtgaacg | ttctttttcg | caacgggttt | gccgccagaa | cacagctgaa gcttcgaggg | 3120 |
| gctcgcatct | ctccttcacg | cgcccgccgc | cctacctgag | gccgccatcc acgccggttg | 3180 |
| agtcgcgttc | tgccgcctcc | cgcctgtggt | gcctcctgaa | ctgcgtccgc cgtctaggta | 3240 |
| agtcgactcg | ttggatcccc | actacccgga | tcaacgccct | aggtttatgt ttggatgaac | 3300 |
| tgacatacgc | gtatccgtct | taagaatctt | ttcaaacact | agtagtgaaa tatattaa | 3360 |
| actagtgttt | gaaaagattc | ttattacggt | aacgcggaat | tcgaactat tttatcaatt | 3420 |
| ttttgcgtcg | acacttcaag | gggcttgcgg | ccgcaaccat | ctccatggct gtttgaatga | 3480 |
| ggcttcagta | ctttacagaa | tcgttgcctg | cacatcttgg | aaacacttgc tgggattact | 3540 |
| tcgacttctt | aacccaacag | aaggctcgag | aaggtatatt | gctgttgaca gtgagcgcca | 3600 |
| gtgtgaagct | cttgtcagat | agtgaagcca | cagatgtatc | tgacaagagc ttcacactga | 3660 |
| tgcctactgc | ctcggacttc | aaggggctag | aattcgcagca | attatcttgt ttactaaaac | 3720 |
| tgaatacctt | gctatctctt | tgatacattt | ttacaaagct | gaattaaaat ggtataaatt | 3780 |
| aaatcacttt | gacggtgact | taggagtatg | ccggatcaac | gccctaggtt tatgtttgga | 3840 |
| tgaactgaca | tacgcgtatc | cgtctaaaaa | tcaatctcat | ttcctggtag tgaaatatat | 3900 |
| attaaaccag | gaaatgagat | tgatttttt | acggtaagcg | acatttttat | 3960 |
| caattttttg | cgtcgacgac | tgtgacagca | gagtatgccg | gatcaacgcc ctaggttat | 4020 |
| gtttggatga | actgacatac | gcgtatccgt | cttatgtaaa | agacaacaa tgcgtagtga | 4080 |
| aatatatatt | aaacgcattg | tttgtctttt | acatattacg | gtaacgcgga attcgcaact | 4140 |
| attttatcaa | ttttttgcgt | cgaccggaac | tatcttgaag | agtagtagtg gactagtgtg | 4200 |
| acgctgctga | ccccttctt | tccctctac | agatccaagc | tgtgaccggc gcctacacct | 4260 |

```
gcagcccaag cttaccatgg ccttaccagt gaccgccttg ctcctgccgc tggccttgct    4320
gctccacgcc gccaggcctg agatcgtgct gacccagtct cccgccaccc tgtccctgtc    4380
tcccggcgaa agggctaccc tgtcttgcgg cgcctcccag tccgtgagca gcagctacct    4440
ggcctggtat cagcaaaagc ccggcctggc tcccaggctg ctgatctacg acgccagcag    4500
cagggctaca ggaataccag accggttcag cggcagcggc agcggcaccg acttcacact    4560
gacaataagc cggctggaac ccgaggactt cgccgtgtac tattgtcaac agtacgcag    4620
cagcccttac accttcggcc agggaaccaa gctcgagatc aagggcggcg gaggatctgg    4680
cggaggagga tctggaggag gaggcagcca agtgcaactg gtgcagagcg gcgccgaagt    4740
gaagaagccc ggcgccagcg tgaaagtgtc ctgcaaagcc agcggataca cattcagctc    4800
ctacggcgtg agctgggtgc gacaggctcc cggagtgga tgggctggat    4860
cagcaagtat aacggcaaca ccaactacgc ccagaagttc cagggaaggg tgacaatgac    4920
caccgacacc agcaccagca ccgcctacat ggagctgagg agcctcagga gcgacgacac    4980
cgcagtgtac ttctgcgcac gcggcggcat ccacggcgac agctactact tctattacct    5040
ggacgtgtgg ggcaagggca ccaccgtgac cgtgtccgga gcaaccacaa cacccgctcc    5100
cagacctccc acaccagcac caacaatagc aagtcaaccc ttgagcttgc gccctgaggc    5160
ctgcttcatg tacgtggccg ccgccgcctt cgtgttgctg ttcttcgtgg gctgtggcgt    5220
gctgttgtcc agaaagcgcc gccgccagca cggacagctc tggttccctg agggcttcaa    5280
agtgtcagag gccagcaaga gaagcggcg cgaacctgtc ggcgaggaca gcgtgggcct    5340
gaagcctctg aaaaacgcta tggtgtcaaa gctcagccag ctccagacag agctgctggc    5400
cgccctgctg aaaagcggcc tgagcaagga ggccctgttg caggctctgg agagccagg    5460
cccttacctg ctggctggcg agggacctt ggataagggc gagagctgcg gaggcggacg    5520
cggagagctg gccgaactgc ctaatggctt gggcgagaca cgcggcagcg aggacgagac    5580
agacgacgac ggcgaggatt tcacacctcc catcctcaag gagttggaga atctgtctcc    5640
cgaggaggcc gcccaccaga aggccgtggt ggagacactg ctgcaagagg acccttggcg    5700
cgtggccaag atggtgaaga gctacctgca acagcacaac atccctcagc gcgaggtggt    5760
ggataccacc ggcctgaacc agagccacct gtcccagcac ctgaacaagg gcacacccat    5820
gaagacccca aagcgcgcc ccctctacac ctggtacgtg cgcaagcagc gcgaggttgc    5880
tcaacagttc acccacgccg gccagggcgg cttgattgag gaaccacagg cgacgagct    5940
gcccaccaag aagggccgcc gcaaccgctt caaatgggga cccgcctcgc agcagatact    6000
gttccaagcc tacgagcgcc agaagaatcc cagcaaggag gagcgcgaca cactcgtgga    6060
ggagtgcaac cgcgctgagt gcatccagag gggcgtgagc cctagccaag cccagggctt    6120
gggcagcaac ctggtgacag aagtgcgcgt gtataactgg ttcgcaacc gccgcaagga    6180
ggaggccttc cgcacaagc tggccatgac ttgccgcgac gagttcccta caatggtctt    6240
tcccagcggc cagatcagcc aggcctctgc cctggcacca gcaccaccac aagtgttacc    6300
tcaagctccc gctcccgctc ccgctcctgc tatggtgtcg gcattggctc aagctcctgc    6360
tcccgtgccg gtgttggcac ctggaccgcc tcaagctgtt gctcctcccg ctcccaagcc    6420
cacacaagcc ggcgaaggca ccctgtctga ggccctgctg caactgcaat cgacgacga    6480
ggatctgggc gccctgctgg caacagcac cgatcccgct gtctttaccg atctggccag    6540
cgtggataat agcgagttcc agcagctcct gaaccaggat atccctgtgg cgccgcacac    6600
aacgagcccc atgctgatgg agtaccctga ggccatcacc agactcgtga ctggcgcaca    6660
acgccctcct gatccagcac cagccgtt aggcgcacct ggcctgccta acggcttgct    6720
gagcggcgac gaggatttct ccagcatcgc cgatatggat ttcagcgcac tgctgagtca    6780
aatctccagc cgggccaagc ggtccggatc cggagaggc agggatctc tccttacttg    6840
tggggacgtc gaggaaaacc ctggaccaat gggagccgga gccactggcc gcgctatgga    6900
cggaccaaga cttctcctgc ttctgctgtt gggtgtctct ctaggtgggg cgaaagaagc    6960
ctgtcccact ggtctatata tcattctgg ggagtgctgt aaggcctgta accttggcga    7020
gggagtggca cagccctgtg gggcgaatca gaccgtgtgc gagccttgtc tggacagtgt    7080
gacccttctcg gacgtagtgt ctgccactga accttgtaaa ccgtgcacag agtgcgtagg    7140
gctccaatca atgtccgctc cctgcgtgga agcagacgac gccgtgtgcc gatgcgcata    7200
cggctattac caggatgaaa ccacaggccg ctgcgaggcc tgtagggttt gcgaggccgg    7260
aagcggatta gtgttttcat gccaagacaa gcagaatacg gtgtgcgagg agtgccctga    7320
cggaacttac tctgatgagg ccaaccacgt cgatccctgt ttgccgtgta cggttttgtga    7380
ggataccgaa cgacagctca gagagtgcac ccggtgggct gatgcagaat gcgaggagat    7440
cccagggcgt tggatcacca ggtcaacacc acccgaaggg tccgacagta ccgctcctag    7500
tacccaggaa ccagaagctc caccggagca ggatctgatt gcgagtacag tagccggcgt    7560
ggtcacaaca gttatgggaa gcagccaacc tgtcgtgaca cgcggaacta cagataatct    7620
catacccgtg tattgttcaa tcctggccgc cgtagtggtc ggtctggtgg cttacattgc    7680
gttcaagcgg tggaactcct aaaggacggg tggcatccct gtgaccctc ccagtgcct    7740
ctcctggccc tggaagttgc cactccagtg cccaccagcc ttgtcctaat aaaattaagt    7800
tgcatcattt tgtctgacta ggtgtccttc tataatatta tggggtggag ggggtggta    7860
tggagcaagg ggcaagttgg gaagacaacc tgtagggcct gcggggtcta ttgggaacca    7920
agctggagtg cagtggcaca atcttggctc actgcaatct ccgcctcctg gttcaagcg    7980
attctcctgc ctcagcctcc cgagttgttg ggattccagg catgcatgac caggctcagc    8040
taattttgt tttttggta gaacgggggt ttcaccatgt tggccaggct ggtctccaac    8100
tcctaatctc aggtgatcta cccaccttgg cctcccaaat tgctgggatt acaggcgtga    8160
accactgctc cctcctgt cctccgagg gcaatctggc ccatcaagtg gccttcgcct    8220
ctgggagtaa caaaaatgca cttcaaaata gcttctgtaa tcaagctgca tgggtggagt    8280
actcccagc tgactccagg aagttctcta tccaaagtca ttcattaggc cagagctgtg    8340
caaataatta gtcacccact tgctccataa ccctccatga cagccaggc attgagtcca    8400
ggtgggacca tcaagccatg ctctggtggc tcatgcatta tcatagaaat ggggaggcttt    8460
attttattta ctaaaagaa caaaaacaac agactgctgt cctttagaca ataggatcac    8520
gtcatctgag ccctctgtgc cccaggtgac aagcccagcc ccaagttctc tttcctcagc    8580
ctccccacac atgttctgga ggagatgggc ccagcaggct gctctgaggc ctggcccctc    8640
gtaagccaag catggctca                                                 8659

SEQ ID NO: 148        moltype = DNA   length = 6492
FEATURE               Location/Qualifiers
source                1..6492
                      mol_type = other DNA
``` organism = synthetic construct
SEQUENCE: 148

```
ggcggctagg gaggtggggc gaggcgaggt ttgctgggt gaggcagcgg cgcggccggg   60
ccgggccggg ccacaggcgg tggcggcggg accatggagg cggcggtcgc tgctccgcgt  120
ccccggctgc tcctcctcgt gctggcggcg gcggcggcgg cggccgggc gctgctcccg   180
ggggcgacgg cgttacagtg tttctgccac ctctgtacaa aagacaattt tacttgtgtg  240
acagatgggc tctgctttgt ctctgtcaca gagaccacag acaaagttat acacaacagc  300
atgtgtatag ctgaaattga cttaattcct cgagataggc cgtttgtatg tgcaccctct  360
tcaaaaactg ggtctgtgac tacaacatat tgctgcaatc aggaccattg caataaaata  420
gaacttccaa ctactgtaaa gtcatcacct ggccttggtc ctgtggaact ggcagctgtc  480
attgctggac cagtgtgctt cgtctgcatc tcactcatgt tgatggtcta tatctgccac  540
aaccgcactg tcattcacca tcgagtgcca aatgaagagg acccttcatt agatcgccct  600
tttatttcag agggtactac gttgaaagac ttaatttatg atatgacaac gtcaggttct  660
ggctcaggtt taccattgct tgttcagaga acaattgcga gaactattgt gttacaagaa  720
agcattggca aaggtcgatt tggagaagtt tggagaggaa agtggcgggg agaagaagtt  780
gctgttaaga tattctcctc tagagaagaa cgttcgtggt tccgtgaggc agagatttat  840
caaactgtaa tgttacgtca tgaaaacatc ctgggatta tagcagcaga caataaagac  900
aatggtactt ggactcagct ctggttggtg tcagattatc atgagcatgg atcccttttt  960
gattacttaa acagatacac agttactgtg gaaggaatga taaaacttgc tctgtccacg 1020
gcgagcggtc ttgcccatct tcacatggag attgttggta cccaaggaaa gccagccatt 1080
gctcatagag atttgaaatc aaagaatatc ttggtaaaga agaatggaac ttgctgtatt 1140
gcagacttag gactggcagt aagcatgat tcagccacag ataccattga tattgctcca 1200
aaccacagag tgggaacaaa aaggtacatg gcccctgaag ttctcgatga ttccataaat 1260
atgaaacatt ttgaatcctt caaacgtgct gacatctatg caatgggctt agtattctgg 1320
gaaattgctc gacgatgttc cattggtgga attcatgaag attccaact gccttattat 1380
gatcttgtac cttctgaccc atcagttgaa gaaatgagaa aagttgtttg tgaacagaag 1440
ttaaggccaa atatcccaaa cagatgcag agctgtgaag ccttgagagt aatggctaaa 1500
attatgagag aatgttggta tgccaatgga gcagctaggc ttacagcatt gcggattaag 1560
aaaacattat cgcaactcag tcaacaggaa ggcatcaaaa tgtaattcta cagctttgcc 1620
tgaactctcc tttttcttc agatctgctc ctgggttta atttgggagg tcaattgttc 1680
tacctcactg agagggaaca gaaggatatt gcttcctttt gcagcagtga ataaagtca 1740
attaaaaact tcccaggatt tctttggacc caggaaacag ccatgtgggt cctttctgtg 1800
cactatgaac gcttctttcc caggacagaa aatgtgtagt ctacctttat tttttattaa 1860
caaaacttgt tttttaaaaa gatgattgct ggtcttaact ttaggtaact ctgctgtgt 1920
ggagatcatc tttaagggca aaggagttgg attgctgaat tacaatgaaa catgtcttat 1980
tactaaagaa agtgatttac tcctggttag tacattctca gaggattctg aaccactaga 2040
gtttccttga ttcagacttt gaatgtactg ttctatagtt tttcaggatc ttaaaactaa 2100
cacttataaa actcttatct tgagtctaaa aatgacctca tatagtagtg aggaacataa 2160
ttcatgcaat tgtattttgt atactattat tgttctttca cttattcaga acattacatg 2220
ccttcaaaat gggattgtac tataccagta agtgccactt ctgtgtcttt ctaatgaaa  2280
tgagtagaat tgctgaaagt ctctatgtta aacctatag tgtttgaatt caaaagctt  2340
atttatctgg gtaacccaaa cttttctgt tttgttttg gaagggtttt tgtggtatgt 2400
catttggtat tctattctga aaatgcettt ctcctaccaa aatgtgctta agccactaaa 2460
gaaatgaagt ggcattaatt agtaaattat tagcatggtc atgtttgaat attctcacat 2520
caagcttttg cattttaatt gtgttgtcta agtatacttt taaaaaatca agtggcactc 2580
tagatgctta tagtacttta atatttgtag catacagact aattttttcta aaagggaaag 2640
tctgtctagc tgcttgtgaa aagttatgtg gtattctgta agccattttt ttcttttatct 2700
gttcaaagac ttatttttta agacatgaat tacatttaaa attagaatat ggttaatatt 2760
aaataatagg ccttttttcta ggaaggcgaa ggtagttaat aatttgaata gataacagat 2820
gtgcaagaaa gtcacatttg ttatgtatgt aggagtaaac gttcggtgga tcctctgtct 2880
ttgtaactga ggttagagct agtgtggttt tgaggtctca ctacactttg aggaaggcag 2940
cttttaattc agtgtttcct tatgtgtgcg tacattgcaa ctgcttacat gtaatttatg 3000
taatgcattc agtgcaccct tgttacttcg gagaggtggt agctaaagaa cattctgagt 3060
ataggttttt ctccatttac agatgtcttt ggtcaaatat tgaaagcaaa cttgtcatgg 3120
tcttcttaca ttaagttgaa actagcttat aataactgtt ttttacttcc aatgctatga 3180
agtctctgca gggcttttac agttttcgaa gtccttttat cactgtgatc ttattctgag 3240
gggagaaaaa actatcatag ctctgaggca agacttcgac tttatagtgc tatcagttcc 3300
ccgatacagg gtcagagtaa cccatacagt attttggtca ggaagagaaa gtggccattt 3360
acactgaatg agttgcattc tgataatgtc ttatctctta tacgtaagat aaatttgaaa 3420
gactatttga tcttaaaacc aaagtaattt tagaatgagt gacatattac ataggaattt 3480
agtgtcaatt tcatgtgttt aaaaaacatca tgggaaaaat gcttagaggt tactattttg 3540
actacaaagt tgagtttttt tctgtagtta ccataatttc attgaagcaa atgaatgagt 3600
ttgagaggtt tgttttttata gttgtgttgt attacttgtt taataataat ctctaattct 3660
gtgatcaggt acttttttg tgggggttt tttttttt gttgttgttt 3720
ttgggccatt tctaagccta ccagatctgc tttatgaaat ccaggggacc aatgcatttt 3780
atcactaaaa ctattttat ataatttaa gaatatacca aaagttgtct gatttaaagt 3840
tgtaatacat gatttctcac tttcatgtaa ggttatccac ttttgctgaa gatatttttt 3900
attgaatcaa agattgagtt acaattatac ttttcttacc taagtggata aaatgtactt 3960
ttgatgaatc agggaatttt tttaaagttg gagtttagtt ctaaattgac tttacgtatt 4020
actgcagtta attccttttt tggctaggga tggtttgata aaccacaatt ggctgatatt 4080
gaaaatgaaa gaaacttaaa aggtgggatg gatcatgatt actgtcgata actgcagata 4140
aatttgatta gagtaataat tttgtcattt aaaaacacag ttgtttatac tgcccatcct 4200
aggatgctca ccttccaaga ttcaacgtgg ctaaaacatc ttctggtaaa ttgtgcgtcc 4260
atattcattt tgtcagtagc caggagaaat gggatgggag gaaatacgac ttagtgaggc 4320
atagacatcc ctggtccatc ctttctgtct ccagctgttt cttggaacct gctctcctgc 4380
ttgctggtcc ctgacgcaga gaccgttgcc tcccccacag ccgtttgact gaaggctgct 4440
ctggagacct agagtaaaac ggctgatgga agttgtggga cccacttcca tttccttcag 4500
tcattagagg tggaagggag gggtctccaa gtttggagat tgagcagatg aggcttggga 4560
tgcccctgct ttgacttcag ccatggatga ggagtgggat ggcagcaagg tggctcctgt 4620
```

```
ggcagtggag ttgtgccaga aacagtggcc agttgtatcg cctataagac agggtaaggt   4680
ctgaagagct gagcctgtaa ttctgctgta ataatgatag tgctcaagaa gtgccttgag   4740
ttggtgtaca gtgccatggc catcaagaat cccagatttc aggttttatt acaaaatgta   4800
agtggtcact tggcgatttt gtagtacatg catgagttac ctttttttctc tatgtctgag  4860
aactgtcaga ttaaaacaag atggcaaaga gatcgttaga gtgcacaaca aaatcactat   4920
cccattagac acatcatcaa aagcttattt ttattcttgc actggaagaa tcgtaagtca   4980
actgtttctt gaccatggca gtgttctggc tccaaatggt agtgattcca ataatggtt    5040
ctgttaacac tttggcagaa aatgccagct cagatatttt gagatactaa ggattatctt   5100
tggacatgta ctgcagcttc ttgtctctgt tttggattac tggaataccc atgggccctc   5160
tcaagagtgc tggacttcta ggacattaag atgattgtca gtacattaaa cttttcaatc   5220
ccattatgca atcttgtttg taaatgtaaa cttctaaaaa tatggttaat aacattcaac   5280
ctgtttatta caactaaaaa ggaacttcag tgaatttgtt tttattttttt aacaagattt  5340
gtgaactgaa tatcatgaac catgttttga taccccttttt tcacgttgtg ccaacggaat  5400
agggtgtttg atatttcttc atatgttaag gagatgcttc aaaatgtcaa ttgctttaaa   5460
cttaaattac ctctcaagag accaaggtac atttacctca ttgtgtatat aatgttaat    5520
atttgtcaga gcattctcca ggtttgcagt tttatttcta taaagtatgg gtattatgtt   5580
gctcagttac tcaaatggta ctgtattgtt tatatttgta ccccaaataa catcgtctgt   5640
actttctgtt ttctgtattg tatttgtgca ggattcttca ggctttatca gtgtaatctc   5700
tgccttttaa gatatgtaca gaaaatgtcc atataaattt ccattgaagt cgaatgatac   5760
tgagaagcct gtaaagagga gaaaaaaaca taagctgtgt ttccccataa gttttttaa    5820
attgtatatt gtatttgtag taatattcca aagaatgta aataggaaat agaagagtga    5880
tgcttatgtt aagtcctaac actacagtag aagaatgaca gcagtgcaaa taaattacat   5940
ttttcccaag tgccagtggc atattttaaa ataaagtgta tacgttggaa tgagtcatgc   6000
catatgtagt tgctgtagat ggcaactaga acctttgagt tacaagagtc tttagaagtt   6060
ttctaaccct gccagtgca agttacaata ttatagcgtg ttcggggagt gccctcctgt    6120
ctgcaggtgt gtctcctgc ctgggggctt ttctccacat gcttagggtg gtgggtcttc    6180
cattggggca tgatggacct gtctacaggt gatctctgtt gcctttgggt cagcacatttt  6240
gttagtctcc tgggggtgaa aacttggctt acaagagaac tggaaaaatg atgagatgtg   6300
gtccccaaac ccttgattga ctctggggag gggctttgtg aataggattg ctctcacatt   6360
aaagatagtt acttcaattt gaaggctgga tttagggatt ttttttttttc cttataacaa   6420
agacatcacc aggatatgaa gcttttgttg aaagttggaa aaaagtgaa attaaagaca    6480
ttcccagaca aa                                                       6492

SEQ ID NO: 149         moltype = DNA  length = 22
FEATURE                Location/Qualifiers
source                 1..22
                       mol_type = other DNA
                       organism = synthetic construct
SEQUENCE: 149
ttaaatgtaa ttcatgtctt aa                                             22

SEQ ID NO: 150         moltype = DNA  length = 22
FEATURE                Location/Qualifiers
source                 1..22
                       mol_type = other DNA
                       organism = synthetic construct
SEQUENCE: 150
ttcaatgaaa ttatggtaac ta                                             22

SEQ ID NO: 151         moltype = DNA  length = 22
FEATURE                Location/Qualifiers
source                 1..22
                       mol_type = other DNA
                       organism = synthetic construct
SEQUENCE: 151
tataattgta actcaatctt tg                                             22

SEQ ID NO: 152         moltype = DNA  length = 22
FEATURE                Location/Qualifiers
source                 1..22
                       mol_type = other DNA
                       organism = synthetic construct
SEQUENCE: 152
tttgattcca aatctctatg ag                                             22

SEQ ID NO: 153         moltype = DNA  length = 22
FEATURE                Location/Qualifiers
source                 1..22
                       mol_type = other DNA
                       organism = synthetic construct
SEQUENCE: 153
tttaaatgta attcatgtct ta                                             22

SEQ ID NO: 154         moltype = DNA  length = 22
FEATURE                Location/Qualifiers
source                 1..22
                       mol_type = other DNA
                       organism = synthetic construct
SEQUENCE: 154
```

```
ttaagttgta ataaacaggt tg                                              22

SEQ ID NO: 155         moltype = DNA   length = 22
FEATURE                Location/Qualifiers
source                 1..22
                       mol_type = other DNA
                       organism = synthetic construct
SEQUENCE: 155
tttaattgac tttattacac tg                                              22

SEQ ID NO: 156         moltype = DNA   length = 22
FEATURE                Location/Qualifiers
source                 1..22
                       mol_type = other DNA
                       organism = synthetic construct
SEQUENCE: 156
ttagtatctc aaaatatctg ag                                              22

SEQ ID NO: 157         moltype = DNA   length = 22
FEATURE                Location/Qualifiers
source                 1..22
                       mol_type = other DNA
                       organism = synthetic construct
SEQUENCE: 157
ttaattgact ttattacact gc                                              22

SEQ ID NO: 158         moltype = DNA   length = 22
FEATURE                Location/Qualifiers
source                 1..22
                       mol_type = other DNA
                       organism = synthetic construct
SEQUENCE: 158
ttaaatgaca aaattattac tc                                              22

SEQ ID NO: 159         moltype = DNA   length = 22
FEATURE                Location/Qualifiers
source                 1..22
                       mol_type = other DNA
                       organism = synthetic construct
SEQUENCE: 159
ttagtaataa gacatgtttc at                                              22

SEQ ID NO: 160         moltype = DNA   length = 22
FEATURE                Location/Qualifiers
source                 1..22
                       mol_type = other DNA
                       organism = synthetic construct
SEQUENCE: 160
tattcaaatt attaactacc tt                                              22

SEQ ID NO: 161         moltype = DNA   length = 22
FEATURE                Location/Qualifiers
source                 1..22
                       mol_type = other DNA
                       organism = synthetic construct
SEQUENCE: 161
taagtaatca aaagggatc ca                                               22

SEQ ID NO: 162         moltype = DNA   length = 22
FEATURE                Location/Qualifiers
source                 1..22
                       mol_type = other DNA
                       organism = synthetic construct
SEQUENCE: 162
ttgtgtataa ctttgtctgt gg                                              22

SEQ ID NO: 163         moltype = DNA   length = 22
FEATURE                Location/Qualifiers
source                 1..22
                       mol_type = other DNA
                       organism = synthetic construct
SEQUENCE: 163
ttttaaatgt aattcatgtc tt                                              22

SEQ ID NO: 164         moltype = DNA   length = 22
FEATURE                Location/Qualifiers
source                 1..22
                       mol_type = other DNA
                       organism = synthetic construct
```

```
SEQUENCE: 164
ttaacataag catcactctt ct                                                      22

SEQ ID NO: 165          moltype = DNA   length = 22
FEATURE                 Location/Qualifiers
source                  1..22
                        mol_type = other DNA
                        organism = synthetic construct
SEQUENCE: 165
ttaaagtact ataagcatct ag                                                      22

SEQ ID NO: 166          moltype = DNA   length = 22
FEATURE                 Location/Qualifiers
source                  1..22
                        mol_type = other DNA
                        organism = synthetic construct
SEQUENCE: 166
tatctattca aattattaac ta                                                      22

SEQ ID NO: 167          moltype = DNA   length = 22
FEATURE                 Location/Qualifiers
source                  1..22
                        mol_type = other DNA
                        organism = synthetic construct
SEQUENCE: 167
tcttgtaaca caatagttct cg                                                      22

SEQ ID NO: 168          moltype = DNA   length = 22
FEATURE                 Location/Qualifiers
source                  1..22
                        mol_type = other DNA
                        organism = synthetic construct
SEQUENCE: 168
ttaaacaagt aatacaacac aa                                                      22

SEQ ID NO: 169          moltype = DNA   length = 22
FEATURE                 Location/Qualifiers
source                  1..22
                        mol_type = other DNA
                        organism = synthetic construct
SEQUENCE: 169
taataaaacc tgaaatctgg ga                                                      22

SEQ ID NO: 170          moltype = DNA   length = 22
FEATURE                 Location/Qualifiers
source                  1..22
                        mol_type = other DNA
                        organism = synthetic construct
SEQUENCE: 170
tacattttgt aataaaacct ga                                                      22

SEQ ID NO: 171          moltype = DNA   length = 22
FEATURE                 Location/Qualifiers
source                  1..22
                        mol_type = other DNA
                        organism = synthetic construct
SEQUENCE: 171
tagaattaca ttttgatgcc tt                                                      22

SEQ ID NO: 172          moltype = DNA   length = 22
FEATURE                 Location/Qualifiers
source                  1..22
                        mol_type = other DNA
                        organism = synthetic construct
SEQUENCE: 172
tttaagatca aatagtcttt ca                                                      22

SEQ ID NO: 173          moltype = DNA   length = 22
FEATURE                 Location/Qualifiers
source                  1..22
                        mol_type = other DNA
                        organism = synthetic construct
SEQUENCE: 173
tacaatttaa aaaaacttat gg                                                      22

SEQ ID NO: 174          moltype = DNA   length = 22
FEATURE                 Location/Qualifiers
source                  1..22
                        mol_type = other DNA
```

```
                       organism = synthetic construct
SEQUENCE: 174
taaaattgtc ttttgtacag ag                                             22

SEQ ID NO: 175         moltype = DNA  length = 22
FEATURE                Location/Qualifiers
source                 1..22
                       mol_type = other DNA
                       organism = synthetic construct
SEQUENCE: 175
taagttgtaa taaacaggtt ga                                             22

SEQ ID NO: 176         moltype = DNA  length = 22
FEATURE                Location/Qualifiers
source                 1..22
                       mol_type = other DNA
                       organism = synthetic construct
SEQUENCE: 176
taatgtactg acaatcatct ta                                             22

SEQ ID NO: 177         moltype = DNA  length = 22
FEATURE                Location/Qualifiers
source                 1..22
                       mol_type = other DNA
                       organism = synthetic construct
SEQUENCE: 177
tttcattttc aatatcagcc aa                                             22

SEQ ID NO: 178         moltype = DNA  length = 22
FEATURE                Location/Qualifiers
source                 1..22
                       mol_type = other DNA
                       organism = synthetic construct
SEQUENCE: 178
ttttaagatc aaatagtctt tc                                             22

SEQ ID NO: 179         moltype = DNA  length = 374
FEATURE                Location/Qualifiers
source                 1..374
                       mol_type = other DNA
                       organism = synthetic construct
SEQUENCE: 179
ggatctgcga tcgctccggt gcccgtcagt gggcagagcg cacatcgccc acagtccccg    60
agaagttggg gggaggggtc ggcaattgaa cgggtgccta gagaaggtgg cgcggggtaa   120
actgggaaag tgatgtcgtg tactggctcc gccttttttcc cgagggtggg ggagaaccgt  180
atataagtgc agtagtcgcc gtgaacgttc ttttttcgcaa cgggtttgcc gccagaacac  240
agctgaagct tcgaggggct cgcatctctc cttcacgcgc ccgccgccct acctgaggcc  300
gccatccacg ccggttgagt cgcgttctgc cgcctcccgc ctgtggtgcc tcctgaactg  360
cgtccgccgt ctag                                                    374

SEQ ID NO: 180         moltype = DNA  length = 479
FEATURE                Location/Qualifiers
source                 1..479
                       mol_type = other DNA
                       organism = synthetic construct
SEQUENCE: 180
cgggtggcat ccctgtgacc cctcccagt gcctctcctg gccctggaag ttgccactcc    60
agtgcccacc agccttgtcc taataaaatt aagttgcatc attttgtctg actaggtgtc   120
cttctataat attatgggt ggagggggt ggtatggagc aaggggcaag ttgggaagac   180
aacctgtagg gcctgcgggg tctattggga accaagctgg agtgcagtgg cacaatcttg   240
gctcactgca atctccgcct cctgggttca agcgattctc ctgcctcagc ctcccgagtt   300
gttgggattc caggcatgca tgaccaggct cagctaattt ttgttttttt ggtagaaacg   360
gggtttcacc atattggcca ggctggtctc caactcctaa tctcaggtga tctacccacc   420
ttggcctccc aaattgctgg gattacaggc gtgaaccact gctcccttcc ctgtccttc   479

SEQ ID NO: 181         moltype = DNA  length = 613
FEATURE                Location/Qualifiers
source                 1..613
                       mol_type = other DNA
                       organism = synthetic construct
SEQUENCE: 181
gtaagtcgac tcgttggatc cccactaccc ggatcaacgc cctaggttta tgtttggatg    60
aactgacata cgcgtatccg tcttaagaat cttttcaaac actagtagtg aaatatatat   120
taaactagtg tttgaaaaga ttcttattac ggtaacgcgg aattcgcaac tatttttatca  180
atttttttgcg tcgacacttc aaggggcttg cggccgcaac catctccatg gctgtttgaa   240
tgaggcttca gtactttaca gaatcgttgc ctgcacatct tggaaacact tgctgggatt   300
acttcgactt cttaacccaa cagaaggctc gagaaggtat attgctgttg acagtgagcg   360
ccagtgtgaa gctcttgtca gatagtgaag ccacagatgt atctgacaag agcttcacac   420
tgatgcctac tgcctcggac ttcaagggc tagaattcga gcaattatct tgtttactaa   480
```

```
aactgaatac cttgctatct ctttgataca ttttttacaaa gctgaattaa aatggtataa    540
attaaatcac ttttttcatct gaccagtagt ggactagtgt gacgctgctg accccttttct   600
ttcccttcta cag                                                        613

SEQ ID NO: 182          moltype = DNA   length = 354
FEATURE                 Location/Qualifiers
source                  1..354
                        mol_type = other DNA
                        organism = synthetic construct
SEQUENCE: 182
ccggatcaac gccctaggtt tatgtttgga tgaactgaca tacgcgtatc cgtctaaaaa    60
tcaatctcat ttcctggtag tgaaatatat attaaaccag gaaatgagat tgattttttt   120
acggtaacgc ggaattcgca actattttat caattttttg cgtcgacgac tgtgacagca   180
gagtatgccg gatcaacgcc ctaggtttat gtttggatga actgacatac gcgtatccgt   240
cttatgtaaa agacaaacaa tgcgtagtga aatatatatt aaacgcattg tttgtctttt   300
acatattacg gtaacgcgga attcgcaact attttatcaa ttttttgcgt cgac         354

SEQ ID NO: 183          moltype = DNA   length = 906
FEATURE                 Location/Qualifiers
source                  1..906
                        mol_type = other DNA
                        organism = synthetic construct
SEQUENCE: 183
ccactacccg gatcaacgcc ctaggtttat gtttggatga actgacatac gcgtatccgt    60
cttaagaatc tttttcaaaca ctagtagtga aatatatatt aaactagtgt ttgaaaagat  120
tcttattacg gtaacgcgga attcgcaact attttatcaa ttttttgcgt cgacacttca   180
aggggcttgc ggccgcaacc atctccatgg ctgtttgaat gaggcttcag tactttacag   240
aatcgttgcc tgcacatctt ggaaacactt gctgggatta cttcgacttc ttaacccaac   300
agaaggctcg agaaggtata ttgctgttga cagtgagcgc cagtgtgaag ctcttgtcag   360
atagtgaagc cacagatgta tctgacaaga gcttcacact gatgcctact gcctcggact   420
tcaaggggct agaattcgag caattatctt gtttactaaa actgaatacc ttgctatctc   480
tttgatacat ttttacaaag ctgaattaaa atggtataaa ttaaatcact ttgacggtga   540
cttaggagta tgccggatca acgccctagg tttatgtttg gatgaactga catacgcgta   600
tccgtctaaa aatcaatctc atttcctggt agtgaaatat atattaaacc aggaaatgag   660
attgattttt ttacggtaac gcggaattcg caactatttt atcaattttt tgcgtcgacg   720
actgtgacag cagagtatgc cggatcaacg ccctaggttt atgtttggat gaactgacat   780
acgcgtatcc gtcttatgta aaagacaaac aatgcgtagt gaaatatata ttaaacgcat   840
tgtttgtctt tacatatta cggtaacgcg gaattcgcaa ctattttatc aattttttgc    900
gtcgac                                                               906

SEQ ID NO: 184          moltype = RNA   length = 1541
FEATURE                 Location/Qualifiers
source                  1..1541
                        mol_type = other RNA
                        organism = synthetic construct
SEQUENCE: 184
ggatctgcga tcgctccggt gcccgtcagt gggcagagcg cacatcgccc acagtcccg     60
agaagttggg gggaggggtc ggcaattgaa cgggtgccta gagaaggtgg cgcggggtaa   120
actgggaaag tgatgtcgtg tactggctcc gccttttttcc cgagggtggg ggagaaccgt   180
atataagtgc agtagtcgcc gtgaacgttc ttttcgcaa cggggtttgcc gccagaacac   240
agctgaagct tcgagggct cgcatctctc cttcacgcgc ccgccgcctc acctgaggcc   300
gccatccacg ccggttgagt cgcgttctgc cgcctcccgc ctgtggtgcc tcctgaactg   360
cgtccgccgt ctaggtaagt cgactcgttg gatcccact acccgggatca acgccctagg    420
tttatgtttg gatgaactga catacgcgta tccgtcttaa gaatctttttc aaacactagt   480
agtgaaatat atattaaact agtgtttgaa aagattctta ttacggtaac gcggaattcg    540
caactatttt atcaattttt tgcgtcgacg acggtgactt aggagtatgc cggatcaacg    600
ccctaggttt atgtttggat gaactgacat acgcgtatcc gtctaaaaat caatctcatt   660
tcctggtagt gaaatatata ttaaaccagg aaatgagatt gattttttta cggtaacgcg   720
gaattcgcaa ctattttatc aattttttgc gtcgacgact gtgacagcag agtatgccgg   780
atcaacgccc taggtttatg tttggatgaa ctgacatacg cgtatccgtc ttatgtaaaa   840
gacaaacaat gcgtagtgaa atatatatta aacgcattgt ttgtcttttA catattacgg   900
taacgcggaa ttcgcaacta ttttatcaat ttttgcgtc gaccggaact atcttgaaga   960
gtagtagtgg actagtgtga cgctgctgac ccctttcttt ccccttctaca gatccaagct  1020
gtgaccggcg cctacacctg cagcccaagc ttacctaaag ggctgctctc atccgctgta  1080
cccctccca gtgcctctcc tggccctgga agttgccact ccagtgccca ccagccttgt   1140
cctaataaaa ttaagttgca tcattttgtc tgactaggtg tccttctata atattatggg   1200
gtggaggggg gtggtatgga gcaagggca agttgggaag acaacctgta gggcctgcgg   1260
ggtctattgg gaaccaagct ggagtgcagt ggcacaatct tggctcactg caatcctccg   1320
ctcctgggtt caagcgattc tcctgcctca gcctcccgag ttgttgggat tccaggcatg   1380
catgaccagg ctcagctaat tttttgttttt ttggtagaaa cggggtttca ccatattggc   1440
caggctggtc tccaactcct aatctcaggt gatctaccca ccttggcctc ccaaattgct   1500
gggattacag gcgtgaacca ctgctccctt ccctgtcctt c                       1541

SEQ ID NO: 185          moltype = RNA   length = 1055
FEATURE                 Location/Qualifiers
source                  1..1055
                        mol_type = other RNA
                        organism = synthetic construct
SEQUENCE: 185
```

```
ggatctgcga tcgctccggt gcccgtcagt gggcagagcg cacatcgccc acagtcccg   60
agaagttggg gggaggggtc ggcaattgaa cgggtgccta gagaaggtgg cgcggggtaa  120
actgggaaag tgatgtcgtg tactggctcc gccttttttcc cgagggtggg ggagaaccgt  180
atataagtgc agtagtcgcc gtgaacgttc tttttcgcaa cgggtttgcc gccagaacac  240
agctgaagct tcgaggggct cgcatctctc cttcacgcgc ccgccgccct acctgaggcc  300
gccatccacg ccggttgagt cgcgttctgc cgcctcccgc ctgtggtgcc tcctgaactg  360
cgtccgccgt ctaggtaagt cgactcgttg gatcccact acccggatca acgccctagg  420
tttatgtttg gatgaactga catacgcgta tccgtcttaa gaatcttttc aaacactagt  480
agtgaaatat atattaaact agtgtttgaa aagattctta ttacggtaac gcggaattcg  540
caactatttt atcaattttt tgcgtcgacg acggtgactt aggagtatgc ggatcaacg   600
ccctaggttt atgtttggat gaactgacat acgcgtatcc gtctaaaaat caatctcatt  660
tcctggtagt gaaatatata ttaaaccagg aaatgagatt gattttttta cggtaacgcg  720
gaattcgcaa ctatttttatc aatttttttgc gtcgacgact gtgacagcag agtatgccgg  780
atcaacgccc taggtttatg tttggatgaa ctgacatacg cgtatccgtc ttatgtaaaa  840
gacaaacaat gcgtagtgaa atatatatta aacgcattgt ttgtctttta catattacgg  900
taacgcggaa ttcgcaacta ttttatcaat tttttgcgtc gaccgaaact atcttgaaga  960
gtagtagtgg actagtgtga cgctgctgac ccctttctttt cccttctaca gatccaagct 1020
gtgaccggcg cctacacctg cagcccaagc ttacc                             1055

SEQ ID NO: 186        moltype = RNA   length = 486
FEATURE               Location/Qualifiers
source                1..486
                      mol_type = other RNA
                      organism = synthetic construct
SEQUENCE: 186
taaaggacgg gtggcatccc tgtgaccccct ccccagtgcc tctcctggcc ctggaagttg  60
ccactccagt gcccaccagc cttgtcctaa taaaattaag ttgcatcatt ttgtctgact 120
aggtgtcctt ctataatatt atgggggtgga ggggggtggt atggagcaag ggcaagttg  180
ggaagacaac ctgtagggcc tgcggggtct attgggaacc aagctggagt gcagtggcac 240
aatcttggct cactgcaatc tccgcctcct gggttcaagc gattctcctg cctcagcctc 300
ccgagttgtt gggattccag gcatgcatga ccaggctcag ctaatttttg ttttttttggt 360
agaaacgggg tttcaccata ttggccaggc tggtctccaa ctcctaatct caggtgatct 420
acccaccttg gcctcccaaa ttgctgggat tacaggcgtg aaccactgct ccctttccctg 480
tccttc                                                             486

SEQ ID NO: 187        moltype = RNA   length = 1578
FEATURE               Location/Qualifiers
source                1..1578
                      mol_type = other RNA
                      organism = synthetic construct
SEQUENCE: 187
ggatctgcga tcgctccggt gcccgtcagt gggcagagcg cacatcgccc acagtcccg   60
agaagttggg gggaggggtc ggcaattgaa cgggtgccta gagaaggtgg cgcggggtaa  120
actgggaaag tgatgtcgtg tactggctcc gccttttttcc cgagggtggg ggagaaccgt  180
atataagtgc agtagtcgcc gtgaacgttc tttttcgcaa cgggtttgcc gccagaacac  240
agctgaagct tcgaggggct cgcatctctc cttcacgcgc ccgccgccct acctgaggcc  300
gccatccacg ccggttgagt cgcgttctgc cgcctcccgc ctgtggtgcc tcctgaactg  360
cgtccgccgt ctaggtaagt cgactcgttg gatcccact acccggatca acgccctagg  420
tttatgtttg gatgaactga catacgcgta tccgtctaaa aatcaatctc atttcctggt  480
agtgaaatat atattaaacc aggaaatgag attgattttt ttacggtaac gcggaattcg  540
caactatttt atcaattttt tgcgtcgaca ctttcaaggg cttgcggccg caaccatctc  600
catggcgacg gtgactagg agtatgccgg atcaacgccc taggtttatg tttggatgaa  660
ctgacatacg cgtatccgtc ttatgtaaaa gacaaacaat gcgtagtgaa atatatatta  720
aacgcattgt ttgtctttta catattacgg taacgcggaa ttcgcaacta ttttatcaat  780
tttttgcgtc gacgactgtg acagcagagt atgccggatc aacgccctag gtttatgttt  840
ggatgaactg acatacgcgt atccgtctta agaatctttt caaacactag tagtgaaata  900
tatattaaac tagtgtttga aaagattctt attacggtaa cgcggaattc gcaactatttt  960
tatcaatttt ttgcgtcgac cggaactatc ttgaagagta gtagtggact agtgtgacgc 1020
tgctgaccccc tttcttttccc ttctacagat ccaagctgtg accggcgcct acacctgcag 1080
cccaagctta cctaaaggac ggtggcatcc ctgtgacccc tccccagtgt cctctcctg  1140
ccctggaagt tgccactcca gtgcccacca gccttgtcct aataaaatta gttgcatca  1200
ttttgtctga ctaggtgtcc ttctataata ttatggggtg gaggggggtg gtatggagca  1260
aggggcaagt tgggaagaca acctgtaggg cctgcggggt ctattgggaa ccaagctgga 1320
gtgcagtggc acaatcttgg ctcactgcaa tctccgcctc ctgggttcaa gcgattctc  1380
tgcctcagcc tcccgagttg ttgggattcc aggcatgcat gaccaggctc agctaattttt 1440
tgttttttttg gtagaaacgg ggtttcacca tattggccag gctggtctcc aactcctaat 1500
ctcaggtgat ctacccacct tggcctccca aattgctggg attacaggcg tgaaccactg 1560
ctcccttccc tgtccttc                                                1578

SEQ ID NO: 188        moltype = RNA   length = 1092
FEATURE               Location/Qualifiers
source                1..1092
                      mol_type = other RNA
                      organism = synthetic construct
SEQUENCE: 188
ggatctgcga tcgctccggt gcccgtcagt gggcagagcg cacatcgccc acagtcccg   60
agaagttggg gggaggggtc ggcaattgaa cgggtgccta gagaaggtgg cgcggggtaa  120
actgggaaag tgatgtcgtg tactggctcc gccttttttcc cgagggtggg ggagaaccgt  180
atataagtgc agtagtcgcc gtgaacgttc tttttcgcaa cgggtttgcc gccagaacac  240
```

```
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt cgactcgttg gatcccact accccggatca acgccctagg    420
tttatgtttg gatgaactga catacgcgta tccgtctaaa aatcaatctc atttcctggt    480
agtgaaatat atattaaacc aggaaatgag attgattttt ttacggtaac gcggaattcg    540
caactatttt atcaattttt tgcgtcgaca cttcaagggg cttgcggccg caaccatctc    600
catggcgacg gtgacttagg agtatgccgg atcaacgccc taggtttatg tttgatgaa    660
ctgacatacg cgtatccgtc ttatgtaaaa gacaaacaat gcgtagtgaa atatatatta    720
aacgcattgt ttgtctttta catattacgg taacgcggaa ttcgcaacta ttttatcaat    780
tttttgcgtc gacgactgtg acagcagagt atgccggatc aacgccctag gtttatgttt    840
ggatgaactg acatacgcgt atccgtctta agaatctttt caaacactag tagtgaaata    900
tatattaaac tagtgtttga aaagattctt attacggtaa cgcggaattc gcaactattt    960
tatcaatttt ttgcgtcgac cggaactatc ttgaagagta gtagtggact agtgtgacgc    1020
tgctgacccc tttctttccc ttctacagat ccaagctgtg accggcgcct acacctgcag    1080
cccaagctta cc                                                       1092

SEQ ID NO: 189         moltype = RNA   length = 486
FEATURE                Location/Qualifiers
source                 1..486
                       mol_type = other RNA
                       organism = synthetic construct
SEQUENCE: 189
taaaggacgg gtggcatccc tgtgacccct ccccagtgcc tctcctgacc ctggaagttg    60
ccactccagt gcccaccagc cttgtcctaa taaaattaag ttgcatcatt ttgtctgact    120
aggtgtcctt ctataatatt atgggtgga ggggggtggt atggagcaag gggcaagttg    180
ggaagacaac ctgtagggcc tgcggggtct atttgggaac aagctggagt gcagtggcac    240
aatcttggct cactgcaatc tccgcctcct gggttcaagc gattctcctg cctcagcctc    300
ccgagttgtt gggattccag gcatgcatga ccaggctcag ctaattttg tttttttggt    360
agaaacgggg tttcaccata ttggccaggc tggtctccaa ctcctaatct caggtgatct    420
acccaccttg gcctcccaaa ttgctgggat tacaggcgtg aaccactgct cccttccctg    480
tccttc                                                              486

SEQ ID NO: 190         moltype = RNA   length = 1732
FEATURE                Location/Qualifiers
source                 1..1732
                       mol_type = other RNA
                       organism = synthetic construct
SEQUENCE: 190
ggatctgcga tcgctccggt gcccgtcagt gggcagagcg cacatcgccc acagtccccg    60
agaagttggg gggagggtc ggcaattgaa cgggtgccta gagaaggtgg cgcggggtaa    120
actgggaaag tgatgtcgtg tactggctcc gccttttcc cgagggtggg ggagaaccgt    180
atataagtgc agtagtcgcc gtgaacgttc ttttcgcaa cgggttgcc gccagaacac    240
agctgaagct cgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt cgactcgttg gatcccact accccggatca acgccctagg    420
tttatgtttg gatgaactga catacgcgta tccgtctaa gaatcttttc aaacactagt    480
agtgaaatat atattaaact agtgtttgaa aagattctta ttacggtaac gcggaattcg    540
caactatttt atcaattttt tgcgtcgaca cttcaagggg cttgcggccg caaccatctc    600
catggcgacg gtgacttagg agtatgtgtt tgaatgaggc ttcagtactt tacagaatcg    660
ttgcctgcac atcttggaaa cacttgctgg gattacttcg acttcttaac ccaacagaag    720
gctcgagaag gtatattgct gttgacagtg agcgcaggaa atgagattga ttttttagt    780
gaagccacag atgtataaaa atcaatctca tttcctgtgc ctactgcctc ggacttcaag    840
gggctagaat tcgagcaatt atcttgttta ctaaaactga ataccttgct atctctttga    900
tacatttta caaagctgaa ttaaaatggt ataaattaaa tcactttgac tgtgacagca    960
gagtatgccg gatcaacgcc ctaggtttat gtttggatga actgacatac gcgtatccgt    1020
cttatgtaaa agacaaacaa tgcgtagtga aatatatatt aaacgcattg tttgtctttt    1080
acatattacg gtaacgcgga attcgcaact attttatcaa ttttttgcgt cgaccggaac    1140
tatcttgaag agtagtagtg gactagtgtg acgctgctga ccccttcct tcccttctac    1200
agatccaagc tgtgaccggc gcctacacct gcagcccaag cttacctaaa ggacggggtc    1260
catccctgtg acccctcccc agtgcctctc ctggccctgg aagttgccac tccagtgccc    1320
accagcttg tcctaataaa attaagtgc atcattttgt ctgactaggt gtccttctat    1380
aatattatgg ggtggagggg ggtggtatgg agcaaggggc aagttgggaa gacaacctgt    1440
agggcctgcg gggtctattg gaaccaagc tggagtgcag tggcacaatc ttggctcact    1500
gcaatctccg cctcctgggt tcaagcgatt ctcctgcctc agctcccgag ttgtttggga    1560
ttccaggcat gcatgaccag gctcagctaa ttttgttt ttttggtagaa acggggtttc    1620
accatattgg ccaggctggt ctccaactcc taatctcagg tgatctaccc accttggcct    1680
cccaaattgc tgggattaca ggcgtgaacc actgctccct ccctgtcct tc           1732

SEQ ID NO: 191         moltype = RNA   length = 1246
FEATURE                Location/Qualifiers
source                 1..1246
                       mol_type = other RNA
                       organism = synthetic construct
SEQUENCE: 191
ggatctgcga tcgctccggt gcccgtcagt gggcagagcg cacatcgccc acagtccccg    60
agaagttggg gggagggtc ggcaattgaa cgggtgccta gagaaggtgg cgcggggtaa    120
actgggaaag tgatgtcgtg tactggctcc gccttttcc cgagggtggg ggagaaccgt    180
atataagtgc agtagtcgcc gtgaacgttc ttttcgcaa cgggttgcc gccagaacac    240
agctgaagct cgaggggct cgcatctctc cttcacgcgc ccgccgccct acctgaggcc    300
```

```
gccatccacg ccggttgagt cgcgttctgc cgcctcccgc ctgtggtgcc tcctgaactg   360
cgtccgccgt ctaggtaagt cgactcgttg gatccccact acccggatca acgccctagg   420
tttatgtttg gatgaactga catacgcgta tccgtcttaa gaatcttttc aaacactagt   480
agtgaaatat atattaaact agtgtttgaa aagattctta ttacggtaac gcggaattcg   540
caactatttt atcaattttt tgcgtcgaca cttcaagggg cttgcggccg caaccatctc   600
catggcgacg gtgacttagg agtatgtgtt tgaatgaggc ttcagtactt tacagaatcg   660
ttgcctgcac atcttggaaa cacttgctgg gattacttcg acttcttaac ccaacagaag   720
gctcgagaag gtatattgct gttgacagtg agcgcaggaa atgagattga tttttttagt   780
gaagccacag atgtataaaa atcaatctca tttcctgtgc ctactgcctc ggacttcaag   840
gggctagaat tcgagcaatt atcttgttta ctaaaactga ataccttgct atctctttga   900
tacatttta caaagctgaa ttaaaatggt ataattaaa tcactttgac tgtgacagca   960
gagtatgccg gatcaacgcc ctaggtttat gtttggatga actgacatac gcgtatccgt  1020
cttatgtaaa agacaaacaa tgcgtagtga aatatatatt aaacgcattg tttgtctctt  1080
acatattacg gtaacgcgga attcgcaact attttatcaa tttttgcgt cgaccggaac  1140
tatcttgaag agtagtagtg gactagtgtg acgctgctga ccccttcttt tcccttctac  1200
agatccaagc tgtgaccggc gcctacacct gcagcccaag cttacc                 1246

SEQ ID NO: 192        moltype = RNA    length = 486
FEATURE               Location/Qualifiers
source                1..486
                      mol_type = other RNA
                      organism = synthetic construct
SEQUENCE: 192
taaaggacgg gtggcatccc tgtgacccct ccccagtgcc tctcctggcc ctggaagttg    60
ccactccagt gcccaccagc cttgtcctaa taaaattaag ttgcatcatt ttgtctgact   120
aggtgtcctt ctataatatt atggggtgga gggggtgatg ggagcaagg gggcaagttg   180
ggaagacaac ctgtagggcc tgcggggtct attgggaacc aagctggagt gcagtggcac   240
aatcttggct cactgcaatc tccgcctcct gggttcaagc gattctcctg cctcagcctc   300
ccgagttgtt gggattccag gcatgcatga ccaggctcag ctaattttg ttttttttggt   360
agaaacgggg tttcaccata ttggccaggc tggtctccaa ctcctaatct caggtgatct   420
acccaccttg gcctcccaaa ttgctgggat tacaggcgtg aaccactgct cccttccctg   480
tccttc                                                              486

SEQ ID NO: 193        moltype = RNA    length = 731
FEATURE               Location/Qualifiers
source                1..731
                      mol_type = other RNA
                      organism = synthetic construct
SEQUENCE: 193
cggatcaacg ccctaggttt atgtttggat gaactgacat acgcgtatcc gtcttaagaa    60
tcttttcaaa cactagtagt gaaatatata ttaaactagt gtttgaaaag attcttatta   120
cggtaacgcg gaattcgcaa ctattttatc aatttttgc gtcgacactt caaggggctt   180
gcggccgcaa ccatctccat ggcgacggtg acttaggagt atgtgtttga atgaggcttc   240
agtactttac agaatcgttg cctgcacatc ttggaaacac ttgctgggat tacttcgact   300
tcttaaccca acagaaggct cgagaaggta tattgctgtt gacagtgagc gcaggaaatg   360
agattgattt ttttagtgaa gccacagatg tataaaaatc aatctcattt cctgtgccta   420
ctgcctcgga cttcaagggg ctagaattcg agcaattatc ttgttttacta aaactgaata   480
ccttgctatc tctttgatac attttttacaa agctgaatta aaatggtata attaaaatca   540
ctttgactgt gacagcagag tatgccggat caacgcccta ggtttatgtt tggatgaact   600
gacatacgcg tatccgtctt atgtaaagaa caaacaatgc gtagtgaaat atatattaaa   660
cgcattgttt gtctttttaca tattacggta acgcggaatt cgcaactatt ttatcaattt   720
tttgcgtcga c                                                        731

SEQ ID NO: 194        moltype = DNA    length = 508
FEATURE               Location/Qualifiers
source                1..508
                      mol_type = other DNA
                      organism = synthetic construct
SEQUENCE: 194
tgtttgaatg aggcttcagt actttacaga atcgttgcct gcacatcttg gaaacacttg    60
ctgggattac ttcgacttct taacccaaca gaaggctcga gaaggtatat tgctgttgac   120
agtgagcgca ggaaatgaga ttgatttttt tagtgaagcc acagatgtat aaaaatcaat   180
ctcatttcct gtgcctactg cctcggactt caaggggcta gaattcgagc aattatcttg   240
tttactaaaa ctgaatacct tgctatctct ttgatacatt tttacaaagc tgaattaaaa   300
tggtataaat taaatcactt tgactgtgac agcagagtat gccggatcaa cgccctaggt   360
ttatgtttgg atgaactgac atacgcgtat ccgtcttatg taaagacaa acaatgcgta   420
gtgaaatata tattaaacgc attgtttgtc ttttacatat tacggtaacg cggaattcgc   480
aactatttta tcaattttt gcgtcgac                                       508

SEQ ID NO: 195        moltype = RNA    length = 578
FEATURE               Location/Qualifiers
source                1..578
                      mol_type = other RNA
                      organism = synthetic construct
SEQUENCE: 195
ccggatcaac gccctaggtt tatgtttgga tgaactgaca tacgcgtatc cgtctaaaaa    60
tcaatctcat ttcctggtag tgaaatatat attaaaccag gaaatgagat tgattttttt   120
acggtaacgc ggaattcgca actattttat caatttttg cgtcgacact tcaaggggct   180
tgcggccgca accatctcca tggcgacggt gacttaggag tatgccggat caacgcccta   240
```

```
ggtttatgtt tggatgaact gacatacgcg tatccgtctt atgtaaaaga caaacaatgc    300
gtagtgaaat atatattaaa cgcattgttt gtcttttaca tattacggta acgcggaatt    360
cgcaactatt ttatcaattt tttgcgtcga cgactgtgac agcagagtat gccggatcaa    420
cgccctaggt ttatgtttgg atgaactgac atacgcgtat ccgtcttaag aatcttttca    480
aacactagta gtgaaatata tattaaacta gtgtttgaaa agattcttat tacggtaacg    540
cggaattcgc aactatttta tcaattttt gcgtcgac                             578

SEQ ID NO: 196          moltype = RNA    length = 1899
FEATURE                 Location/Qualifiers
source                  1..1899
                        mol_type = other RNA
                        organism = synthetic construct
SEQUENCE: 196
ggatctgcga tcgctccggt gcccgtcagt gggcagagcg cacatcgccc acagtccccg     60
agaagttggg gggaggggtc ggcaattgaa cgggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc tttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt cgactcgttg gatcccact accccggatca acgcctagg    420
tttatgtttg gatgaactga catacgcgta tccgtcttaa gaatcttttc aaacactagt    480
agtgaaatat atattaaact agtgtttgaa aagattctta ttacggtaac gcggaattcg    540
caactatttt atcaattttt gcgtcgaca cttcaagggg cttgcggccg caaccatctc    600
catggctgtt tgaatgaggc ttcagtactt tacagaatcg ttgcctgcac atcttggaaa    660
cacttgctgg gattacttcg acttcttaac ccaacagaag gctcgagaag gtatattgct    720
gttgacagtg agcgccagtg tgaagctctt gtcagatagt gaagccacag atgtatctga    780
caagagcttc acactgatgc ctactgcctc ggacttcaag gggctagaat tcgagcaatt    840
atcttgttta ctaaaactga ataccttgct atctctttga tacattttta caaagctgaa    900
ttaaaatggt ataaattaaa tcactttgac ggtgacttag gagtatgccg gatcaacgcc    960
ctaggtttat gtttggatga actgacatac gcgtatccgt ctaaaaatca atctcatttc   1020
ctggtagtga aatatatatt aaaccaggaa atgagattga tttttttacg gtaacgcgga   1080
attcgcaact attttatcaa ttttttgcgt cgacgactgt gacagcagag tatgccggat   1140
caacgcccta ggtttatgtt tggatgaact gacatacgcg tatccgtctt atgtaaaaga   1200
caaacaatgc gtagtgaaat atattaaaa cgcattgttt gtcttttaca tattacggta   1260
acgcggaatt cgcaactatt ttatcaattt tttgcgtcga ccggaactat cttgaagagt   1320
agtagtggac tagtgtgacg ctgctgaccc ctttctttcc cttctacaga tccaagctgt   1380
gaccggcgcc tacacctgca gcccaagctt acctaaagga cgggtggcat ccctgtgacc   1440
cctccccagt gcctctcctg gccctggaag ttgccactcc agtgcccacc agccttgtcc   1500
taataaaatt aagttgcatc atttttgtctg actaggtgtc cttctataat attatggagt   1560
ggagggggt ggtatggagc aaggggcaag ttgggaagac aacctgtagg gcctgcgggg   1620
tctattggga accaagctgg agtgcagtgg cacaatcttg gctcactgca atctccgcct   1680
cctgggttca agcgattctc ctgcctcagc ctcccgagtt gttgggattc caggcatgca   1740
tgaccaggct cagctaattt ttgttttttt ggtagaaacg gggtttcacc atattggcca   1800
ggctggtctc caactcctaa tctcaggtga tctacccacc ttggcctccc aaattgctgg   1860
gattacaggc gtgaaccact gctcccttcc ctgtccttc                          1899

SEQ ID NO: 197          moltype = RNA    length = 1413
FEATURE                 Location/Qualifiers
source                  1..1413
                        mol_type = other RNA
                        organism = synthetic construct
SEQUENCE: 197
ggatctgcga tcgctccggt gcccgtcagt gggcagagcg cacatcgccc acagtccccg     60
agaagttggg gggaggggtc ggcaattgaa cgggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc tttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt cgactcgttg gatcccact accccggatca acgcctagg    420
tttatgtttg gatgaactga catacgcgta tccgtcttaa gaatcttttc aaacactagt    480
agtgaaatat atattaaact agtgtttgaa aagattctta ttacggtaac gcggaattcg    540
caactatttt atcaattttt gcgtcgaca cttcaagggg cttgcggccg caaccatctc    600
catggctgtt tgaatgaggc ttcagtactt tacagaatcg ttgcctgcac atcttggaaa    660
cacttgctgg gattacttcg acttcttaac ccaacagaag gctcgagaag gtatattgct    720
gttgacagtg agcgccagtg tgaagctctt gtcagatagt gaagccacag atgtatctga    780
caagagcttc acactgatgc ctactgcctc ggacttcaag gggctagaat tcgagcaatt    840
atcttgttta ctaaaactga ataccttgct atctctttga tacattttta caaagctgaa    900
ttaaaatggt ataaattaaa tcactttgac ggtgacttag gagtatgccg gatcaacgcc    960
ctaggtttat gtttggatga actgacatac gcgtatccgt ctaaaaatca atctcatttc   1020
ctggtagtga aatatatatt aaaccaggaa atgagattga tttttttacg gtaacgcgga   1080
attcgcaact attttatcaa ttttttgcgt cgacgactgt gacagcagag tatgccggat   1140
caacgcccta ggtttatgtt tggatgaact gacatacgcg tatccgtctt atgtaaaaga   1200
caaacaatgc gtagtgaaat atattaaaa cgcattgttt gtcttttaca tattacggta   1260
acgcggaatt cgcaactatt ttatcaattt tttgcgtcga ccggaactat cttgaagagt   1320
agtagtggac tagtgtgacg ctgctgaccc ctttctttcc cttctacaga tccaagctgt   1380
gaccggcgcc tacacctgca gcccaagctt acc                                1413

SEQ ID NO: 198          moltype = RNA    length = 486
FEATURE                 Location/Qualifiers
```

```
source                  1..486
                        mol_type = other RNA
                        organism = synthetic construct
SEQUENCE: 198
taaaggacgg gtggcatccc tgtgacccct ccccagtgcc tctcctggcc ctggaagttg    60
ccactccagt gcccaccagc cttgtcctaa taaaattaag ttgcatcatt ttgtctgact   120
aggtgtcctt ctataatatt atggggtgga ggggggtggt atggagcaag ggcaagttg    180
ggaagacaac ctgtagggcc tgcggggtct attgggaacc aagctggagt gcagtggcac   240
aatcttggct cactgcaatc tccgcctcct gggttcaagc gattctcctg cctcagcctc   300
ccgagttgtt gggattccag gcatgcatga ccaggctcag ctaattttg tttttttggt   360
agaaacgggg tttcaccata ttggccaggc tggtctccaa ctcctaatct caggtgatct   420
acccaccttg gcctcccaaa ttgctgggat tacaggcgtg aaccactgct cccttccctg   480
tccttc                                                              486

SEQ ID NO: 199          moltype = AA  length = 10
FEATURE                 Location/Qualifiers
source                  1..10
                        mol_type = protein
                        organism = synthetic construct
SEQUENCE: 199
GYTFTSYGIT                                                          10

SEQ ID NO: 200          moltype = AA  length = 5
FEATURE                 Location/Qualifiers
source                  1..5
                        mol_type = protein
                        organism = synthetic construct
SEQUENCE: 200
SYGIT                                                               5

SEQ ID NO: 201          moltype = AA  length = 6
FEATURE                 Location/Qualifiers
source                  1..6
                        mol_type = protein
                        organism = synthetic construct
SEQUENCE: 201
TSYGIT                                                              6

SEQ ID NO: 202          moltype = AA  length = 8
FEATURE                 Location/Qualifiers
source                  1..8
                        mol_type = protein
                        organism = synthetic construct
SEQUENCE: 202
GYTFTSYG                                                            8

SEQ ID NO: 203          moltype = AA  length = 10
FEATURE                 Location/Qualifiers
source                  1..10
                        mol_type = protein
                        organism = synthetic construct
SEQUENCE: 203
WISEYNGNTN                                                          10

SEQ ID NO: 204          moltype = AA  length = 17
FEATURE                 Location/Qualifiers
source                  1..17
                        mol_type = protein
                        organism = synthetic construct
SEQUENCE: 204
WISEYNGNTN YAQKFQG                                                  17

SEQ ID NO: 205          moltype = AA  length = 13
FEATURE                 Location/Qualifiers
source                  1..13
                        mol_type = protein
                        organism = synthetic construct
SEQUENCE: 205
WMGWISEYNG NTN                                                      13

SEQ ID NO: 206          moltype = AA  length = 8
FEATURE                 Location/Qualifiers
source                  1..8
                        mol_type = protein
                        organism = synthetic construct
SEQUENCE: 206
ISEYNGT                                                             8

SEQ ID NO: 207          moltype = AA  length = 15
```

```
FEATURE              Location/Qualifiers
source               1..15
                     mol_type = protein
                     organism = synthetic construct
SEQUENCE: 207
ARGGILPYYF FYYMD                                                    15

SEQ ID NO: 208       moltype = AA  length = 16
FEATURE              Location/Qualifiers
source               1..16
                     mol_type = protein
                     organism = synthetic construct
SEQUENCE: 208
ARGGILPYYF FYYMDV                                                   16

SEQ ID NO: 209       moltype = AA  length = 8
FEATURE              Location/Qualifiers
source               1..8
                     mol_type = protein
                     organism = synthetic construct
SEQUENCE: 209
SSSYLAWY                                                             8

SEQ ID NO: 210       moltype = AA  length = 7
FEATURE              Location/Qualifiers
source               1..7
                     mol_type = protein
                     organism = synthetic construct
SEQUENCE: 210
QSVSSSY                                                              7

SEQ ID NO: 211       moltype = AA  length = 10
FEATURE              Location/Qualifiers
source               1..10
                     mol_type = protein
                     organism = synthetic construct
SEQUENCE: 211
LLIYGASSRA                                                          10

SEQ ID NO: 212       moltype = AA  length = 8
FEATURE              Location/Qualifiers
source               1..8
                     mol_type = protein
                     organism = synthetic construct
SEQUENCE: 212
QQYGSSPY                                                             8

SEQ ID NO: 213       moltype = AA  length = 5
FEATURE              Location/Qualifiers
source               1..5
                     mol_type = protein
                     organism = synthetic construct
SEQUENCE: 213
SYGVS                                                                5

SEQ ID NO: 214       moltype = AA  length = 6
FEATURE              Location/Qualifiers
source               1..6
                     mol_type = protein
                     organism = synthetic construct
SEQUENCE: 214
SSYGVS                                                               6

SEQ ID NO: 215       moltype = AA  length = 8
FEATURE              Location/Qualifiers
source               1..8
                     mol_type = protein
                     organism = synthetic construct
SEQUENCE: 215
GYTFSSYG                                                             8

SEQ ID NO: 216       moltype = AA  length = 10
FEATURE              Location/Qualifiers
source               1..10
                     mol_type = protein
                     organism = synthetic construct
SEQUENCE: 216
WISKYNGNTN                                                          10
```

-continued

```
SEQ ID NO: 217        moltype = AA  length = 17
FEATURE               Location/Qualifiers
source                1..17
                      mol_type = protein
                      organism = synthetic construct
SEQUENCE: 217
WISKYNGNTN YAQKFQG                                                    17

SEQ ID NO: 218        moltype = AA  length = 13
FEATURE               Location/Qualifiers
source                1..13
                      mol_type = protein
                      organism = synthetic construct
SEQUENCE: 218
WMGWISKYNG NTN                                                        13

SEQ ID NO: 219        moltype = AA  length = 8
FEATURE               Location/Qualifiers
source                1..8
                      mol_type = protein
                      organism = synthetic construct
SEQUENCE: 219
ISKYNGNT                                                              8

SEQ ID NO: 220        moltype = AA  length = 16
FEATURE               Location/Qualifiers
source                1..16
                      mol_type = protein
                      organism = synthetic construct
SEQUENCE: 220
ARGGIHGDSY YFYYLD                                                     16

SEQ ID NO: 221        moltype = AA  length = 17
FEATURE               Location/Qualifiers
source                1..17
                      mol_type = protein
                      organism = synthetic construct
SEQUENCE: 221
ARGGIHGDSY YFYYLDV                                                    17

SEQ ID NO: 222        moltype = AA  length = 8
FEATURE               Location/Qualifiers
source                1..8
                      mol_type = protein
                      organism = synthetic construct
SEQUENCE: 222
SSSYLAWY                                                              8

SEQ ID NO: 223        moltype = AA  length = 7
FEATURE               Location/Qualifiers
source                1..7
                      mol_type = protein
                      organism = synthetic construct
SEQUENCE: 223
QSVSSSY                                                               7

SEQ ID NO: 224        moltype = AA  length = 10
FEATURE               Location/Qualifiers
source                1..10
                      mol_type = protein
                      organism = synthetic construct
SEQUENCE: 224
LLIYDASSRA                                                            10

SEQ ID NO: 225        moltype = AA  length = 8
FEATURE               Location/Qualifiers
source                1..8
                      mol_type = protein
                      organism = synthetic construct
SEQUENCE: 225
QQYGSSPY                                                              8

SEQ ID NO: 226        moltype = AA  length = 10
FEATURE               Location/Qualifiers
source                1..10
                      mol_type = protein
                      organism = synthetic construct
SEQUENCE: 226
GYTFTSYYMH                                                            10
```

```
SEQ ID NO: 227            moltype = AA   length = 5
FEATURE                   Location/Qualifiers
source                    1..5
                          mol_type = protein
                          organism = synthetic construct
SEQUENCE: 227
SYYMH                                                                    5

SEQ ID NO: 228            moltype = AA   length = 6
FEATURE                   Location/Qualifiers
source                    1..6
                          mol_type = protein
                          organism = synthetic construct
SEQUENCE: 228
TSYYMH                                                                   6

SEQ ID NO: 229            moltype = AA   length = 8
FEATURE                   Location/Qualifiers
source                    1..8
                          mol_type = protein
                          organism = synthetic construct
SEQUENCE: 229
GYTFTSYY                                                                 8

SEQ ID NO: 230            moltype = AA   length = 10
FEATURE                   Location/Qualifiers
source                    1..10
                          mol_type = protein
                          organism = synthetic construct
SEQUENCE: 230
IINPSRGSAS                                                              10

SEQ ID NO: 231            moltype = AA   length = 17
FEATURE                   Location/Qualifiers
source                    1..17
                          mol_type = protein
                          organism = synthetic construct
SEQUENCE: 231
IINPSRGSAS YAQKFQG                                                      17

SEQ ID NO: 232            moltype = AA   length = 13
FEATURE                   Location/Qualifiers
source                    1..13
                          mol_type = protein
                          organism = synthetic construct
SEQUENCE: 232
WMGIINPSRG SAS                                                          13

SEQ ID NO: 233            moltype = AA   length = 8
FEATURE                   Location/Qualifiers
source                    1..8
                          mol_type = protein
                          organism = synthetic construct
SEQUENCE: 233
INPSRGSA                                                                 8

SEQ ID NO: 234            moltype = AA   length = 11
FEATURE                   Location/Qualifiers
source                    1..11
                          mol_type = protein
                          organism = synthetic construct
SEQUENCE: 234
ARDRNYYYYM D                                                            11

SEQ ID NO: 235            moltype = AA   length = 12
FEATURE                   Location/Qualifiers
source                    1..12
                          mol_type = protein
                          organism = synthetic construct
SEQUENCE: 235
ARDRNYYYYM DV                                                           12

SEQ ID NO: 236            moltype = AA   length = 7
FEATURE                   Location/Qualifiers
source                    1..7
                          mol_type = protein
                          organism = synthetic construct
SEQUENCE: 236
```

```
SSNLAWY                                                                    7

SEQ ID NO: 237          moltype = AA  length = 6
FEATURE                 Location/Qualifiers
source                  1..6
                        mol_type = protein
                        organism = synthetic construct SEQUENCE: 237
QNISSN                                                                     6

SEQ ID NO: 238          moltype = AA  length = 10
FEATURE                 Location/Qualifiers
source                  1..10
                        mol_type = protein
                        organism = synthetic construct SEQUENCE: 238
LLIYGASTRA                                                                10

SEQ ID NO: 239          moltype = AA  length = 7
FEATURE                 Location/Qualifiers
source                  1..7
                        mol_type = protein
                        organism = synthetic construct SEQUENCE: 239
QQYITWY                                                                    7

SEQ ID NO: 240          moltype = AA  length = 11
FEATURE                 Location/Qualifiers
source                  1..11
                        mol_type = protein
                        organism = synthetic construct SEQUENCE: 240
GFSFSDYSGM S                                                              11

SEQ ID NO: 241          moltype = AA  length = 6
FEATURE                 Location/Qualifiers
source                  1..6
                        mol_type = protein
                        organism = synthetic construct SEQUENCE: 241
DYSGMS                                                                     6

SEQ ID NO: 242          moltype = AA  length = 7
FEATURE                 Location/Qualifiers
source                  1..7
                        mol_type = protein
                        organism = synthetic construct SEQUENCE: 242
SDYSGMS                                                                    7

SEQ ID NO: 243          moltype = AA  length = 9
FEATURE                 Location/Qualifiers
source                  1..9
                        mol_type = protein
                        organism = synthetic construct SEQUENCE: 243
GFSFSDYSG                                                                  9

SEQ ID NO: 244          moltype = AA  length = 10
FEATURE                 Location/Qualifiers
source                  1..10
                        mol_type = protein
                        organism = synthetic construct SEQUENCE: 244
AISPGGGDTY                                                                10

SEQ ID NO: 245          moltype = AA  length = 17
FEATURE                 Location/Qualifiers
source                  1..17
                        mol_type = protein
                        organism = synthetic construct SEQUENCE: 245
AISPGGGDTY YADSVKG                                                        17

SEQ ID NO: 246          moltype = AA  length = 13
FEATURE                 Location/Qualifiers
source                  1..13
                        mol_type = protein
                        organism = synthetic construct
```

```
SEQUENCE: 246
LVSAISPGGG DTY                                                           13

SEQ ID NO: 247          moltype = AA   length = 8
FEATURE                 Location/Qualifiers
source                  1..8
                        mol_type = protein
                        organism = synthetic construct
SEQUENCE: 247
ISPGGGDT                                                                  8

SEQ ID NO: 248          moltype = AA   length = 18
FEATURE                 Location/Qualifiers
source                  1..18
                        mol_type = protein
                        organism = synthetic construct
SEQUENCE: 248
ARRWWYYSNH SGDYDYFD                                                      18

SEQ ID NO: 249          moltype = AA   length = 19
FEATURE                 Location/Qualifiers
source                  1..19
                        mol_type = protein
                        organism = synthetic construct
SEQUENCE: 249
ARRWWYYSNH SGDYDYFDY                                                     19

SEQ ID NO: 250          moltype = AA   length = 463
FEATURE                 Location/Qualifiers
source                  1..463
                        mol_type = protein
                        organism = synthetic construct
SEQUENCE: 250
QVQLVQSGAE VKKPGASVKV SCKASGYTFT SYYMHWVRQA PGQGLEWMGI INPSRGSASY         60
AQKFQGRVTM ARDTSTSTVY MELSSLRSED TAVYYCARDR NYYYYMDVWG KGTTVTVSSG        120
GGGSGGGGSG GGGSEIVMTQ SPATLSVSPG ERATLSCRAS QNISSNLAWY QQKPGQAPRL        180
LIYGASTRAT DIPARFSGSG SGTEFTLTIS SLQSEDFAVY YCQQYITWYT FGQGTKLEIK        240
AAAIEVMYPP PYLDNEKSNG TIIHVKGKHL CPSPLFPGPS KPFWVLVVVG GVLACYSLLV        300
TVAFIIFWVK RGRKKLLYIF KQPFMRPVQT TQEEDGCSCR FPEEEEGGCE LRVKFSRSAD        360
APAYQQGQNQ LYNELNLGRR EEYDVLDKRR GRDPEMGGKP RRKNPQEGLY NELQKDKMAE        420
AYSEIGMKGE RRRGKGHDGL YQGLSTATKD TYDALHMQAL PPR                         463

SEQ ID NO: 251          moltype = AA   length = 353
FEATURE                 Location/Qualifiers
source                  1..353
                        mol_type = protein
                        organism = synthetic construct
SEQUENCE: 251
EVQLVESGGG LVQPGGSLRL SCAASGFSFS DYSGMSWVRQ APGKGEELVS AISPGGGDTY         60
YADSVKGRFT ISRDNSKNTL YLQMNSLRAE DTAVYYCARR WWYYSNHSGD YDYFDYRGQG        120
TLVTVSSAAA TTTPAPRPPT PAPTIASQPL SLRPEACRPA AGGAVHTRGL DFACDIYIWA        180
PLAGTCGVLL LSLVITLYCK RGRKKLLYIF KQPFMRPVQT TQEEDGCSCR FPEEEEGGCE        240
LRVKFSRSAD APAYQQGQNQ LYNELNLGRR EEYDVLDKRR GRDPEMGGKP RRKNPQEGLY        300
NELQKDKMAE AYSEIGMKGE RRRGKGHDGL YQGLSTATKD TYDALHMQAL PPR               353

SEQ ID NO: 252          moltype = AA   length = 816
FEATURE                 Location/Qualifiers
source                  1..816
                        mol_type = protein
                        organism = synthetic construct
SEQUENCE: 252
EIVLTQSPGT LSLSPGERAT VSCRASQSVS SSYLAWYQQK PGQAPRLLIY GASSRATGIP         60
DRFSGSGSGT DFTLTISRLE PEDFAVYYCQ QYGSSPYTFG QGTKLEIKGG GGSGGGGSGG        120
GGSQVQLVQS GPEVKKPGAS VKVSCKASGY TFTSYGITWV RQAPGQGLEW MGWISEYNGN        180
TNYAQKFQGR VTMTIDTSTT TAYMELRSLR SDDTAVYFCA RGGILPYYFF YYMDVWGKGT        240
TVTVSSATTT PAPRPPTPAP TIASQPLSLR PEACFMYVAA AAFVLLFFVG CGVLLSRKRR        300
RQHGQLWFPE GFKVSEASKK KRREPLGEDS VGLKPLKNAM VSKLSQLQTE LLAALLESGL        360
SKEALLQALG EPGPYLLAGE GPLDKGESCG GGRELAELP NGLGETRGSE DETDDDGEDF        420
TPPILKELEN LSPEEAAHQK AVVETLLQED PWRVAKMVKS YLQQHNIPQR EVVDTTGLNQ        480
SHLSQHLNKG TPMKTQKRAA LYTWYVRKQR EVAQQFTHAG QGGLIEEPTG DELPTKGRR         540
NRFKWGPASQ QILFQAYERQ KNPSKEERET LVEECNRAEC IQRGVSPSQA QGLGSNLVTE        600
VRVYNWFANR RKEEAFRHKL AMTCRDEFPT MVFPSGQISQ ASALAPAPPQ VLPQAPAPAP        660
APAMVSALAQ APAVPVLAP GPPQAVAPPA PKPTQAGEGT LSEALLQLQF DDEDLGALLG        720
NSTDPAVFTD LASVDNSEFQ QLLNQGIPVA PHTTEPMLME YPEAITRLVT GAQRPPDPAP        780
APLGAPGLPN GLLSGDEDFS SIADMDFSAL LSQISS                                 816

SEQ ID NO: 253          moltype = AA   length = 816
FEATURE                 Location/Qualifiers
source                  1..816
```

-continued

```
                          mol_type = protein
                          organism = synthetic construct
SEQUENCE: 253
EIVLTQSPAT LSLSPGERAT LSCGASQSVS SSYLAWYQQK PGLAPRLLIY DASSRATGIP   60
DRFSGSGSGT DFTLTISRLE PEDFAVYYCQ QYGSSPYTFG QGTKLEIKGG GGSGGGGSGG  120
GGSQVQLVQS GAEVKKPGAS VKVSCKASGY TFSSYGVSWV RQAPGQGLEW MGWISKYNGN  180
TNYAQKFQGR VTMTTDTSTS TAYMELRSLR SDDTAVYFCA RGGIHGDSYY FYYLDVWGKG  240
TTVTVSSATT TPAPRPPTPA PTIASQPLSL RPEACFMYVA AAAFVLLFFV GCGVLLSRKR  300
RRQHGQLWFP EGFKVSEASK KKRREPLGED SVGLKPLKNA MVSKLSQLQT ELLAALLESG  360
LSKEALLQAL GEPGPYLLAG EGPLDKGESC GGGRGELAEL PNGLGETRGS EDETDDDGED  420
FTPPILKELE NLSPEEAAHQ KAVVETLLQE DPWRVAKMVK SYLQQHNIPQ REVVDTTGLN  480
QSHLSQHLNK GTPMKTQKRA ALYTWYVRKQ REVAQQFTHA GQGGLIEEPT GDELPTKKGR  540
RNRFKWGPAS QQILFQAYER QKNPSKEERE TLVEECNRAE CIQRGVSPSQ AQGLGSNLVT  600
EVRVYNWFAN RRKEEAFRHK LAMTCRDEFP TMVFPSGQIS QASALAPAPP QVLPQAPAPA  660
PAPAMVSALA QAPAPVPVLA PGPPQAVAPP APKPTQAGEG TLSEALLQLQ FDDEDLGALL  720
GNSTDPAVFT DLASVDNSEF QQLLNQGIPV APHTTEPMLM EYPEAITRLV TGAQRPPDPA  780
PAPLGAPGLP NGLLSGDEDF SSIADMDFSA LLSQIS                            816

SEQ ID NO: 254            moltype = AA   length = 320
FEATURE                   Location/Qualifiers
source                    1..320
                          mol_type = protein
                          organism = synthetic construct
SEQUENCE: 254
ELPTQGTFSN VSTNVSELCG GAIVVPVCLA FLLTTLLGVL FCFNKRDLIK KHIWPNVPDP   60
SKSHIAQWSP HTPPRHNFNS KDQMYSDGNF TDVSVVEIEA NDKKPFPEDL KSLDLFKKEK  120
INTEGHSSGI GGSSCMSSSR PSISSSDENE SSQNTSSTVQ YSTVVHSGYR HQVPSVQVFS  180
RSESTQPLLD SEERPEDLQL VDHVGGDGI LPRQQYFKQN CSQHESSPDI SHFERSKQVS   240
SVNEEDFVRL KQQISDHISQ SCGSGQMKMF QEVSAADAFG PGTEGQVERF ETVGMEAATD  300
EGMPKSYLPQ TVRQGGYMPQ                                             320

SEQ ID NO: 255            moltype = AA   length = 249
FEATURE                   Location/Qualifiers
source                    1..249
                          mol_type = protein
                          organism = synthetic construct
SEQUENCE: 255
KEACPTGLYT HSGECCKACN LGEGVAQPCG ANQTVCEPCL DSVTFSDVVS ATEPCKPCTE   60
CVGLQSMSAP CVEADDAVCR CAYGYYQDET TGRCEACRVC EAGSGLVFSC QDKQNTVCEE  120
CPDGTYSDEA NHVDPCLPCT VCEDTERQLR ECTRWADAEC EEIPGRWITR STPPEGSDST  180
APSTQEPEAP PEQDLIASTV AGVVTTVMGS SQPVVTRGTT DNLIPVYCSI LAAVVVGLVA  240
YIAFKRWNS                                                         249

SEQ ID NO: 256            moltype = DNA   length = 140
FEATURE                   Location/Qualifiers
source                    1..140
                          mol_type = other DNA
                          organism = synthetic construct
SEQUENCE: 256
gttaataatt aacatatatg ttaatcatta acatatagtt aattattaac cgctatgtta   60
atgattaaca acgttaata attaacatat atgttaatca ttaacatata actagtctag  120
agggtatata atgggggcca                                             140

SEQ ID NO: 257            moltype = AA   length = 277
FEATURE                   Location/Qualifiers
source                    1..277
                          mol_type = protein
                          organism = synthetic construct
SEQUENCE: 257
NKRDLIKKHI WPNVPDPSKS HIAQWSPHTP PRHNFNSKDQ MYSDGNFTDV SVVEIEANDK   60
KPFPEDLKSL DLFKKEKINT EGHSSGIGGS SCMSSSRPSI SSSDENESSQ NTSSTVQYST  120
VVHSGYRHQV PSVQVFSRSE STQPLLDSEE RPEDLQLVDH VDGGDILPR QQYFKQNCSQ  180
HESSPDISHF ERSKQVSSVN EEDFVRLKQQ ISDHISQSCG SGQMKMFQEV SAADAFGPGT  240
EGQVERFETV GMEAATDEGM PKSYLPQTVR QGGYMPQ                           277

SEQ ID NO: 258            moltype = AA   length = 22
FEATURE                   Location/Qualifiers
source                    1..22
                          mol_type = protein
                          organism = synthetic construct
SEQUENCE: 258
AIVVPVCLAF LLTTLLGVLF CF                                           22

SEQ ID NO: 259            moltype = AA   length = 378
FEATURE                   Location/Qualifiers
source                    1..378
                          mol_type = protein
                          organism = synthetic construct
SEQUENCE: 259
```

```
MALPVTALLL PLALLLHAAR PDYKDDDDKE LCGGRIARLE EKVKTLKAQN SELASTANML    60
REQVAQLKQK VMNAQGEIEA IVVPVCLAFL LTTLLGVLFC FNKRDLIKKH IWPNVPDPSK   120
SHIAQWSPHT PPRHNFNSKD QMYSDGNFTD VSVVEIEAND KKPFPEDLKS LDLFKKEKIN   180
TEGHSSGIGG SSCMSSSRPS ISSSDENESS QNTSSTVQYS TVVHSGYRHQ VPSVQVFSRS   240
ESTQPLLDSE ERPEDLQLVD HVDGGDGILP RQQYFKQNCS QHESSPDISH FERSKQVSSV   300
NEEDFVRLKQ QISDHISQSC GSGQMKMFQE VSAADAFGPG TEGQVERFET VGMEAATDEG   360
MPKSYLPQTV RQGGYMPQ                                                 378

SEQ ID NO: 260            moltype = AA   length = 16
FEATURE                   Location/Qualifiers
source                    1..16
                          mol_type = protein
                          organism = synthetic construct
SEQUENCE: 260
ELPTQGTFSN VSTNVS                                                    16

SEQ ID NO: 261            moltype = DNA  length = 960
FEATURE                   Location/Qualifiers
source                    1..960
                          mol_type = other DNA
                          organism = synthetic construct
SEQUENCE: 261
gagctgccca cacaaggcac attcagcaac gtgtccacca acgtgtccga gctgtgcggc    60
ggcgctatcg tggtgccgt gtgcttggcc ttcctgctga ccaccctgct gggcgtgctg   120
ttctgcttca acaagcggga cctgattaag aagcacatct ggcccaacgt gcccgaccct   180
agcaagagcc acatcgccca gtggagccct cacacacaca ccaggcacaa cttcaacagc   240
aaggaccaga tgtactccga cggcaacttc accgacgtgt ccgtggtgga gatcgaggcc   300
aacgacaaga gcccttccc tgaggacctg aagtccctgg acctgttcaa gaaggagaag   360
atcaacaccg agggacacag cagcggcatc ggcggctcta gctgtatgag cagcagcagg   420
cccagcatct ccagcagcga cgagaacgag agcagccaga ccgtgcag                480
tacagcaccg tggtgcacag cggctacagg caccaggtgc catcagtgca agtgttcagc   540
cgatccgagt ccacccagcc tctgctggac agcgaggaga ggcccgagga cctgcaactg   600
gtggaccacg tggacggagg cgacggcatc ctgcctaggc agcaatactt caagcagaat   660
tgccagccagc acgagagcag ccctgacatc agccacttcg agaggagcaa gcaagtgtcc   720
agcgtgaacg aggaggactt cgtgaggctg aagcagcaga tcagcgacca catcagccag   780
agctgcggca gcggccagat gaagatgttc caggaagtgt ccgccgccga cgccttcggc   840
cctggcacaa aggacaagt ggagaggttc gaaaccgtgg gcatgaggc cgccaccgac    900
gagggaatgc ccaagagcta cctgcctcag accgtgcggc agggcggcta catgcctcag   960

SEQ ID NO: 262            moltype = DNA  length = 1023
FEATURE                   Location/Qualifiers
source                    1..1023
                          mol_type = other DNA
                          organism = synthetic construct
SEQUENCE: 262
atggccctgc ccgtgacagc cctgctcctg cctctggccc tgttgctgca tgcagcacgg    60
cctgagctgc ccacacaagg cacattcagc aacgtgtcc ccaacgtgtc gctgtgtgc   120
ggcggcgcta tcgtggtgcc cgtgtgcttg gccttcctgc tgaccaccct gctgggcgtg   180
ctgttctgct tcaacaagcg ggacctgatt aagaagcaca tctggcccaa cgtgcccgac   240
cctagcaaga gccacatcgc ccagtggagc cctcacacac tcccaggca aacttcaac    300
agcaaggacc agatgtactc cgacggcaac ttcaccgacg tccgtggt ggagatcgag   360
gccaacgaca gaagccctt ccctgaggac ctgaagtccc tggacctgtt caagaaggag   420
aagatcaaca ccgagggaca cagcagcggc atcggcggct ctagctgtat gagcagcagc   480
aggcccagca tctccagcag cgacgagaac gagagcagcc agaacaccag cagcaccgtg   540
cagtacagca ccgtggtgca cagcggctac aggcaccagg tgccatcagt gcaagtgttc   600
agccgatccg agtccaccca gcctctgctg gacagcgagg agaggcccga ggacctgcaa   660
ctggtggacc acgtggacgg aggcgacggc atcctgccta ggcagcaata cttcaagcag   720
aattgcagcc agcacgagag cagccctgac atcagccact cgagaggag caagcaagtg   780
tccagcgtga acgaggagga cttcgtgagg ctgaagcagc agatcagcga ccacatcagc   840
cagagctgcg gcagcggcca gatgaagatg ttccaggaag tgtccgccgc cgacgccttc   900
ggccctggca cagaaggaca gtggagagg ttcgaaaccg tgggcatgga ggccgccacc   960
gacgagggaa tgcccaagag ctacctgcct cagaccgtgc ggcagggcgg ctacatgcct  1020
cag                                                                1023

SEQ ID NO: 263            moltype = AA   length = 10
FEATURE                   Location/Qualifiers
source                    1..10
                          mol_type = protein
                          organism = synthetic construct
SEQUENCE: 263
GYTFSSYGVS                                                           10

SEQ ID NO: 264            moltype = AA   length = 7
FEATURE                   Location/Qualifiers
source                    1..7
                          mol_type = protein
                          organism = synthetic construct
SEQUENCE: 264
ENLYTQS                                                               7
```

| | | |
|---|---|---|
| SEQ ID NO: 265 | moltype = AA   length = 5 | |
| FEATURE | Location/Qualifiers | |
| source | 1..5 | |
| | mol_type = protein | |
| | organism = synthetic construct | |
| SEQUENCE: 265 | | |
| DDDDK | | 5 |
| | | |
| SEQ ID NO: 266 | moltype = AA   length = 4 | |
| FEATURE | Location/Qualifiers | |
| source | 1..4 | |
| | mol_type = protein | |
| | organism = synthetic construct | |
| SEQUENCE: 266 | | |
| LVPR | | 4 |
| | | |
| SEQ ID NO: 267 | moltype = AA   length = 4 | |
| FEATURE | Location/Qualifiers | |
| source | 1..4 | |
| | mol_type = protein | |
| | organism = synthetic construct | |
| SEQUENCE: 267 | | |
| CPPC | | 4 |
| | | |
| SEQ ID NO: 268 | moltype = RNA   length = 103 | |
| FEATURE | Location/Qualifiers | |
| source | 1..103 | |
| | mol_type = other RNA | |
| | organism = synthetic construct | |

SEQUENCE: 268
ggggccacta gggacaggat gttttagagc tagaaatagc aagttaaaat aaggctagtc   60
cgttatcaac ttgaaaaagt ggcaccgagt cggtgctttt ttt                    103

| | | |
|---|---|---|
| SEQ ID NO: 269 | moltype = DNA   length = 20 | |
| FEATURE | Location/Qualifiers | |
| source | 1..20 | |
| | mol_type = genomic DNA | |
| | organism = Adeno-associated virus | |
| SEQUENCE: 269 | | |
| ggggccacta gggacaggat | | 20 |
| | | |
| SEQ ID NO: 270 | moltype = RNA   length = 20 | |
| FEATURE | Location/Qualifiers | |
| source | 1..20 | |
| | mol_type = other RNA | |
| | organism = synthetic construct | |
| SEQUENCE: 270 | | |
| gcacctgaat accacgcctg | | 20 |
| | | |
| SEQ ID NO: 271 | moltype = RNA   length = 20 | |
| FEATURE | Location/Qualifiers | |
| source | 1..20 | |
| | mol_type = other RNA | |
| | organism = synthetic construct | |
| SEQUENCE: 271 | | |
| cgcctgcgat gtagtcgatg | | 20 |
| | | |
| SEQ ID NO: 272 | moltype = RNA   length = 20 | |
| FEATURE | Location/Qualifiers | |
| source | 1..20 | |
| | mol_type = other RNA | |
| | organism = synthetic construct | |
| SEQUENCE: 272 | | |
| caggacgggc gagatgtccc | | 20 |
| | | |
| SEQ ID NO: 273 | moltype = RNA   length = 20 | |
| FEATURE | Location/Qualifiers | |
| source | 1..20 | |
| | mol_type = other RNA | |
| | organism = synthetic construct | |
| SEQUENCE: 273 | | |
| ctgaatcttt ggagtacctg | | 20 |
| | | |
| SEQ ID NO: 274 | moltype = RNA   length = 20 | |
| FEATURE | Location/Qualifiers | |
| source | 1..20 | |
| | mol_type = other RNA | |
| | organism = synthetic construct | |

```
SEQUENCE: 274
ggccacggag cgagacatct                                               20

SEQ ID NO: 275          moltype = RNA  length = 20
FEATURE                 Location/Qualifiers
source                  1..20
                        mol_type = other RNA
                        organism = synthetic construct
SEQUENCE: 275
aagtcaactt caatgtcgga                                               20

SEQ ID NO: 276          moltype = RNA  length = 20
FEATURE                 Location/Qualifiers
source                  1..20
                        mol_type = other RNA
                        organism = synthetic construct
SEQUENCE: 276
gcttggaggc ctgatcagcg                                               20

SEQ ID NO: 277          moltype = RNA  length = 20
FEATURE                 Location/Qualifiers
source                  1..20
                        mol_type = other RNA
                        organism = synthetic construct
SEQUENCE: 277
cttatctctt cgcagcgagg                                               20

SEQ ID NO: 278          moltype = RNA  length = 20
FEATURE                 Location/Qualifiers
source                  1..20
                        mol_type = other RNA
                        organism = synthetic construct
SEQUENCE: 278
cacacattac tccaacattg                                               20

SEQ ID NO: 279          moltype = RNA  length = 20
FEATURE                 Location/Qualifiers
source                  1..20
                        mol_type = other RNA
                        organism = synthetic construct
SEQUENCE: 279
ttccgcaaaa tagagcccca                                               20

SEQ ID NO: 280          moltype = RNA  length = 20
FEATURE                 Location/Qualifiers
source                  1..20
                        mol_type = other RNA
                        organism = synthetic construct
SEQUENCE: 280
tgcacagaac tatcgtacca                                               20

SEQ ID NO: 281          moltype = RNA  length = 20
FEATURE                 Location/Qualifiers
source                  1..20
                        mol_type = other RNA
                        organism = synthetic construct
SEQUENCE: 281
gcaataagac tctttaaaga                                               20

SEQ ID NO: 282          moltype = RNA  length = 20
FEATURE                 Location/Qualifiers
source                  1..20
                        mol_type = other RNA
                        organism = synthetic construct
SEQUENCE: 282
caaagagatt acgaatgcct                                               20

SEQ ID NO: 283          moltype = RNA  length = 20
FEATURE                 Location/Qualifiers
source                  1..20
                        mol_type = other RNA
                        organism = synthetic construct
SEQUENCE: 283
caaggcaccc caggtttcca                                               20

SEQ ID NO: 284          moltype = RNA  length = 20
FEATURE                 Location/Qualifiers
source                  1..20
                        mol_type = other RNA
```

```
                          organism = synthetic construct
SEQUENCE: 284
ttacgaatgc cttggaaacc                                                    20

SEQ ID NO: 285            moltype = RNA   length = 20
FEATURE                   Location/Qualifiers
source                    1..20
                          mol_type = other RNA
                          organism = synthetic construct
SEQUENCE: 285
cagagacgca tctgaccctc                                                    20

SEQ ID NO: 286            moltype = RNA   length = 20
FEATURE                   Location/Qualifiers
source                    1..20
                          mol_type = other RNA
                          organism = synthetic construct
SEQUENCE: 286
catgcagttc tcacacactg                                                    20

SEQ ID NO: 287            moltype = RNA   length = 20
FEATURE                   Location/Qualifiers
source                    1..20
                          mol_type = other RNA
                          organism = synthetic construct
SEQUENCE: 287
gtgtgagaac tgcatggaga                                                    20

SEQ ID NO: 288            moltype = RNA   length = 20
FEATURE                   Location/Qualifiers
source                    1..20
                          mol_type = other RNA
                          organism = synthetic construct
SEQUENCE: 288
tctcatttca ggaaaccact                                                    20

SEQ ID NO: 289            moltype = RNA   length = 20
FEATURE                   Location/Qualifiers
source                    1..20
                          mol_type = other RNA
                          organism = synthetic construct
SEQUENCE: 289
agtcatacac cttaaccaag                                                    20

SEQ ID NO: 290            moltype = RNA   length = 20
FEATURE                   Location/Qualifiers
source                    1..20
                          mol_type = other RNA
                          organism = synthetic construct
SEQUENCE: 290
ttcaaggaaa ccagttgagg                                                    20

SEQ ID NO: 291            moltype = RNA   length = 20
FEATURE                   Location/Qualifiers
source                    1..20
                          mol_type = other RNA
                          organism = synthetic construct
SEQUENCE: 291
gagccttgcc tggaaatctg                                                    20

SEQ ID NO: 292            moltype = RNA   length = 20
FEATURE                   Location/Qualifiers
source                    1..20
                          mol_type = other RNA
                          organism = synthetic construct
SEQUENCE: 292
aagcgtcaaa agtctgccag                                                    20

SEQ ID NO: 293            moltype = RNA   length = 20
FEATURE                   Location/Qualifiers
source                    1..20
                          mol_type = other RNA
                          organism = synthetic construct
SEQUENCE: 293
cgttccaact cgaagtgcca                                                    20

SEQ ID NO: 294            moltype = RNA   length = 20
FEATURE                   Location/Qualifiers
source                    1..20
```

```
                         mol_type = other RNA
                         organism = synthetic construct
SEQUENCE: 294
gagcgactgg gacacggtga                                                 20

SEQ ID NO: 295           moltype = RNA   length = 20
FEATURE                  Location/Qualifiers
source                   1..20
                         mol_type = other RNA
                         organism = synthetic construct
SEQUENCE: 295
gctgcgcaag aagggcccta                                                 20

SEQ ID NO: 296           moltype = RNA   length = 20
FEATURE                  Location/Qualifiers
source                   1..20
                         mol_type = other RNA
                         organism = synthetic construct
SEQUENCE: 296
ttgttctggc cagcagcccc                                                 20

SEQ ID NO: 297           moltype = RNA   length = 20
FEATURE                  Location/Qualifiers
source                   1..20
                         mol_type = other RNA
                         organism = synthetic construct
SEQUENCE: 297
cttccagagc cacatcatcg                                                 20

SEQ ID NO: 298           moltype = RNA   length = 20
FEATURE                  Location/Qualifiers
source                   1..20
                         mol_type = other RNA
                         organism = synthetic construct
SEQUENCE: 298
gggactcacc agagagaggt                                                 20

SEQ ID NO: 299           moltype = RNA   length = 20
FEATURE                  Location/Qualifiers
source                   1..20
                         mol_type = other RNA
                         organism = synthetic construct
SEQUENCE: 299
cggtcgaaat agaagcccta                                                 20

SEQ ID NO: 300           moltype = RNA   length = 20
FEATURE                  Location/Qualifiers
source                   1..20
                         mol_type = other RNA
                         organism = synthetic construct
SEQUENCE: 300
aaaaggatat tgtgcaactg                                                 20

SEQ ID NO: 301           moltype = RNA   length = 20
FEATURE                  Location/Qualifiers
source                   1..20
                         mol_type = other RNA
                         organism = synthetic construct
SEQUENCE: 301
tgtgcatatt tattacatcg                                                 20

SEQ ID NO: 302           moltype = RNA   length = 20
FEATURE                  Location/Qualifiers
source                   1..20
                         mol_type = other RNA
                         organism = synthetic construct
SEQUENCE: 302
tttgtgaaga tcttgaccaa                                                 20

SEQ ID NO: 303           moltype = RNA   length = 20
FEATURE                  Location/Qualifiers
source                   1..20
                         mol_type = other RNA
                         organism = synthetic construct
SEQUENCE: 303
tgtcatgctg aaccgcattg                                                 20

SEQ ID NO: 304           moltype = RNA   length = 20
FEATURE                  Location/Qualifiers
```

```
source                        1..20
                              mol_type = other RNA
                              organism = synthetic construct
SEQUENCE: 304
ccactctatg aggatagtca                                                         20

SEQ ID NO: 305                moltype = RNA   length = 20
FEATURE                       Location/Qualifiers
source                        1..20
                              mol_type = other RNA
                              organism = synthetic construct
SEQUENCE: 305
ttgacataga agaggcacaa                                                         20

SEQ ID NO: 306                moltype = RNA   length = 20
FEATURE                       Location/Qualifiers
source                        1..20
                              mol_type = other RNA
                              organism = synthetic construct
SEQUENCE: 306
gagtactaca ctcagcagca                                                         20

SEQ ID NO: 307                moltype = RNA   length = 20
FEATURE                       Location/Qualifiers
source                        1..20
                              mol_type = other RNA
                              organism = synthetic construct
SEQUENCE: 307
tcacgcacaa gaaacgtcca                                                         20

SEQ ID NO: 308                moltype = RNA   length = 20
FEATURE                       Location/Qualifiers
source                        1..20
                              mol_type = other RNA
                              organism = synthetic construct
SEQUENCE: 308
aggtctcggt gaaaccacct                                                         20

SEQ ID NO: 309                moltype = RNA   length = 20
FEATURE                       Location/Qualifiers
source                        1..20
                              mol_type = other RNA
                              organism = synthetic construct
SEQUENCE: 309
agcattatcc aaagagtccg                                                         20

SEQ ID NO: 310                moltype = RNA   length = 20
FEATURE                       Location/Qualifiers
source                        1..20
                              mol_type = other RNA
                              organism = synthetic construct
SEQUENCE: 310
atattaattc ttaccagtgg                                                         20

SEQ ID NO: 311                moltype = RNA   length = 20
FEATURE                       Location/Qualifiers
source                        1..20
                              mol_type = other RNA
                              organism = synthetic construct
SEQUENCE: 311
agctttaaat caaggttcat                                                         20

SEQ ID NO: 312                moltype = RNA   length = 20
FEATURE                       Location/Qualifiers
source                        1..20
                              mol_type = other RNA
                              organism = synthetic construct
SEQUENCE: 312
atcccgagcc ctaaggtgca                                                         20

SEQ ID NO: 313                moltype = RNA   length = 20
FEATURE                       Location/Qualifiers
source                        1..20
                              mol_type = other RNA
                              organism = synthetic construct
SEQUENCE: 313
ggcagcgcgg aggacagcgt                                                         20

SEQ ID NO: 314                moltype = RNA   length = 20
```

```
FEATURE                 Location/Qualifiers
source                  1..20
                        mol_type = other RNA
                        organism = synthetic construct
SEQUENCE: 314
ctcagggggc tactaccacc                                               20

SEQ ID NO: 315          moltype = RNA   length = 20
FEATURE                 Location/Qualifiers
source                  1..20
                        mol_type = other RNA
                        organism = synthetic construct
SEQUENCE: 315
gtcaccgacg agaccagaag                                               20

SEQ ID NO: 316          moltype = RNA   length = 20
FEATURE                 Location/Qualifiers
source                  1..20
                        mol_type = other RNA
                        organism = synthetic construct
SEQUENCE: 316
gtcgtggact tcgtactgct                                               20

SEQ ID NO: 317          moltype = RNA   length = 20
FEATURE                 Location/Qualifiers
source                  1..20
                        mol_type = other RNA
                        organism = synthetic construct
SEQUENCE: 317
taattttag gcaagtgtcg                                                20

SEQ ID NO: 318          moltype = RNA   length = 20
FEATURE                 Location/Qualifiers
source                  1..20
                        mol_type = other RNA
                        organism = synthetic construct
SEQUENCE: 318
ttagctgtta gacttgaata                                               20

SEQ ID NO: 319          moltype = RNA   length = 20
FEATURE                 Location/Qualifiers
source                  1..20
                        mol_type = other RNA
                        organism = synthetic construct
SEQUENCE: 319
cgagagccgt caacttgcgt                                               20

SEQ ID NO: 320          moltype = RNA   length = 20
FEATURE                 Location/Qualifiers
source                  1..20
                        mol_type = other RNA
                        organism = synthetic construct
SEQUENCE: 320
cggcttcaac tgcaaaggtg                                               20

SEQ ID NO: 321          moltype = RNA   length = 20
FEATURE                 Location/Qualifiers
source                  1..20
                        mol_type = other RNA
                        organism = synthetic construct
SEQUENCE: 321
tatgaaaaag cagagcgact                                               20

SEQ ID NO: 322          moltype = RNA   length = 20
FEATURE                 Location/Qualifiers
source                  1..20
                        mol_type = other RNA
                        organism = synthetic construct
SEQUENCE: 322
tctggcgggc gagctcacgc                                               20

SEQ ID NO: 323          moltype = RNA   length = 20
FEATURE                 Location/Qualifiers
source                  1..20
                        mol_type = other RNA
                        organism = synthetic construct
SEQUENCE: 323
ctcacgctgg ttaccgccta                                               20
```

| | | |
|---|---|---|
| SEQ ID NO: 324<br>FEATURE<br>source | moltype = RNA   length = 20<br>Location/Qualifiers<br>1..20<br>mol_type = other RNA<br>organism = synthetic construct | |
| SEQUENCE: 324<br>aaagattacg aacttccctg | | 20 |
| SEQ ID NO: 325<br>FEATURE<br>source | moltype = RNA   length = 20<br>Location/Qualifiers<br>1..20<br>mol_type = other RNA<br>organism = synthetic construct | |
| SEQUENCE: 325<br>gttaaaaaca gacatgccta | | 20 |
| SEQ ID NO: 326<br>FEATURE<br>source | moltype = RNA   length = 20<br>Location/Qualifiers<br>1..20<br>mol_type = other RNA<br>organism = synthetic construct | |
| SEQUENCE: 326<br>atgcctaagg aggttgtacc | | 20 |
| SEQ ID NO: 327<br>FEATURE<br>source | moltype = RNA   length = 20<br>Location/Qualifiers<br>1..20<br>mol_type = other RNA<br>organism = synthetic construct | |
| SEQUENCE: 327<br>ctccaggtat cccatcgaaa | | 20 |
| SEQ ID NO: 328<br>FEATURE<br>source | moltype = RNA   length = 20<br>Location/Qualifiers<br>1..20<br>mol_type = other RNA<br>organism = synthetic construct | |
| SEQUENCE: 328<br>caccaaatac gatagatcag | | 20 |
| SEQ ID NO: 329<br>FEATURE<br>source | moltype = RNA   length = 20<br>Location/Qualifiers<br>1..20<br>mol_type = other RNA<br>organism = synthetic construct | |
| SEQUENCE: 329<br>tggcggcgtg aatggcaaga | | 20 |
| SEQ ID NO: 330<br>FEATURE<br>source | moltype = RNA   length = 20<br>Location/Qualifiers<br>1..20<br>mol_type = other RNA<br>organism = synthetic construct | |
| SEQUENCE: 330<br>taggatggta gcacacaacc | | 20 |
| SEQ ID NO: 331<br>FEATURE<br>source | moltype = RNA   length = 20<br>Location/Qualifiers<br>1..20<br>mol_type = other RNA<br>organism = synthetic construct | |
| SEQUENCE: 331<br>cagcagcaga gccccgacgg | | 20 |
| SEQ ID NO: 332<br>FEATURE<br>source | moltype = RNA   length = 20<br>Location/Qualifiers<br>1..20<br>mol_type = other RNA<br>organism = synthetic construct | |
| SEQUENCE: 332<br>cggcgtgcga acggaatgtg | | 20 |
| SEQ ID NO: 333<br>FEATURE<br>source | moltype = RNA   length = 20<br>Location/Qualifiers<br>1..20<br>mol_type = other RNA<br>organism = synthetic construct | |
| SEQUENCE: 333<br>tatagacgct gcccgacgtc | | 20 |

```
SEQ ID NO: 334           moltype = RNA  length = 20
FEATURE                  Location/Qualifiers
source                   1..20
                         mol_type = other RNA
                         organism = synthetic construct
SEQUENCE: 334
tccaaagaag ggtactgtgg                                                    20

SEQ ID NO: 335           moltype = RNA  length = 20
FEATURE                  Location/Qualifiers
source                   1..20
                         mol_type = other RNA
                         organism = synthetic construct
SEQUENCE: 335
acagtaccct tctttggaat                                                    20

SEQ ID NO: 336           moltype = RNA  length = 20
FEATURE                  Location/Qualifiers
source                   1..20
                         mol_type = other RNA
                         organism = synthetic construct
SEQUENCE: 336
gcgacgggcg catctacgtg                                                    20

SEQ ID NO: 337           moltype = RNA  length = 20
FEATURE                  Location/Qualifiers
source                   1..20
                         mol_type = other RNA
                         organism = synthetic construct
SEQUENCE: 337
cccgacctcc ataagtcctg                                                    20

SEQ ID NO: 338           moltype = RNA  length = 20
FEATURE                  Location/Qualifiers
source                   1..20
                         mol_type = other RNA
                         organism = synthetic construct
SEQUENCE: 338
ggggtcctcg aagcgcacga                                                    20

SEQ ID NO: 339           moltype = RNA  length = 20
FEATURE                  Location/Qualifiers
source                   1..20
                         mol_type = other RNA
                         organism = synthetic construct
SEQUENCE: 339
tgctctgttt agaagatgac                                                    20

SEQ ID NO: 340           moltype = RNA  length = 20
FEATURE                  Location/Qualifiers
source                   1..20
                         mol_type = other RNA
                         organism = synthetic construct
SEQUENCE: 340
atattctttt ctagttaaag                                                    20

SEQ ID NO: 341           moltype = RNA  length = 20
FEATURE                  Location/Qualifiers
source                   1..20
                         mol_type = other RNA
                         organism = synthetic construct
SEQUENCE: 341
cctgtaaaga aacaaaagac                                                    20

SEQ ID NO: 342           moltype = RNA  length = 20
FEATURE                  Location/Qualifiers
source                   1..20
                         mol_type = other RNA
                         organism = synthetic construct
SEQUENCE: 342
tggagaaaga cgtaacttcg                                                    20

SEQ ID NO: 343           moltype = RNA  length = 20
FEATURE                  Location/Qualifiers
source                   1..20
                         mol_type = other RNA
                         organism = synthetic construct
SEQUENCE: 343
```

```
tctgccctga ggtatgcgat                                              20

SEQ ID NO: 344          moltype = RNA   length = 20
FEATURE                 Location/Qualifiers
source                  1..20
                        mol_type = other RNA
                        organism = synthetic construct
SEQUENCE: 344
attccgcttg gtgaaaacga                                              20

SEQ ID NO: 345          moltype = RNA   length = 20
FEATURE                 Location/Qualifiers
source                  1..20
                        mol_type = other RNA
                        organism = synthetic construct
SEQUENCE: 345
caggcacaat agaaacaacg                                              20

SEQ ID NO: 346          moltype = RNA   length = 20
FEATURE                 Location/Qualifiers
source                  1..20
                        mol_type = other RNA
                        organism = synthetic construct
SEQUENCE: 346
ccatttgtaa tgctgacttg                                              20

SEQ ID NO: 347          moltype = RNA   length = 20
FEATURE                 Location/Qualifiers
source                  1..20
                        mol_type = other RNA
                        organism = synthetic construct
SEQUENCE: 347
ctgggtcact tgtgccgtgg                                              20

SEQ ID NO: 348          moltype = RNA   length = 20
FEATURE                 Location/Qualifiers
source                  1..20
                        mol_type = other RNA
                        organism = synthetic construct
SEQUENCE: 348
gtcagggttc tggatatctg                                              20

SEQ ID NO: 349          moltype = RNA   length = 20
FEATURE                 Location/Qualifiers
source                  1..20
                        mol_type = other RNA
                        organism = synthetic construct
SEQUENCE: 349
tggatttaga gtctctcagc                                              20

SEQ ID NO: 350          moltype = RNA   length = 20
FEATURE                 Location/Qualifiers
source                  1..20
                        mol_type = other RNA
                        organism = synthetic construct
SEQUENCE: 350
ctgcggctgt ggtccagctg                                              20

SEQ ID NO: 351          moltype = RNA   length = 20
FEATURE                 Location/Qualifiers
source                  1..20
                        mol_type = other RNA
                        organism = synthetic construct
SEQUENCE: 351
acaaaactgt gctagacatg                                              20

SEQ ID NO: 352          moltype = RNA   length = 20
FEATURE                 Location/Qualifiers
source                  1..20
                        mol_type = other RNA
                        organism = synthetic construct
SEQUENCE: 352
ttcttcccca gcccaggtaa                                              20

SEQ ID NO: 353          moltype = RNA   length = 20
FEATURE                 Location/Qualifiers
source                  1..20
                        mol_type = other RNA
                        organism = synthetic construct
```

```
SEQUENCE: 353
cgtcatgagc agattaaacc                                                     20

SEQ ID NO: 354          moltype = RNA   length = 20
FEATURE                 Location/Qualifiers
source                  1..20
                        mol_type = other RNA
                        organism = synthetic construct
SEQUENCE: 354
gagagcgcct gcgacccgag                                                     20

SEQ ID NO: 355          moltype = RNA   length = 20
FEATURE                 Location/Qualifiers
source                  1..20
                        mol_type = other RNA
                        organism = synthetic construct
SEQUENCE: 355
ccagcgggtg aagtacacca                                                     20

SEQ ID NO: 356          moltype = RNA   length = 20
FEATURE                 Location/Qualifiers
source                  1..20
                        mol_type = other RNA
                        organism = synthetic construct
SEQUENCE: 356
ggagcgcttt tcgccgccag                                                     20

SEQ ID NO: 357          moltype = RNA   length = 20
FEATURE                 Location/Qualifiers
source                  1..20
                        mol_type = other RNA
                        organism = synthetic construct
SEQUENCE: 357
tgaggcctgg accttatgca                                                     20

SEQ ID NO: 358          moltype = RNA   length = 20
FEATURE                 Location/Qualifiers
source                  1..20
                        mol_type = other RNA
                        organism = synthetic construct
SEQUENCE: 358
cctggtggag tgaaccatga                                                     20

SEQ ID NO: 359          moltype = RNA   length = 20
FEATURE                 Location/Qualifiers
source                  1..20
                        mol_type = other RNA
                        organism = synthetic construct
SEQUENCE: 359
caagcactta ggttcccctg                                                     20

SEQ ID NO: 360          moltype = RNA   length = 20
FEATURE                 Location/Qualifiers
source                  1..20
                        mol_type = other RNA
                        organism = synthetic construct
SEQUENCE: 360
ggtctcccta caattcagcg                                                     20

SEQ ID NO: 361          moltype = RNA   length = 20
FEATURE                 Location/Qualifiers
source                  1..20
                        mol_type = other RNA
                        organism = synthetic construct
SEQUENCE: 361
cacagcgcgt gactgcaatg                                                     20

SEQ ID NO: 362          moltype = RNA   length = 20
FEATURE                 Location/Qualifiers
source                  1..20
                        mol_type = other RNA
                        organism = synthetic construct
SEQUENCE: 362
tctggggcac caattctagg                                                     20

SEQ ID NO: 363          moltype = RNA   length = 20
FEATURE                 Location/Qualifiers
source                  1..20
                        mol_type = other RNA
```

-continued

```
                         organism = synthetic construct
SEQUENCE: 363
gagccatgct tggcttacga                                                    20

SEQ ID NO: 364           moltype = RNA   length = 20
FEATURE                  Location/Qualifiers
source                   1..20
                         mol_type = other RNA
                         organism = synthetic construct
SEQUENCE: 364
gtacaagtac ttatctcatg                                                    20

SEQ ID NO: 365           moltype = RNA   length = 20
FEATURE                  Location/Qualifiers
source                   1..20
                         mol_type = other RNA
                         organism = synthetic construct
SEQUENCE: 365
gagataacaa cataacaaca                                                    20

SEQ ID NO: 366           moltype = RNA   length = 20
FEATURE                  Location/Qualifiers
source                   1..20
                         mol_type = other RNA
                         organism = synthetic construct
SEQUENCE: 366
catattccat agtctttggg                                                    20

SEQ ID NO: 367           moltype = RNA   length = 20
FEATURE                  Location/Qualifiers
source                   1..20
                         mol_type = other RNA
                         organism = synthetic construct
SEQUENCE: 367
ctgccccttia gcaacttagg                                                   20

SEQ ID NO: 368           moltype = RNA   length = 20
FEATURE                  Location/Qualifiers
source                   1..20
                         mol_type = other RNA
                         organism = synthetic construct
SEQUENCE: 368
tgtttaaaaa tatgttgaca                                                    20

SEQ ID NO: 369           moltype = RNA   length = 20
FEATURE                  Location/Qualifiers
source                   1..20
                         mol_type = other RNA
                         organism = synthetic construct
SEQUENCE: 369
ccaggaatgg aaactcacgc                                                    20

SEQ ID NO: 370           moltype = RNA   length = 20
FEATURE                  Location/Qualifiers
source                   1..20
                         mol_type = other RNA
                         organism = synthetic construct
SEQUENCE: 370
gaggccgctg aattaacccg                                                    20

SEQ ID NO: 371           moltype = RNA   length = 20
FEATURE                  Location/Qualifiers
source                   1..20
                         mol_type = other RNA
                         organism = synthetic construct
SEQUENCE: 371
atacacgcac acttgcagaa                                                    20

SEQ ID NO: 372           moltype = RNA   length = 20
FEATURE                  Location/Qualifiers
source                   1..20
                         mol_type = other RNA
                         organism = synthetic construct
SEQUENCE: 372
gagcagacag aaacccaggg                                                    20

SEQ ID NO: 373           moltype = RNA   length = 20
FEATURE                  Location/Qualifiers
source                   1..20
```

```
                        mol_type = other RNA
                        organism = synthetic construct
SEQUENCE: 373
tgagtctcca aacagaacag                                               20

SEQ ID NO: 374          moltype = RNA   length = 20
FEATURE                 Location/Qualifiers
source                  1..20
                        mol_type = other RNA
                        organism = synthetic construct
SEQUENCE: 374
taatatcact gacttcacgg                                               20

SEQ ID NO: 375          moltype = RNA   length = 20
FEATURE                 Location/Qualifiers
source                  1..20
                        mol_type = other RNA
                        organism = synthetic construct
SEQUENCE: 375
tacacacaat gtaagcagca                                               20

SEQ ID NO: 376          moltype = RNA   length = 20
FEATURE                 Location/Qualifiers
source                  1..20
                        mol_type = other RNA
                        organism = synthetic construct
SEQUENCE: 376
gggagctcaa ttcgaaacca                                               20

SEQ ID NO: 377          moltype = RNA   length = 20
FEATURE                 Location/Qualifiers
source                  1..20
                        mol_type = other RNA
                        organism = synthetic construct
SEQUENCE: 377
ttggacaggt gagacagtcg                                               20

SEQ ID NO: 378          moltype = RNA   length = 20
FEATURE                 Location/Qualifiers
source                  1..20
                        mol_type = other RNA
                        organism = synthetic construct
SEQUENCE: 378
aagctcactc agatagtgtg                                               20

SEQ ID NO: 379          moltype = RNA   length = 20
FEATURE                 Location/Qualifiers
source                  1..20
                        mol_type = other RNA
                        organism = synthetic construct
SEQUENCE: 379
caggagaacc accttacacg                                               20

SEQ ID NO: 380          moltype = RNA   length = 20
FEATURE                 Location/Qualifiers
source                  1..20
                        mol_type = other RNA
                        organism = synthetic construct
SEQUENCE: 380
ggacagaccc tgattcacaa                                               20

SEQ ID NO: 381          moltype = RNA   length = 20
FEATURE                 Location/Qualifiers
source                  1..20
                        mol_type = other RNA
                        organism = synthetic construct
SEQUENCE: 381
acatggcagt ctatgaacag                                               20

SEQ ID NO: 382          moltype = RNA   length = 20
FEATURE                 Location/Qualifiers
source                  1..20
                        mol_type = other RNA
                        organism = synthetic construct
SEQUENCE: 382
cctatagaga gtactacttg                                               20

SEQ ID NO: 383          moltype = RNA   length = 20
FEATURE                 Location/Qualifiers
```

```
SEQ ID NO: 383
FEATURE                 moltype = RNA  length = 20
                        Location/Qualifiers
source                  1..20
                        mol_type = other RNA
                        organism = synthetic construct
SEQUENCE: 383
ccaaccgggt cttcattacg                                              20

SEQ ID NO: 384          moltype = RNA  length = 20
FEATURE                 Location/Qualifiers
source                  1..20
                        mol_type = other RNA
                        organism = synthetic construct
SEQUENCE: 384
tcaagcgtag agttccgagt                                              20

SEQ ID NO: 385          moltype = RNA  length = 20
FEATURE                 Location/Qualifiers
source                  1..20
                        mol_type = other RNA
                        organism = synthetic construct
SEQUENCE: 385
tcatgcaatt atggacccag                                              20

SEQ ID NO: 386          moltype = RNA  length = 20
FEATURE                 Location/Qualifiers
source                  1..20
                        mol_type = other RNA
                        organism = synthetic construct
SEQUENCE: 386
cgggaaagtg actggccatg                                              20

SEQ ID NO: 387          moltype = RNA  length = 20
FEATURE                 Location/Qualifiers
source                  1..20
                        mol_type = other RNA
                        organism = synthetic construct
SEQUENCE: 387
tgagattgaa atcaaatcgg                                              20

SEQ ID NO: 388          moltype = RNA  length = 20
FEATURE                 Location/Qualifiers
source                  1..20
                        mol_type = other RNA
                        organism = synthetic construct
SEQUENCE: 388
tatgcaatat tcatcacgcg                                              20

SEQ ID NO: 389          moltype = RNA  length = 20
FEATURE                 Location/Qualifiers
source                  1..20
                        mol_type = other RNA
                        organism = synthetic construct
SEQUENCE: 389
aatgtgttaa atcaaatgca                                              20
```

SYSTEMS TARGETING PSMA AND CA9

CROSS REFERENCE TO RELATED APPLICATIONS

This application claims the benefit of U.S. Provisional Application No. 63/488,386, filed Mar. 3, 2023; U.S. Provisional Application No. 63/489,837, filed Mar. 13, 2023; U.S. Provisional Application No. 63/495,869, filed Apr. 13, 2023; U.S. Provisional Application No. 63/578,854, filed Aug. 25, 2023; U.S. Provisional Application No. 63/601,617, filed Nov. 21, 2023; U.S. Provisional Application No. 63/613,712, filed Dec. 21, 2023; and U.S. Provisional Application No. 63/618,233, filed Jan. 5, 2024, each of which are hereby incorporated in their entirety by reference.

SEQUENCE LISTING

The instant application contains a Sequence Listing which is hereby incorporated by reference in its entirety. Said XML copy, created on Feb. 23, 2024, is named ANB-221WO_SL.XML, and is 443,727 bytes in size.

BACKGROUND

Cancer is a disease characterized by uncontrollable growth of cells. Many approaches to treating cancer have been tried, including drugs and radiation therapies. Recent cancer treatments have sought to use the body's own immune cells to attack cancer cells. One promising approach uses T cells that are taken from a patient and genetically engineered to produce chimeric antigen receptors, or CARs, receptor proteins that give the T cells a new ability to target a specific protein. The receptors are chimeric because they combine antigen-binding and T-cell activating functions into a single receptor.

Immunotherapy using CAR-T cells is promising because the modified T cells have the potential to recognize cancer cells in order to more effectively target and destroy them.

After the T cells are engineered with the CARs, the resulting CAR-T cells are introduced into patients to attack tumor cells. CAR-T cells can be either derived from T cells in a patient's own blood (autologous) or derived from the T cells of another healthy donor (allogeneic). Once CAR-T cells are infused into a patient, they come in contact with their targeted antigen on a cell. The CAR-T cells bind to the antigen and become activated. Upon antigen engagement, CAR T cells can proliferate exponentially, initiate antitumor cytokine production, and target tumor cell killing.

However, there remain some concerns and limitations to CAR T cell-based immunotherapy. Some CAR T cells may engage with normal cells expressing low levels of target antigens, leading to off target toxicity. For example, both primary and metastatic sites of ccRCC are highly vascularized, with the majority of tumor cells expressing elevated levels of carbonic anhydrase IX (CA9). However, CA9 is also expressed in healthy bile ducts and stomach tissue which has led to on-target, off-tumor toxicities in patients treated with constitutive CA9 CAR T cells. Thus, additional therapies that reduce off-target toxicity remain desirable.

SUMMARY

In one aspect, provided herein are isolated antibodies or antigen binding fragments thereof that binds to Carbonic Anhydrase IX (CA9) (SEQ ID NO: 1), comprising a variable heavy (VH) chain sequence comprising three heavy chain CDR sequences, CDR-H1, CDR-H2, and CDR-H3, of the VH sequences set forth in SEQ ID NOs: 99 or 110, and, optionally, a variable light (VL) chain sequence comprising three light chain CDR sequences, CDR-L1, CDR-L2, and CDR-L3, of the VL sequence set forth in SEQ ID NO: 100, optionally wherein:
  i. CDR-H1 comprises the sequence set forth in SEQ ID NO: 101, CDR-H2 comprises the sequence set forth in SEQ ID NO: 102, CDR-H3 comprises the sequence set forth in SEQ ID NO: 103, CDR-L1 comprises the sequence set forth in SEQ ID NO: 104, CDR-L2 comprises the sequence set forth in SEQ ID NO: 105, and CDR-L3 comprises the sequence set forth in SEQ ID NO: 106; or
  ii. CDR-H1 comprises the sequence set forth in SEQ ID NO: 111, CDR-H2 comprises the sequence set forth in SEQ ID NO: 112, CDR-H3 comprises the sequence set forth in SEQ ID NO: 113.

In some embodiments, the VH chain sequence comprises the VH sequence set forth in SEQ ID NO: 99, and the VL chain sequence comprises the VL sequence set forth in SEQ ID NO: 100.

In some embodiments, the antibody comprises an scFv.

In some embodiments, the scFv comprises the sequence set forth in SEQ ID NO: 98.

In some embodiments, the VH chain sequence comprises the VH sequence set forth in SEQ ID NO: 110.

In one aspect, provided herein are isolated receptors comprising an extracellular antigen-binding domain that binds to Carbonic Anhydrase IX (CA9) (SEQ ID NO: 1), comprising a variable heavy (VH) chain sequence comprising three heavy chain CDR sequences, CDR-H1, CDR-H2, and CDR-H3, of the VH sequence set forth in SEQ ID NO: 99 or 110, and, optionally, a variable light (VL) chain sequence comprising three light chain CDR sequences, CDR-L1, CDR-L2, and CDR-L3, of the VL sequence set forth in SEQ ID NO: 100, optionally wherein:
  i. CDR-H1 comprises the sequence set forth in SEQ ID NO: 101, CDR-H2 comprises the sequence set forth in SEQ ID NO: 102, CDR-H3 comprises the sequence set forth in SEQ ID NO: 103, CDR-L1 comprises the sequence set forth in SEQ ID NO: 104, CDR-L2 comprises the sequence set forth in SEQ ID NO: 105, and CDR-L3 comprises the sequence set forth in SEQ ID NO: 106; or
  ii. CDR-H1 comprises the sequence set forth in SEQ ID NO: 111, CDR-H2 comprises the sequence set forth in SEQ ID NO: 112, CDR-H3 comprises the sequence set forth in SEQ ID NO: 113.

In some embodiments, the VH chain sequence comprises the VH sequence set forth in SEQ ID NO: 99, and the VL chain sequence comprises the VL sequence set forth in SEQ ID NO: 100.

In some embodiments, the CAR comprises an scFv.

In some embodiments, the scFv comprises the sequence set forth in SEQ ID NO: 98.

In some embodiments, the VH chain sequence comprises the VH sequence set forth in SEQ ID NO: 110.

In some embodiments, the receptor is a chimeric antigen receptor (CAR) comprising, from N-terminus to C-terminus,
  i. the extracellular antigen-binding domain;
  ii. a transmembrane domain;
  iii. an optional intracellular co-stimulatory domain; and
  iv. an intracellular activation domain.

In some embodiments, the CAR further comprises a hinge domain.

In some embodiments, the hinge domain comprises a CD8α, truncated CD8α, or CD28 hinge domain.

In some embodiments, the transmembrane domain comprises a CD8α transmembrane domain or a CD28 transmembrane domain.

In some embodiments, the intracellular co-stimulatory domain comprises a 4-1BB domain.

In some embodiments, the intracellular activation domain comprises a CD3ζ domain.

In some embodiments, the CAR comprises a sequence as set forth in SEQ ID NOs: 108, 115, 250, or 251.

In one aspect, provided herein are isolated antibodies or antigen binding fragments thereof that binds to Prostate-Specific Membrane Antigen (PSMA) (SEQ ID NO: 2), comprising a variable heavy (VH) chain sequence comprising three heavy chain CDR sequences, CDR-H1, CDR-H2, and CDR-H3, of the VH sequences set forth in SEQ ID NOs: 118 or 130, and a variable light (VL) chain sequence comprising three light chain CDR sequences, CDR-L1, CDR-L2, and CDR-L3, of the VL sequences set forth in SEQ ID NOs: 119 or 131, optionally wherein:
  i. CDR-H1 comprises the sequence set forth in SEQ ID NO: 120, CDR-H2 comprises the sequence set forth in SEQ ID NO: 121, CDR-H3 comprises the sequence set forth in SEQ ID NO: 122, CDR-L1 comprises the sequence set forth in SEQ ID NO: 123, CDR-L2 comprises the sequence set forth in SEQ ID NO: 124, and CDR-L3 comprises the sequence set forth in SEQ ID NO: 125; or
  ii. CDR-H1 comprises the sequence set forth in SEQ ID NO: 132, CDR-H2 comprises the sequence set forth in SEQ ID NO: 133, CDR-H3 comprises the sequence set forth in SEQ ID NO: 134, CDR-L1 comprises the sequence set forth in SEQ ID NO: 135, CDR-L2 comprises the sequence set forth in SEQ ID NO: 136, and CDR-L3 comprises the sequence set forth in SEQ ID NO: 137.

In some embodiments, the VH chain sequence comprises the VH sequence set forth in SEQ ID NO: 118, and the VL chain sequence comprises the VL sequence set forth in SEQ ID NO: 119.

In some embodiments, the VH chain sequence comprises the VH sequence set forth in SEQ ID NO: 130, and the VL chain sequence comprises the VL sequence set forth in SEQ ID NO: 131.

In some embodiments, the antibody comprises an scFv.

In some embodiments, the scFv comprises the sequence set forth in SEQ ID NO: 117 or 129.

In one aspect, provided herein are isolated receptors comprising an extracellular antigen-binding domain that binds to Prostate-Specific Membrane Antigen (PSMA) (SEQ ID NO: 2), comprising a variable heavy (VH) chain sequence comprising three heavy chain CDR sequences, CDR-H1, CDR-H2, and CDR-H3, of the VH sequences set forth in SEQ ID NOs: 118 or 130, and a variable light (VL) chain sequence comprising three light chain CDR sequences, CDR-L1, CDR-L2, and CDR-L3, of the VL sequences set forth in SEQ ID NOs: 119 or 131, optionally wherein:
  i. CDR-H1 comprises the sequence set forth in SEQ ID NO: 120, CDR-H2 comprises the sequence set forth in SEQ ID NO: 121, CDR-H3 comprises the sequence set forth in SEQ ID NO: 122, CDR-L1 comprises the sequence set forth in SEQ ID NO: 123, CDR-L2 comprises the sequence set forth in SEQ ID NO: 124, and CDR-L3 comprises the sequence set forth in SEQ ID NO: 125; or
  ii. CDR-H1 comprises the sequence set forth in SEQ ID NO: 132, CDR-H2 comprises the sequence set forth in SEQ ID NO: 133, CDR-H3 comprises the sequence set forth in SEQ ID NO: 134, CDR-L1 comprises the sequence set forth in SEQ ID NO: 135, CDR-L2 comprises the sequence set forth in SEQ ID NO: 136, and CDR-L3 comprises the sequence set forth in SEQ ID NO: 137.

In some embodiments, the VH chain sequence comprises the VH sequence set forth in SEQ ID NO: 118, and the VL chain sequence comprises the VL sequence set forth in SEQ ID NO: 119.

In some embodiments, the VH chain sequence comprises the VH sequence set forth in SEQ ID NO: 130, and the VL chain sequence comprises the VL sequence set forth in SEQ ID NO: 131.

In some embodiments, the priming receptor comprises an scFv.

In some embodiments, the scFv comprises the sequence set forth in SEQ ID NO: 117 or 129.

In some embodiments, the receptor is a priming receptor comprising, from N-terminus to C-terminus,
  i. the extracellular antigen-binding domain;
  ii. a transmembrane domain comprising one or more ligand-inducible proteolytic cleavage sites; and
  iii. an intracellular domain comprising a human or humanized transcriptional effector, wherein binding of PSMA by the first extracellular antigen-binding domain results in cleavage at the one or more ligand-inducible proteolytic cleavage sites.

In some embodiments, the priming receptor further comprises a hinge domain positioned between the extracellular antigen-binding domain and the transmembrane domain.

In some embodiments, the hinge domain comprises a CD8α or truncated CD8α hinge domain.

In some embodiments, the hinge domain comprises the sequence as set forth in SEQ ID NO: 85.

In some embodiments, the transmembrane domain comprises a Notch1 transmembrane domain.

In some embodiments, the transmembrane domain comprises the sequence as set forth in SEQ ID NO: 86.

In some embodiments, the intracellular domain comprises an HNF1α/p65 domain or a Gal4/VP64 domain.

In some embodiments, the intracellular domain comprises the sequence as set forth in SEQ ID NO: 88, 89, or 90.

In some embodiments, rein the priming receptor further comprises a stop-transfer-sequence or juxtamembrane domain between the transmembrane domain and the intracellular domain.

In some embodiments, the stop-transfer-sequence or juxtamembrane domain comprises the sequence as set forth in SEQ ID NO: 87.

In some embodiments, the priming receptor comprises a sequence as set forth in SEQ ID NO: 127, 138, 252, or 253.

In one aspect, provided herein are systems comprising:
  i. a first chimeric polypeptide comprises a priming receptor comprising a first extracellular antigen-binding domain that specifically binds Prostate-Specific Membrane Antigen (PSMA) (SEQ ID NO: 2);
  ii. a second chimeric polypeptide comprising a chimeric antigen receptor (CAR) comprising a second extracellular antigen-binding domain that specifically binds to Carbonic Anhydrase IX (CA9) (SEQ ID NO: 1);
  iii. an optional third chimeric polypeptide comprising a synthetic pathway activator (SPA); and iv. at least one or more nucleic acids comprising a nucleic acid sequence at least 15 nucleotides in length complementary to:
   1. a nucleic acid encoding human Fas Cell Surface Death Receptor (FAS) comprising the sequence set forth in SEQ ID NO: 3; and
   2. a nucleic acid encoding human Transforming Growth factor (TGF)-β Receptor 2 (TGFBR2) comprising the sequence set forth in SEQ ID NO: 4.

In some embodiments, the first extracellular antigen-binding domain comprises a first variable heavy (VH) chain sequence comprising three heavy chain CDR sequences, CDR-H1, CDR-H2, and CDR-H3, of the VH sequences set forth in SEQ ID NOs: 118 or 130, and a first variable light (VL) chain sequence comprising three light chain CDR sequences, CDR-L1, CDR-L2, and CDR-L3, of the VL sequences set forth in SEQ ID NOs: 119 or 131, optionally wherein:
   i. CDR-H1 comprises the sequence set forth in SEQ ID NO: 120, CDR-H2 comprises the sequence set forth in SEQ ID NO: 121, CDR-H3 comprises the sequence set forth in SEQ ID NO: 122, CDR-L1 comprises the sequence set forth in SEQ ID NO: 123, CDR-L2 comprises the sequence set forth in SEQ ID NO: 124, and CDR-L3 comprises the sequence set forth in SEQ ID NO: 125; or
   ii. CDR-H1 comprises the sequence set forth in SEQ ID NO: 132, CDR-H2 comprises the sequence set forth in SEQ ID NO: 133, CDR-H3 comprises the sequence set forth in SEQ ID NO: 134, CDR-L1 comprises the sequence set forth in SEQ ID NO: 135, CDR-L2 comprises the sequence set forth in SEQ ID NO: 136, and CDR-L3 comprises the sequence set forth in SEQ ID NO: 137.

In some embodiments, the first VH chain sequence comprises the sequence set forth in SEQ ID NO: 118 or 130.

In some embodiments, the first VL chain sequence comprises the sequence set forth in SEQ ID NO: 119 or 131.

In some embodiments, the first extracellular antigen-binding domain comprises the sequence set forth in SEQ ID NO: 117 or 129.

In some embodiments, the second extracellular antigen-binding domain comprises a second variable heavy (VH) chain sequence comprising three heavy chain CDR sequences, CDR-H1, CDR-H2, and CDR-H3, of the VH sequences set forth in SEQ ID NOs: 99 or 110, and, optionally, a second variable light (VL) chain sequence comprising three light chain CDR sequences, CDR-L1, CDR-L2, and CDR-L3, of the VL sequence set forth in SEQ ID NO: 100, optionally wherein:
   i. CDR-H1 comprises the sequence set forth in SEQ ID NO: 101, CDR-H2 comprises the sequence set forth in SEQ ID NO: 102, CDR-H3 comprises the sequence set forth in SEQ ID NO: 103, CDR-L1 comprises the sequence set forth in SEQ ID NO: 104, CDR-L2 comprises the sequence set forth in SEQ ID NO: 105, and CDR-L3 comprises the sequence set forth in SEQ ID NO: 106; or
   ii. CDR-H1 comprises the sequence set forth in SEQ ID NO: 111, CDR-H2 comprises the sequence set forth in SEQ ID NO: 112, CDR-H3 comprises the sequence set forth in SEQ ID NO: 113.

In some embodiments, the second VH comprises the sequence as set forth in SEQ ID NO: 99 or 110.

In some embodiments, the second VL comprises the sequence set forth in SEQ ID NO: 100.

In some embodiments, the second extracellular domain comprises the sequence set forth in SEQ ID NO: 98 or 110.

In one aspect, provided herein are systems comprising:
   i. a first chimeric polypeptide comprises a priming receptor comprising a first extracellular antigen-binding domain that specifically binds Prostate-Specific Membrane Antigen (PSMA) (SEQ ID NO: 2), wherein the first extracellular antigen-binding domain comprises a variable heavy (VH) chain sequence comprising three heavy chain CDR sequences, CDR-H1, CDR-H2, and CDR-H3, of the VH sequences set forth in SEQ ID NOs: 118 or 130, and a variable light (VL) chain sequence comprising three light chain CDR sequences, CDR-L1, CDR-L2, and CDR-L3, of the VL sequences set forth in SEQ ID NOs: 119 or 131, optionally wherein:
   ii. CDR-H1 comprises the sequence set forth in SEQ ID NO: 120, CDR-H2 comprises the sequence set forth in SEQ ID NO: 121, CDR-H3 comprises the sequence set forth in SEQ ID NO: 122, CDR-L1 comprises the sequence set forth in SEQ ID NO: 123, CDR-L2 comprises the sequence set forth in SEQ ID NO: 124, and CDR-L3 comprises the sequence set forth in SEQ ID NO: 125; or
   iii. CDR-H1 comprises the sequence set forth in SEQ ID NO: 132, CDR-H2 comprises the sequence set forth in SEQ ID NO: 133, CDR-H3 comprises the sequence set forth in SEQ ID NO: 134, CDR-L1 comprises the sequence set forth in SEQ ID NO: 135, CDR-L2 comprises the sequence set forth in SEQ ID NO: 136, and CDR-L3 comprises the sequence set forth in SEQ ID NO: 137.
   iv. a second chimeric polypeptide comprises a chimeric antigen receptor (CAR);
   v. an optional third chimeric polypeptide comprising a synthetic pathway activator (SPA); and
   vi. at least one or more nucleic acids comprising a nucleic acid sequence at least 15 nucleotides in length complementary to:
      1. a nucleic acid encoding human Fas Cell Surface Death Receptor (FAS) comprising the sequence set forth in SEQ ID NO: 3; and
      2. a nucleic acid encoding human Transforming Growth factor (TGF)-β Receptor 2 (TGFBR2) comprising the sequence set forth in SEQ ID NO: 4.

In some embodiments, the VH chain sequence comprises the sequence set forth in SEQ ID NO: 118 or 130.

In some embodiments, the VL chain sequence comprises the sequence set forth in SEQ ID NO: 119 or 131.

In some embodiments, the first extracellular antigen-binding domain comprises the sequence set forth in SEQ ID NO: 117 or 129.

In some embodiments, the CAR comprises a second extracellular antigen-binding domain that specifically binds to Carbonic Anhydrase IX (CA9) (SEQ ID NO: 1).

In some embodiments, the second extracellular antigen-binding domain comprises a variable heavy (VH) chain sequence comprising three heavy chain CDR sequences, CDR-H1, CDR-H2, and CDR-H3, of the VH sequences set forth in SEQ ID NOs: 99 or 110, and optionally, a variable light (VL) chain sequence comprising three light chain CDR sequences, CDR-L1, CDR-L2, and CDR-L3, of the VL sequence set forth in SEQ ID NO: 100, optionally wherein:
   i. CDR-H1 comprises the sequence set forth in SEQ ID NO: 101, CDR-H2 comprises the sequence set forth in SEQ ID NO: 102, CDR-H3 comprises the sequence set forth in SEQ ID NO: 103, CDR-L1 comprises the sequence set forth in SEQ ID NO: 104, CDR-L2 comprises the sequence set forth in SEQ ID NO: 105, and CDR-L3 comprises the sequence set forth in SEQ ID NO: 106; or ii. CDR-H1 comprises the sequence set forth in SEQ ID NO: 111, CDR-H2 comprises the sequence set forth in SEQ ID NO: 112, CDR-H3 comprises the sequence set forth in SEQ ID NO: 113.

In some embodiments, the VH comprises the sequence as set forth in SEQ ID NO: 99 or 110.

In some embodiments, the VL comprises the sequence set forth in SEQ ID NO: 100.

In some embodiments, the second extracellular domain comprises the sequence set forth in SEQ ID NO: 98 or 110.

In one aspect, provided herein are systems comprising:
i. a first chimeric polypeptide comprises a priming receptor, and
ii. a second chimeric polypeptide comprises a chimeric antigen receptor (CAR) comprising a second extracellular antigen-binding domain that specifically binds to Carbonic Anhydrase IX (CA9) (SEQ ID NO: 1), wherein the extracellular antigen-binding domain comprises a single domain antibody comprising a variable heavy (VH) chain sequence comprising three heavy chain CDR sequences, CDR-H1, CDR-H2, and CDR-H3 of the VH sequences set forth in SEQ ID NOs: 99 or 110, and optionally a variable light (VL) chain sequence comprising three light chain CDR sequences, CDR-L1, CDR-L2, and CDR-L3 of the VL sequence set forth in SEQ ID NOs: 110, optionally wherein:
iii. CDR-H1 comprises the sequence set forth in SEQ ID NO: 101, CDR-H2 comprises the sequence set forth in SEQ ID NO: 102, CDR-H3 comprises the sequence set forth in SEQ ID NO: 103, CDR-L1 comprises the sequence set forth in SEQ ID NO: 104, CDR-L2 comprises the sequence set forth in SEQ ID NO: 105, and CDR-L3 comprises the sequence set forth in SEQ ID NO: 106; or
iv. CDR-H1 comprises the sequence set forth in SEQ ID NO: 111, CDR-H2 comprises the sequence set forth in SEQ ID NO: 112, CDR-H3 comprises the sequence set forth in SEQ ID NO: 113;
v. an optional third chimeric polypeptide comprising a synthetic pathway activator (SPA); and
vi. at least one or more nucleic acids comprising a nucleic acid sequence at least 15 nucleotides in length complementary to:
1. a nucleic acid encoding human Fas Cell Surface Death Receptor (FAS) comprising the sequence set forth in SEQ ID NO: 3; and
2. a nucleic acid encoding human Transforming Growth factor (TGF)-β Receptor 2 (TGFBR2) comprising the sequence set forth in SEQ ID NO: 4.

In some embodiments, the VH chain sequence comprises the sequence set forth in SEQ ID NO: 99 or 110.

In some embodiments, the VL comprises the sequence set forth in SEQ ID NO: 100.

In some embodiments, the second extracellular domain comprises the sequence set forth in SEQ ID NO: 98 or 110.

In some embodiments, the priming receptor comprises a first extracellular antigen-binding domain that specifically binds to Prostate-Specific Membrane Antigen (PSMA).

In some embodiments, the first extracellular antigen-binding domain comprises a variable heavy (VH) chain sequence comprising three heavy chain CDR sequences, CDR-H1, CDR-H2, and CDR-H3, of the VH sequences set forth in SEQ ID NOs: 118 or 130, and a variable light (VL) chain sequence comprising three light chain CDR sequences, CDR-L1, CDR-L2, and CDR-L3, of the VL sequences set forth in SEQ ID NOs: 119 or 131, optionally wherein:

i. CDR-H1 comprises the sequence set forth in SEQ ID NO: 120, CDR-H2 comprises the sequence set forth in SEQ ID NO: 121, CDR-H3 comprises the sequence set forth in SEQ ID NO: 122, CDR-L1 comprises the sequence set forth in SEQ ID NO: 123, CDR-L2 comprises the sequence set forth in SEQ ID NO: 124, and CDR-L3 comprises the sequence set forth in SEQ ID NO: 125; or ii. CDR-H1 comprises the sequence set forth in SEQ ID NO: 132, CDR-H2 comprises the sequence set forth in SEQ ID NO: 133, CDR-H3 comprises the sequence set forth in SEQ ID NO: 134, CDR-L1 comprises the sequence set forth in SEQ ID NO: 135, CDR-L2 comprises the sequence set forth in SEQ ID NO: 136, and CDR-L3 comprises the sequence set forth in SEQ ID NO: 137.

In some embodiments, the VH comprises the sequence as set forth in SEQ ID NO: 118 or 130.

In some embodiments, the VL comprises the sequence set forth in SEQ ID NO: 119 or 131.

In some embodiments, the first extracellular domain comprises the sequence set forth in SEQ ID NO: 117 or 129.

In some embodiments, the priming receptor comprises, from N-terminus to C-terminus,
i. the first extracellular antigen-binding domain;
ii. a first transmembrane domain comprising one or more ligand-inducible proteolytic cleavage sites; and
iii. an intracellular domain comprising a human or humanized transcriptional effector, wherein binding of PSMA by the first extracellular antigen-binding domain results in cleavage at the one or more ligand-inducible proteolytic cleavage sites.

In some embodiments, the priming receptor further comprises a first hinge domain positioned between the first extracellular antigen-binding domain and the first transmembrane domain.

In some embodiments, the first hinge domain comprises a CD8α or truncated CD8α hinge domain.

In some embodiments, the first hinge comprises the sequence as set forth in SEQ ID NO: 85.

In some embodiments, the first transmembrane domain comprises a Notch1 transmembrane domain.

In some embodiments, the transmembrane domain comprises the sequence as set forth in SEQ ID NO: 86.

In some embodiments, the intracellular domain comprises an HNF1α/p65 domain or a Gal4/VP64 domain.

In some embodiments, the intracellular domain comprises the sequence as set forth in SEQ ID NO: 88, 89, or 90.

In some embodiments, the priming receptor further comprises a stop-transfer-sequence or juxtamembrane domain between the first transmembrane domain and the intracellular domain.

In some embodiments, the stop-transfer-sequence or juxtamembrane domain comprises the sequence as set forth in SEQ ID NO: 87.

In some embodiments, the priming receptor comprises a sequence as set forth in SEQ ID NO: 127, 138, 252, or 253.

In some embodiments, the CAR comprises, from N-terminus to C-terminus,
i. a second extracellular antigen-binding domain;
ii. a second transmembrane domain;
iii. an intracellular co-stimulatory domain; and
iv. an intracellular activation domain.

In some embodiments, the CAR comprises a second hinge domain.

In some embodiments, the second hinge domain comprises a CD8α or truncated CD8α hinge domain.

In some embodiments, the second transmembrane domain comprises a CD8α transmembrane domain.

In some embodiments, the intracellular co-stimulatory domain comprises a 4-1BB domain.

In some embodiments, the intracellular activation domain comprises a CD3ζ domain.

In some embodiments, the CAR comprises a sequence as set forth in SEQ ID NOs: 108, 115, 250, or 251.

In some embodiments, the priming receptor and the CAR are capable of binding to a same target cell if the target cell expresses PSMA and CA9.

In some embodiments, the at least one or more nucleic acid sequences are at least 16, 17, 18, 19, 20, 21, or 22 nucleotides in length.

In some embodiments, the at least one or more nucleic acid sequences are a short hairpin RNA (shRNA), a small interfering RNA (siRNA), a double stranded RNA (dsRNA), or an antisense oligonucleotide.

In some embodiments, the at least one or more nucleic acid sequences are shRNA.

In some embodiments, the at least one or more nucleic acids comprises a sequence selected from the group consisting of the sequences set forth in SEQ ID NOs: 6-82.

In some embodiments, the nucleic acid sequence complementary to human FAS comprises a sequence selected from the group consisting of the sequences set forth in SEQ ID NOs: 6-20.

In some embodiments, the nucleic acid reduces expression of FAS in the immune cell by at least 10%, 15%, 20%, 25%, 30%, 35%, 40%, 45%, 50%, 55%, 60%, 65%, 75%, 80%, 85%, 90%, 95%, or 99% as compared to a control cell that does not comprise the nucleic acid.

In some embodiments, the nucleic acid sequence complementary to human TGFBR2 comprises a sequence selected from the group consisting of the sequences set forth in SEQ ID NOs: 34-82.

In some embodiments, the nucleic acid reduces expression of TGFBR2 in the immune cell by at least 10%, 15%, 20%, 25%, 30%, 35%, 40%, 45%, 50%, 55%, 60%, 65%, 75%, 80%, 85%, 90%, 95%, or 99% as compared to a control cell that does not comprise the nucleic acid.

In some embodiments, the system comprises at least two nucleic acid sequences complementary to human TGFBR2 selected from the group consisting of the sequences set forth in SEQ ID NOs: 34-82.

In some embodiments, the system comprises at least a first nucleic acid sequence complementary to a nucleic acid encoding human FAS comprising the sequence set forth in SEQ ID NO: 3, a second nucleic acid sequence complementary to a nucleic acid encoding human TGF-β Receptor 2 (TGFBR2) comprising the sequence set forth in SEQ ID NO: 4.

In some embodiments, the nucleic acid sequence is complementary to nucleotides 1126 to 1364 of a nucleic acid encoding human FAS comprising the sequence set forth in SEQ ID NO: 3.

In some embodiments, the first nucleic acid reduces expression of FAS in the immune cell by at least 10%, 15%, 20%, 25%, 30%, 35%, 40%, 45%, 50%, 55%, 60%, 65%, 75%, 80%, 85%, 90%, 95%, or 99% as compared to a control cell that does not comprise the nucleic acid and the second nucleic acid reduces expression of TGFBR2 in the immune cell by at least 10%, 15%, 20%, 25%, 30%, 35%, 40%, 45%, 50%, 55%, 60%, 65%, 75%, 80%, 85%, 90%, 95%, or 99% as compared to a control cell that does not comprise the nucleic acid.

In some embodiments, the system further comprises a third nucleic acid sequence complementary to mRNA encoding human TGF-β Receptor 2 (TGFBR2) comprising the sequence set forth in SEQ ID NO: 4.

In some embodiments, the third nucleic acid reduces expression of TGFBR2 in the immune cell by at least 10%, 15%, 20%, 25%, 30%, 35%, 40%, 45%, 50%, 55%, 60%, 65%, 75%, 80%, 85%, 90%, 95%, or 99% as compared to a control cell that does not comprise the nucleic acid.

In some embodiments, further comprising at least one nucleic acid sequence complementary to a nucleic acid encoding human Protein Tyrosine Phosphatase Non-Receptor Type 2 (PTPN2) comprising the sequence set forth in SEQ ID NO: 5.

In some embodiments, the nucleic acid sequence is complementary to nucleotides 518 to 559 of a nucleic acid encoding human Protein Tyrosine Phosphatase Non-Receptor Type 2 (PTPN2) comprising the sequence set forth in SEQ ID NO: 5.

In some embodiments, the nucleic acid sequence complementary to human PTPN2 comprises a sequence selected from the group consisting of the sequences set forth in SEQ ID NOs: 21-33.

In some embodiments, the nucleic acid reduces expression of PTPN2 in the immune cell by at least 10%, 15%, 20%, 25%, 30%, 35%, 40%, 45%, 50%, 55%, 60%, 65%, 75%, 80%, 85%, 90%, 95%, or 99% as compared to a control cell that does not comprise the nucleic acid.

In some embodiments, the SPA is an activator of STAT phosphorylation, optionally STAT1, STAT3, and/or STAT5 phosphorylation.

In some embodiments, the SPA comprises an extracellular domain linked to an intracellular signaling domain.

In some embodiments, the intracellular signaling domain comprises an intracellular signaling region derived from a cytokine receptor.

In some embodiments, the intracellular signaling domain comprises a polypeptide sequence derived from an interleukin receptor.

In some embodiments, the cytokine receptor comprises interleukin-6 signal transducer (IL6ST).

In some embodiments, the SPA comprises the sequence as set forth in SEQ ID NO: 141 or 254.

In some embodiments, the extracellular domain conveys constitutive activity to the intracellular signaling domain.

In some embodiments, the target cell is a human cell.

In some embodiments, the target cell is a cancer cell.

In some embodiments, the cancer cell is a solid cancer cell or a liquid cancer cell.

In some embodiments, the cancer cell is a kidney cell, a colon cell, or a lung cell.

In one aspect, provided herein are nucleic acids comprising a nucleotide sequence encoding the antibodies disclosed herein.

In one aspect, provided herein are nucleic acids comprising a nucleotide sequence encoding the antibodies disclosed herein.

In one aspect, provided herein are nucleic acids comprising a nucleotide sequence encoding the chimeric antigen receptors disclosed herein.

In one aspect, provided herein are nucleic acids comprising a nucleotide sequence encoding the priming receptors disclosed herein.

In one aspect, provided herein are one or more nucleic acids comprising at least one nucleic acid fragment comprising a nucleotide sequence encoding the systems disclosed herein.

In one aspect, provided herein are one or more nucleic acids, wherein the one or more nucleic acids encode:
  i. a first chimeric polypeptide comprising a priming receptor comprising a first extracellular antigen-binding domain that specifically binds Prostate-Specific Membrane Antigen (PSMA);
  ii. a second chimeric polypeptide comprising a chimeric antigen receptor (CAR) comprising a second extracellular antigen-binding domain that specifically binds to Carbonic Anhydrase IX (CA9);
  iii. an optional third chimeric polypeptide comprising a synthetic pathway activator (SPA) and
  iv. at least one nucleic acid sequence at least 15 nucleotides in length complementary to:
    1. a nucleic acid encoding human Fas Cell Surface Death Receptor (FAS) comprising the sequence set forth in SEQ ID NO: 3; and
    2. a nucleic acid encoding human Transforming Growth factor (TGF)-β Receptor 2 (TGFBR2) comprising the sequence set forth in SEQ ID NO: 4.

In some embodiments, the nucleic acid sequence is complementary to nucleotides 1126 to 1364 of a nucleic acid encoding human FAS comprising the sequence set forth in SEQ ID NO: 3.

In some embodiments, the first extracellular antigen-binding domain comprises a heavy chain comprising a first variable heavy (VH) chain sequence comprising three heavy chain CDR sequences, CDR-H1, CDR-H2, and CDR-H3, of the VH sequences set forth in SEQ ID NOs: 118 or 130, and a light chain comprising a first variable light (VL) chain sequence comprising three light chain CDR sequences, CDR-L1, CDR-L2, and CDR-L3, of the VL sequences set forth in SEQ ID NOs: 119 or 131, optionally wherein:
  i. CDR-H1 comprises the sequence set forth in SEQ ID NO: 120, CDR-H2 comprises the sequence set forth in SEQ ID NO: 121, CDR-H3 comprises the sequence set forth in SEQ ID NO: 122, CDR-L1 comprises the sequence set forth in SEQ ID NO: 123, CDR-L2 comprises the sequence set forth in SEQ ID NO: 124, and CDR-L3 comprises the sequence set forth in SEQ ID NO: 125; or
  ii. CDR-H1 comprises the sequence set forth in SEQ ID NO: 132, CDR-H2 comprises the sequence set forth in SEQ ID NO: 133, CDR-H3 comprises the sequence set forth in SEQ ID NO: 134, CDR-L1 comprises the sequence set forth in SEQ ID NO: 135, CDR-L2 comprises the sequence set forth in SEQ ID NO: 136, and CDR-L3 comprises the sequence set forth in SEQ ID NO: 137.

In some embodiments, the first VH chain sequence comprises the VH sequence set forth in SEQ ID NO: 118 or 130, and the first VL chain sequence comprises the VL sequence set forth in SEQ ID NO: 119 or 131.

In some embodiments, the first extracellular antigen-binding domain comprises the sequence set forth in SEQ ID NO: 117 or 129.

In some embodiments, the second extracellular antigen-binding domain comprises a heavy chain comprising a second variable heavy (VH) chain sequence comprising three heavy chain CDR sequences, CDR-H1, CDR-H2, and CDR-H3, of the VH sequences set forth in SEQ ID NOs: 99 or 110, and, optionally, a light chain comprising a second variable light (VL) chain sequence comprising three light chain CDR sequences, CDR-L1, CDR-L2, and CDR-L3, of the VL sequence set forth in SEQ ID NO: 100, optionally wherein
  i. CDR-H1 comprises the sequence set forth in SEQ ID NO: 101, CDR-H2 comprises the sequence set forth in SEQ ID NO: 102, CDR-H3 comprises the sequence set forth in SEQ ID NO: 103, CDR-L1 comprises the sequence set forth in SEQ ID NO: 104, CDR-L2 comprises the sequence set forth in SEQ ID NO: 105, and CDR-L3 comprises the sequence set forth in SEQ ID NO: 106; or
  ii. CDR-H1 comprises the sequence set forth in SEQ ID NO: 111, CDR-H2 comprises the sequence set forth in SEQ ID NO: 112, CDR-H3 comprises the sequence set forth in SEQ ID NO: 113.

In some embodiments, the second VH comprises the sequence as set forth in SEQ ID NO: 99 or 110.

In some embodiments, the second VL comprises the sequence set forth in SEQ ID NO: 100.

In some embodiments, the second extracellular domain comprises the sequence set forth in SEQ ID NO: 98 or 110.

In some embodiments, the at least one nucleic acid sequences are at least 16, 17, 18, 19, 20, 21, or 22 nucleotides in length.

In some embodiments, the at least one nucleic acid sequences are a short hairpin RNA (shRNA), a small interfering RNA (siRNA), a double stranded RNA (dsRNA), or an antisense oligonucleotide.

In some embodiments, the at least one nucleic acid sequences are shRNA.

In some embodiments, the at least one or more nucleic acids comprises a sequence selected from the group consisting of the sequences set forth in SEQ ID NOs: 6-82.

In some embodiments, the at least one or more nucleic acids comprises a sequence selected from the group consisting of the sequences set forth in SEQ ID NOs: 6-20.

In some embodiments, the at least one or more nucleic acid reduces expression of FAS in the immune cell by at least 10%, 15%, 20%, 25%, 30%, 35%, 40%, 45%, 50%, 55%, 60%, 65%, 75%, 80%, 85%, 90%, 95%, or 99% as compared to a control cell that does not comprise the nucleic acid.

In some embodiments, the at least one or more nucleic acid comprises a sequence selected from the group consisting of the sequences set forth in SEQ ID NOs: 34-82.

In some embodiments, the at least one or more nucleic acid reduces expression of TGFBR2 in the immune cell by at least 10%, 15%, 20%, 25%, 30%, 35%, 40%, 45%, 50%, 55%, 60%, 65%, 75%, 80%, 85%, 90%, 95%, or 99% as compared to a control cell that does not comprise the nucleic acid.

In some embodiments, the at least one or more nucleic acids further comprise at least one nucleic acid sequence complementary to a nucleic acid encoding human Protein Tyrosine Phosphatase Non-Receptor Type 2 (PTPN2) comprising the sequence set forth in SEQ ID NO: 5.

In some embodiments, the nucleic acid sequence is complementary to nucleotides 518 to 559 of a nucleic acid encoding human Protein Tyrosine Phosphatase Non-Receptor Type 2 (PTPN2) comprising the sequence set forth in SEQ ID NO: 5.

In some embodiments, the nucleic acid sequence complementary to human PTPN2 comprises a sequence selected from the group consisting of the sequences set forth in SEQ ID NOs: 21-33.

In some embodiments, the nucleic acid reduces expression of PTPN2 in the immune cell by at least 10%, 15%, 20%, 25%, 30%, 35%, 40%, 45%, 50%, 55%, 60%, 65%, 75%, 80%, 85%, 90%, 95%, or 99% as compared to a control cell that does not comprise the nucleic acid In some embodiments, the at least one or more nucleic acid sequence is encoded in at least one intron region of the nucleic acid.

In some embodiments, the nucleic acid is selected from the group consisting of the sequences set forth in SEQ ID NOs: 143-147.

In one aspect, provided herein are one or more nucleic acids comprising at least one nucleic acid fragment comprising a nucleotide sequence encoding a priming receptor comprising a first extracellular antigen-binding domain that specifically binds to PSMA, a nucleotide sequence encoding a chimeric antigen receptor comprising an second extracellular antigen-binding domain that specifically binds to CA9, a synthetic pathway activator (SPA); and at least one nucleic acid sequence at least 15 nucleotides in length, wherein the at least one nucleic acid sequence comprises one or more of: (1) a first nucleic acid sequence complementary to a nucleic acid encoding human Fas Cell Surface Death Receptor (FAS) comprising the sequence set forth in SEQ ID NO: 3, and (2) a second nucleic acid sequence complementary to a nucleic acid encoding human Transforming Growth factor (TGF)-β Receptor 2 (TGFBR2) comprising the sequence set forth in SEQ ID NO: 4.

In some embodiments, the nucleic acid sequence is complementary to nucleotides 1126 to 1364 of a nucleic acid encoding human FAS comprising the sequence set forth in SEQ ID NO: 3.

In one aspect, provided herein are one or more nucleic acids comprising at least one nucleic acid fragment comprising the nucleic acid(s) disclosed herein.

In some embodiments, the nucleic acid comprises two or more nucleic acid fragments.

In some embodiments, the nucleic acid further comprises an inducible promoter operably linked to the nucleotide sequence encoding the CAR.

In some embodiments, the nucleic acid further comprises a constitutive promoter operably linked to the nucleotide sequence encoding the priming receptor.

In some embodiments, the nucleic acid further comprises an inducible promoter operably linked to the nucleotide sequence encoding the chimeric antigen receptor and a constitutive promoter operably linked to the nucleotide sequence encoding the priming receptor.

In some embodiments, the constitutive promoter is EF1α.

In some embodiments, the EF1α promoter comprises a sequence as set forth in SEQ ID NO: 179.

In some embodiments, the inducible promoter comprises one or more Hepatocyte Nuclear Factor 1α (HNF1α) enhancer element(s).

In some embodiments, the inducible promoter the inducible promoter further comprises a YB-TATA promoter sequence.

In some embodiments, the inducible promoter comprises a sequence as set forth in SEQ ID NO: 256.

In some embodiments, the nucleic acid comprises, in a 5' to 3' direction,
  i. the constitutive promoter;
  ii. the nucleotide sequence encoding priming receptor;
  iii. the inducible promoter;
  iv. the nucleotide sequence encoding chimeric antigen receptor; and
  v. the optional nucleotide sequence encoding the SPA.

In some embodiments, the nucleic acid comprises, in a 5' to 3' direction,
  i. the inducible promoter;
  ii. the nucleotide sequence encoding chimeric antigen receptor;
  iii. the constitutive promoter; and
  iv. the nucleotide sequence encoding priming receptor; and
  v. the optional nucleotide sequence encoding the SPA.

In some embodiments, the nucleic acid comprises, in a 5' to 3' direction,
  i. the first constitutive promoter;
  ii. the nucleotide sequence encoding the priming receptor;
  iii. the second constitutive promoter;
  iv. the nucleotide sequence encoding the at least one nucleic acid complementary to human FAS or human TGFBR2;
  v. the inducible promoter;
  vi. the optional nucleotide sequence encoding the chimeric antigen receptor; and
  vii. the nucleotide sequence encoding the SPA.

In some embodiments, the nucleic acid comprises, in a 5' to 3' direction,
  i. the first constitutive promoter;
  ii. the nucleotide sequence encoding the priming receptor;
  iii. the second constitutive promoter;
  iv. the nucleotide sequence encoding the first nucleic acid complementary to human FAS or the nucleotide sequence encoding the second nucleic acid complementary to human TGFBR2;
  v. the nucleotide sequence encoding the first nucleic acid complementary to human FAS or the nucleotide sequence encoding the second nucleic acid complementary to human TGFBR2;
  vi. the inducible promoter;
  vii. the nucleotide sequence encoding the chimeric antigen receptor; and
  viii. the optional nucleotide sequence encoding the SPA.

In some embodiments, the nucleic acid comprises, in a 5' to 3' direction,
  i. the inducible promoter;
  ii. the nucleotide sequence encoding the chimeric antigen receptor;
  iii. the second constitutive promoter;
  iv. the nucleotide sequence encoding the first nucleic acid complementary to human FAS or the nucleotide sequence encoding the second nucleic acid complementary to human TGFBR2;
  v. the nucleotide sequence encoding the first nucleic acid complementary to human FAS or the nucleotide sequence encoding the second nucleic acid complementary to human TGFBR2;
  vi. the first constitutive promoter; and
  vii. the nucleotide sequence encoding the priming receptor; and
  viii. the optional nucleotide sequence encoding the SPA.

In some embodiments, the nucleic acid is selected from the group consisting of the sequences set forth in SEQ ID NOs: 143-147.

In some embodiments, the nucleic acid further comprises a 5' homology directed repair arm and a 3' homology directed repair arm complementary to an insertion site in a host cell chromosome.

In some embodiments, the nucleic acid further comprises a nucleotide sequence encoding a self-excising 2A peptide (P2A).

In some embodiments, the P2A is at the 3' end of the nucleotide sequence encoding chimeric antigen receptor.

In some embodiments, the P2A is at the 3' end of the nucleotide sequence encoding priming receptor.

In some embodiments, the nucleic acid further comprises a woodchuck hepatitis virus post-translational regulatory element (WPRE).

In some embodiments, the WPRE is at the 3' end of the nucleotide sequence encoding chimeric antigen receptor and at the 5' end of the nucleotide sequence encoding priming receptor or wherein the WPRE is at the 3' end of the nucleotide sequence encoding priming receptor and at the 5' end of the nucleotide sequence encoding chimeric antigen receptor.

In some embodiments, the nucleic acid further comprises an SV40 or a human growth hormone (GH1) polyA element.

In some embodiments, the nucleic acid is incorporated into an expression cassette or an expression vector.

In some embodiments, the expression vector is a non-viral vector.

In one aspect, provided herein are vectors comprising the nucleic acids disclosed herein.

In some embodiments, the 5' and 3' ends of the nucleic acid comprise nucleotide sequences that are homologous to genomic sequences flanking an insertion site in a genome of a primary cell.

In some embodiments, the insertion site is located at a T Cell Receptor Alpha Constant (TRAC) locus or a genomic safe harbor (GSH) locus.

In one aspect, provided herein are cells comprising:
i. the systems disclosed herein;
ii. at least one nucleic acids disclosed herein; and/or
iii. the vectors disclosed herein.

In some embodiments, the cell is an immune cell.

In one aspect, provided herein are immune cells comprising:
i. the systems disclosed herein;
ii. at least one nucleic acids disclosed herein; and/or
iii. the vectors disclosed herein.

In some embodiments, the immune cell is a primary human immune cell.

In some embodiments, the immune cell is an allogeneic immune cell.

In some embodiments, the immune cell is an autologous immune cell.

In some embodiments, the primary immune cell is a natural killer (NK) cell, a T cell, a CD8+ T cell, a CD4+ T cell, a primary T cell, or a T cell progenitor.

In some embodiments, the primary immune cell is a primary T cell.

In some embodiments, the primary immune cell is a primary human T cell.

In some embodiments, the primary immune cell is virus-free. A primary immune cell comprising at least one nucleic acid comprising a priming receptor comprising a first extracellular antigen-binding domain that specifically binds to PSMA, a chimeric antigen receptor comprising a second extracellular antigen-binding domain that specifically binds to CA9, and optionally a synthetic pathway activator inserted into a target region of the genome of the primary immune cell, and wherein the primary immune cell does not comprise a viral vector for introducing the nucleic acid into the primary immune cell.

In one aspect, provided herein are primary immune cells comprising at least one nucleic acid comprising a priming receptor comprising a first extracellular antigen-binding domain that specifically binds to PSMA, a chimeric antigen receptor comprising a second extracellular antigen-binding domain that specifically binds to CA9, and optionally a synthetic pathway activator inserted into a target region of the genome of the primary immune cell, and wherein the primary immune cell does not comprise a viral vector for introducing the nucleic acid into the primary immune cell.

In one aspect, provided herein are viable, virus-free, primary cells comprising a ribonucleoprotein complex (RNP)-nucleic acid complex, wherein the RNP comprises a nuclease domain and a guide RNA, wherein nucleic acid comprises a priming receptor comprising a first extracellular antigen-binding domain that specifically binds to PSMA and a chimeric antigen receptor comprising a second extracellular antigen-binding domain that specifically binds to CA9, and optionally a synthetic pathway activator and wherein the 5' and 3' ends of the nucleic acid comprise nucleotide sequences that are homologous to genomic sequences flanking an insertion site in the genome of the primary cell.

In some embodiments, the cell further comprises at least one nucleic acid sequence at least 15 nucleotides in length, wherein the at least one nucleic acid sequence comprises one or more of a first nucleic acid sequence complementary to a nucleic acid encoding human Fas Cell Surface Death Receptor (FAS) comprising the sequence set forth in SEQ ID NO: 3, and a second nucleic acid sequence complementary a nucleic acid encoding human Transforming Growth factor (TGF)-β Receptor 2 (TGFBR2) comprising the sequence set forth in SEQ ID NO: 4.

In some embodiments, the nucleic acid comprising a sequence with at least 80%, 85%, 90%, 91%, 92%, 93%, 94%, 95%, 96%, 97%, 98%, 99%, or 100% identity to a sequence selected from the group consisting of the sequences set forth in SEQ ID NOs: 143-147.

In one aspect, provided herein are populations of cells comprising a plurality of cells or immune cells disclosed herein.

In one aspect, provided herein are pharmaceutical compositions comprising the cells or immune cell disclosed herein or the population of cells or immune cells disclosed herein, and a pharmaceutically acceptable excipient.

In one aspect, provided herein are pharmaceutical compositions comprising the nucleic acid disclosed herein or the vector disclosed herein, and a pharmaceutically acceptable excipient.

In one aspect, provided herein are methods of editing a cell, comprising: inserting the nucleic acid disclosed herein into an insertion site in the genome of the cell.

In some embodiments, the nucleic acid is introduced to the cell non-virally.

In one aspect, provided herein are methods of editing a cell, comprising:
i. providing a nuclease domain and a guide RNA, wherein the nucleic acid comprises the nucleic acid disclosed herein, and wherein the 5' and 3' ends of the nucleic acid comprise nucleotide sequences that are homologous to genomic sequences flanking an insertion site in the genome of the cell;
ii. introducing the nuclease domain and nucleic acid into the cell, wherein the guide RNA specifically hybridizes to a target region of the genome of the cell, and wherein the nuclease domain cleaves the target region to create the insertion site in the genome of the cell; and
iii. editing the cell via insertion of the nucleic acid into the insertion site in the genome of the cell.

In some embodiments, the nuclease domain and nucleic acid are introduced to the cell non-virally.

In one aspect, provided herein are methods of editing an immune cell, comprising:
  i. providing a ribonucleoprotein complex (RNP)-nucleic acid complex, wherein the RNP comprises a nuclease domain and a guide RNA, wherein the nucleic acid comprises the nucleic acids disclosed herein, and wherein the 5' and 3' ends of the nucleic acid comprise nucleotide sequences that are homologous to genomic sequences flanking an insertion site in the genome of the immune cell;
  ii. non-virally introducing the RNP-nucleic acid complex into the immune cell, wherein the guide RNA specifically hybridizes to a target region of the genome of the primary immune cell, and wherein the nuclease domain cleaves the target region to create the insertion site in the genome of the immune cell; and
  iii. editing the immune cell via insertion of the nucleic acids disclosed herein into the insertion site in the genome of the immune cell.

In some embodiments, non-virally introducing comprises electroporation.

In some embodiments, the nuclease domain comprises a CRISPR-associated endonuclease (Cas), optionally a Cas9 nuclease.

In some embodiments, the target region of the genome of the cell is a T Cell Receptor Alpha Constant (TRAC) locus or a genomic safe harbor (GSH) locus.

In some embodiments, the nucleic acid is a double-stranded nucleic acid or a single-stranded nucleic acid.

In some embodiments, the nucleic acid is a linear nucleic acid or a circular nucleic acid, optionally wherein the circular nucleic acid is a plasmid.

In some embodiments, the immune cell is a primary human immune cell.

In some embodiments, the immune cell is an autologous immune cell.

In some embodiments, the immune cell is an allogeneic immune cell.

In some embodiments, the immune cell is a natural killer (NK) cell, a T cell, a CD8+ T cell, a CD4+ T cell, a primary T cell, or a T cell progenitor.

In some embodiments, the immune cell is a primary T cell.

In some embodiments, the immune cell is a primary human T cell.

In some embodiments, the immune cell is virus-free.

In some embodiments, further comprising obtaining the immune cell from a patient and introducing the nucleic acid in vitro.

In one aspect, provided herein are methods of treating a disease in a subject comprising administering the immune cells disclosed herein or the pharmaceutical compositions disclosed herein to the subject.

In some embodiments, the disease is cancer.

In some embodiments, the cancer is a solid cancer or a liquid cancer.

In some embodiments, the cancer is kidney cancer, clear cell renal cell carcinoma (ccRcc), colorectal cancer, or lung cancer.

In some embodiments, the administration of the immune cell enhances an immune response in the subject.

In some embodiments, the enhanced immune response is an adaptive immune response.

In some embodiments, the enhanced immune response is an innate immune response.

In some embodiments, the enhanced immune response is an increased expression of at least one cytokine or chemokine.

In some embodiments, the cytokine is interferon-gamma (IFNγ).

In some embodiments, the method further comprises administering an immunotherapy to the subject concurrently with the immune cell or subsequently to the immune cell.

In one aspect, provided herein are methods of inhibiting a target cell in a subject comprising administering the immune cells disclosed herein to the subject, wherein the immune cell inhibits the target cell.

In some embodiments, the target cell expresses PSMA and CA9.

In some embodiments, the target cell is a cancer cell.

In one aspect, provided herein are methods of inducing expression of a chimeric antigen receptor with a priming receptor in a cell or immune cell comprising:
  i. obtaining a cell or immune cell comprising:
  ii. the systems disclosed herein;
  iii. the nucleic acids disclosed herein; and/or
  iv. the vectors disclosed herein; and
  v. contacting the immune cell with a target cell expressing PSMA and CA9, wherein binding of the priming receptor to PSMA on the target cell induces activation of the priming receptor and expression of the chimeric antigen receptor.

In one aspect, provided herein are methods of modulating the activity of a cell or immune cell comprising:
  i. obtaining a cell or immune cell comprising:
  ii. the systems disclosed herein;
  iii. the nucleic acids disclosed herein; and/or
  iv. the vectors disclosed herein; and
  v. contacting the cell or immune cell with a target cell expressing PSMA and CA9, wherein binding of the priming receptor to PSMA on the target cell induces activation of the priming receptor and expression of the chimeric antigen receptor and wherein binding of the chimeric antigen receptor to CA9 on the target cell modulates the activity of the immune cell.

In some embodiments, the modulation of the immune cell activity comprises enhancing an immune response.

In some embodiments, the enhanced immune response is an adaptive immune response.

In some embodiments, the enhanced immune response is an innate immune response.

In some embodiments, the immune cell activity is an increased expression of at least one cytokine or chemokine.

In some embodiments, the cytokine is interferon-gamma (IFNγ).

In one aspect, provided herein are methods of treating a disease in a subject comprising:
  i. determining or having determined the presence of PSMA-positive (PSMA+) cells from a cancer sample obtained from the subject;
  ii. determining or having determined the presence of CA9-positive (CA+) cells from a cancer sample obtained from the subject; and
  iii. administering a cell or immune cell disclosed herein or a pharmaceutical composition disclosed herein to the subject.

In some embodiments, the disease is cancer.

In some embodiments, the cancer is a solid cancer or a liquid cancer.

In some embodiments, the cancer is kidney cancer, clear cell renal cell carcinoma (ccRcc), colorectal cancer, or lung cancer.

In some embodiments, the administration of the immune cell enhances an immune response in the subject.

In some embodiments, the enhanced immune response is an adaptive immune response.

In some embodiments, the enhanced immune response is an innate immune response.

In some embodiments, the enhanced immune response is an increased expression of at least one cytokine or chemokine.

In some embodiments, the cytokine is interferon-gamma (IFNγ).

In some embodiments, the method further comprises administering an immunotherapy to the subject concurrently with the immune cell or subsequently to the immune cell.

BRIEF DESCRIPTION OF THE SEVERAL VIEWS OF THE DRAWINGS

These and other features, aspects, and advantages of the present disclosure will become better understood with regard to the following description, and accompanying drawings, where:

FIG. 2C shows that CA9 1 antigen biding fragment had no interaction with HEK293T-ASGR1+ cells across a range of concentration up to 5 ug/mL. FIG. 2D shows that CA9 1 and CA9 2 both bound to wt CA9-expressing cells (293T-LP81-CA9) as well as cells expressing three different isoforms of CA9: 91-96del CA9, R131Q CA9, and Q326R CA9.

FIG. 3A shows binding of the PSMA 1 antigen biding fragment to HEK293T-PSMA (expressing human PSMA) cells but not HEK293T parental cells. FIG. 3B shows that the PSMA 1 antigen biding fragment did not bind to HEK293T-mPSMA cells (expressing mouse PSMA9).

FIG. 7A shows cytotoxicity against parental K562 cells expressing neither CA9 or PSMA, FIG. 7B shows cytotoxicity against K562 cells expressing only CA9, FIG. 7C cytotoxicity against K562 cells expressing only PSMA. FIG. 7D shows cytotoxicity against K562 cells expressing both PSMA and CA9.

FIG. 11A shows that ICT cytotoxicity was not affected by soluble CA9. FIG. 11B shows that ICT cytotoxicity was not affected by soluble PSMA.

DETAILED DESCRIPTION

Definitions

Figure 1A:
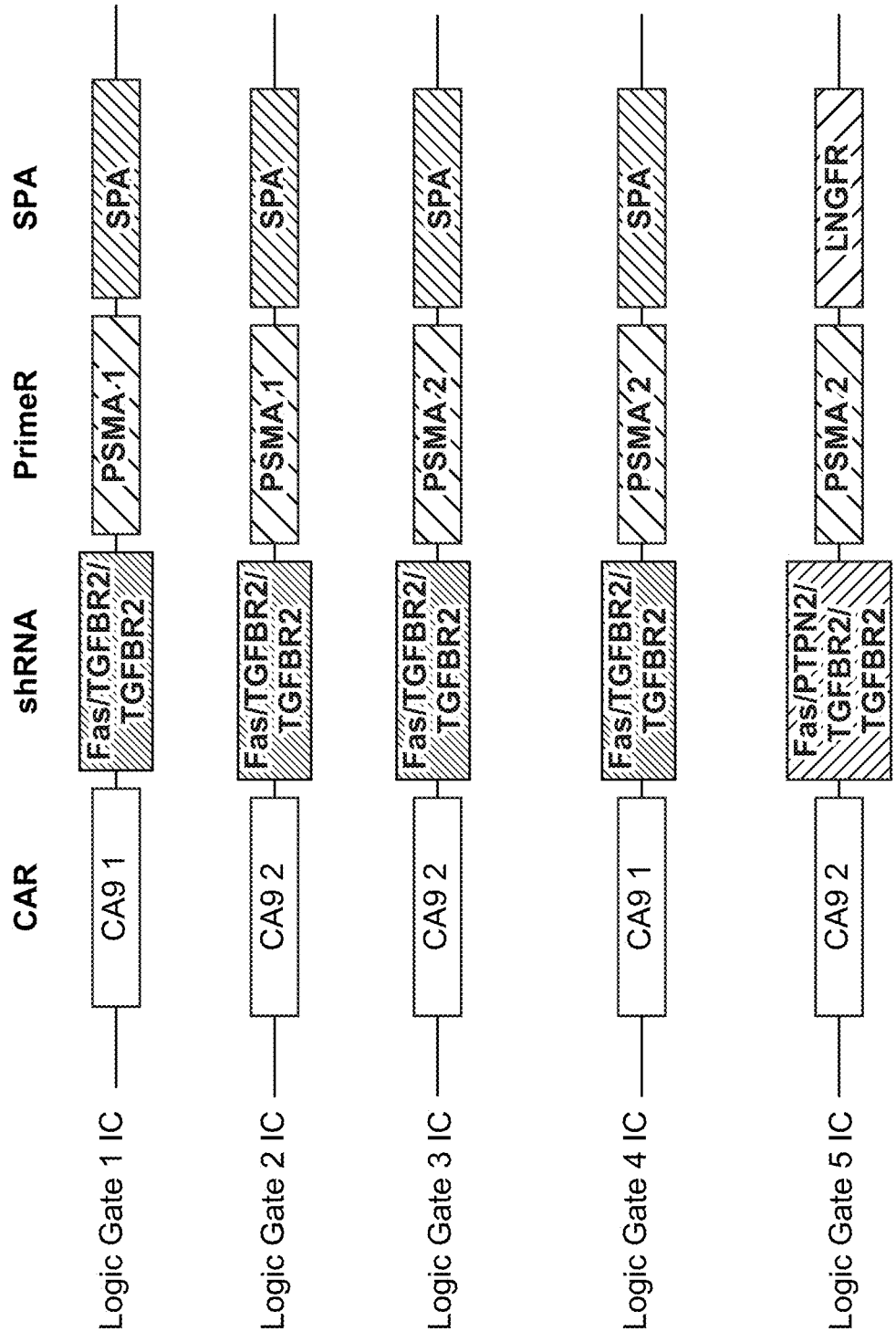
FIG. 1A provides diagram of the various ICT transgene cassettes expressing Logic Gate 1-5 Integrated Circuits (ICs), shRNA, and SPAs.

Terms used in the claims and specification are defined as set forth below unless otherwise specified.

As used herein, the term "gene" refers to the basic unit of heredity, consisting of a segment of DNA arranged along a chromosome, which codes for a specific protein or segment of protein. A gene typically includes a promoter, a 5' untranslated region, one or more coding sequences (exons), optionally introns, and a 3' untranslated region. The gene may further comprise a terminator, enhancers and/or silencers.

As used herein, the term "locus" refers to a specific, fixed physical location on a chromosome where a gene or genetic marker is located.

The term "safe harbor locus" refers to a locus at which genes or genetic elements can be incorporated without disruption to expression or regulation of adjacent genes. These safe harbor loci are also referred to as safe harbor sites (SHS). As used herein, a safe harbor locus refers to an "integration site" or "knock-in site" at which a sequence encoding a transgene, as defined herein, can be inserted. In some embodiments the insertion occurs with replacement of a sequence that is located at the integration site. In some embodiments, the insertion occurs without replacement of a sequence at the integration site. Examples of integration sites contemplated are provided in Table D.

As used herein, the term "insert" refers to a nucleotide sequence that is integrated (inserted) at a target locus or safe harbor site. The insert can be used to refer to the genes or genetic elements that are incorporated at the target locus or safe harbor site using, for example, homology-directed repair (HDR) CRISPR/Cas9 genome-editing or other methods for inserting nucleotide sequences into a genomic region known to those of ordinary skill in the art.

The term "inserting" refers to a manipulation of a nucleotide sequence to introduce a non-native sequence. This is done, for example, via the use of restriction enzymes and ligases whereby the DNA sequence of interest, usually encoding the gene of interest, can be incorporated into another nucleic acid molecule by digesting both molecules with appropriate restriction enzymes in order to create compatible overlaps and then using a ligase to join the molecules together. One skilled in the art is very familiar with such manipulations and examples may be found in Sambrook et al. (Sambrook, Fritsch, & Maniatis, "Molecular Cloning: A Laboratory Manual", 2nd ed., Cold Spring Harbor Laboratory, 1989), which is hereby incorporated by reference in its entirety including any drawings, figures and tables.

The "CRISPR/Cas" system refers to a widespread class of bacterial systems for defense against foreign nucleic acid. CRISPR/Cas systems are found in a wide range of eubacterial and archaeal organisms. CRISPR/Cas systems include type I, II, and III sub-types. Wild-type type II CRISPR/Cas systems utilize an RNA-mediated nuclease, Cas9 in complex with guide and activating RNA to recognize and cleave foreign nucleic acid. Guide RNAs having the activity of both a guide RNA and an activating RNA are also known in the art. In some cases, such dual activity guide RNAs are referred to as a small guide RNA (sgRNA).

Cas9 homologs are found in a wide variety of eubacteria, including, but not limited to bacteria of the following taxonomic groups: *Actinobacteria, Aquificae, Bacteroidetes-Chlorobi, Chlamydiae-Verrucomicrobia, Chiroflexi, Cyanobacteria, Firmicutes, Proteobacteria, Spirochaetes*, and *Thermotogae*. An exemplary Cas9 protein is the *Streptococcus pyogenes* Cas9 protein. Additional Cas9 proteins and homologs thereof are described in, e.g., Chylinksi, et al., RNA Biol. 2013 May 1; 10(5): 726-737; Nat. Rev. Microbiol. 2011 June; 9(6): 467-477; Hou, et al., Proc Natl Acad Sci USA. 2013 Sep. 24; 110(39):15644-9; Sampson et al., Nature. 2013 May 9; 497(7448):254-7; and Jinek, et al., Science. 2012 Aug. 17; 337(6096):816-21. The Cas9 nuclease domain can be optimized for efficient activity or enhanced stability in the host cell.

As used herein, the term "Cas9" refers to an RNA-mediated nuclease (e.g., of bacterial or archeal orgin, or derived therefrom). Exemplary RNA-mediated nucleases include the foregoing Cas9 proteins and homologs thereof, and include but are not limited to, CPF1 (See, e.g., Zetsche et al., Cell, Volume 163, Issue 3, p759-771, 22 Oct. 2015). Similarly, as used herein, the term "Cas9 ribonucleoprotein" complex and the like refers to a complex between the Cas9 protein, and a crRNA (e.g., guide RNA or small guide RNA), the Cas9 protein and a trans-activating crRNA (tracrRNA), the Cas9 protein and a small guide RNA, or a combination thereof (e.g., a complex containing the Cas9 protein, a tracrRNA, and a crRNA guide RNA).

As used herein, the phrase "immune cell" is inclusive of all cell types that can give rise to immune cells, including hematopoietic cells such hematopoietic stem cells, pluripotent stem cells, and induced pluripotent stem cells (iPSCs). In some embodiments, the immune cell is a B cell, macrophage, a natural killer (NK) cell, an induced pluripotent stem cell (iPSC), a human pluripotent stem cell (HSPC), a T cell or a T cell progenitor or dendritic cell. In some embodiments, the cell is an innate immune cell.

As used herein, the term "primary" in the context of a primary cell or primary stem cell refers to a cell that has not been transformed or immortalized. Such primary cells can be cultured, sub-cultured, or passaged a limited number of times (e.g., cultured 0, 1, 2, 3, 4, 5, 6, 7, 8, 9, 10, 11, 12, 13, 14, 15, 16, 17, 18, 19, or 20 times). In some cases, the primary cells are adapted to in vitro culture conditions. In some cases, the primary cells are isolated from an organism, system, organ, or tissue, optionally sorted, and utilized, e.g., directly without culturing or sub-culturing. In some cases, the primary cells are stimulated, activated, or differentiated. For example, primary T cells can be activated by contact with (e.g., culturing in the presence of) CD3, CD28 agonists, IL-2, IFN-γ, or a combination thereof.

As used herein, the terms "T lymphocyte" and "T cell" are used interchangeably and refer to cells that have completed maturation in the thymus, and identify certain foreign antigens in the body. The terms also refer to the major leukocyte types that have various roles in the immune system, including activation and deactivation of other immune cells. The T cell can be any T cell such as a cultured T cell, e.g., a primary T cell, or a T cell derived from a cultured T cell line, e.g., a Jurkat, SupT1, etc., or a T cell obtained from a mammal. T cells include, but are not limited to, naïve T cells, stimulated T cells, primary T cells (e.g., uncultured), cultured T cells, immortalized T cells, helper T cells, cytotoxic T cells, memory T cells, regulatory T cells, natural killer T cells, combinations thereof, or sub-populations thereof. The T cell can be a CD3+ cell. T cells can be CD4+, CD8+, or CD4+ and CD8+. The T cell can be any type of T cell, CD4+/CD8+ double positive T cells, CD4+ helper T cells (e.g. Th1 and Th2 cells), CD8+ T cells (e.g. cytotoxic T cells), peripheral Including but not limited to blood mononuclear cells (PBMC), peripheral blood leukocytes (PBL), tumor infiltrating lymphocytes (TIL), memory T cells, naive T cells, regulatory T cells, γδ T cells, etc. It can be any T cell at any stage of development. Additional types of helper T cells include Th3 (Treg) cells, Th17 cells, Th9 cells, or Tfh cells. Additional types of memory T cells include cells such as central memory T cells (Tcm cells), effector memory T cells (Tem cells and TEMRA cells). A T cell can also refer to a genetically modified T cell, such as a T cell that has been modified to express a T cell receptor (TCR) or a chimeric antigen receptor (CAR). T cells can also be differentiated from stem cells or progenitor cells.

"CD4+ T cells" refers to a subset of T cells that express CD4 on their surface and are associated with a cellular immune response. CD4+ T cells are characterized by a post-stimulation secretion profile that can include secretion of cytokines such as IFN-γ, TNF-α, IL-2, IL-4 and IL-10. "CD4" is a 55 kD glycoprotein originally defined as a differentiation antigen on T lymphocytes, but was also found on other cells including monocytes/macrophages. The CD4 antigen is a member of the immunoglobulin superfamily and has been implicated as an associative recognition element in MHC (major histocompatibility complex) class II restricted immune responses. On T lymphocytes, the CD4 antigen defines a helper/inducer subset.

"CD8+ T cells" refers to a subset of T cells that express CD8 on their surface, are MHC class I restricted, and function as cytotoxic T cells. The "CD8" molecule is a differentiation antigen present on thymocytes, as well as on cytotoxic and suppressor T lymphocytes. The CD8 antigen is a member of the immunoglobulin superfamily and is an associative recognition element in major histocompatibility complex class I restriction interactions.

As used herein, the phrase "hematopoietic stem cell" refers to a type of stem cell that can give rise to a blood cell. Hematopoietic stem cells can give rise to cells of the myeloid or lymphoid lineages, or a combination thereof. Hematopoietic stem cells are predominantly found in the bone marrow, although they can be isolated from peripheral blood, or a fraction thereof. Various cell surface markers can be used to identify, sort, or purify hematopoietic stem cells. In some cases, hematopoietic stem cells are identified as c-kit+ and lin−. In some cases, human hematopoietic stem cells are identified as CD34+, CD59+, Thy1/CD90+, CD38$^{lo/-}$, C-kit/CD117+, lin−. In some cases, human hematopoietic stem cells are identified as CD34−, CD59+, Thy1/CD90+, CD38$^{lo/-}$, C-kit/CD117+, lin−. In some cases, human hematopoietic stem cells are identified as CD133+, CD59+, Thy1/CD90+, CD38$^{lo/-}$, C-kit/CD117+, lin−. In some cases, mouse hematopoietic stem cells are identified as CD34$^{lo/-}$, SCA-1+, Thy1$^{+/lo}$, CD38+, C-kit+, lin−. In some cases, the hematopoietic stem cells are CD150+CD48−CD244−.

As used herein, the phrase "hematopoietic cell" refers to a cell derived from a hematopoietic stem cell. The hematopoietic cell may be obtained or provided by isolation from an organism, system, organ, or tissue (e.g., blood, or a fraction thereof). Alternatively, an hematopoietic stem cell can be isolated and the hematopoietic cell obtained or provided by differentiating the stem cell. Hematopoietic cells include cells with limited potential to differentiate into further cell types. Such hematopoietic cells include, but are not limited to, multipotent progenitor cells, lineage-restricted progenitor cells, common myeloid progenitor cells, granulocyte-macrophage progenitor cells, or megakaryocyte-erythroid progenitor cells. Hematopoietic cells include cells of the lymphoid and myeloid lineages, such as lymphocytes, erythrocytes, granulocytes, monocytes, and thrombocytes.

As used herein, the term "construct" refers to a complex of molecules, including macromolecules or polynucleotides.

As used herein, the term "integration" refers to the process of stably inserting one or more nucleotides of a construct into the cell genome, i.e., covalently linking to a nucleic acid sequence in the chromosomal DNA of the cell. It may also refer to nucleotide deletions at a site of integration. Where there is a deletion at the insertion site, "integration" may further include substitution of the endogenous sequence or nucleotide deleted with one or more inserted nucleotides.

As used herein, the term "exogenous" refers to a molecule or activity that has been introduced into a host cell and is not native to that cell. The molecule can be introduced, for example, by introduction of the encoding nucleic acid into host genetic material, such as by integration into a host chromosome, or as non-chromosomal genetic material, such as a plasmid. Thus, the term, when used in connection with expression of an encoding nucleic acid, refers to the introduction of the encoding nucleic acid into a cell in an expressible form. The term "endogenous" refers to a molecule or activity that is present in a host cell under natural, unedited conditions. Similarly, the term, when used in connection with expression of the encoding nucleic acid, refers to expression of the encoding nucleic acid that is contained within the cell and not introduced exogenously.

The term "heterologous" refers to a nucleic acid or polypeptide sequence or domain which is not native to a flanking sequence, e.g., wherein the heterologous sequence is not found in nature coupled to the nucleic acid or polypeptide sequences occurring at one or both ends.

The term "homologous" refers to a nucleic acid or polypeptide sequence or domain which is native to a flanking sequence, e.g., wherein the homologous sequence is found in nature coupled to the nucleic acid or polypeptide sequences occurring at one or both ends.

As used herein, a "polynucleotide donor construct" refers to a nucleotide sequence (e.g. DNA sequence) that is genetically inserted into a polynucleotide and is exogenous to that polynucleotide. The polynucleotide donor construct is transcribed into RNA and optionally translated into a polypeptide. The polynucleotide donor construct can include prokaryotic sequences, cDNA from eukaryotic mRNA, genomic DNA sequences from eukaryotic (e.g., mammalian) DNA, and synthetic DNA sequences. For example, the polynucleotide donor construct can be a miRNA, shRNA, natural polypeptide (i.e., a naturally occurring polypeptide) or fragment thereof or a variant polypeptide (e.g. a natural polypeptide having less than 100% sequence identity with the natural polypeptide) or fragments thereof.

As used herein, the term "complementary" or "complementarity" refers to specific base pairing between nucleotides or nucleic acids. Complementary nucleotides are, generally, A and T (or A and U), and G and C. The guide RNAs described herein can comprise sequences, for example, DNA targeting sequence that are perfectly complementary or substantially complementary (e.g., having 1-4 mismatches) to a genomic sequence in a cell.

As used herein, the term "transgene" refers to a polynucleotide that has been transferred naturally, or by any of a number of genetic engineering techniques from one organism to another. It is optionally translated into a polypeptide. As used, transgene can refer to a polynucleotide that encodes a polypeptide.

The terms "protein," "polypeptide," and "peptide" are used herein interchangeably.

As used herein, the term "operably linked" or "operatively linked" refers to the binding of a nucleic acid sequence to a single nucleic acid fragment such that one function is affected by the other. For example, if a promoter is capable of affecting the expression of a coding sequence or functional RNA (i.e., the coding sequence or functional RNA is under transcriptional control by the promoter), the promoter is operably linked thereto. Coding sequences can be operably linked to control sequences in both sense and antisense orientation.

As used herein, the term "developmental cell states" refers to, for example, states when the cell is inactive, actively expressing, differentiating, senescent, etc. developmental cell state may also refer to a cell in a precursor state (e.g., a T cell precursor).

As used, the term "encoding" refers to a sequence of nucleic acids which codes for a protein or polypeptide of interest. The nucleic acid sequence may be either a molecule of DNA or RNA. In preferred embodiments, the molecule is a DNA molecule. In other preferred embodiments, the molecule is a RNA molecule. When present as a RNA molecule, it will comprise sequences which direct the ribosomes of the host cell to start translation (e.g., a start codon, ATG) and direct the ribosomes to end translation (e.g., a stop codon). Between the start codon and stop codon is an open reading frame (ORF). Such terms are known to one of ordinary skill in the art.

As used herein, the term "subject" refers to a mammalian subject. Exemplary subjects include humans, monkeys, dogs, cats, mice, rats, cows, horses, camels, goats, rabbits, pigs and sheep. In certain embodiments, the subject is a human. In some embodiments the subject has a disease or condition that can be treated with an engineered cell provided herein or population thereof. In some aspects, the disease or condition is a cancer.

As used herein, the term "promoter" refers to a nucleotide sequence (e.g. DNA sequence) capable of controlling the expression of a coding sequence or functional RNA. The promoter sequence consists of proximal and more distal upstream elements, the latter elements often referred to as enhancers. A promoter can be derived from natural genes in its entirety, can be composed of different elements from different promoters found in nature, and/or may comprise synthetic DNA segments. A promoter, as contemplated herein, can be endogenous to the cell of interest or exogenous to the cell of interest. It is appreciated by those skilled in the art that different promoters can induce gene expression in different tissue or cell types, or at different developmental stages, or in response to different environmental conditions. As is known in the art, a promoter can be selected according to the strength of the promoter and/or the conditions under which the promoter is active, e.g., constitutive promoter, strong promoter, weak promoter, inducible/repressible promoter, tissue specific Or developmentally regulated promoters, cell cycle-dependent promoters, and the like.

A promoter can be an inducible promoter (e.g., a heat shock promoter, tetracycline-regulated promoter, steroid-regulated promoter, metal-regulated promoter, estrogen receptor-regulated promoter, Hepatocyte Nuclear Factor 1α (HNF1α), etc.). The promoter can be a constitutive promoter (e.g., CMV promoter, UBC promoter, EF1α promoter). In some embodiments, the promoter can be a spatially restricted and/or temporally restricted promoter (e.g., a tissue specific promoter, a cell type specific promoter, etc.). See for example US Publication 20180127786, the disclosure of which is herein incorporated by reference in its entirety.

Gene editing, as contemplated herein, may involve a gene (or nucleotide sequence) knock-in or knock-out. As used herein, the term "knock-in" refers to an addition of a DNA sequence, or fragment thereof into a genome. Such DNA sequences to be knocked-in may include an entire gene or genes, may include regulatory sequences associated with a gene or any portion or fragment of the foregoing. For example, a polynucleotide donor construct encoding a protein may be inserted into the genome of a cell carrying a mutant gene. In some embodiments, a knock-in strategy involves substitution of an existing sequence with the provided sequence, e.g., substitution of a mutant allele with a wild-type copy. On the other hand, the term "knock-out" refers to the elimination of a gene or the expression of a gene. For example, a gene can be knocked out by either a deletion or an addition of a nucleotide sequence that leads to a disruption of the reading frame. As another example, a gene may be knocked out by replacing a part of the gene with an irrelevant (e.g., non-coding) sequence.

As used herein, the term "non-homologous end joining" or NHEJ refers to a cellular process in which cut or nicked ends of a DNA strand are directly ligated without the need for a homologous template nucleic acid. NHEJ can lead to the addition, the deletion, substitution, or a combination thereof, of one or more nucleotides at the repair site.

As used herein, the term "homology directed repair" or HDR refers to a cellular process in which cut or nicked ends of a DNA strand are repaired by polymerization from a homologous template nucleic acid. Thus, the original sequence is replaced with the sequence of the template. The homologous template nucleic acid can be provided by homologous sequences elsewhere in the genome (sister chromatids, homologous chromosomes, or repeated regions on the same or different chromosomes). Alternatively, an exogenous template nucleic acid can be introduced to obtain a specific HDR-induced change of the sequence at the target site. In this way, specific mutations can be introduced at the cut site.

As used herein, a "DNA template," "DNA template insert," "single-stranded DNA template," a "single-stranded DNA template insert," a "double-stranded DNA template," or a "double-stranded DNA template insert" refers to a DNA oligonucleotide that can be used by a cell as a template for HDR. Generally, the single-stranded DNA template or a double-stranded DNA template has at least one region of homology to a target site. In some cases, the single-stranded DNA template or double-stranded DNA template has two homologous regions flanking a region that contains a heterologous sequence to be inserted at a target cut site. In some embodiments, the DNA template or DNA template insert comprises a cassette or expression cassette comprising one or more modules that encode for transgenes and/or RNAi molecules disclosed herein.

The terms "expression vector," "vector," and "plasmid" are used interchangeably and as used herein refer to polynucleotide vehicles useful to introduce genetic material into a cell. Vectors can be linear or circular. Vectors can integrate into a target genome of a host cell or replicate independently in a host cell. Vectors can comprise, for example, an origin of replication, a multicloning site, and/or a selectable marker. An expression vector typically comprises an expression cassette or cassette. Vectors and plasmids include, but are not limited to, integrating vectors, prokaryotic plasmids, eukaryotic plasmids, plant synthetic chromosomes, episomes, cosmids, and artificial chromosomes.

As used herein, the phrase "introducing" in the context of introducing a nucleic acid or a complex comprising a nucleic acid, for example, an RNP-DNA template complex, refers to the translocation of the nucleic acid sequence or the RNP-DNA template complex from outside a cell to inside the cell. In some cases, introducing refers to translocation of the nucleic acid or the complex from outside the cell to inside the nucleus of the cell. Various methods of such translocation are contemplated, including but not limited to, electroporation, contact with nanowires or nanotubes, receptor mediated internalization, translocation via cell penetrating peptides, liposome mediated translocation, and the like.

As used herein the term "expression cassette" or "cassette" is a polynucleotide construct, generated recombinantly or chemically synthesized, comprising regulatory sequences operably linked to a selected polynucleotide to facilitate expression of the selected polynucleotide in a host cell. Such cassettes may include one or more modules comprising the selected polynucleotide, such as the transgenes (e.g., a CAR, priming receptor, and/or synthetic pathway activator described herein) and/or RNAi molecules (e.g., an shRNA) disclosed herein. For example, the regulatory sequences can facilitate transcription of the selected polynucleotide in a host cell, or transcription and translation of the selected polynucleotide in a host cell. An expression cassette can, for example, be integrated in the genome of a host cell or be present in an expression vector. In some embodiments, the cassette is part of a DNA template insert.

As used herein, the phrase "subject in need thereof" refers to a subject that exhibits and/or is diagnosed with one or more symptoms or signs of a disease or disorder as described herein.

A "chemotherapeutic agent" refers to a chemical compound useful in the treatment of cancer. Chemotherapeutic agents include "anti-hormonal agents" or "endocrine therapeutics" which act to regulate, reduce, block, or inhibit the effects of hormones that can promote the growth of cancer.

The term "composition" refers to a mixture that contains, e.g., an engineered cell or protein contemplated herein. In some embodiments, the composition may contain additional components, such as adjuvants, stabilizers, excipients, and the like. The term "composition" or "pharmaceutical composition" refers to a preparation which is in such form as to permit the biological activity of an active ingredient contained therein to be effective in treating a subject, and which contains no additional components which are unacceptably toxic to the subject in the amounts provided in the pharmaceutical composition.

The term "in situ" refers to processes that occur in a living cell growing separate from a living organism, e.g., growing in tissue culture.

The term "in vivo" refers to processes that occur in a living organism.

As used herein, the term "ex vivo" generally includes experiments or measurements made in or on living tissue, preferably in an artificial environment outside the organism, preferably with minimal differences from natural conditions.

The term "mammal" as used herein includes both humans and non-humans and include but is not limited to humans, non-human primates, canines, felines, murines, bovines, equines, and porcines.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (ncbi.nlm.nih.gov/).

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease.

The term "ameliorating" refers to any therapeutically beneficial result in the treatment of a disease state, e.g., a cancer disease state, lessening in the severity or progression, remission, or cure thereof.

As used herein, the term "effective amount" refers to the amount of a compound (e.g., a compositions described herein, cells described herein) sufficient to effect beneficial or desired results. An effective amount can be administered in one or more administrations, applications or dosages and is not intended to be limited to a particular formulation or administration route.

As used herein, the term "treating" includes any effect, e.g., lessening, reducing, modulating, ameliorating or eliminating, that results in the improvement of the condition, disease, disorder, and the like, or ameliorating a symptom thereof.

The terms "modulate" and "modulation" refer to reducing or inhibiting or, alternatively, activating or increasing, a recited variable.

The terms "increase" and "activate" refer to an increase of 10%, 20%, 30%, 40%, 50%, 60%, 70%, 75%, 80%, 85%, 90%, 95%, 100%, 2-fold, 3-fold, 4-fold, 5-fold, 10-fold, 20-fold, 50-fold, 100-fold, or greater in a recited variable.

The terms "reduce" and "inhibit" refer to a decrease of 10%, 20%, 30%, 40%, 50%, 60%, 70%, 75%, 80%, 85%, 90%, 95%, 2-fold, 3-fold, 4-fold, 5-fold, 10-fold, 20-fold, 50-fold, 100-fold, or greater in a recited variable.

With regard to the binding of an antibody to a target molecule, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). For example, an antibody that "selectively binds" or "specifically binds" an antigen is an antigen-binding moiety that binds the antigen with high affinity and does not significantly bind other unrelated antigens. Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the antibody to the target molecule is competitively inhibited by the control molecule.

"Affinity" refers to the strength of the sum total of non-covalent interactions between a single binding site of a molecule (e.g., an antibody) and its binding partner (e.g., an antigen or epitope). Unless indicated otherwise, as used herein, "affinity" refers to intrinsic binding affinity, which reflects a 1:1 interaction between members of a binding pair (e.g., antibody and antigen or epitope). The affinity of a molecule X for its partner Y can be represented by the dissociation equilibrium constant ($K_D$). The kinetic components that contribute to the dissociation equilibrium constant are described in more detail below. Affinity can be measured by common methods known in the art, including, but not limited to, surface plasmon resonance (SPR) technology (e.g., BIACORE®) or biolayer interferometry (e.g., FORTEBIO®).

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen-binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

The term "CDR" denotes a complementarity determining region as defined by at least one manner of identification to one of skill in the art.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia" numbering scheme); Martin (Enhanced Chothia or AbM) Abhinandan and Martin, *Mol Immunol.* 2008 August; 45(14):3832-9; MacCallum et al., 1996, *J. Mol. Biol.* 262: 732-745 ("Contact" numbering scheme); Lefranc et al., *Dev. Comp. Immunol.*, 2003, 27:55-77 ("IMGT" numbering scheme); and Honegger and Plückthun, *J. Mol. Biol.*, 2001, 309:657-70 ("AHo" numbering scheme); each of which is incorporated by reference in its entirety.

Table A provides the positions of CDR-L1, CDR-L2, CDR-L3, CDR-H1, CDR-H2, and CDR-H3 as identified by the Kabat, Chothia, AbM, Contact, and IMGT schemes. For CDR-H1, residue numbering is provided using both the Kabat and Chothia numbering schemes.

CDRs may be assigned, for example, using antibody numbering software, such as Abnum, available at bioinf.org.uk/abs/abnum/and described in Abhinandan and Martin, *Immunology*, 2008, 45:3832-3839, incorporated by reference in its entirety, and AbYsis, available at abysis.org/abysis/sequence_input/key_annotation/key_annotation.cgi.

TABLE A

Residues in CDRs according to Kabat, Chothia, AbM, Contact, and IMGT numbering schemes.

| CDR | Kabat | Chothia | AbM | Contact | IMGT |
|---|---|---|---|---|---|
| L1 | L24-L34 | L24-L34 | L24-L34 | L30-L36 | L27-L32 |
| L2 | L50-L56 | L50-L56 | L50-L56 | L46-L55 | L50-L51 |
| L3 | L89-L97 | L89-L97 | L89-L97 | L89-L96 | L89-L97 |
| H1 (Kabat Numbering) | H31-H35B | H26-H32 or H34* | H26-H35B | H30-H35B | H26-H35B |
| H1 (Chothia/Martin Numbering) | H31-H35 | H26-H32 | H26-H35 | H30-H35 | H26-H33 |
| H2 | H50-H65 | H52-H56 | H50-H58 | H47-H58 | H51-H56 |
| H3 | H95-H102 | H95-H102 | H95-H102 | H93-H101 | H93-H102 |

*The C-terminus of CDR-H1, when numbered using the Kabat numbering convention, varies between H32 and H34, depending on the length of the CDR.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

As used herein, the term "single-chain" refers to a molecule comprising amino acid monomers linearly linked by peptide bonds. In a particular such embodiment, the C-terminus of the Fab light chain is connected to the N-terminus of the Fab heavy chain in the single-chain Fab molecule. As described in more detail herein, an scFv has a variable domain of light chain (VL) connected from its C-terminus to the N-terminal end of a variable domain of heavy chain (VH) by a polypeptide chain. Alternately the scFv comprises of polypeptide chain where in the C-terminal end of the VH is connected to the N-terminal end of VL by a polypeptide chain.

The "Fab fragment" (also referred to as fragment antigen-binding) contains the constant domain (CL) of the light chain and the first constant domain (CH1) of the heavy chain along with the variable domains VL and VH on the light and heavy chains respectively. The variable domains comprise the complementarity determining loops (CDR, also referred to as hypervariable region) that are involved in antigen-binding. Fab' fragments differ from Fab fragments by the addition of a few residues at the carboxy terminus of the heavy chain CH1 domain including one or more cysteines from the antibody hinge region.

"F(ab')$_2$" fragments contain two Fab' fragments joined, near the hinge region, by disulfide bonds. F(ab')$_2$ fragments may be generated, for example, by recombinant or synthetic methods or by pepsin digestion of an intact antibody. The F(ab') fragments can be dissociated, for example, by treatment with β-mercaptoethanol.

"Fv" fragments comprise a non-covalently-linked dimer of one heavy chain variable domain and one light chain variable domain.

The "Single-chain Fv" or "scFv" includes the VH and VL domains of an antibody, wherein these domains are present in a single polypeptide chain. In one embodiment, the Fv polypeptide further comprises a polypeptide linker between the VH and VL domains which enables the scFv to form the desired structure for antigen-binding. For a review of scFv see Pluckthun in *The Pharmacology of Monoclonal Antibodies*, vol. 113, Rosenburg and Moore eds., Springer-Verlag, New York, pp. 269-315 (1994). HER2 antibody scFv fragments are described in WO93/16185; U.S. Pat. Nos. 5,571,894; and 5,587,458.

The term "single domain antibody" or "sdAb" refers to a molecule in which one variable domain of an antibody specifically binds to an antigen without the presence of the other variable domain. Single domain antibodies, and fragments thereof, are described in Arabi Ghahroudi et al., *FEBS Letters*, 1998, 414:521-526 and Muyldermans et al., *Trends in Biochem. Sci.*, 2001, 26:230-245, each of which is incorporated by reference in its entirety. Single domain antibodies are also known as sdAbs or nanobodies. Sdabs are fairly stable and easy to express as fusion partner with the Fc chain of an antibody (Harmsen M M, De Haard H J (2007). "Properties, production, and applications of camelid single-domain antibody fragments". Appl. Microbiol Biotechnol. 77(1): 13-22). The terms "single domain antibody" and "sdAb" are used interchangeably herein to refer to an antibody comprising at least one monomeric domain, such as a VHH domain, or a VNAR domain (from a shark antibody) without a light chain, and an Fc region.

The term "VHH" or "VHH domain" or "VHH antigen-binding domain" as used herein refers to the antigen-binding portion of a single-domain antibody (sdAb), such as a camelid antibody. In some embodiments, a VHH comprises three CDRs and four framework regions, designated FR1, CDR1, FR2, CDR2, FR3, CDR3, and FR4.

It must be noted that, as used in the specification and the appended claims, the singular forms "a," "an" and "the" include plural referents unless the context clearly dictates otherwise.

Antibodies and Antigen Binding Fragments

PSMA Antibodies, Antigen Binding Fragments, CDRs, VH, and VL Domains

In some aspects, provided herein are isolated antibodies or antigen binding fragments thereof that bind to Prostate-Specific Membrane Antigen (PSMA) (SEQ ID NO: 2). PSMA is also known as FOLH1 or Folate Hydrolase 1 (HGNC: 3788, NCBI Entrez Gene: 2346, Ensembl: ENSG00000086205, UniProtKB/Swiss-Prot: Q04609). The amino acid sequence of PSMA is provided in SEQ ID NO: 3.

In some aspects, provided herein are antibodies or antigen binding fragments thereof that bind to PSMA. In some aspects, provided herein are means for binding to PSMA. In some embodiments, the means for binding to PSMA comprises an antibody or antigen-binding fragment provided herein. In some embodiments, a PSMA antibody or antigen-binding fragment or equivalent thereof comprises means for binding a PSMA protein, optionally binding a human PSMA protein in the region(s) of human PSMA bound by the PSMA binders (e.g., as described in the Examples below). In some embodiments, the means binds a PSMA protein. In some embodiments, the means binds a human PSMA protein. In some embodiments, the means is a PSMA antibody or antigen-binding fragment or equivalent thereof (e.g., a full length antibody or a F(ab')2 fragment, a Fab fragment, a single chain variable fragment (scFv), and a single domain antibody (sdAb), or a functional fragment thereof) means for binding a PSMA protein. In some embodiments, the means for binding PSMA includes the anti-PSMA antibodies and antigen-binding fragments or equivalents thereof described herein.

In some embodiments, a PSMA antibody or antigen-binding fragment or equivalent thereof provided herein binds to human PSMA. In some embodiments, a PSMA antibody or antigen-binding fragment or equivalent thereof provided herein does not bind to mouse PSMA. In some embodiments, a PSMA antibody or antigen-binding fragment or equivalent thereof provided herein binds to isoforms of human PSMA, including, but not limited to, a PSMA protein comprising a Y75H single nucleotide polymorphism (SNP) as compared to SEQ ID NO: 2.

In some aspects, the PSMA antibody or antigen-binding fragment or equivalent thereof comprises a variable heavy (VH) chain sequence comprising three heavy chain CDR sequences, CDR-H1, CDR-H2, and CDR-H3, of the VH sequences set forth in SEQ ID NOs: 118 or 130, and a variable light (VL) chain sequence comprising three light chain CDR sequences, CDR-L1, CDR-L2, and CDR-L3, of the VL sequences set forth in SEQ ID NOs: 119 or 131. In some embodiments, CDR-H1 comprises the sequence set forth in SEQ ID NO: 120, CDR-H2 comprises the sequence set forth in SEQ ID NO: 121, CDR-H3 comprises the sequence set forth in SEQ ID NO: 122, CDR-L1 comprises the sequence set forth in SEQ ID NO: 123, CDR-L2 comprises the sequence set forth in SEQ ID NO: 124, and CDR-L3 comprises the sequence set forth in SEQ ID NO: 125. In some embodiments, CDR-H1 comprises the sequence set forth in SEQ ID NO: 132, CDR-H2 comprises the sequence set forth in SEQ ID NO: 133, CDR-H3 comprises the sequence set forth in SEQ ID NO: 134, CDR-L1 comprises the sequence set forth in SEQ ID NO: 135, CDR-L2 comprises the sequence set forth in SEQ ID NO: 136, and CDR-L3 comprises the sequence set forth in SEQ ID NO: 137. In some embodiments, CDR-H1, CDR-H2, CDR-H3, CDR-L1, CDR-L2, and CDR-L3 comprise a sequence as set forth in Table B.

TABLE B

PSMA binder CDR sequences according to different definitions

| SEQ ID NO | Name | Definition | Sequence |
|---|---|---|---|
| 120 | PSMA 1 CDR-H1 | Chothia | GYTFTSY--- |
| 199 | PSMA 1 CDR-H1 | AbM | GYTFTSYGIT |
| 200 | PSMA 1 CDR-H1 | Kabat | -----SYGIT |
| 201 | PSMA 1 CDR-H1 | Contact | ----TSYGIT |
| 202 | PSMA 1 CDR-H1 | IMGT | GYTFTSYG-- |
| 121 | PSMA 1 CDR-H2 | Chothia | -----SEYNGN--------- |
| 203 | PSMA 1 CDR-H2 | AbM | ---WISEYNGNTN------- |
| 204 | PSMA 1 CDR-H2 | Kabat | ---WISEYNGNTNYAQKFQG |
| 205 | PSMA 1 CDR-H2 | Contact | WMGWISEYNGNTN------- |
| 206 | PSMA 1 CDR-H2 | IMGT | ----ISEYNGNT-------- |
| 122 | PSMA 1 CDR-H3 | Chothia | --GGILDYYFFYYMDV |
| 122 | PSMA 1 CDR-H3 | AbM | --GGILPYYFFYYMDV |
| 122 | PSMA 1 CDR-H3 | Kabat | --GGILPYYFFYYMDV |
| 207 | PSMA 1 CDR-H3 | Contact | ARGGILPYYFFYYMD- |
| 208 | PSMA 1 CDR-H3 | IMGT | ARGGILPYYFFYYMDV |
| 123 | PSMA 1 CDR-L1 | Chothia | RASQSVSSSYLA-- |
| 123 | PSMA 1 CDR-L1 | AbM | RASQSVSSSYLA-- |
| 123 | PSMA 1 CDR-L1 | Kabat | RASQSVSSSYLA-- |
| 209 | PSMA 1 CDR-L1 | Contact | ------SSSYLAWY |
| 210 | PSMA 1 CDR-L1 | IMGT | ---QSVSSSY---- |
| 124 | PSMA 1 CDR-L2 | Chothia | ----GASSRAT |
| 124 | PSMA 1 CDR-L2 | AbM | ----GASSRAT |
| 124 | PSMA 1 CDR-L2 | Kabat | ----GASSRAT |
| 211 | PSMA 1 CDR-L2 | Contact | LLIYGASSRA- |
|  | PSMA 1 CDR-L2 | IMGT | ----GA----- |
| 125 | PSMA 1 CDR-L3 | Chothia | QQYGSSPYT |
| 125 | PSMA 1 CDR-L3 | AbM | QQYGSSPYT |
| 125 | PSMA 1 CDR-L3 | Kabat | QQYGSSPYT |
| 212 | PSMA 1 CDR-L3 | Contact | QQYGSSPY- |
| 125 | PSMA 1 CDR-L3 | IMGT | QQYGSSPYT |
| 132 | PSMA 2 CDR-H1 | Chothia | GYTFSSY--- |
| 263 | PSMA 2 CDR-H1 | AbM | GYTFSSYGVS |
| 213 | PSMA 2 CDR-H1 | Kabat | -----SYGVS |
| 214 | PSMA 2 CDR-H1 | Contact | ----SSYGVS |
| 215 | PSMA 2 CDR-H1 | IMGT | GYTFSSYG-- |
| 133 | PSMA 2 CDR-H2 | Chothia | -----SKYNGN--------- |
| 216 | PSMA 2 CDR-H2 | AbM | ---WISKYNGNTN------- |
| 217 | PSMA 2 CDR-H2 | Kabat | ---WISKYNGNTNYAQKFQG |
| 218 | PSMA 2 CDR-H2 | Contact | WMGWISKYNGNTN------- |
| 219 | PSMA 2 CDR-H2 | IMGT | ----ISKYNGNT-------- |
| 134 | PSMA 2 CDR-H3 | Chothia | --GGIHGDSYYFYYLDV |
| 134 | PSMA 2 CDR-H3 | AbM | --GGIHGDSYYFYYLDV |
| 134 | PSMA 2 CDR-H3 | Kabat | --GGIHGDSYYFYYLDV |
| 220 | PSMA 2 CDR-H3 | Contact | ARGGIHGDSYYFYYLD- |
| 221 | PSMA 2 CDR-H3 | IMGT | ARGGIHGDSYYFYYLDV |
| 135 | PSMA 2 CDR-L1 | Chothia | GASQSVSSSYLA-- |
| 135 | PSMA 2 CDR-L1 | AbM | GASQSVSSSYLA-- |
| 135 | PSMA 2 CDR-L1 | Kabat | GASQSVSSSYLA-- |
| 222 | PSMA 2 CDR-L1 | Contact | ------SSSYLAWY |
| 223 | PSMA 2 CDR-L1 | IMGT | ---QSVSSSY---- |
| 136 | PSMA 2 CDR-L2 | Chothia | ----DASSRAT |
| 136 | PSMA 2 CDR-L2 | AbM | ----DASSRAT |
| 136 | PSMA 2 CDR-L2 | Kabat | ----DASSRAT |
| 224 | PSMA 2 CDR-L2 | Contact | LLIYDASSRA- |
|  | PSMA 2 CDR-L2 | IMGT | ----DA----- |
| 137 | PSMA 2 CDR-L3 | Chothia | QQYGSSPYT |
| 137 | PSMA 2 CDR-L3 | AbM | QQYGSSPYT |
| 137 | PSMA 2 CDR-L3 | Kabat | QQYGSSPYT |
| 225 | PSMA 2 CDR-L3 | Contact | QQYGSSPY- |
| 137 | PSMA 2 CDR-L3 | IMGT | QQYGSSPYT |

In some embodiments, the VH chain sequence comprises the sequence set forth in SEQ ID NO: 118. In some embodiments, the VH chain sequence comprises the sequence set forth in SEQ ID NO: 130. In some embodiments, the VL comprises the sequence set forth in SEQ ID NO: 119. In some embodiments, the VL comprises the sequence set forth in SEQ ID NO: 131. In some embodiments, the PSMA antibody or antigen-binding fragment or equivalent thereof comprises an extracellular domain comprises the sequence set forth in SEQ ID NO: 117. In some embodiments, the PSMA antibody or antigen-binding fragment or equivalent thereof comprises an extracellular domain comprises the sequence set forth in SEQ ID NO: 129.

In some embodiments, the PSMA antibody or antigen-binding fragment or equivalent thereof CDR-H3 has at least about 50%, 75%, 80%, 85%, 90%, or 95% identity with a CDR-H3 of SEQ ID NO: 122 or 134, the CDR-H2 has at least about 50%, 75%, 80%, 85%, 90%, or 95% identity with a CDR-H2 of SEQ ID NO: 121 or 133, the CDR-H1 has at least about 50%, 75%, 80%, 85%, 90%, or 95% identity with a CDR-H1 of SEQ ID NO: 120 or 132, the CDR-L3 has at least about 50%, 75%, 80%, 85%, 90%, or 95% identity with a CDR-L3 of SEQ ID NO: 125 or 137, the CDR-L2 has at least about 50%, 75%, 80%, 85%, 90%, or 95% identity with a CDR-L2 of SEQ ID NO: 124 or 136, and the CDR-L1 has at least about 50%, 75%, 80%, 85%, 90%, or 95% identity with a CDR-L1 of SEQ ID NO: 123 or 135. In some embodiments, the CDR-H3 is a CDR-H3 of SEQ ID NO: 122 or 134, with up to 1, 2, 3, 4, 5, 6, 7, or 8 amino acid substitutions; the CDR-H2 is a CDR-H2 of SEQ ID NO: 121 or 133, with up to 1, 2, 3, 4, 5, 6, 7, or 8 amino acid substitutions; the CDR-H1 is a CDR-H1 of SEQ ID NO: 120 or 132, with up to 1, 2, 3, 4, or 5 amino acid substitutions; the CDR-L3 is a CDR-L3 of SEQ ID NO: 125 or 137, with up to 1, 2, 3, 4, or 5 amino acid substitutions; the CDR-L2 is a CDR-L2 of SEQ ID NO: 124 or 136, with up to 1, 2, 3, or 4 amino acid substitutions; and the CDR-L1 is a CDR-L1 of SEQ ID NO: 123 or 135 with up to 1, 2, 3, 4, 5, or 6 amino acid substitutions.

In some embodiments, a PSMA antibody or antigen-binding fragment or equivalent thereof provided herein comprises one to three CDRs of a VH domain as set forth in SEQ ID NO: 118 or 130. In some embodiments, a PSMA antibody or antigen-binding fragment or equivalent thereof provided herein comprises two to three CDRs of a VH domain as set forth in SEQ ID Nos: 118 or 130. In some embodiments, a PSMA antibody or antigen-binding fragment or equivalent thereof provided herein comprises three CDRs of a VH domain as set forth in SEQ ID NO: 118 or 130. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, a PSMA antibody or antigen-binding fragment or equivalent thereof provided herein comprises a VH sequence having at least about 50%, 60%, 70%, 80%, 90%, 95%, or 99% identity to an VH sequence set forth in SEQ ID NO: 118 or 130. In some embodiments, an antigen-binding domain provided herein comprises a VH sequence provided in SEQ ID NO: 118 or 130, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antigen-binding domains described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies or antigen-binding domains.

In some embodiments, a PSMA antibody or antigen-binding fragment or equivalent thereof provided herein comprises one to three CDRs of a VL domain as set forth in SEQ ID NO: 119 or 131. In some embodiments, an antigen-binding domain provided herein comprises two to three CDRs of a VL domain as set forth in SEQ ID NO: 119 or 131. In some embodiments, an antigen-binding domain provided herein comprises three CDRs of a VL domain as set forth in SEQ ID NO: 119 or 131. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, a PSMA antibody or antigen-binding fragment or equivalent thereof provided herein comprises a VL sequence having at least about 50%, 60%, 70%, 80%, 90%, 95%, or 99% identity to an VL sequence set forth in SEQ ID NO: 119 or 131. In some embodiments, a PSMA antibody or antigen-binding fragment or equivalent thereof provided herein comprises a VL sequence provided in SEQ ID NO: 119 or 131, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies or antigen-binding domains.

In some embodiments, a PSMA antibody or antigen-binding fragment or equivalent thereof provided herein comprises a sequence having at least about 50%, 60%, 70%, 80%, 90%, 95%, or 99% identity to the sequence set forth in SEQ ID NO: 117 or 129. In some embodiments, a PSMA antibody or antigen-binding fragment or equivalent thereof antigen-binding domain provided herein comprises an scFv sequence provided in SEQ ID NO: 117 or 129, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies or antigen-binding domains.

In some embodiments, an PSMA antibody or antigen-binding fragment or equivalent thereof comprises means for binding a PSMA protein, optionally binding a human PSMA protein in the region(s) of human PSMA bound by the PSMA 1 or PSMA 2 binders (e.g., as described in the Examples below). In some embodiments, the means binds human PSMA protein. In some embodiments, the means is a PSMA antibody or antigen-binding fragment or equivalent thereof (e.g., a full length antibody or a F(ab')2 fragment, a Fab fragment, a single chain variable fragment (scFv), and a single domain antibody (sdAb), or a functional fragment thereof) means for binding human PSMA protein. In some embodiments, the means for binding PSMA includes the anti-PSMA antibodies and antigen-binding fragments or equivalents thereof described herein.

CA9 Antibodies, Antigen Binding Fragments, CDRs, VH, and VL Domains

In some aspects, provided herein are isolated antibodies or antigen binding fragments thereof that bind to Carbonic Anhydrase IX (CA9) (SEQ ID NO: 1). The amino acid sequence of CA9 (HGNC: 1383, NCBI Entrez Gene: 768, Ensembl: ENSG00000107159, UniProtKB/Swiss-Prot: Q16790) is provided in SEQ ID NO: 1.

In some aspects, provided herein are antibodies or antigen binding fragments thereof that bind to CA9. In some aspects, provided herein are means for binding to CA9. In some embodiments, the means for binding to CA9 comprises an antibody or antigen-binding fragment provided herein. In some embodiments, a CA9 antibody or antigen-binding fragment or equivalent thereof comprises means for binding a CA9 protein, optionally binding a human CA9 protein in the region(s) of human CA9 bound by the CA9 binders (e.g., as described in the Examples below). In some embodiments, the means binds a CA9 protein. In some embodiments, the means binds a human CA9 protein. In some embodiments, the means is a CA9 antibody or antigen-binding fragment or equivalent thereof (e.g., a full length antibody or a F(ab')2 fragment, a Fab fragment, a single chain variable fragment (scFv), and a single domain antibody (sdAb), or a functional fragment thereof) means for binding a CA9 protein. In some embodiments, the means for binding CA9 includes the anti-CA9 antibodies and antigen-binding fragments or equivalents thereof described herein.

In some embodiments, a CA9 antibody or antigen-binding fragment or equivalent thereof provided herein binds to human CA9. In some embodiments, a CA9 antibody or antigen-binding fragment or equivalent thereof provided herein does not bind to mouse CA9. In some embodiments, a CA9 antibody or antigen-binding fragment or equivalent thereof provided herein binds to isoforms of human CA9, including, but not limited to, a CA9 protein comprising a R131 W single nucleotide polymorphism (SNP), a Q326R SNP or a 91-96 deletion (91-96del) as compared to SEQ ID NO: 1.

In some aspects, the CA9 antibody or antigen-binding fragment or equivalent thereof comprises a variable heavy (VH) chain sequence comprising three heavy chain CDR sequences, CDR-H1, CDR-H2, and CDR-H3, of the VH sequences set forth in SEQ ID NOs: 99 or 110. In some embodiments, the CA9 antibody or antigen-binding fragment or equivalent thereof comprises a variable light (VL) chain sequence comprising three light chain CDR sequences, CDR-L1, CDR-L2, and CDR-L3, of the VL sequence set forth in SEQ ID NO: 100. In some embodiments, CDR-H1, CDR-H2, CDR-H3, CDR-L1, CDR-L2, CDR-L3 comprise s sequence set forth in Table C. In some embodiments, CDR-H1 comprises the sequence set forth in SEQ ID NO: 101, CDR-H2 comprises the sequence set forth in SEQ ID NO: 102, CDR-H3 comprises the sequence set forth in SEQ ID NO: 103, CDR-L1 comprises the sequence set forth in SEQ ID NO: 104, CDR-L2 comprises the sequence set forth in SEQ ID NO: 105, and CDR-L3 comprises the sequence set forth in SEQ ID NO: 106. In some embodiments, CDR-H1 comprises the sequence set forth in SEQ ID NO: 111, CDR-H2 comprises the sequence set forth in SEQ ID NO: 112, CDR-H3 comprises the sequence set forth in SEQ ID NO: 113.

TABLE C

CA9 binder CDR sequences

| SEQ ID NO | Name | Definition | Sequence |
|---|---|---|---|
| 101 | CA9 1 CDR-H1 | Chothia | GYTFTSY--- |
| 226 | CA9 1 CDR-H1 | AbM | GYTFTSYYMH |
| 227 | CA9 1 CDR-H1 | Kabat | -----SYYMH |
| 228 | CA9 1 CDR-H1 | Contact | ----TSYYMH |
| 229 | CA9 1 CDR-H1 | IMGT | GYTFTSYY-- |
| 102 | CA9 1 CDR-H2 | Chothia | -----NPSRGS--------- |
| 230 | CA9 1 CDR-H2 | AbM | ---IINPSRGSAS------- |
| 231 | CA9 1 CDR-H2 | Kabat | ---IINPSRGSASYAQKFQG |
| 232 | CA9 1 CDR-H2 | Contact | WMGIINPSRGSAS------- |
| 233 | CA9 1 CDR-H2 | IMGT | ----INPSRGSA-------- |
| 103 | CA9 1 CDR-H3 | Chothia | --DRNYYYYMDV |
| 103 | CA9 1 CDR-H3 | AbM | --DRNYYYYMDV |
| 103 | CA9 1 CDR-H3 | Kabat | --DRNYYYYMDV |
| 234 | CA9 1 CDR-H3 | Contact | ARDRNYYYYMD- |
| 235 | CA9 1 CDR-H3 | IMGT | ARDRNYYYYMDV |
| 104 | CA9 1 CDR-L1 | Chothia | RASQNISSNLA-- |
| 104 | CA9 1 CDR-L1 | AbM | RASQNISSNLA-- |
| 104 | CA9 1 CDR-L1 | Kabat | RASQNISSNLA-- |
| 236 | CA9 1 CDR-L1 | Contact | ------SSNLAWY |
| 237 | CA9 1 CDR-L1 | IMGT | ---QNISSN---- |
| 105 | CA9 1 CDR-L2 | Chothia | ----GASTRAT |
| 105 | CA9 1 CDR-L2 | AbM | ----GASTRAT |
| 105 | CA9 1 CDR-L2 | Kabat | ----GASTRAT |
| 238 | CA9 1 CDR-L2 | Contact | LLIYGASTRA- |
|  | CA9 1 CDR-L2 | IMGT | ----GA----- |
| 106 | CA9 1 CDR-L3 | Chothia | QQYITWYT |
| 106 | CA9 1 CDR-L3 | AbM | QQYITWYT |
| 106 | CA9 1 CDR-L3 | Kabat | QQYITWYT |
| 239 | CA9 1 CDR-L3 | Contact | QQYITWY- |
| 106 | CA9 1 CDR-L3 | IMGT | QQYITWYT |
| 111 | CA9 2 CDR-H1 | Chothia | GFSFSDYS--- |
| 240 | CA9 2 CDR-H1 | AbM | GFSFSDYSGMS |
| 241 | CA9 2 CDR-H1 | Kabat | -----DYSGMS |
| 242 | CA9 2 CDR-H1 | Contact | ----SDYSGMS |
| 243 | CA9 2 CDR-H1 | IMGT | GFSFSDYSG-- |
| 112 | CA9 2 CDR-H2 | Chothia | -----SPGGGD--------- |
| 244 | CA9 2 CDR-H2 | AbM | ---AISPGGGDTY------- |

TABLE C-continued

CA9 binder CDR sequences

| SEQ ID NO | Name | Definition | Sequence |
|---|---|---|---|
| 245 | CA9 2 CDR-H2 | Kabat | ---AISPGGGDTYYADSVKG |
| 246 | CA9 2 CDR-H2 | Contact | LVSAISPGGGDTY------- |
| 247 | CA9 2 CDR-H2 | IMGT | ----ISPGGGDT-------- |
| 113 | CA9 2 CDR-H3 | Chothia | --RWWYYSNHSGDYDYFDY |
| 113 | CA9 2 CDR-H3 | AbM | --RWWYYSNHSGDYDYFDY |
| 113 | CA9 2 CDR-H3 | Kabat | --RWWYYSNHSGDYDYFDY |
| 248 | CA9 2 CDR-H3 | Contact | ARRWWYYSNHSGDYDYFD- |
| 249 | CA9 2 CDR-H3 | IMGT | ARRWWYYSNHSGDYDYFDY |

In some embodiments, the VH chain sequence comprises the sequence set forth in SEQ ID NO: 99. In some embodiments, the VH chain sequence comprises the sequence set forth in SEQ ID NO: 110. In some embodiments, the VL comprises the sequence set forth in SEQ ID NO: 100. In some embodiments, the CA9 antibody or antigen-binding fragment or equivalent thereof comprises an extracellular domain comprises the sequence set forth in SEQ ID NO: 98. In some embodiments, the CA9 antibody or antigen-binding fragment or equivalent thereof comprises an extracellular domain comprises the sequence set forth in SEQ ID NO: 110.

In some embodiments, the CA9 antibody or antigen-binding fragment or equivalent thereof CDR-H3 has at least about 50%, 75%, 80%, 85%, 90%, or 95% identity with a CDR-H3 of SEQ ID NO: 103 or 113, the CDR-H2 has at least about 50%, 75%, 80%, 85%, 90%, or 95% identity with a CDR-H2 of SEQ ID NO: 102 or 112, the CDR-H1 has at least about 50%, 75%, 80%, 85%, 90%, or 95% identity with a CDR-H1 of SEQ ID NO: 101 or 111, the CDR-L3 has at least about 50%, 75%, 80%, 85%, 90%, or 95% identity with a CDR-L3 of SEQ ID NO: 106, the CDR-L2 has at least about 50%, 75%, 80%, 85%, 90%, or 95% identity with a CDR-L2 of SEQ ID NO: 105, and the CDR-L1 has at least about 50%, 75%, 80%, 85%, 90%, or 95% identity with a CDR-L1 of SEQ ID NO: 104. In some embodiments, the CDR-H3 is a CDR-H3 of SEQ ID NO: 103 or 113, with up to 1, 2, 3, 4, 5, 6, 7, or 8 amino acid substitutions; the CDR-H2 is a CDR-H2 of SEQ ID NO: 102 or 112, with up to 1, 2, 3, 4, 5, 6, 7, or 8 amino acid substitutions; the CDR-H1 is a CDR-H1 of SEQ ID NO: 101 or 111, with up to 1, 2, 3, 4, or 5 amino acid substitutions; the CDR-L3 is a CDR-L3 of SEQ ID NO: 106, with up to 1, 2, 3, 4, or 5 amino acid substitutions; the CDR-L2 is a CDR-L2 of SEQ ID NO: 105, with up to 1, 2, 3, or 4 amino acid substitutions; and the CDR-L1 is a CDR-L1 of SEQ ID NO: 104 with up to 1, 2, 3, 4, 5, or 6 amino acid substitutions.

In some embodiments, a CA9 antibody or antigen-binding fragment or equivalent thereof provided herein comprises one to three CDRs of a VH domain as set forth in SEQ ID NO: 99 or 110. In some embodiments, a CA9 antibody or antigen-binding fragment or equivalent thereof provided herein comprises two to three CDRs of a VH domain as set forth in SEQ ID Nos: 99 or 110. In some embodiments, a CA9 antibody or antigen-binding fragment or equivalent thereof provided herein comprises three CDRs of a VH domain as set forth in SEQ ID NO: 99 or 110. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, a CA9 antibody or antigen-binding fragment or equivalent thereof provided herein comprises a VH sequence having at least about 50%, 60%, 70%, 80%, 90%, 95%, or 99% identity to an VH sequence set forth in SEQ ID NO: 99 or 110. In some embodiments, an antigen-binding domain provided herein comprises a VH sequence provided in SEQ ID NO: 99 or 110, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antigen-binding domains described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies or antigen-binding domains.

In some embodiments, a CA9 antibody or antigen-binding fragment or equivalent thereof provided herein comprises one to three CDRs of a VL domain as set forth in SEQ ID NO: 100. In some embodiments, an antigen-binding domain provided herein comprises two to three CDRs of a VL domain as set forth in SEQ ID NO: 100. In some embodiments, an antigen-binding domain provided herein comprises three CDRs of a VL domain as set forth in SEQ ID NO: 100. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, a CA9 antibody or antigen-binding fragment or equivalent thereof provided herein comprises a VL sequence having at least about 50%, 60%, 70%, 80%, 90%, 95%, or 99% identity to an VL sequence set forth in SEQ ID NO: 100. In some embodiments, a CA9 antibody or antigen-binding fragment or equivalent thereof provided herein comprises a VL sequence provided in SEQ ID NO: 100, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies or antigen-binding domains.

In some embodiments, a CA9 antibody or antigen-binding fragment or equivalent thereof provided herein comprises a sequence having at least about 50%, 60%, 70%, 80%, 90%, 95%, or 99% identity to the sequence set forth in SEQ ID NO: 98 or 110. In some embodiments, a CA9 antibody or antigen-binding fragment or equivalent thereof antigen-binding domain provided herein comprises an scFv sequence provided in SEQ ID NO: 98 or 110, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies or antigen-binding domains.

In some embodiments, a CA9 antibody or antigen-binding fragment or equivalent thereof comprises means for binding a CA9 protein, optionally binding human CA9 protein in the region(s) of human CA9 protein bound by the CA9 1 or CA9 2 binders (e.g., as described in the Examples below). In some embodiments, the means binds human CA9. In some embodiments, the means is a CA9 antibody or antigen-binding fragment or equivalent thereof (e.g., a full length antibody or a F(ab')2 fragment, a Fab fragment, a single chain variable fragment (scFv), a VHH, and a single domain antibody (sdAb), or a functional fragment thereof) means for binding CA9. In some embodiments, the means for binding CA9 includes the anti-CA9 antibodies and antigen-binding fragments or equivalents thereof described herein.

Logic Gate Systems

As used herein, a "logic gate," "circuit," "circuit receptor," "system" or "system receptor" refers to a two part protein expression system comprising a priming receptor and a chimeric antigen receptor. The system can be encoded on at least one nucleic acid inserted into a cell, where the priming receptor is expressed in the cell. The intracellular domain of the priming receptor is cleaved from the transmembrane domain upon binding of the priming receptor to its target antigen. The intracellular domain is then capable of translocating into a cell nucleus where it induces expression of the chimeric antigen receptor.

In one aspect, provided herein are systems comprising a priming receptor that binds to PSMA and a chimeric antigen receptor that binds to CA9, wherein the transcription factor of the intracellular domain of the priming receptor is capable of inducing expression of the CAR. Such systems are alternatively termed "logic gates" or "circuits." In some aspects, the system is encoded by nucleic acid transgenes inserted into an immune cell. The system can be encoded on a single nucleic acid insert or fragment that comprises both transgenes, or can be encoded on two nucleic acids that encode the system transgenes individually. The priming receptor and CAR of the system can be placed in any order on the single nucleic acid. For example, the priming receptor can be at the 5' end and the CAR can be at the 3' end, or the CAR can be at the 5' end and the priming receptor can be at the 3' end.

A constitutive promoter can be operably linked to the nucleotide sequence encoding the priming receptor. An inducible promoter can also be operably linked to the nucleotide sequence encoding the CAR. In some embodiments, when the system is encoded on a single nucleic acid insert or fragment that comprises both transgenes, the nucleic acid can comprise, in a 5' to 3' direction, the constitutive promoter; the nucleotide sequence encoding priming receptor; the inducible promoter; and the nucleotide sequence encoding chimeric antigen receptor. Alternatively, the nucleic acid can comprise, in a 5' to 3' direction, the inducible promoter; the nucleotide sequence encoding chimeric antigen receptor; the constitutive promoter; the nucleotide sequence encoding priming receptor.

In some embodiments, the constitutive promoter is an EF1α promoter. In some embodiments, the constitutive promoter comprises the sequence of SEQ ID NO: 179.

In some embodiments, the inducible promoter comprises one or more Hepatocyte Nuclear Factor 1α (HNF1α) enhancer element(s). For example, the inducible promoter can comprise 1, 2, 3, 4, 5, 6, 7, or more HNF1α enhancer element(s). In some embodiments, the inducible promoter further comprises a YB-TATA promoter sequence. In some embodiments, the inducible promoter comprises the sequence as set forth in SEQ ID NO: 256.

In some embodiments, the logic gate is encoded on a nucleic acid. In some embodiments, the nucleic acid is selected from the group consisting of the sequences set forth in SEQ ID NOs: 143-147. In some embodiments, the nucleic acid is a sequence as set forth in SEQ ID NO: 143. In some embodiments, the nucleic acid is a sequence as set forth in SEQ ID NO: 144. In some embodiments, the nucleic acid is a sequence as set forth in SEQ ID NO: 145. In some embodiments, the nucleic acid is a sequence as set forth in SEQ ID NO: 146. In some embodiments, the nucleic acid is a sequence as set forth in SEQ ID NO: 147.

In some embodiments, the nucleic acid comprises a sequence as set forth in SEQ ID NO: 143. In some embodiments, the nucleic acid comprises a sequence at least 80%, 85%, 90%, 91%, 92%, 93%, 94%, 95%, 96%, 97%, 98%, 99%, or 100% identical to a sequence as set forth in SEQ ID NO: 143.

In some embodiments, the nucleic acid comprises a sequence as set forth in SEQ ID NO: 144. In some embodiments, the nucleic acid comprises a sequence at least 80%, 85%, 90%, 91%, 92%, 93%, 94%, 95%, 96%, 97%, 98%, 99%, or 100% identical to a sequence as set forth in SEQ ID NO: 144.

In some embodiments, the nucleic acid comprises a sequence as set forth in SEQ ID NO: 145. In some embodiments, the nucleic acid comprises a sequence at least 80%, 85%, 90%, 91%, 92%, 93%, 94%, 95%, 96%, 97%, 98%, 99%, or 100% identical to a sequence as set forth in SEQ ID NO: 145.

In some embodiments, the nucleic acid comprises a sequence as set forth in SEQ ID NO: 146. In some embodiments, the nucleic acid comprises a sequence at least 80%, 85%, 90%, 91%, 92%, 93%, 94%, 95%, 96%, 97%, 98%, 99%, or 100% identical to a sequence as set forth in SEQ ID NO: 146.

In some embodiments, the nucleic acid comprises a sequence as set forth in SEQ ID NO: 147. In some embodiments, the nucleic acid comprises a sequence at least 80%, 85%, 90%, 91%, 92%, 93%, 94%, 95%, 96%, 97%, 98%, 99%, or 100% identical to a sequence as set forth in SEQ ID NO: 147.

Synthetic Receptors

In one aspect, synthetic receptors disclosed herein comprises a domain that specifically binds Prostate-Specific Membrane Antigen (PSMA). In one aspect, synthetic receptors disclosed herein comprises a domain that specifically binds (CA9). In some embodiments, the domain is an extracellular domain. In some embodiments, the domain includes the ligand-binding portion of a receptor. In some embodiments, the domain includes an antigen-binding moiety that binds to one or more target antigens. In some embodiments, the antigen-binding moiety includes one or more antigen-binding determinants of an antibody or a functional antigen-binding fragment or equivalent thereof.

In some embodiments, the antigen-binding moiety is selected from the group consisting of an antibody, a nanobody, a diabody, a triabody, or a minibody, a F(ab')2 fragment, a Fab fragment, a single chain variable fragment (scFv), a VHH, and a single domain antibody (sdAb), or a functional fragment thereof. In some embodiments, the antigen-binding moiety comprises an scFv. The antigen-binding moiety can include naturally-occurring amino acid sequences or can be engineered, designed, or modified so as to provide desired and/or improved properties, e.g., increased binding affinity.

In some embodiments, the synthetic receptor is a chimeric antigen receptor or a priming receptor.

PSMA Receptors

In some embodiments, the antigen-binding domain specifically binds to Prostate-Specific Membrane Antigen. In some embodiments, the antigen-binding domain includes an antigen-binding moiety that binds to Prostate-Specific Membrane Antigen.

In some embodiments, provided herein are isolated synthetic receptors comprising an antigen-binding domain that binds to Prostate-Specific Membrane Antigen (PSMA) (SEQ ID NO: 2).

In some embodiments, the isolated synthetic receptor comprises the PSMA antibody or antigen binding fragments disclosed herein. In some embodiments, the isolated synthetic receptor comprises the sequence set forth in SEQ ID NO: 127. In some embodiments, the isolated synthetic receptor comprises the sequence set forth in SEQ ID NO: 138. In some embodiments, the isolated synthetic receptor comprises the sequence set forth in SEQ ID NO: 252. In some embodiments, the isolated synthetic receptor comprises the sequence set forth in SEQ ID NO: 253.

In some embodiments, the isolated receptor's extracellular antigen-binding domains comprises the variable heavy (VH) chain sequence comprising three heavy chain CDR sequences, CDR-H1, CDR-H2, and CDR-H3, and the variable light (VL) chain sequence comprising three light chain CDR sequences, CDR-L1, CDR-L2, and CDR-L3 of the PSMA antibody or antigen binding fragments disclosed herein.

CA9 Receptors

In some embodiments, the antigen-binding domain specifically binds to Carbonic Anhydrase IX (CA9) (SEQ ID NO: 1). In some embodiments, the domain includes an antigen-binding moiety that binds to Carbonic Anhydrase IX (CA9) (SEQ ID NO: 1).

In some embodiments, provided herein are isolated synthetic receptors comprising an antigen-binding domain that binds to Carbonic Anhydrase IX (CA9) (SEQ ID NO: 1).

In some embodiments, the isolated synthetic receptor comprises any CA9 antibody or antigen binding fragments disclosed herein. In some embodiments, the isolated synthetic receptor comprises the sequence as set forth in SEQ ID NO: 98. In some embodiments, the isolated synthetic receptor comprises the sequence as set forth in SEQ ID NO: 108. In some embodiments, the isolated synthetic receptor comprises the sequence as set forth in SEQ ID NO: 250. In some embodiments, the isolated synthetic receptor comprises the sequence as set forth in SEQ ID NO: 110. In some embodiments, the isolated synthetic receptor comprises the sequence as set forth in SEQ ID NO: 115. In some embodiments, the isolated synthetic receptor comprises the sequence as set forth in SEQ ID NO: 251.

In some embodiments, the isolated synthetic receptor's extracellular antigen-binding domains comprises the variable heavy (VH) chain sequence comprising three heavy chain CDR sequences, CDR-H1, CDR-H2, and CDR-H3, of any CA9 antibody or antigen binding fragments disclosed herein. In some embodiments, the isolated receptor's extracellular antigen-binding domains comprises the variable light (VL) chain sequence comprising three light chain CDR sequences, CDR-L1, CDR-L2, and CDR-L3 of any CA9 antibody or antigen binding fragments disclosed herein.

Priming Receptors

Provided herein are priming receptors comprising an extracellular antigen-binding domain that specifically binds Prostate-Specific Membrane Antigen (PSMA). In some embodiments, the priming receptor comprises an extracellular antigen-binding domain that specifically binds Prostate-Specific Membrane Antigen (PSMA). PSMA is also known as FOLH1 or Folate Hydrolase 1 (HGNC: 3788, NCBI Entrez Gene: 2346, Ensembl: ENSG00000086205, UniProtKB/Swiss-Prot: Q04609). The amino acid sequence of PSMA is provided in SEQ ID NO: 2.

In certain aspects of the present disclosure, the priming receptor is a synthetic receptor based on the Notch protein. Binding of a natural Notch receptor to a cognate ligand, such as those from the Delta family of proteins, causes intramembrane proteolysis that cleaves an intracellular fragment of the Notch protein. This intracellular fragment is a transcriptional regulator that only functions when cleaved from Notch. Cleavage may occur by sequential proteolysis by ADAM metalloprotease and the gamma-secretase complex. This intracellular fragment enters the nucleus of a cell and activates cell-cell signaling genes. In contrast to a natural Notch protein, a synthetic notch priming receptor replaces the natural Notch intracellular fragment with one that causes a gene encoding a protein of choice, such as a CAR, to be transcribed upon release of the intracellular fragment from the priming receptor.

Notch receptors have a modular domain organization. The ectodomains of Notch receptors consist of a series of N-terminal epidermal growth factor (EGF)-like repeats that are responsible for ligand binding. In synthetic Notch receptors or priming receptors, the Notch ligand-binding domain is replaced with a ligand binding domain that binds a selected target ligand or antigen. The EGF repeats are followed by three LIN-12/Notch repeat (LNR) modules, which are unique to Notch receptors, and are widely reported to participate in preventing premature receptor activation. The heterodimerization (HD) domain of Notch1 is divided by furin cleavage, so that its N-terminal part terminates the extracellular subunit, and its C-terminal half constitutes the beginning of the transmembrane subunit. Following the extracellular region, the receptor has a transmembrane segment and an intracellular domain (ICD), which includes a transcriptional regulator.

Multiple forms of priming receptors can be used in the methods, cells, and nucleic acids as described herein. One type of priming receptor contemplated for use in the methods and cells herein comprise a heterologous extracellular ligand binding domain, a linking polypeptide having substantial sequence identity with a Notch receptor including the NRR, a TMD, and an ICD. "Fn Notch" receptors comprise a heterologous extracellular ligand binding domain, a linking polypeptide having substantial sequence identity with a Robo receptor (such as a mammalian Robo1, Robo2, Robo3, or Robo4), followed by 1, 2, or 3 fibronectin repeats ("Fn"), a TMD, and an ICD. "Mini Notch" receptors comprise a heterologous extracellular ligand binding domain, a linking polypeptide having substantial sequence identity with a Notch receptor (lacking the NRR), a TMD, and an ICD. "Minimal Linker Notch" receptors comprise a heterologous extracellular ligand binding domain, a linking polypeptide lacking substantial sequence identity with a Notch receptor (e.g., a synthetic (GGS)n polypeptide sequence), a TMD, and an ICD. "Hinge Notch" receptors comprise a heterologous extracellular ligand binding domain, a hinge sequence comprising an oligomerization domain (i.e., a domain that promotes dimerization, trimerization, or higher order multimerization with a synthetic receptor and/or an existing host receptor), a TMD, and an ICD. All of these receptor classes are synthetic, recombinant, and do not occur in nature. In some embodiments, the non-naturally occurring receptors disclosed herein bind a target cell-surface displayed ligand, which triggers proteolytic cleavage of the receptors and release of a transcriptional regulator that modulates a custom transcriptional program in the cell. In some embodiments, the priming receptor does not include a LIN-12-Notch repeat (LNR) and/or a heterodimerization domain (HD) of a Notch receptor.

Priming Receptor Extracellular Domain

The priming receptor disclosed herein comprises an extracellular domain that specifically binds Prostate-Specific Membrane Antigen (PSMA). In some embodiments, provided herein are priming receptors comprising an extracellular antigen-binding domain that binds to Prostate-Specific Membrane Antigen (PSMA) (SEQ ID NO: 2). In some embodiments, the priming receptor extracellular antigen-binding domains comprises a variable heavy (VH) chain sequence comprising three heavy chain CDR sequences, CDR-H1, CDR-H2, and CDR-H3, and a variable light (VL) chain sequence comprising three light chain CDR sequences, CDR-L1, CDR-L2, and CDR-L3 of any PSMA antibody or antigen binding fragments disclosed herein.

In some embodiments, the extracellular domain includes the ligand-binding portion of a receptor. In some embodiments, the extracellular domain includes an antigen-binding moiety that binds to one or more target antigens. In some embodiments, the antigen-binding moiety includes one or more antigen-binding determinants of an antibody or a functional antigen-binding fragment or equivalent thereof. In some embodiments, the antigen-binding moiety is selected from the group consisting of an antibody, a nanobody, a diabody, a triabody, or a minibody, a F(ab')2 fragment, a Fab fragment, a single chain variable fragment (scFv), a VHH, and a single domain antibody (sdAb), or a functional fragment thereof. In some embodiments, the antigen-binding moiety comprises an scFv. The antigen-binding moiety can include naturally-occurring amino acid sequences or can be engineered, designed, or modified so as to provide desired and/or improved properties, e.g., increased binding affinity.

In some embodiments, the extracellular antigen-binding domain specifically binds to Prostate-Specific Membrane Antigen. In some embodiments, the extracellular domain includes an antigen-binding moiety that binds to Prostate-Specific Membrane Antigen.

In some embodiments, the priming receptor comprises the PSMA antibody or antigen binding fragments disclosed herein. In some embodiments, the isolated receptor comprises the sequence set forth in SEQ ID NO: 127. In some embodiments, the priming receptor comprises the sequence set forth in SEQ ID NO: 138. In some embodiments, the isolated receptor comprises the sequence set forth in SEQ ID NO: 252. In some embodiments, the isolated receptor comprises the sequence set forth in SEQ ID NO: 253.

The PSMA priming receptor sequence provided in SEQ ID NO: 127 includes the leader sequence, while the PSMA priming receptor sequence provided in SEQ ID NO: 252 excludes the leader sequence. The PSMA priming receptor sequence provided in SEQ ID NO: 138 includes the leader sequence, while the PSMA priming receptor sequence provided in SEQ ID NO: 253 excludes the leader sequence.

In various embodiments, a priming receptor comprises means for binding a PSMA protein, optionally binding a human PSMA protein in the region(s) of human PSMA bound by the PSMA binders (e.g., as described in the Examples below). In some embodiments, the means binds a PSMA protein. In some embodiments, the means binds a human PSMA protein. In some embodiments, the means is a PSMA antibody or antigen-binding fragment or equivalent thereof (e.g., a full length antibody or a F(ab')2 fragment, a Fab fragment, a single chain variable fragment (scFv), and a single domain antibody (sdAb), or a functional fragment thereof). In some embodiments, the means for binding PSMA includes the anti-PSMA antibodies and antigen-binding fragments or equivalents thereof described herein.

The extracellular domain of the priming receptor can further comprise a signal sequence, such as a CD8α signal sequence. In some embodiments, the priming receptor comprises a CD8α signal sequence as set forth in SEQ ID NO: 91.

Transmembrane Domain

In some embodiments, the priming receptor comprises a hinge domain. In some embodiments, the hinge domain is a CD8 or a CD8α hinge. In some embodiments, the priming receptor hinge domain comprises the sequence as set forth in SEQ ID NO: 85.

As described above, the priming receptor comprises a transmembrane domain (TMD) comprising one or more ligand-inducible proteolytic cleavage sites.

In some embodiments, the TMD comprises a Notch1 transmembrane domain.

Generally, the TMD suitable for the chimeric receptors disclosed herein can be any transmembrane domain of a Type 1 transmembrane receptor including at least one gamma-secretase cleavage site. Detailed description of the structure and function of the gamma-secretase complex as well as its substrate proteins, including amyloid precursor protein (APP) and Notch, can, for example, be found in a recent review by Zhang et al, Frontiers Cell Neurosci (2014). Non limiting suitable TMDs from Type 1 transmembrane receptors include those from CLSTN1, CLSTN2, APLP1, APLP2, LRP8, APP, BTC, TGBR3, SPN, CD44, CSF1R, CXCL16, CX3CL1, DCC, DLL1, DSG2, DAG1, CDH1, EPCAM, EPHA4, EPHB2, EFNB1, EFNB2, ErbB4, GHR, HLA-A, and IFNAR2, wherein the TMD includes at least one gamma secretase cleavage site. Additional TMDs suitable for the compositions and methods described herein include, but are not limited to, transmembrane domains from Type 1 transmembrane receptors IL1R1, IL1R2, IL6R, INSR, ERN1, ERN2, JAG2, KCNE1, KCNE2, KCNE3, KCNE4, KL, CHL1, PTPRF, SCN1B, SCN3B, NPR3, NGFR, PLXDC2, PAM, AGER, ROBO1, SORCS3, SORCS1, SORL1, SDC1, SDC2, SPN, TYR, TYRP1, DCT, YASN, FLT1, CDH5, PKHD1, NECTIN1, PCDHGC3, NRG1, LRP1B, CDH2, NRG2, PTPRK, SCN2B, Nradd, and PTPRM. In some embodiments, the TMD of the chimeric polypeptides or Notch receptors of the disclosure is a TMD derived from the TMD of a member of the calsyntenin family, such as, alcadein alpha and alcadein gamma. In some embodiments, the TMD of the chimeric polypeptides or Notch receptors of the disclosure is a TMD known for Notch receptors. In some embodiments, the TMD of the chimeric polypeptides or Notch receptors of the disclosure is a TMD derived from a different Notch receptor. For example, in a Mini Notch based on human Notch1, the Notch1 TMD can be substituted with a Notch2 TMD, Notch3 TMD, Notch4 TMD, or a Notch TMD from a non-human animal such as *Danio rerio, Drosophila melanogaster, Xenopus laevis*, or *Gallus gallus*.

In some embodiments, the priming receptor comprises a Notch cleavage site, such as S2 or S3. Additional proteolytic cleavage sites suitable for the compositions and methods disclosed herein include, but are not limited to, ADAM10, a metalloproteinase cleavage site for a MMP selected from collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). Another example of a suitable protease cleavage site is a plasminogen activator cleavage site, e.g., a urokinase plasminogen activator (uPA) or a tissue plasminogen activator (tPA) cleavage site. Another example of a suitable protease cleavage site is a prolactin cleavage site. Specific examples of cleavage sequences of uPA and tPA include sequences comprising Yal-Gly-Arg. Another example of a protease cleavage site that can be included in a proteolytically cleavable linker is a tobacco etch vims (TEV) protease cleavage site, e.g., Glu-Asn-Leu-Tyr-Thr-Gln-Ser (SEQ ID NO: 264), where the protease cleaves between the glutamine and the serine. Another example of a protease cleavage site that can be included in a proteolytically cleavable linker is an enterokinase cleavage site, e.g., Asp-Asp-Asp-Asp-Lys (SEQ ID NO: 265), where cleavage occurs after the lysine residue. Another example of a protease cleavage site that can be included in a proteolytically cleavable linker is a thrombin cleavage site, e.g., Leu-Val-Pro-Arg (SEQ ID NO: 266). Additional suitable linkers comprising protease cleavage sites include sequences cleavable by the following proteases: a PreScission™ protease (a fusion protein comprising human rhinovirus 3C protease and glutathione-S-transferase), a thrombin, cathepsin B, Epstein-Barr vims proteas, MMP-3 (stromelysin), MMP-7 (matrilysin), MMP-9; thermolysin-like MMP, matrix metalloproteinase 2 (MMP-2), cathepsin L; cathepsin D, matrix metalloproteinase 1 (MMP-1), urokinase-type plasminogen activator, membrane type 1 matrixmetalloprotemase (MT-MMP), stromelysin 3 (or MMP-11), thermo lysin, fibroblast collagenase and stromelysin-1, matrix metalloproteinase 13 (collagenase-3), tissue-type plasminogen activator(tPA), human prostate-specific antigen, kallikrein (hK3), neutrophil elastase, and calpain (calcium activated neutral protease). Proteases that are not native to the host cell in which the receptor is expressed (for example, TEV) can be used as a further regulatory mechanism, in which activation of the receptor is reduced until the protease is expressed or otherwise provided. Additionally, a protease may be tumor-associated or disease-associated (expressed to a significantly higher degree than in normal tissue), and serve as an independent regulatory mechanism. For example, some matrix metalloproteases are highly expressed in certain cancer types.

In some embodiments, the amino acid substitution(s) within the TMD includes one or more substitutions within a "GV" motif of the TMD. In some embodiments, at least one of such substitution(s) comprises a substitution to alanine. Additional sequences and substitutions are described in WO2021061872, hereby incorporated by reference in its entirety.

In some embodiments, the TMD domain comprises the sequence as set forth in SEQ ID NO: 86.

Intracellular Domain

In some embodiments, the priming receptor comprises one or more intracellular domains from or derived from a transcriptional regulator and/or a DNA-binding domain. In some embodiments, the intracellular domain comprises means for modulating transcription of one or more genes. In some embodiments, the means for modulating transcription of one or more genes comprises a transcriptional regulator, e.g., a transcriptional regulator provided herein or an equivalent thereof. In some embodiments, the priming receptor comprises one or more intracellular domains from or derived from a transcriptional regulator and/or a DNA-binding domain. In some embodiments, the intracellular domain comprises an HNF1α/p65 domain or a Gal4/VP64 domain.

Transcriptional regulators either activate or repress transcription from cognate promoters. Transcriptional activators typically bind nearby to transcriptional promoters and recruit RNA polymerase to directly initiate transcription. Transcriptional repressors bind to transcriptional promoters and sterically hinder transcriptional initiation by RNA polymerase. Other transcriptional regulators serve as either an activator or a repressor depending on where it binds and cellular conditions. Accordingly, as used herein, a "transcriptional activation domain" or "TAD" refers to the domain of a transcription factor that interacts with transcriptional control elements and/or transcriptional regulatory proteins (i.e., transcription factors, RNA polymerases, etc.) to increase and/or activate transcription of one or more genes. Non-limiting examples of transcriptional activation domains include: a herpes simplex virus VP16 activation domain, VP64 (which is a tetrameric derivative of VP16), HIV TAT, a NFkB p65 activation domain, p53 activation domains 1 and 2, a CREB (cAMP response element binding protein) activation domain, an E2A activation domain, NFAT (nuclear factor of activated T-cells) activation domain, yeast Gal4, yeast GCN4, yeast HAP1, MLL, RTG3, GLN3, OAF1, PIP2, PDR1, PDR3, PHO4, LEU3 glucocorticoid receptor transcription activation domain, B-cell POU homeodomain protein Oct2, plant Ap2, or any others known to one or ordinary skill in the art. In some embodiments, the transcriptional regulator is selected from Gal4-VP16, Gal4-VP64, tetR-VP64, ZFHD1-YP64, Gal4-KRAB, and HAP1-VP16. In some embodiments, the transcriptional regulator is Gal4-VP64. In some embodiments, the transcriptional regulator is p65. A transcriptional activation domain can comprise a wild-type or naturally occurring sequence, or it can be a modified, mutant, or derivative version of the original transcriptional activation domain that has the desired ability to increase and/or activate transcription of one or more genes. In some embodiments, the transcriptional regulator can further include a nuclear localization signal.

In some embodiments, the priming receptor comprises one or more intracellular "DNA-binding domains" (or "DB domains"). Such "DNA-binding domains" refer to sequence-specific DNA binding domains that bind a particular DNA sequence element. Accordingly, as used herein, a "sequence-specific DNA-binding domain" refers to a protein domain portion that has the ability to selectively bind DNA having a specific, predetermined sequence. A sequence-specific DNA binding domain can comprise a wild-type or naturally occurring sequence, or it can be a modified, mutant, or derivative version of the original domain that has the desired ability to bind to a desired sequence. In some embodiments, the sequence-specific DNA binding domain is engineered to bind a desired sequence. Non-limiting examples of proteins having sequence-specific DNA binding domains that can be used in synthetic proteins described herein include HNF1α, Gal4, GCN4, reverse tetracycline receptor, THY1, SYN1, NSE/ RU5', AGRP, CALB2, CAMK2A, CCK, CHAT, DLX6A, EMX1, zinc finger proteins or domains thereof, CRISPR/ Cas proteins, such as Cas9, Cas3, Cas4, Cas5, Cas5e (or CasD), Cash, Cas6e, Cas6f, Cas7, Cas8a1, Cas8a2, Cas8b, Cas8c, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu196, and TALES. In some embodiments the DNA binding domain (DBD) is HNF1α.

In those embodiments where a CRISPR/Cas-like protein is used, the CRISPR/Cas-like protein can be a wild type CRISPR/Cas protein, a modified CRISPR/Cas protein, or a fragment of a wild type or modified CRISPR/Cas protein. The CRISPR/Cas-like protein can be modified to increase nucleic acid binding affinity and/or specificity, alter an enzymatic activity, and/or change another property of the protein. For example, nuclease (i.e., DNase, RNase) domains of the CRISPR/Cas-like protein can be modified, deleted, or inactivated. Alternatively, the CRISPR/Cas-like protein can be truncated to remove domains that are not essential for the functions of the systems described herein. For example, a CRISPR enzyme that is used as a DNA binding protein or domain thereof can be mutated with respect to a corresponding wild-type enzyme such that the mutated CRISPR or domain thereof lacks the ability to cleave a nucleic acid sequence containing a DNA binding domain target site. For example, a D10A mutation can be combined with one or more of H840A, N854A, or N863A mutations to produce a Cas9 enzyme substantially lacking all DNA cleavage activity.

In some embodiments, the intracellular domain comprises the sequence as set forth in SEQ ID NOs: 88, 89, or 90. In some embodiments, the intracellular domain comprises an HNF1α DNA binding domain (DBD) sequence as set forth in SEQ ID NO: 88. In some embodiments, the intracellular domain comprises a p65 transcriptional activation domain (TAD) sequence as set forth in SEQ ID NO: 89. In some embodiments, the intracellular domain comprises an HNF1α/p65 DBD-TAD domain sequence as set forth in SEQ ID NO: 90.

Juxtamembrane Domain

The ECD and the TMD, or the TMD and the ICD, can be linked to each other with a linking polypeptide, such as a juxtamembrane domain. "SynNotch" or synthetic notch receptors comprise a heterologous extracellular ligand-binding domain, a linking polypeptide having substantial sequence identity with a Notch receptor JMD (including the NRR), a TMD, and an ICD. "Fn Notch" receptors comprise a heterologous extracellular ligand binding domain, a linking polypeptide having substantial sequence identity with a Robo receptor (such as a mammalian Robo1, Robo2, Robo3, or Robo4), followed by 1, 2, or 3 fibronectin repeats ("Fn"), a TMD, and an ICD. "Mini Notch" receptors comprise a heterologous extracellular ligand binding domain, a linking polypeptide having substantial sequence identity with a Notch receptor JMD but lacking the NRR (the LIN-12-Notch repeat (LNR) modules, and the heterodimerization domain), a TMD, and an ICD. "Minimal Linker Notch" receptors comprise a heterologous extracellular ligand-binding domain, a linking polypeptide lacking substantial sequence identity with a Notch receptor (for example, without limitation, having a synthetic (GGS)$_n$ polypeptide sequence), a TMD, and an ICD. "Hinge Notch" receptors comprise a heterologous extracellular ligand-binding domain, a hinge sequence comprising an oligomerization domain (i.e., a domain that promotes dimerization, trimerization, or higher order multimerization with a synthetic receptor and/or an existing host receptor), a TMD, and an ICD.

In some embodiments, the priming receptor comprises a juxtamembrane domain (JMD) peptide in between the extracellular domain and the transmembrane domain. In some embodiments, the priming receptor comprises a juxtamembrane domain (JMD) peptide in between the transmembrane domain and the intracellular domain. In some embodiments, the JMD peptide comprises an LWF motif. The use of LWF motifs in receptor constructs is described in U.S. Pat. No. 10,858,443, hereby incorporated by reference in its entirety. In some embodiments, the JMD peptide has substantial sequence identity to the JMD of Notch1, Notch2, Notch3, and/or Notch4. In some embodiments, the JMD peptide has substantial sequence identity to the Notch1, Notch2, Notch3, and/or Notch4 JMD, but does not include a LIN-12-Notch repeat (LNR) and/or a heterodimerization domain (HD) of a Notch receptor. In some embodiments, the JMD peptide does not have substantial sequence identity to the Notch1, Notch2, Notch3, and/or Notch4 JMD. In some embodiments, the JMD peptide includes an oligimerization domain which promotes formation of dimers, trimers, or higher order assemblages of the receptor. Such JMD peptides are described in WO2021061872, hereby incorporated by reference in its entirety.

In the Mini Notch receptor, the linking polypeptide is derived from a Notch JMD sequence after deletion of the NRR and HD domain. The Notch JMD sequence may be the sequence from Notch1, Notch2, Notch3, or Notch4, and can be derived from a non-human homolog, such as those from *Drosophila, Gallus, Danio*, and the like. Four to 50 amino acid residues of the remaining Notch sequence can be used as a polypeptide linker. In some embodiments, the length and amino acid composition of the linker polypeptide sequence are varied to alter the orientation and/or proximity of the ECD and the TMD relative to one another to achieve a desired activity of the chimeric polypeptide, such as the signal transduction level when ligand induced or in the absence of ligand.

In the Minimal Linker Notch receptor, the linking polypeptide does not have substantial sequence identity to a Notch JMD sequence, including the Notch JMD sequence from Notch1, Notch2, Notch3, or Notch4, or a non-human homolog thereof. Four to 50 amino acid residues can be used as a polypeptide linker. In some embodiments, the length and amino acid composition of the linker polypeptide sequence are varied to alter the orientation and/or proximity of the ECD and the TMD relative to one another to achieve a desired activity of the chimeric polypeptide of the disclosure. The Minimal Linker sequence can be designed to include or omit a protease cleavage site, and can include or omit a glycosylation site or sites for other types of post-translational modification. In some embodiments, the Minimal Linker does not comprise a protease cleavage site or a glysosylation site.

In some embodiments, the priming receptor further comprises a hinge. Hinge linkers that can be used in the priming receptor can include an oligomerization domain (e.g., a hinge domain) containing one or more polypeptide motifs that promote oligomer formation of the chimeric polypeptides via intermolecular disulfide bonding. In these instances, within the chimeric receptors disclosed herein, the hinge domain generally includes a flexible polypeptide connector region disposed between the ECD and the TMD. Thus, the hinge domain provides flexibility between the ECD and TMD and also provides sites for intermolecular disulfide bonding between two or more chimeric polypeptide monomers to form an oligomeric complex. In some embodiments, the hinge domain includes motifs that promote dimer formation of the chimeric polypeptides disclosed herein. In some embodiments, the hinge domain includes motifs that promote trimer formation of the chimeric polypeptides disclosed herein (e.g., a hinge domain derived from OX40). Hinge polypeptide sequences suitable for the compositions and methods of the disclosure can be naturally-occurring hinge polypeptide sequences (e.g., those from naturally-occurring immunoglobulins) or can be engineered, designed, or modified so as to provide desired and/or improved properties, e.g., modulating transcription. Suitable hinge polypeptide sequences include, but are not limited to, those derived from IgA, IgD, and IgG subclasses, such as IgG1 hinge domain, IgG2 hinge domain, IgG3 hinge domain, and IgG4 hinge domain, or a functional variant thereof. In some embodiments, the hinge polypeptide sequence contains one or more CXXC motifs. In some embodiments, the hinge polypeptide sequence contains one or more CPPC motifs (SEQ ID NO: 267).

Hinge polypeptide sequences can also be derived from a CD8α hinge domain, a CD28 hinge domain, a CD152 hinge domain, a PD-1 hinge domain, a CTLA4 hinge domain, an OX40 hinge domain, and functional variants thereof. In some embodiments, the hinge domain includes a hinge polypeptide sequence derived from a CD8α hinge domain or a functional variant thereof. In some embodiments, the hinge domain includes a hinge polypeptide sequence derived from a CD28 hinge domain or a functional variant thereof. In some embodiments, the hinge domain includes a hinge polypeptide sequence derived from an OX40 hinge domain or a functional variant thereof. In some embodiments, the hinge domain includes a hinge polypeptide sequence derived from an IgG4 hinge domain or a functional variant thereof.

The Fn Notch linking polypeptide is derived from the Robo1 JMD, which contains a fibronectin repeat (Fn) domain, with a short polypeptide sequence between the Fn repeats and the TMD. The Fn Notch linking polypeptide does not contain a Notch negative regulatory region (NRR), or the Notch HD domain. The Fn linking polypeptide can contain 1, 2, 3, 4, or 5 Fn repeats. In some embodiments, the chimeric receptor comprises a Fn linking polypeptide having about 1 to about 5 Fn repeats, about 1 to about 3 Fn repeats, or about 2 to about 3 Fn repeats. The short polypeptide sequence between the Fn repeats and the TMD can be from about 2 to about 30 amino acid residues. In some embodiments, the short polypeptide sequence can be between about 5 and about 20 amino acids, of any sequence. In some embodiments, the short polypeptide sequence can be between about 5 and about 20 naturally-occurring amino acids, of any sequence. In some embodiments, the short polypeptide sequence can be between about 5 and about 20 amino acids, of any sequence but having no more than one proline. In some embodiments, the short polypeptide sequence can be between about 5 and about 20 amino acids, and about 50% or more of the amino acids are glycine. In some embodiments, the short polypeptide sequence can be between about 5 and about 20 amino acids, where the amino acids are selected from glycine, serine, threonine, and alanine. In some embodiments, the length and amino acid composition of the Fn linking polypeptide sequence can be varied to alter the orientation and/or proximity of the ECD and the TMD relative to one another to achieve a desired activity of the chimeric polypeptide of the disclosure.

Stop-Transfer Sequence

In some embodiments, the priming receptor further comprises a stop-transfer sequence (STS) in between the transmembrane domain and the intracellular domains. The STS comprises a charged, lipophobic sequence. Without being bound by any theory, the STS serves as a membrane anchor, and is believed to prevent passage of the intracellular domain into the plasma membrane. The use of STS domains in priming receptors is described in WO2021061872, hereby incorporated by reference in its entirety. Non-limiting exemplary STS sequences include APLP1, APLP2, APP, TGBR3, CSF1R, CXCL16, CX3CL1, DAG1, DCC, DNER, DSG2, CDH1, GHR, HLA-A, IFNAR2, IGF1R, IL1R1, ERN2, KCNE1, KCNE2, CHL1, LRP1, LRP2, LRP18, PTPRF, SCN1B, SCN3B, NPR3, NGFR, PLXDC2, PAM, AGER, ROBO1, SORCS3, SORCS1, SORL1, SDC1, SDC2, SPN, TYR, TYRP1, DCT, VASN, FLT1, CDH5, PKTFD1, NECTIN1, KL, IL6R, EFNB1, CD44, CLSTN1, LRP8, PCDHGC3, NRG1, LRP1B, JAG2, EFNB2, DLL1, CLSTN2, EPCAM, ErbB4, KCNE3, CDH2, NRG2, PTPRK, BTC, EPHA4, IL1R2, KCNE4, SCN2B, Nradd, PTPRM, Notch1, Notch2, Notch3, and Notch4 STS sequences. In some embodiments, the STS is heterologous to the transmembrane domain. In some embodiments, the STS is homologous to the transmembrane domain. STS sequences are described in WO2021061872, hereby incorporated by reference in its entirety.

In some embodiments, the STS domain comprises the sequence as set forth in SEQ ID NO: 87.

Chimeric Antigen Receptors

In another aspect, provided herein are chimeric antigen receptors comprising an extracellular antigen-binding domain that specifically binds to Carbonic Anhydrase IX (CA9). The CAR can be a human CAR, comprising fully human sequences, e.g., natural human sequences. The amino acid sequence of CA9 (HGNC: 1383, NCBI Entrez Gene: 768, Ensembl: ENSG00000107159, UniProtKB/Swiss-Prot: Q16790) is provided in SEQ ID NO: 1.

In some embodiments, the chimeric antigen receptor includes an extracellular portion comprising an antigen binding domain. The antigen recognition domain of a receptor such as a CAR can be linked to one or more intracellular signaling components, such as signaling components that mimic activation through an antigen receptor complex, such as a TCR complex, in the case of a CAR, and/or signal via another cell surface receptor. Thus, in some embodiments, the extracellular binding component (e.g., ligand-binding or antigen-binding domain) is linked to one or more transmembrane and intracellular signaling domains. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

In some aspects, the chimeric antigen receptor includes an extracellular portion comprising an antigen binding domain described herein and an intracellular signaling domain. In some embodiments, an antibody or fragment includes an scFv, a VH, or a single-domain VH antibody and the intracellular domain contains an ITAM. In some aspects, the intracellular signaling domain includes a signaling domain of a zeta chain of a CD3-zeta (CD3) chain. In some embodiments, the chimeric antigen receptor includes a transmembrane domain linking the extracellular domain and the intracellular signaling domain.

In some aspects, the transmembrane domain contains a transmembrane portion of CD8α or CD28. The extracellular domain and transmembrane can be linked directly or indirectly. In some embodiments, the extracellular domain and transmembrane are linked by a spacer, such as any described herein. In some embodiments, the chimeric antigen receptor contains an intracellular domain of a T cell costimulatory molecule, such as between the transmembrane domain and intracellular signaling domain. In some aspects, the T cell costimulatory molecule is CD28 or 41BB.

Chimeric Antigen Receptor Extracellular Domain

The chimeric antigen receptors disclosed herein comprises an extracellular domain that specifically binds Carbonic Anhydrase IX (CA9). In some embodiments, provided herein are chimeric antigen receptors comprising an extracellular antigen-binding domain that binds to Carbonic Anhydrase IX (CA9) (SEQ ID NO: 1). In some embodiments, the chimeric antigen receptors extracellular antigen-binding domains comprises a variable heavy (VH) chain sequence comprising three heavy chain CDR sequences, CDR-H1, CDR-H2, and CDR-H3. In some embodiments, the chimeric antigen receptors extracellular antigen-binding domains comprises a variable light (VL) chain sequence comprising three light chain CDR sequences, CDR-L1, CDR-L2, and CDR-L3 of any CA9 antibody or antigen binding fragments disclosed herein.

In some embodiments, the chimeric antigen receptor comprises the sequence as set forth in SEQ ID NO: 98. In some embodiments, the chimeric antigen receptor comprises the sequence as set forth in SEQ ID NO: 108 or 250. In some embodiments, the chimeric antigen receptor comprises the sequence as set forth in SEQ ID NO: 110. In some embodiments, the chimeric antigen receptor comprises the sequence as set forth in SEQ ID NO: 115 or 251. The CA9 CAR sequence provided in SEQ ID NO: 108 includes the leader sequence, while the CA9 CAR sequence provided in SEQ ID NO: 250 excludes the leader sequence. The CA9 CAR sequence provided in SEQ ID NO: 115 includes the leader sequence, while the CA9 CAR sequence provided in SEQ ID NO: 251 excludes the leader sequence.

In some embodiments, the extracellular domain includes the ligand-binding portion of a receptor. In some embodiments, the extracellular domain includes an antigen-binding moiety that binds to one or more target antigens. In some embodiments, the antigen-binding moiety includes one or more antigen-binding determinants of an antibody or a functional antigen-binding fragment or equivalent thereof. In some embodiments, the antigen-binding moiety is selected from the group consisting of an antibody, a nanobody, a diabody, a triabody, or a minibody, a F(ab')2 fragment, a Fab fragment, a single chain variable fragment (scFv), a VHH, and a single domain antibody (sdAb), or a functional fragment thereof. In some embodiments, the antigen-binding moiety comprises an scFv. The antigen-binding moiety can include naturally-occurring amino acid sequences or can be engineered, designed, or modified so as to provide desired and/or improved properties, e.g., increased binding affinity.

In some embodiments, the extracellular antigen-binding domain specifically binds to Carbonic Anhydrase IX (CA9). In some embodiments, the extracellular domain includes an antigen-binding moiety that binds to Carbonic Anhydrase IX (CA9).

In various embodiments, a CAR comprises means for binding a CA9 protein, optionally binding a human CA9 protein in the region(s) of human CA9 bound by the CA9 binders (e.g., as described in the Examples below). In some embodiments, the means binds a CA9 protein. In some embodiments, the means binds a human CA9 protein. In some embodiments, the means is a CA9 antibody or antigen-binding fragment or equivalent thereof (e.g., a full length antibody or a F(ab')2 fragment, a Fab fragment, a single chain variable fragment (scFv), and a single domain antibody (sdAb), or a functional fragment thereof) means for binding a CA9 protein. In some embodiments, the means for binding CA9 includes the anti-CA9 antibodies and antigen-binding fragments or equivalents thereof described herein.

The extracellular domain of the CAR can further comprise a signal sequence, such as a CD8α signal sequence. In some embodiments, the CAR comprises a CD8α signal sequence as set forth in SEQ ID NO: 91.

CAR Transmembrane Domain

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD 16, CD22, CD33, CD37, CD64, CD80, CD86, CD 134, CD137, and/or CD 154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

In some embodiments, the transmembrane domain (TMD) of the receptor, e.g., the CAR, is a transmembrane domain of human CD28 or variant thereof, e.g., a 27-amino acid transmembrane domain of a human CD28 (UniProt Accession No.: P10747).

In some embodiments, the transmembrane domain (TMD) of the receptor, e.g., the CAR, is a transmembrane domain of human CD8α or variant thereof, e.g., a 24-amino acid transmembrane domain of a human CD8α (UniProt Accession No.: P01732).

In some embodiments, the CAR comprises a CD8α or CD28 TMD. In some embodiments, the CD8α TMD comprises the sequence set forth in SEQ ID NO: 93. In some embodiments, the CD28 TMD comprises the sequence set forth in SEQ ID NO: 95.

CAR Hinge

In some embodiments, the CAR further includes a spacer, which may be or include at least a portion of an immunoglobulin constant region or variant or modified version thereof, such as a hinge region, e.g., a CD8α hinge, a CD28 hinge, an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include CD8α hinge, CD28 hinge, IgG4 hinge alone, IgG4 hinge linked to CH2 and CH3 domains, or IgG4 hinge linked to the CH3 domain. Exemplary spacers include, but are not limited to, those described in Hudecek et al. (2013) Clin. Cancer Res., 19:3153 or international patent application publication number WO2014031687. In some embodiments, the CAR hinge comprises a CD8α, truncated CD8α, or CD28 hinge domain. In some embodiments, the hinge domain comprises a CD8α hinge comprising the sequence as set forth in SEQ ID NO: 92. In some embodiments, the hinge domain comprises a CD28 hinge comprising the sequence as set forth in SEQ ID NO: 94.

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the receptor.

CAR Intracellular Domain

In some embodiments, upon ligation of the CAR, the cytoplasmic domain or intracellular signaling domain of the receptor activates at least one of the normal effector functions or responses of the immune cell, e.g., T cell engineered to express the receptor. In some embodiments, the CAR comprises means for activating at least one of the normal effector functions or responses of the immune cell, e.g., T cell engineered to express the receptor. For example, in some contexts, the receptor induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability. In some embodiments, the means for at least one of the normal effector functions or responses of the immune cell comprises an CAR intracellular activation domain, e.g., an intracellular activation domain provided herein or an equivalent thereof. In some embodiments, the means for at least one of the normal effector functions or responses of the immune cell comprises an CAR intracellular activation domain and a CAR co-stimulatory domain, e.g., a co-stimulatory domain provided herein or an equivalent thereof.

In some aspects, the receptor includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR or CD3 zeta, FcR gamma, FcR beta, CD3 gamma, CD3 delta, CD3 epsilon, CD5, CD22, CD79a, CD79b, and CD66d.

The receptor, e.g., the CAR, can include at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the extracellular domain is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor-gamma, CD8, CD4, CD25, or CD16. For example, in some aspects, the CAR includes a chimeric molecule between CD3-zeta or Fc receptor-gamma and CD8, CD4, CD25 or CD16.

In some embodiments, the intracellular signaling domain comprises a human CD3 zeta stimulatory signaling domain or functional variant thereof, such as a 112 AA cytoplasmic domain of isoform 3 of human CD3 zeta. (UniProt Accession No.: P20963.2) or a CD3 zeta signaling domain as described in U.S. Pat. No. 7,446,190 or U.S. Pat. No. 8,911,993.

In some embodiments, cytoplasmic signaling molecule(s) in the CAR contain(s) a cytoplasmic signaling domain, portion thereof, or sequence derived from CD3 zeta. In some embodiments, the intracellular activation domain comprises a CD3ζ domain. In some embodiments, the intracellular activation domain comprises a CD3ζ domain set forth in SEQ ID NO: 97.

In some embodiments, the intracellular domain comprises an intracellular costimulatory signaling domain of 41BB or functional variant or portion thereof, such as a 42-amino acid cytoplasmic domain of a human 4-1BB (UniProt Accession No. Q07011.1) or functional variant or portion thereof.

In some embodiments, the receptor encompasses one or more, e.g., two or more, costimulatory domains and an activation domain, e.g., primary activation domain, in the cytoplasmic portion. Exemplary receptors include intracellular components of CD3-zeta, CD28, and 4-1BB. In some embodiments, the chimeric antigen receptor contains an intracellular domain of a T cell costimulatory molecule. In some aspects, the T cell costimulatory molecule is 4-1BB.

In some embodiments, the receptor includes a signaling domain and/or transmembrane portion of a costimulatory receptor, such as CD28, 4-1BB, OX40, DAP10, and ICOS. In some aspects, the same receptor includes both the activating and costimulatory components.

In certain embodiments, the intracellular signaling domain comprises a CD8a transmembrane and signaling domain linked to a CD3 (e.g., CD3-zeta) intracellular domain. In some embodiments, the intracellular signaling domain comprises a 4-1BB (CD137, TNFRSF9) co-stimulatory domains, linked to a CD3 zeta intracellular domain. In some embodiments, the CAR comprises a 4-1BB co-stimulatory domain. In some embodiments, the 4-1BB co-stimulatory domain comprises the sequence as set forth in SEQ ID NO: 96.

In some embodiments, the CAR or other antigen receptor further includes a marker, such as a cell surface marker, which may be used to confirm transduction or engineering of the cell to express the receptor, such as a truncated version of a cell surface receptor, such as truncated EGFR (tEGFR). In some aspects, the marker includes all or part (e.g., truncated form) of CD34, a nerve growth factor receptor (NGFR), or epidermal growth factor receptor (e.g., tEGFR). In some embodiments, the nucleic acid encoding the marker is operably linked to a polynucleotide encoding for a linker sequence, such as a cleavable linker sequence or a ribosomal skip sequence, e.g., T2A. See WO2014031687. In some embodiments, introduction of a construct encoding the CAR and EGFRt separated by a T2A ribosome switch can express two proteins from the same construct, such that the EGFRt can be used as a marker to detect cells expressing such construct. In some embodiments, a marker, and optionally a linker sequence, can be any as disclosed in published patent application No. WO2014031687. For example, the marker can be a truncated EGFR (tEGFR) that is, optionally, linked to a linker sequence, such as a T2A ribosomal skip sequence.

In some embodiments, the marker is a molecule, e.g., cell surface protein, not naturally found on T cells or not naturally found on the surface of T cells, or a portion thereof.

In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

The CAR may comprise one or modified synthetic amino acids in place of one or more naturally-occurring amino acids. Exemplary modified amino acids include, but are not limited to, aminocyclohexane carboxylic acid, norleucine, α-amino n-decanoic acid, homoserine, S-acetylaminomethylcysteine, trans-3- and trans-4-hydroxyproline, 4-aminophenylalanine, 4-nitrophenylalanine, 4-chlorophenylalanine, 4-carboxyphenylalanine, (3-phenylserine (3-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbomane)-carboxylic acid, α,γ-diaminobutyric acid, α,γ-diaminopropionic acid, homophenylalanine, and α-tertbutylglycine.

For example, in some embodiments, the CAR includes an antibody or fragment thereof, including single chain antibodies (sdAbs, e.g. containing only the VH region, also called a VHH), VH domains, and scFvs, described herein, a spacer such as a CD8a hinge, a CD8a transmembrane domain, a 4-1BB intracellular signaling domain, and a CD3 zeta signaling domain. In some embodiments, the CAR includes an antibody or fragment, including sdAbs and scFvs described herein, a spacer such as a CD8a hinge, a CD8a transmembrane domain, a 4-1BB intracellular signaling domain, and a CD3 zeta signaling domain.

Transgenes expressing the priming receptor and CAR system may be introduced into cells, such as a T cell, using, for example, a site-specific technique. With site specific integration of the transgenes (e.g. priming receptor and CAR), the transgenes may be targeted to a safe harbor locus or TRAC. Examples of site-specific techniques for integration into the safe harbor loci include, without limitation, homology-dependent engineering using nucleases and homology independent targeted insertion using Cas9.

The engineered cells have applications to immune-oncology. The priming receptor and CAR, for example, can be selected to target different specific tumor antigens. Examples of cancers that can be effectively targeted using such cells are blood cancers or solid cancers. In some embodiments, immune cell therapy can be used to treat solid tumors.

Synthetic Pathway Activators

In various aspects, systems disclosed herein employ one or more "synthetic pathway activators" (SPAs). CAR-expressing immune cells can be limited by the necessity for in vivo expansion following infusion. To achieve robust expansion, T cells require three signals: antigen-stimulation, co-stimulation, and cytokine-induced stimulation. Activation of CARs is sufficient to induce the first two signals, but cannot recapitulate cytokine signaling. Furthermore, the tumor microenvironment is often immunosuppressive and devoid of pro-inflammatory cytokines. SPAs can thus be used to stimulate robust in vivo expansion and enhance desirable properties (i.e., increased survival, persistence, and potency) of T cells expressing priming receptors and/or CARs as described herein.

SPA Structure

In various embodiments, SPAs mimic activation of interleukin signaling. Interleukin receptors are cytokine receptors that signal through Signal Transducer and Activator of Transcription (STAT) transcription factors (e.g., STAT3 and STAT5). Interleukin receptors typically function by dimerization in response to ligand binding. Once dimerized, receptors can bind janus-associated kinases (JAKs) to induce JAK cross-phosphorylation and downstream "JAK/STAT" signaling. Accordingly, induced receptor agonism or ligand-independent dimerization of receptors can be utilized to induce constitutive receptor activity and thus, constitutive cytokine signaling.

In various embodiments, SPAs comprise interleukin receptors or functional fragments thereof. In some embodiments, SPAs comprise or are derived from interleukin receptor intracellular signaling domains or functional fragments thereof. In some embodiments, SPAs comprise or are derived from interleukin-6 signal transducer (IL6ST) polypeptides or functional fragments thereof. Interleukin-6 signal transducer (IL6ST) is also known as glycoprotein 130 (gp130)

In various embodiments, one or more structural alterations can be made to confer constitutive activity to a SPA or functional fragment thereof. In some embodiments, structures or mutations can be added to induce SPA multimerization. In some embodiments, one or more amino acids can be mutated to a cysteine to allow formation of one or more disulfide bond(s), e.g., between two receptor monomers. In some embodiments, one or more amino acids can be inserted into a wild-type receptor polypeptide to promote dimerization, e.g., through formation of one or more disulfide bond(s).

In some embodiments, an exogenous polypeptide is operatively linked to a cytokine receptor or functional fragment thereof to cause their multimerization. In some embodiments, a leucine zipper polypeptide is operatively linked to a cytokine receptor or functional fragment thereof. In some embodiments, the leucine zipper polypeptide is a c-Jun leucine zipper. In some embodiments, an exogenous scaffold is operatively linked to a cytokine receptor or functional fragment thereof (e.g., IL6ST or gp130).

In some embodiments, SPAs can comprise a ligand agonist (e.g., a cytokine, e.g., an interleukin) that allows constitutive activation of the SPA. In some embodiments, the cytokine receptor and a soluble agonist are expressed simultaneously. In some embodiments, the cytokine receptor and a membrane-bound agonist are expressed simultaneously.

In various embodiments, SPAs are anchored to the cellular membrane. In some embodiments SPAs comprise an extracellular domain, a transmembrane domain, and an intracellular signaling domain. In some embodiments, SPAs comprise a transmembrane domain of an interleukin receptor.

Exemplary SPAs

In some embodiments, the SPA comprises a leucine zipper-gp130 (referred to herein as "L-gp130") or an L-gp130 intracellular signaling domain. L-gp130 comprises a homodimer, with each monomer comprising (a) an extracellular domain comprising an inserted cysteine residue that forms a disulfide linkage with another monomer and a c-Jun leucine zipper; and (b) an IL6ST transmembrane domain and intracellular signaling domain. The cysteine residue and the leucine zipper on each polypeptide can induce the formation of stable homodimers that mimic constitutive IL-6R activation. Additional details on the construction of L-gp130 are described in Stuhlmann-Laeisz et al. Mol Biol Cell. 2006 July; 17(7):2986-95 and in WO2020200325, which are hereby incorporated by reference in their entirety. The sequence of L-gp130 is provided in SEQ ID NO: 259. In some embodiments, the SPA comprises L-gp130 comprising a sequence as set forth in SEQ ID NO: 259.

In some embodiments, the SPA comprises an extracellular domain comprising a CD34 epitope or CD34 extracellular domain or fragment thereof. In some embodiments, the SPA comprises an extracellular domain comprising a CD34 epitope, an unpaired cysteine residue for multimerization, an IL6ST (gp130) transmembrane domain, and an IL6ST (gp130) intracellular domain. In some embodiments, the SPA comprises a sequence as set forth in SEQ ID NO: 141 or 254. The IL6ST (gp130) transmembrane domain sequence is provided in SEQ ID NO: 258. In some embodiments, the SPA comprises an IL6ST (gp130) transmembrane domain sequence as set forth in SEQ ID NO: 258. The IL6ST (gp130) intracellular signaling domain sequence is provided in SEQ ID NO: 257. In some embodiments, the SPA comprises an IL6ST (gp130) intracellular signaling domain sequence as set forth in SEQ ID NO: 257. In some embodiments, the SPA comprises an extracellular domain comprising the sequence as set forth in SEQ ID NO: 260. A nucleotide sequence encoding an exemplary SPA is provided in SEQ ID NO: 261. A nucleotide sequence encoding the exemplary SPA protein with an N-terminus leader sequence is provided in SEQ ID NO: 262. In some embodiments, the one or more nucleic acid(s) encoding the system discloses herein comprise SPA comprising a nucleic acid as set forth in SEQ ID NOs: 261 or 262.

Nucleic Acids and Vectors

In another aspect, provided herein are one or more nucleic acids, wherein the one or more nucleic acids encode: a first chimeric polypeptide comprises a priming receptor comprising a first extracellular antigen-binding domain that specifically binds Prostate-Specific Membrane Antigen (PSMA); a second chimeric polypeptide comprising a chimeric antigen receptor (CAR) comprising a second extracellular antigen-binding domain that specifically binds to Carbonic Anhydrase IX (CA9); an optional third chimeric polypeptide comprising a synthetic pathway activator (SPA); and at least one or more nucleic acids comprising a nucleic acid sequence at least 15 nucleotides in length complementary to: a nucleic acid encoding human Fas Cell Surface Death Receptor (FAS) comprising the sequence set forth in SEQ ID NO: 3; and a nucleic acid encoding human Transforming Growth factor (TGF)-β Receptor 2 (TGFBR2) comprising the sequence set forth in SEQ ID NO: 4. In some embodiments, the nucleic acid sequence at least 15 nucleotides in length is complementary to nucleotides 1126 to 1364 of a nucleic acid encoding human FAS comprising the sequence set forth in SEQ ID NO: 3. In some embodiments, the nucleic acid comprises a nucleic acid sequence at least 15 nucleotides in length complementary to a nucleic acid encoding human Protein Tyrosine Phosphatase Non-Receptor Type 2 (PTPN2) comprising the sequence set forth in SEQ ID NO: 5. In some embodiments, the nucleic acid sequence is complementary to nucleotides 518-559 of a nucleic acid encoding human PTPN2 comprising the sequence set forth in SEQ ID NO: 5.

RNA Interference Molecules

Transforming Growth Factor Beta Receptor 1 (TGF-βR1 or TGFBR1; HGNC: 11772, NCBI Entrez Gene: 7046, UniProtKB/Swiss-Prot: P36897) is a transmembrane serine/threonine protein kinase and forms a heteromeric complex with TGF-beta receptor type II (TGFRB2) when bound to TGF-beta, transducing the TGF-beta signal from the cell surface to the cytoplasm.

Transforming Growth Factor Beta Receptor 2 (TGF-βR2 or TGFBR2; HGNC: 11773, NCBI Entrez Gene: 7048, UniProtKB/Swiss-Prot: P37173) is a transmembrane serine/threonine protein kinase and forms a heterodimeric complex with TGF-beta receptor type-1 (TGFBR1) when bound to TGF-beta, resulting in transduction of the TGF-beta signal from the cell surface to the cytoplasm.

Fas Cell Surface Death Receptor (or Fas Receptor, FAS, CD95, or TNFRSF6; HGNC: 11920, NCBI Entrez Gene: 355; UniProtKB/Swiss-Prot: P25445) is an apoptosis-inducing TNF receptor superfamily member.

Protein Tyrosine Phosphatase Non-Receptor Type 2 (PTPN2; HGNC: 9650, NCBI Entrez Gene: 5771; UniProtKB/Swiss-Prot: P17706) is a phosphatase that regulates interferon and many other signaling pathways.

As used herein, "target gene" refers to a nucleic acid sequence in a cell, wherein the expression of the sequence may be specifically and effectively modulated using the nucleic acid molecules and methods described herein. In certain embodiments, the target gene may be implicated in the growth (proliferation), maintenance (survival), and/or immune behavior of an individual's immune cells. In some embodiments, the target gene is FAS. In some embodiments, the target gene is PTPN2. In some embodiments, the target gene is Transforming Growth Factor Beta Receptor 2 (TGFBR2). In some embodiments, two or more nucleic acid molecules target the TFGBR2 gene. In some embodiments, the target gene is Transforming Growth Factor Beta Receptor 1 (TGFBR1). In some embodiments, more than one target gene is modulated using a nucleic acid molecule and methods described herein. In some embodiments, at least two target gene are modulated using the nucleic acid molecules and methods described herein. In some embodiments, the nucleic acid molecule(s) is an shRNA. In some embodiments, the target genes are at least TGFBR1 and TGFBR2. In some embodiments, the target genes are at least FAS and TGFBR2. In some embodiments, the target genes are at least FAS, TGFBR1, and TGFBR2. In some embodiments, the target genes are at least FAS, TGFBR2, and PTPN2. In some embodiments, the target genes are at least FAS, PTPN2, TGFBR1, and TGFBR2.

In one aspect, provided herein are nucleic acid comprising a nucleic acid sequence at least 15 nucleotides in length complementary to a nucleic acid encoding human Transforming Growth Factor Beta Receptor 2 (TGFBR2) (SEQ ID NO: 4). In some embodiments, the nucleic acid comprises a nucleic acid sequence at least 15 nucleotides in length complementary to nucleotides 2215-2236, 4430-4451, or 3761-3782 of a nucleic encoding human Transforming Growth Factor Beta Receptor 2 (TGFBR2) comprising the sequence set forth in SEQ ID NO: 4. In some embodiments, the nucleic acid comprises a sequence selected from the group consisting of the sequences set forth in SEQ ID NOs: 34-82. In some embodiments, the nucleic acid comprises at least two sequence selected from the group consisting of the sequences set forth in SEQ ID NOs: 34-82.

In one aspect, provided herein are nucleic acid comprising a nucleic acid sequence at least 15 nucleotides in length complementary to a nucleic acid encoding human Transforming Growth Factor Beta Receptor 2 (TGFBR2) (SEQ ID NO: 4), wherein the nucleic acid sequence at least 15 nucleotides in length is at least 80%, 85%, 90%, 91%, 92%, 93%, 94%, 95%, 96%, 97%, 98%, 99%, or 100% complementary to a nucleic acid encoding human Transforming Growth Factor Beta Receptor 2 (TGFBR2) (SEQ ID NO: 4). In some embodiments, the nucleic acid comprises at least 80%, 85%, 90%, 91%, 92%, 93%, 94%, 95%, 96%, 97%, 98%, 99%, or 100% identity to a sequence selected from the group consisting of the sequences set forth in SEQ ID NOs: 34-82. In some embodiments, the nucleic acid comprises at least two sequence with at least 80%, 85%, 90%, 91%, 92%, 93%, 94%, 95%, 96%, 97%, 98%, 99%, or 100% identity to a sequence selected from the group consisting of the sequences set forth in SEQ ID NOs: 34-82.

In one aspect, provided herein are nucleic acid comprising a nucleic acid sequence at least 15 nucleotides in length complementary to a nucleic acid encoding human Transforming Growth Factor Beta Receptor 1 (TGFBR1) (SEQ ID NO: 148). In some embodiments, the nucleic acid comprises a sequence selected from the group consisting of the sequences set forth in SEQ ID NOs: 149-178.

In one aspect, provided herein are nucleic acid comprising a nucleic acid sequence at least 15 nucleotides in length complementary to a nucleic acid encoding human Transforming Growth Factor Beta Receptor 1 (TGFBR1) (SEQ ID NO: 148), wherein the nucleic acid sequence at least 15 nucleotides in length is at least 80%, 85%, 90%, 91%, 92%, 93%, 94%, 95%, 96%, 97%, 98%, 99%, or 100% complementary to a nucleic acid encoding human Transforming Growth Factor Beta Receptor 1 (TGFBR1) (SEQ ID NO: 148). In some embodiments, the nucleic acid comprises at least 80%, 85%, 90%, 91%, 92%, 93%, 94%, 95%, 96%, 97%, 98%, 99%, or 100% identity to a sequence selected from the group consisting of the sequences set forth in SEQ ID NOs: 149-178. In some embodiments, the nucleic acid comprises at least two sequence with at least 80%, 85%, 90%, 91%, 92%, 93%, 94%, 95%, 96%, 97%, 98%, 99%, or 100% identity to a sequence selected from the group consisting of the sequences set forth in SEQ ID NOs: 149-178.

In some embodiments, the nucleic acid comprises a nucleic acid sequence at least 15 nucleotides in length complementary to a nucleic acid encoding human Fas Cell Surface Death Receptor (FAS) comprising the sequence set forth in SEQ ID NO: 3. In some embodiments, the nucleic acid comprises a sequence selected from the group consisting of the sequences set forth in SEQ ID NOs: 6-20. In some embodiments, the nucleic acid sequence is complementary to nucleotides 1126 to 1364 of a nucleic acid encoding human FAS comprising the sequence set forth in SEQ ID NO: 3

In one aspect, provided herein are nucleic acid comprising a nucleic acid sequence at least 15 nucleotides in length complementary to a nucleic acid encoding human FAS comprising the sequence set forth in SEQ ID NO: 3, wherein the nucleic acid sequence at least 15 nucleotides in length is at least 80%, 85%, 90%, 91%, 92%, 93%, 94%, 95%, 96%, 97%, 98%, 99%, or 100% complementary to a nucleic acid encoding human FAS comprising the sequence set forth in SEQ ID NO: 3. In some embodiments, the nucleic acid comprises at least 80%, 85%, 90%, 91%, 92%, 93%, 94%, 95%, 96%, 97%, 98%, 99%, or 100% identity to a sequence selected from the group consisting of the sequences set forth in SEQ ID NOs: 6-20. In some embodiments, the nucleic acid comprises at least two sequence with at least 80%, 85%, 90%, 91%, 92%, 93%, 94%, 95%, 96%, 97%, 98%, 99%, or 100% identity to a sequence selected from the group consisting of the sequences set forth in SEQ ID NOs: 6-20.

In some embodiments, the nucleic acid comprises a nucleic acid sequence at least 15 nucleotides in length complementary to a nucleic acid encoding human Protein Tyrosine Phosphatase Non-Receptor Type 2 (PTPN2) comprising the sequence set forth in SEQ ID NO: 5. In some embodiments, the nucleic acid comprises a sequence selected from the group consisting of the sequences set forth in SEQ ID NOs: 21-33. In some embodiments, the nucleic acid sequence is complementary to nucleotides 518-559 of a nucleic acid encoding human PTPN2 comprising the sequence set forth in SEQ ID NO: 5.

In one aspect, provided herein are nucleic acid comprising a nucleic acid sequence at least 15 nucleotides in length complementary to a nucleic acid encoding human Protein Tyrosine Phosphatase Non-Receptor Type 2 (PTPN2) comprising the sequence set forth in SEQ ID NO: 5, wherein the nucleic acid sequence at least 15 nucleotides in length is at least 80%, 85%, 90%, 91%, 92%, 93%, 94%, 95%, 96%, 97%, 98%, 99%, or 100% complementary to a nucleic acid encoding human Protein Tyrosine Phosphatase Non-Receptor Type 2 (PTPN2) comprising the sequence set forth in SEQ ID NO: 5. In some embodiments, the nucleic acid comprises at least 80%, 85%, 90%, 91%, 92%, 93%, 94%, 95%, 96%, 97%, 98%, 99%, or 100% identity to a sequence selected from the group consisting of the sequences set forth in SEQ ID NOs: 21-33. In some embodiments, the nucleic acid comprises at least two sequence with at least 80%, 85%, 90%, 91%, 92%, 93%, 94%, 95%, 96%, 97%, 98%, 99%, or 100% identity to a sequence selected from the group consisting of the sequences set forth in SEQ ID NOs: 21-33. In some embodiments, the nucleic acid sequence is complementary to nucleotides 518-559 of a nucleic acid encoding human PTPN2 comprising the sequence set forth in SEQ ID NO: 5.

In some embodiments, the nucleic acid comprises a sequence as set forth in SEQ ID NO: 13. In some embodiments, the nucleic acid comprises a sequence at least 80%, 85%, 90%, 91%, 92%, 93%, 94%, 95%, 96%, 97%, 98%, 99%, or 100% identical to a sequence as set forth in SEQ ID NO: 13. In some embodiments, the nucleic acid comprises a sequence as set forth in SEQ ID NO: 49. In some embodiments, the nucleic acid comprises a sequence at least 80%, 85%, 90%, 91%, 92%, 93%, 94%, 95%, 96%, 97%, 98%, 99%, or 100% identical to a sequence as set forth in SEQ ID NO: 49. In some embodiments, the nucleic acid comprises a sequence as set forth in SEQ ID NO: 79. In some embodiments, the nucleic acid comprises a sequence at least 80%, 85%, 90%, 91%, 92%, 93%, 94%, 95%, 96%, 97%, 98%, 99%, or 100% identical to a sequence as set forth in SEQ ID NO: 79. In some embodiments, the nucleic acid comprises a sequence as set forth in SEQ ID NO: 83. In some embodiments, the nucleic acid comprises a sequence at least 80%, 85%, 90%, 91%, 92%, 93%, 94%, 95%, 96%, 97%, 98%, 99%, or 100% identical to a sequence as set forth in SEQ ID NO: 83. In some embodiments, the nucleic acid comprises a sequence as set forth in SEQ ID NO: 84. In some embodiments, the nucleic acid comprises a sequence at least 80%, 85%, 90%, 91%, 92%, 93%, 94%, 95%, 96%, 97%, 98%, 99%, or 100% identical to a sequence as set forth in SEQ ID NO: 84.

In some embodiments, the nucleic acid comprises a sequence as set forth in SEQ ID NO: 182. In some embodiments, the nucleic acid comprises a sequence at least 80%, 85%, 90%, 91%, 92%, 93%, 94%, 95%, 96%, 97%, 98%, 99%, or 100% identical to a sequence as set forth in SEQ ID NO: 182.

In some embodiments, the nucleic acid comprises a sequence as set forth in SEQ ID NO: 181, 183, 193, 194, or 195. In some embodiments, the nucleic acid comprises a sequence at least 80%, 85%, 90%, 91%, 92%, 93%, 94%, 95%, 96%, 97%, 98%, 99%, or 100% identical to a sequence as set forth in SEQ ID NO: 181, 183, 193, 194, or 195.

In some embodiments, the nucleic acid is capable of reducing expression of FAS in the immune cell by at least 10%, 15%, 20%, 25%, 30%, 35%, 40%, 45%, 50%, 55%, 60%, 65%, 75%, 80%, 85%, 90%, 95%, or 99% as compared to a control cell that does not comprise the nucleic acid.

In some embodiments, the nucleic acid is capable of reducing expression of TGFBR2 in the immune cell by at least 10%, 15%, 20%, 25%, 30%, 35%, 40%, 45%, 50%, 55%, 60%, 65%, 75%, 80%, 85%, 90%, 95%, or 99% as compared to a control cell that does not comprise the nucleic acid.

In some embodiments, the nucleic acid is capable of reducing expression of PTPN2 in the immune cell by at least 10%, 15%, 20%, 25%, 30%, 35%, 40%, 45%, 50%, 55%, 60%, 65%, 75%, 80%, 85%, 90%, 95%, or 99% as compared to a control cell that does not comprise the nucleic acid.

In some embodiments, the nucleic acid sequence is at least 16, 17, 18, 19, 20, 21, or 22 nucleotides in length.

In some embodiments, the nucleic acid is an RNA interference (RNAi) molecule. Exemplary RNAi molecules include short hairpin RNA (shRNA), a small interfering RNA (siRNA), a double stranded RNA (dsRNA), or an antisense oligonucleotide. In some embodiments, the nucleic acid is a short hairpin RNA (shRNA), a small interfering RNA (siRNA), a double stranded RNA (dsRNA), or an antisense oligonucleotide. In some embodiments, the nucleic acid is an shRNA.

Single-stranded hairpin ribonucleic acids (shRNAs) are short duplexes where the sense and antisense strands are linked by a hairpin loop. They consist of a stem-loop structure that can be transcribed in cells from an RNA polymerase II or RNA polymerase III promoter on a plasmid construct. Once expressed, shRNAs are processed into RNAi species. Expression of shRNA from a plasmid is known to be relatively stable, thereby providing strong advantages over, for example, the use of synthetic siRNAs. shRNA expression units may be incorporated into a variety of plasmids, liposomes, viral vectors, and other vehicles for delivery and integration into a target cell. Expression of shRNA from a plasmid can be stably integrated for constitutive expression. shRNAs are synthesized in the nucleus of cells, further processed and transported to the cytoplasm, and then incorporated into the RNA-induced silencing complex (RISC) for activity. The shRNAs are converted into active siRNA molecules (which are capable of binding to, sequestering, and/or preventing the translation of mRNA transcripts encoded by target genes).

The Argonaute family of proteins is the major component of RISC. Within the Argonaute family of proteins, only Ago2 contains endonuclease activity that is capable of cleaving and releasing the passenger strand from the stem portion of the shRNA molecule. The remaining three members of Argonaute family, Ago1, Ago3 and Ago4, which do not have identifiable endonuclease activity, are also assembled into RISC and are believed to function through a cleavage-independent manner. Thus, RISC can be characterized as having cleavage-dependent and cleavage-independent pathways.

RNAi (e.g., antisense RNA, siRNA, microRNA, shRNA, etc.) are described in International Publication Nos. WO2018232356A1, WO2019084552A1, WO2019226998A1, WO2020014235A1, WO2020123871A1, and WO2020186219A1, each of which is herein incorporated by reference for all purposes.

Antisense oligonucleotide structure and chemical modifications are described in International PCT Publication No. WO20/132521, which is hereby incorporated by reference.

dsRNA and shRNA molecules and methods of use and production are described in U.S. Pat. Nos. 8,829,264; 9,556,431; and 8,252,526, each of which are hereby incorporated by reference siRNA molecules and methods of use and production are described in U.S. Pat. No. 7,361,752 and US Patent Application No. US20050048647, both of which are hereby incorporated by reference.

Additional methods and compositions for RNA interference such as shRNA, siRNA, dsRNA, and antisense oligonucleotides are generally known in the art, and are further described in U.S. Pat. Nos. 7,361,752; 8,829,264; 9,556,431; 8,252,526, International PCT Publication No. WO00/44895; International PCT Publication No. WO01/36646; International PCT Publication No. WO99/32619; International PCT Publication No. WO00/01846; International PCT Publication No. WO01/29058; and International PCT Publication No. WO00/44914; International PCT Publication No. WO04/030634; each of which are hereby incorporated by reference.

The nucleic acid sequences (or constructs) that may be used to encode the RNAi molecules, such as an shRNA described herein, may comprise a promoter, which is operably linked (or connected), directly or indirectly, to a sequence encoding the RNAi molecules. Such promoters may be selected based on the host cell and the effect sought. Non-limiting examples of suitable promoters include constitutive and inducible promoters, such as EF1α or inducible Hepatocyte Nuclear Factor 1α (HNF1α)-YB TATA or RNA polymerase II (pol II)-based promoters. In some embodiments, the constitutive promoter is EF1α. In some embodiments, the EF1α promoter comprises as sequence as set forth in SEQ ID NO: 179. Non-limiting examples of suitable promoters further include the tetracycline inducible or repressible promoter, RNA polymerase I or III-based promoters, the pol II dependent viral promoters, such as the CMV-IE promoter, and the pol III U6 and H1 promoters, as well as Hepatocyte Nuclear Factor 1α (HNF1α)-YB TATA promotor provided in SEQ ID NO: 256. The bacteriophage T7 promoter may also be used (in which case it will be appreciated that the T7 polymerase must also be present). The nucleic acid sequences need not be restricted to the use of any single promoter, especially since the nucleic acid sequences may comprise two or more shRNAs (i.e., a combination of effectors), including but not limited to incorporated shRNA molecules. Each incorporated promoter may control one, or any combination of, the shRNA molecule components.

In certain embodiments, the promoter may be preferentially active in the targeted cells, e.g., it may be desirable to preferentially express at least one nucleic acid in immune cells using an immune cell-specific promoter. Introduction of such constructs into host cells may be effected under conditions whereby the two or more nucleic acids that are contained within the nucleic acid precursor transcript initially reside within a single primary transcript, such that the separate RNA molecules (for example, shRNA each comprising its own stem-loop structure) are subsequently excised from such precursor transcript by an endogenous ribonuclease. The resulting mature nucleic acids (e.g., shRNAs) may then induce degradation, and/or translation repression, of target gene mRNA transcripts produced in the cell. Alternatively, each of the precursor stem-loop structures may be produced as part of a separate transcript, in which case each nucleic acid sequence will preferably include its own promoter and transcription terminator sequences. Additionally, the multiple nucleic acid precursor transcripts may reside within a single primary transcript.

The stem-loop structures of the shRNA nucleic acids described herein may be about 40 to 100 nucleotides long or, preferably, about 50 to 75 nucleotides long. The stem region may be about 15-45 nucleotides in length (or more), or about 20-30 nucleotides in length. In some embodiments, the stem region is 22 nucleotides in length. In some embodiments, the stem region is 15, 16, 17, 18, 19, 20, 21, 22, 23, 24, 25, 26, 27 28 29, 30, 31, 32, 33, 34, 35, 36, 37, 38, 39, 40, 41, 42, 43, 44, or 45 nucleotides in length.

The stem may comprise a perfectly complementary duplex (but for any 3' tail), however, bulges or interior loops may be present on either arm of the stem. The number of such bulges and asymmetric interior loops are preferably few in number (e.g., 1, 2 or 3) and are about 3 nucleotides or less in size. The terminal loop portion may comprise about 4 or more nucleotides, but preferably not more than about 25. The loop portion will preferably be 6-15 nucleotides in size.

As described herein, the stem regions of the shRNAs comprise passenger strands and guide strands, whereby the guide strands contain sequences complementary to the target mRNA transcript encoded by the target gene(s). Preferably, the G-C content and matching of guide strand and passenger strand is carefully designed for thermodynamically-favorable strand unwind activity with or without endonuclease cleavage. Furthermore, the specificity of the guide strand is preferably confirmed via a BLAST search (www.ncbi.nim.nih.gov/BLAST).

The disclosure herein provides that the expression level of multiple target genes may be modulated using the methods and nucleic acids described herein. For example, the disclosure herein provides that a first set of nucleic acids may be designed to include a sequence (a guide strand) that is designed to reduce the expression level of a first target gene, whereas a second set of nucleic acids may be designed to include a sequence (a guide strand) that is designed to reduce the expression level of a second target gene. The different sets of nucleic acids may be expressed and reside within the same, or separate, preliminary transcripts. In certain embodiments, such multiplex approach, i.e., the use of the nucleic acids described herein to modulate the expression level of two or more target genes, may have an enhanced therapeutic effect on a patient. For example, if a patient is provided with cells expressing the nucleic acid molecules described herein to treat, prevent, or ameliorate the effects of cancer, it may be desirable to provide the patient with two or more types of nucleic acid molecules, which are designed to reduce the expression level of multiple genes that are implicated in activation or repression of immune cells.

The nucleic acid molecule(s) described herein may be capable of reducing target gene expression in a cell by at least more than about 50% as compared to a control cell that does not comprise the nucleic acid molecule(s). For example, the nucleic acid molecule(s) (e.g., shRNA) can be capable of reducing expression of a target gene selected from the group consisting of FAS and TGBFR2 in the immune cell by at least 10%, 15%, 20%, 25%, 30%, 35%, 40%, 45%, 50%, 55%, 60%, 65%, 75%, 80%, 85%, 90%, 95%, 97%, 98%, 99%, or more as compared to a control cell that does not comprise the nucleic acid molecule(s). The nucleic acid molecule(s) can be capable of reducing expression of a target gene selected from the group consisting of FAS and TGBFR2 in the immune cell by at least between about 50-100%, 50-99%, 50-95%, 50-90%, 50-85%, 50-80%, 50-75%, 50-70%, 50-65%, 50-60%, 50-55%, or as compared to a control cell that does not comprise the nucleic acid molecule(s). In some embodiments, the nucleic acid molecule(s) is capable of reducing expression of FAS in the immune cell by at least 10%, 15%, 20%, 25%, 30%, 35%, 40%, 45%, 50%, 55%, 60%, 65%, 75%, 80%, 85%, 90%, 95%, or 99% as compared to a control cell that does not comprise the nucleic acid molecule(s). In some embodiments, the nucleic acid molecule(s) is capable of reducing expression of FAS in the immune cell by at least 10%, 15%, 20%, 25%, 30%, 35%, 40%, 45%, 50%, 55%, 60%, 65%, 75%, 80%, 85%, 90%, 95%, or 99% as compared to a control cell that does not comprise the nucleic acid molecule(s). In some embodiments, the nucleic acid molecule(s) is capable of reducing expression of TGBFR2 in the immune cell by at least 10%, 15%, 20%, 25%, 30%, 35%, 40%, 45%, 50%, 55%, 60%, 65%, 75%, 80%, 85%, 90%, 95%, or 99% as compared to a control cell that does not comprise the nucleic acid molecule(s).

The nucleic acid molecule(s) may be chemically synthesized, or in vitro transcribed, and may further include one or more modifications to phosphate-sugar backbone or nucleosides residues.

Other methods known in the art for introducing nucleic acids to cells may be used, such as lipid-mediated carrier transport, chemical mediated transport, such as calcium phosphate, and the like. Thus, the nucleic acid molecule(s) construct may be introduced along with components that perform one or more of the following activities: enhance RNA uptake by the cell, promote annealing of the duplex strands for shRNA, stabilize the annealed shRNA strands, or otherwise increase inhibition of the target gene.

Additional Elements

In some embodiments, the one or more nucleic acid(s) further comprises a 5' homology directed repair arm and/or a 3' homology directed repair arm complementary to an insertion site in a host cell chromosome. In some embodiments, the one or more nucleic acid(s) comprises the 5' homology directed repair arm and the 3' homology directed repair arm. In some embodiments, the one or more nucleic acid(s) is incorporated into an expression cassette or an expression vector. In some embodiments, the expression cassette or the expression vector further comprises a constitutive promoter upstream of the one or more nucleic acid(s).

In some embodiments, the priming receptor, CAR, first nucleic acid, and the second nucleic acid are incorporated into a single expression cassette or a single expression vector. In some embodiments, the priming receptor, CAR, first nucleic acid, and the second nucleic acid are incorporated into two or more expression cassettes or expression vectors. In some embodiments, the expression vector(s) is a non-viral vector.

In some embodiments, the expression cassette or expression vector comprises a sequence as set forth in SEQ ID NO: 184. In some embodiments, the expression cassette comprises a sequence at least 80%, 85%, 90%, 91%, 92%, 93%, 94%, 95%, 96%, 97%, 98%, 99%, or 100% identical to a sequence as set forth in SEQ ID NO: 184. The expression cassette or expression vector comprising a sequence at least 80%, 85%, 90%, 91%, 92%, 93%, 94%, 95%, 96%, 97%, 98%, 99%, or 100% identical to the sequence as set forth in SEQ ID NO: 184 can further comprise one or more transgenes encoding any priming receptor or CAR as disclosed herein. In some embodiments, the expression cassette or expression vector comprises the sequences as set forth in SEQ ID NO: 185 and 186. In some embodiments, the expression cassette or expression vector comprises a sequence at least 80%, 85%, 90%, 91%, 92%, 93%, 94%, 95%, 96%, 97%, 98%, 99%, or 100% identical to a sequence as set forth in SEQ ID NO: 185 and 186. The expression cassette or expression vector comprising the sequence as set forth in SEQ ID NO: 185 and 186 can further comprise one or more transgenes encoding any priming receptor or CAR as disclosed herein.

In some embodiments, the expression cassette or expression vector comprises a sequence as set forth in SEQ ID NO: 187. In some embodiments, the expression cassette or expression vector comprises a sequence at least 80%, 85%, 90%, 91%, 92%, 93%, 94%, 95%, 96%, 97%, 98%, 99%, or 100% identical to a sequence as set forth in SEQ ID NO: 187. The expression cassette or expression vector comprising a sequence at least 80%, 85%, 90%, 91%, 92%, 93%, 94%, 95%, 96%, 97%, 98%, 99%, or 100% identical to the sequence as set forth in SEQ ID NO: 187 can further comprise one or more transgenes encoding any priming receptor or CAR as disclosed herein. In some embodiments, the expression cassette or expression vector comprises the sequences as set forth in SEQ ID NO: 188 and 189. In some embodiments, the expression cassette or expression vector comprises a sequence at least 80%, 85%, 90%, 91%, 92%, 93%, 94%, 95%, 96%, 97%, 98%, 99%, or 100% identical to a sequence as set forth in SEQ ID NO: 188 and 189. The expression cassette or expression vector comprising the sequence as set forth in SEQ ID NO: 188 and 189 can further comprise one or more transgenes encoding any priming receptor or CAR as disclosed herein.

In some embodiments, the expression cassette or expression vector comprises a sequence as set forth in SEQ ID NO: 190. In some embodiments, the expression cassette or expression vector comprises a sequence at least 80%, 85%, 90%, 91%, 92%, 93%, 94%, 95%, 96%, 97%, 98%, 99%, or 100% identical to a sequence as set forth in SEQ ID NO: 190. The expression cassette or expression vector comprising a sequence at least 80%, 85%, 90%, 91%, 92%, 93%, 94%, 95%, 96%, 97%, 98%, 99%, or 100% identical to the sequence as set forth in SEQ ID NO: 190 can further comprise one or more transgenes encoding any priming receptor or CAR as disclosed herein. In some embodiments, the expression cassette or expression vector comprises the sequences as set forth in SEQ ID NO: 191 and 192. In some embodiments, the expression cassette or expression vector comprises a sequence at least 80%, 85%, 90%, 91%, 92%, 93%, 94%, 95%, 96%, 97%, 98%, 99%, or 100% identical to a sequence as set forth in SEQ ID NO: 191 and 192. The expression cassette or expression vector comprising the sequence as set forth in SEQ ID NO: 191 and 192 can further comprise one or more transgenes encoding any priming receptor or CAR as disclosed herein.

In some embodiments, the expression cassette or expression vector comprises a sequence as set forth in SEQ ID NO: 196. In some embodiments, the expression cassette comprises a sequence at least 80%, 85%, 90%, 91%, 92%, 93%, 94%, 95%, 96%, 97%, 98%, 99%, or 100% identical to a sequence as set forth in SEQ ID NO: 196. The expression cassette or expression vector comprising a sequence at least 80%, 85%, 90%, 91%, 92%, 93%, 94%, 95%, 96%, 97%, 98%, 99%, or 100% identical to the sequence as set forth in SEQ ID NO: 196 can further comprise one or more transgenes encoding any priming receptor or CAR as disclosed herein. In some embodiments, the expression cassette or expression vector comprises the sequences as set forth in SEQ ID NO: 197 and 198. In some embodiments, the expression cassette or expression vector comprises a sequence at least 80%, 85%, 90%, 91%, 92%, 93%, 94%, 95%, 96%, 97%, 98%, 99%, or 100% identical to a sequence as set forth in SEQ ID NO: 197 and 198. The expression cassette or expression vector comprising the sequence as set forth in SEQ ID NO: 197 and 198 can further comprise one or more transgenes encoding any priming receptor or CAR as disclosed herein.

For example, the transgene included in any one of the cassettes as provided in any one of the sequences set forth in SEQ ID NOs: 184, 187, 190, or 196 can comprise an extracellular domain that specifically binds Prostate-Specific Membrane Antigen (PSMA) and/or a chimeric antigen receptor (CAR) that specifically binds Carbonic Anhydrase IX (CA9). For example, a transgene comprising a priming receptor can comprise an extracellular antigen-binding domain comprising a variable heavy (VH) chain sequence comprising three heavy chain CDR sequences, CDR-H1, CDR-H2, and CDR-H3, and a variable light (VL) chain sequence comprising three light chain CDR sequences, CDR-L1, CDR-L2, and CDR-L3 of any PSMA antibody or antigen binding fragments disclosed herein. Similarly, a transgene comprising a chimeric antigen receptor (CAR) can comprise an extracellular antigen-binding domain comprising a variable heavy (VH) chain sequence comprising three heavy chain CDR sequences, CDR-H1, CDR-H2, and CDR-H3, and optionally a a variable light (VL) chain sequence comprising three light chain CDR sequences, CDR-L1, CDR-L2, and CDR-L3 of any CA9 antibody or antigen binding fragments disclosed herein.

In some embodiments, the expression cassette or expression vector comprises a sequence as set forth in SEQ ID NO: 143. In some embodiments, the expression cassette or expression vector comprises a sequence at least 80%, 85%, 90%, 91%, 92%, 93%, 94%, 95%, 96%, 97%, 98%, 99%, or 100% identical to a sequence as set forth in SEQ ID NO: 143.

In some embodiments, the expression cassette or expression vector comprises a sequence as set forth in SEQ ID NO: 144. In some embodiments, the expression cassette or expression vector comprises a sequence at least 80%, 85%, 90%, 91%, 92%, 93%, 94%, 95%, 96%, 97%, 98%, 99%, or 100% identical to a sequence as set forth in SEQ ID NO: 144.

In some embodiments, the expression cassette or expression vector comprises a sequence as set forth in SEQ ID NO: 145. In some embodiments, the expression cassette or expression vector comprises a sequence at least 80%, 85%, 90%, 91%, 92%, 93%, 94%, 95%, 96%, 97%, 98%, 99%, or 100% identical to a sequence as set forth in SEQ ID NO: 145.

In some embodiments, the expression cassette or expression vector comprises a sequence as set forth in SEQ ID NO: 146. In some embodiments, the expression cassette or expression vector comprises a sequence at least 80%, 85%, 90%, 91%, 92%, 93%, 94%, 95%, 96%, 97%, 98%, 99%, or 100% identical to a sequence as set forth in SEQ ID NO: 146.

In some embodiments, the expression cassette or expression vector comprises a sequence as set forth in SEQ ID NO: 147. In some embodiments, the expression cassette or expression vector comprises a sequence at least 80%, 85%, 90%, 91%, 92%, 93%, 94%, 95%, 96%, 97%, 98%, 99%, or 100% identical to a sequence as set forth in SEQ ID NO: 147.

The one or more interfering nucleic acid sequences (e.g., one or more shRNA) can be encoded in the intron regions of the nucleic acid insert, DNA template, module, cassette, single expression cassette, or a single expression vector that also encodes the priming receptor and/or the CAR. For example, if the DNA template includes promoters, such as EF1α, or inducible promoters such as the HNF1α-YB TATA promoter, described herein, to drive expression of the CAR or priming receptor, the one or more nucleic acid sequences (e.g., shRNA sequences) can be encoded in the promoter intronic region. In some embodiments, the one or more nucleic acid sequences is encoded in at least one intron region of the nucleic acid insert, module, cassette, or DNA template. In some embodiments, the one or more nucleic acid sequences is encoded in at least one EF1α intron region of the nucleic acid insert, module, cassette, or DNA template.

In some embodiments, the present disclosure contemplates nucleic acid(s), modules, cassettes, or DNA template inserts that comprise one or more transgenes encoding the priming receptors and/or CARs as described herein. In some embodiments, the DNA template insert or cassette encodes a priming receptor transgene. In some embodiments, the DNA template insert or cassette encodes a chimeric antigen receptor transgene. In some embodiments, the DNA template insert or cassette encodes a first nucleic acid complementary to at least 15 nucleotides of a human FAS mRNA sequence, and a second nucleic acid complementary to at least 15 nucleotides of a human TGBFR2 mRNA sequence. In some embodiments, the DNA template insert or cassette comprises a priming receptor transgene and a chimeric antigen receptor transgene. In some embodiments, the DNA template insert comprises a priming receptor transgene, a chimeric antigen receptor transgene, a first nucleic acid complementary to at least 15 nucleotides of a human FAS mRNA sequence, and a second nucleic acid complementary to at least 15 nucleotides of a human TGBFR2 mRNA sequence. In some embodiments, the DNA template insert comprises a priming receptor transgene, a chimeric antigen receptor transgene, a first nucleic acid complementary to at least 15 nucleotides of a human FAS mRNA sequence, and a second nucleic acid complementary to at least 15 nucleotides of a human TGBFR2 mRNA sequence.

In some embodiments, the one or more nucleic acid(s) are encoded on a single DNA template insert or cassette. In some embodiments, the one or more nucleic acid(s) are encoded on multiple DNA template inserts or cassettes. For example, the one or more nucleic acid(s) can be encoded on two, three, or four DNA template inserts.

The DNA template insert can also comprise a self-cleaving peptide. Examples of self-cleaving peptides include, but are not limited to, self-cleaving viral 2A peptides, for example, a porcine teschovirus-1 (P2A) peptide, a Thosea asigna virus (T2A) peptide, an equine rhinitis A virus (E2A) peptide, or a foot-and-mouth disease virus (F2A) peptide. Self-cleaving 2A peptides allow expression of multiple gene products from a single construct. (See, for example, Chang et al. "Cleavage efficient 2A peptides for high level monoclonal antibody expression in CHO cells," *MAbs* 7(2): 403-412 (2015)).

The DNA template insert can also comprise a WPRE element. WPRE elements are generally described in Higashimoto, T., et al. Gene Ther 14, 1298-1304 (2007); and Zufferey, R., et al. J Virol. 1999 April; 73(4):2886-92, both of which are hereby incorporated by reference.

The DNA template insert can also comprise an SV40 or a human growth hormone (GH1) polyA tail.

Cells

Also provided herein are cells or immune cells comprising at least one DNA template non-virally inserted into a target region of the genome of the cell, wherein DNA template encodes the priming receptor and CAR system as described herein. Also provided herein are immune cells comprising the priming receptor that specifically binds Prostate-Specific Membrane Antigen (PSMA) and the chimeric antigen receptor that specifically binds CA9.

A cell comprising a DNA template insert at a target locus or safe harbor site as described in the present disclosure can be referred to as an engineered cell. In some embodiments, the cell or immune cell is any cell that can give rise to a pluripotent immune cell. In some embodiments, the immune cell is a primary immune cell. In some embodiments, the immune cell can be an induced pluripotent stem cell (iPSC) or a human pluripotent stem cell (HSPC). In some embodiments, the immune cell comprises primary hematopoietic cells or primary hematopoietic stem cells. In some embodiments, that engineered cell is a stem cell, a human cell, a primary cell, an hematopoietic cell, an adaptive immune cell, an innate immune cell, a natural killer (NK) cell, a T cell, a CD8+ cell, a CD4+ cell, or a T cell progenitor. In some embodiments, the immune cells are T cells. In some embodiments, the T cells are regulatory T cells, effector T cells, or naïve T cells. In some embodiments, the T cells are CD8+ T cells. In some embodiments, the T cells are CD4+ T cells. In some embodiments, the T cells are CD4+CD8+ T cells.

In some embodiments, the engineered cell is a stem cell, a human cell, a primary cell, an hematopoietic cell, an hematopoietic stem cell, an adaptive immune cell, an innate immune cell, a T cell or a T cell progenitor. Non-limiting examples of immune cells that are contemplated in the present disclosure include T cell, B cell, natural killer (NK) cell, NKT/iNKT cell, macrophage, myeloid cell, and dendritic cells. Non-limiting examples of stem cells that are contemplated in the present disclosure include pluripotent stem cells (PSCs), embryonic stem cells (ESCs), induced pluripotent stem cells (iPSCs), embryo-derived embryonic stem cells obtained by nuclear transfer (ntES; nuclear transfer ES), male germline stem cells (GS cells), embryonic germ cells (EG cells), hematopoietic stem/progenitor stem cells (HSPCs), somatic stem cells (adult stem cells), hemangioblasts, neural stem cells, mesenchymal stem cells and stem cells of other cells (including osteocyte, chondrocyte, myocyte, cardiac myocyte, neuron, tendon cell, adipocyte, pancreocyte, hepatocyte, nephrocyte and follicle cells and so on). In some embodiments, the engineered cells is a T cell, NK cells, iPSC, and HSPC. In some embodiments, the engineered cells used in the present disclosure are human cell lines grown in vitro (e.g. deliberately immortalized cell lines, cancer cell lines, etc.).

Also provided herein are populations of cells comprising a plurality of the cells or immune cell. In some embodiments, the genome of at least 20%, 30%, 40%, 50%, 60%, 70%, 80%, 90%, 95%, 99% or greater of the cells comprises the priming receptor and CAR system as described herein.

Method of Treating Immune-Related Condition of Disease

In another aspect, the disclosure herein provides methods of treating an immune-related condition (e.g., cancer) in an individual comprising administering to the individual an effective amount of a composition comprising a system comprising a priming receptor that specifically binds to PSMA and a chimeric antigen receptor that specifically binds to CA9, such as a cell composition comprising a system comprising a priming receptor that specifically binds to PSMA and a chimeric antigen receptor that specifically binds to CA9. In another aspect, the disclosure herein provides methods of enhancing an immune response in an individual comprising administering to the individual an effective amount of a composition comprising a system comprising a priming receptor that specifically binds to PSMA and a chimeric antigen receptor that specifically binds to CA9, such as a cell composition comprising a system comprising a priming receptor that specifically binds to PSMA and a chimeric antigen receptor that specifically binds to CA9.

In some embodiments, the target cell is a cell that expresses both PSMA and CA9. In some embodiments, the target cell is a cancer cell that expresses both PSMA and CA9. In some embodiments, the cancerous or diseased cell expresses both PSMA and CA9.

In some embodiments, the methods provided herein are useful for the treatment of an immune-related condition in an individual. In one embodiment, the individual is a human.

In some embodiments, the methods provided herein (such as methods of enhancing an immune response) are useful for the treatment of cancer and as such an individual receiving the system described herein has cancer. In some embodiments, the cancer is a solid cancer. In some embodiments, the cancer is immunoevasive. In some embodiments, the cancer is immunoresponsive. In particular embodiments, the cancer is kidney cancer, renal cell carcinoma, clear cell renal cell carcinoma (ccRcc), colorectal cancer, or lung cancer.

In some embodiments, the treatment results in a decrease in the cancer volume or size. In some embodiments, the treatment is effective at reducing a cancer volume as compared to the cancer volume prior to administration of the antibody. In some embodiments, the treatment results in a decrease in the cancer growth rate. In some embodiments, the treatment is effective at reducing a cancer growth rate as compared to the cancer growth rate prior to administration of the antibody. In some embodiments, the treatment is effective at eliminating the cancer.

In some embodiments, CA9 and PSMA are expressed at a higher level in the cancer as compared to a non-cancer cell. Levels of CA9 and PSMA can be assessed by any technique known in the field, including, but not limited to, protein assays or nucleic assays such as FACS, Western blot, ELISA, immunoprecipitation, immunohistochemistry, immunofluorescence, radioimmunoassay, dot blotting, immunodetection methods, HPLC, surface plasmon resonance, optical spectroscopy, mass spectrometry, HPLC, qPCR, RT-qPCR, multiplex qPCR or RT-qPCR, RNA-seq, microarray analysis, SAGE, MassARRAY technique, and FISH, and combinations thereof.

In some aspects, provided herein are methods of inhibiting a target cell in a subject comprising administering the immune cell or population of immune cells disclosed herein to the subject, wherein the immune cell inhibits the target cell. Inhibition of a target cell includes killing of the cancer cell, or prevention or reduction in cancer cell growth, proliferation, or metastasis.

In some embodiments, the subject is conditioned with 30 mg/m$^2$ fludarabine and 300 mg/m$^2$ cyclophosphamide prior to administering the immune cell or population of immune cells disclosed herein. Administering the immune cell or population of immune cells disclosed herein to a subject without the conditioning may also be performed. In some embodiments, the subjects are conditioned on one or more of Days-3, -4, and/or -5 prior to prior to administering the immune cell or population of immune cells disclosed herein.

In some embodiments, subjects are administered 100×10$^6$, 300×10$^6$ or 1000×10$^6$ of the immune cell or population of immune cells disclosed herein.

Method of Immune Modulation

Methods of administration of a cell comprising a system comprising a priming receptor that specifically binds to PSMA and a chimeric antigen receptor that specifically binds to CA9 as described herein can result in modulation of an immune response. Modulation can be an increase or decrease in an immune response. In some embodiments, modulation is an increase in an immune response.

In one aspect, administration of a cell comprising a system comprising a priming receptor that specifically binds to PSMA and a chimeric antigen receptor that specifically binds to CA9 as described herein can result in induction of pro-inflammatory molecules, such as cytokines or chemokines. Generally, induced pro-inflammatory molecules are present at levels greater than that achieved with isotype control. Such pro-inflammatory molecules in turn result in activation of anti-tumor immunity, including, but not limited to, T cell activation, T cell proliferation, T cell differentiation, M1-like macrophage activation, and NK cell activation. Thus, the administration of a system comprising a priming receptor that specifically binds to PSMA and a chimeric antigen receptor that specifically binds to CA9 can induce multiple anti-tumor immune mechanisms that lead to tumor destruction.

In some embodiments, the target cell is a cell that expresses both PSMA and CA9. In some embodiments, the disease cell expresses both PSMA and CA9.

In another aspect, provided herein are methods of increasing an immune response in an individual comprising administering to the individual an effective amount of a cell comprising a system comprising a priming receptor that specifically binds to PSMA and a chimeric antigen receptor that specifically binds to CA9. In some embodiments, the method of increasing an immune response in a subject comprises administering to the subject a cell comprising a system comprising a priming receptor that specifically binds to PSMA and a chimeric antigen receptor that specifically binds to CA9.

In some embodiments, the cell is present in a pharmaceutical composition further comprising a pharmaceutically acceptable excipient.

In any and all aspects of increasing an immune response as described herein, any increase or decrease or alteration of an aspect of characteristic(s) or function(s) is as compared to a cell not comprising a composition comprising a system comprising a priming receptor that specifically binds to PSMA and a chimeric antigen receptor that specifically binds to CA9.

Increasing an immune response can be both enhancing an immune response or inducing an immune response. For instance, increasing an immune response encompasses both the start or initiation of an immune response, or ramping up or amplifying an on-going or existing immune response. In some embodiments, the treatment induces an immune response. In some embodiments, the induced immune response is an adaptive immune response. In some embodiments, the induced immune response is an innate immune response. In some embodiments, the treatment enhances an immune response. In some embodiments, the enhanced immune response is an adaptive immune response. In some embodiments, the enhanced immune response is an innate immune response. In some embodiments, the treatment increases an immune response. In some embodiments, the increased immune response is an adaptive immune response. In some embodiments, the increased immune response is an innate immune response. In some embodiments, the immune response is started or initiated by administration of a cell comprising a system comprising a priming receptor that specifically binds to PSMA and a chimeric antigen receptor that specifically binds to CA9. In some embodiments, the immune response is enhanced by administration of cell comprising a system comprising a priming receptor that specifically binds to PSMA and a chimeric antigen receptor that specifically binds to CA9.

In another aspect, the present application provides methods of genetically editing a cell with a system comprising a priming receptor that specifically binds to PSMA and a chimeric antigen receptor that specifically binds to CA9, which results in the modulation of the immune function of the cell. The modulation can be increasing an immune response. In some embodiments, the modulation is an increase in immune function. In some embodiments, the modulation of function leads to the expression of an CA9 CAR. In some embodiments, the modulation of function leads to the activation of a cell comprising the system.

In some embodiments, the cell is a natural killer (NK) cell, a T cell, a CD8+ T cell, a CD4+ T cell, a primary T cell, or a T cell progenitor.

In some embodiments, the modulation of function of the cells comprising the priming receptor and CAR system as described herein leads to an increase in the cells' abilities to stimulate both native and activated T-cells, for example, by increasing cytokine or chemokine secretion by the cells expressing the priming receptor and CAR system. In some embodiments, the modulation of function enhances or increases the cells' ability to produce cytokines, chemokines, CARs, or costimulatory or activating receptors. In some embodiments, the modulation increases the T-cell stimulatory function of the cells expressing the priming receptor and CAR system, including, for example, the cells' abilities to trigger T-cell receptor (TCR) signaling, T-cell proliferation, or T-cell cytokine production.

In some embodiments, the increased immune response is secretion of cytokines and chemokines. In some embodiments, the priming receptor and CAR system induces increased expression of at least one cytokine or chemokine in a cell as compared to an isotype control cell. In some embodiments, the at least one cytokine or chemokine is selected from the group consisting of: IL-2 and IFNγ. In some embodiments, the cytokine or chemokine is IL-2. In some embodiments, the cytokine or chemokine is IFNγ. In some embodiments, the cytokine or chemokine secretion is increased a between bout 1-100-fold 1, 5, 10, 20, 30, 40, 50, 60, 70, 80, 90, 100, 1-10, 10-20, 20-30, 30-40, 40-50, 50-60, 60-70, 70-80, 80-90, or 90-100 fold as compared to an untreated cell or a cell treated with an isotype control antibody. In some embodiments, the chemokine is IL-2 and the secretion is increased between about 1-100-fold, 1-fold, 5-fold, 10-fold, 20-fold, 30-fold, 40-fold, 50-fold, 60-fold, 70-fold, 80-fold, 90-fold, 100-fold, 1-10-fold, 10-20-fold, 20-30-fold, 30-40-fold, 40-50-fold, 50-60-fold, 60-70-fold, 70-80-fold, 80-90-fold, or 90-100-fold as compared to an untreated cell or a cell treated with an isotype control antibody. In some embodiments, the cytokine is IFNγ and the secretion is increased between about 1-100-fold, 1-fold, 5-fold, 10-fold, 20-fold, 30-fold, 40-fold, 50-fold, 60-fold, 70-fold, 80-fold, 90-fold, 100-fold, 1-10-fold, 10-20-fold, 20-30-fold, 30-40-fold, 40-50-fold, 50-60-fold, 60-70-fold, 70-80-fold, 80-90-fold, or 90-100-fold as compared to an untreated cell or a cell treated with an isotype control antibody.

In some embodiments, the enhanced immune response is anti-tumor immune cell recruitment and activation.

In some embodiments, the cell expressing the priming receptor and CAR system induces a memory immune response as compared to an isotype control cell. In general, a memory immune response is a protective immune response upon a subsequent exposure to pathogens or antigens that the immune system encountered previously. Exemplary memory immune responses include the immune response after infection or vaccination with an antigen. In general, memory immune responses are mediated by lymphocytes such as T cells or B cells. In some embodiments, the memory immune response is a protective immune response to cancer, including cancer cell growth, proliferation, or metastasis. In some embodiments, the memory immune response inhibits, prevents, or reduces cancer cell growth, proliferation, or metastasis.

Methods of Editing Cells

In some aspects, provide herein are methods of editing a cell, comprising: providing a nuclease domain and a guide RNA, wherein the nucleic acid comprises a nucleic acid disclosed herein, and wherein the 5' and 3' ends of the nucleic acid comprise nucleotide sequences that are homologous to genomic sequences flanking an insertion site in the genome of the cell; introducing the nuclease domain and nucleic acid into the cell, wherein the guide RNA specifically hybridizes to a target region of the genome of the cell, and wherein the nuclease domain cleaves the target region to create the insertion site in the genome of the cell; and editing the cell via insertion of the nucleic acid into the insertion site in the genome of the cell.

The terms "gene editing" or "genome editing", as used herein, refer to a type of genetic manipulation in which DNA is inserted, replaced, or removed from the genome using artificially manipulated nucleases or "molecular scissors". It is a useful tool for elucidating the function and effect of sequence-specific genes or proteins or altering cell behavior (e.g. for therapeutic purposes).

Currently available genome editing tools include zinc finger nucleases (ZFN) and transcription activator-like effector nucleases (TALENs) to incorporate genes at safe harbor loci (e.g. the adeno-associated virus integration site 1 (AAVS1) safe harbor locus). The DICE (dual integrase cassette exchange) system utilizing phiC31 integrase and Bxb1 integrase is a tool for target integration. Additionally, clustered regularly interspaced short palindromic repeat/Cas9 (CRISPR/Cas9) techniques can be used for targeted gene insertion.

Site specific gene editing approaches can include homology dependent mechanisms or homology independent mechanisms.

All methods known in the art for targeted insertion of gene sequences are contemplated in the methods described herein to insert constructs at gene targets or safe harbor loci.

Also provided herein are methods of making an immune cell comprising introducing a nucleic acid comprising the priming receptor and CAR system as described herein into a primary immune cell. In some embodiments, the immune cell is an isolated cell. In some embodiments, the immune cell is a mammalian cell (e.g., a human cell).

Provided herein are methods of inserting nucleotide sequences greater than about 5 kilobases in length into the genome of a cell, in the absence of a viral vector. In some embodiments, the nucleotide sequence greater than about 5 kilobase in length can be inserted into the genome of a primary immune cell, in the absence of a viral vector Integration of large nucleic acids, for example nucleic acids greater than 5 kilobase in size, into cells, can be limited by low efficiency of integration, off-target effects and/or loss of cell viability. Described herein are methods and compositions for achieving integration of a nucleotide sequence, for example, a nucleotide sequence greater than about 5 kilobases in size, into the genome of a cell. In some methods the efficiency of integration is increased, off-target effects are reduced and/or loss of cell viability is reduced.

The plasmid can be introduced into an immune cell with a nuclease, such as a CRISPR-associated system (Cas). The nuclease can be introduced in a ribonucleoprotein format with a guide RNA (gRNA) that targets a specific site on the genome of the immune cell. The nuclease cuts the genomic DNA at this specific site. The specific site may be a portion of the genome that encodes an endogenous immune cell receptor. Thus, cutting the genome at this site will cause the immune cell to no longer express an endogenous immune cell receptor.

The plasmid may include 5' and 3' homology-directed repair arms complementary to sequences at a specific site on the genome of the immune cell. The complementary sequences are on either side of the site cut by the nuclease, which allows the plasmid to be incorporated at a specified insertion site on the immune cell's genome. Once the plasmid is incorporated, the cell will express the priming receptor. However, as explained, the design of the transgene cassette ensures that non-virally delivered circuit system receptors do not express CAR until the priming receptor binds to its cognate ligand and releases the cleavable transcription factor.

Initially, a T cell is isolated and optionally activated. The T cell may be obtained from a patient. Thus, the present disclosure provides methods in which immune cells, such as T cells, are harvested from a patient. Then, the plasmid that encodes the CAR and priming receptor are introduced into a T cell. Advantageously, the plasmids of the present disclosure can be introduced using electroporation. When introducing the plasmid via electroporation, the nuclease may also be introduced. By using electroporation, methods of the present disclosure avoid the use of viral vectors for introducing transgenes, which is a known bottleneck in immune cell engineering. The T cells are then expanded and co-cultured to create a sufficient quantity of engineered immune cells to be used as a therapeutic treatment.

Methods for editing the genome of a cell can include a) providing a Cas9 ribonucleoprotein complex (RNP) and a nucleic acid, comprising: (i) the RNP, wherein the RNP comprises a Cas9 nuclease domain and a guide RNA, wherein the guide RNA specifically hybridizes to a target region of the genome of the cell, and wherein the Cas9 nuclease domain cleaves the target region to create an insertion site in the genome of the cell; and (ii) a double-stranded or single-stranded a nucleic acid, such as a DNA template, wherein the size of the nucleic acid (e.g., DNA template) is greater than about 200 nucleotides, wherein the 5' and 3' ends of the nucleic acid (e.g., DNA template) comprise nucleotide sequences that are homologous to genomic sequences flanking the insertion site, and wherein the molar ratio of RNP to nucleic acid (e.g., DNA template) in the complex is from about 3:1 to about 100:1; and b) introducing the RNP complex and nucleic acid (e.g., DNA template) into the cell.

In some embodiments, the methods described herein provide an efficiency of delivery of the RNP complex and the nucleic acid (e.g., DNA template) of at least about 10%, 15%, 20%, 25%, 30%, 35%, 40%, 45%, 50%, 55%, 60%, 65%, 70%, 75%, 80%, 85%, 90%, 95%, 97.5%, 99%, 99.5%, 99%, or higher. In some cases, the efficiency is determined with respect to cells that are viable after introducing the RNP complex and the nucleic acid (e.g., DNA template) into the cell. In some cases, the efficiency is determined with respect to the total number of cells (viable or non-viable) in which the RNP complex and the nucleic acid (e.g., DNA template) is introduced into the cell.

As another example, the efficiency of delivery can be determined by quantifying the number of genome edited cells in a population of cells (as compared to total cells or total viable cells obtained after the introducing step). Various methods for quantifying genome editing can be utilized. These methods include, but are not limited to, the use of a mismatch-specific nuclease, such as T7 endonuclease I; sequencing of one or more target loci (e.g., by sanger sequencing of cloned target locus amplification fragments); and high-throughput deep sequencing.

In some embodiments, loss of cell viability is reduced as compared to loss of cell viability after introduction of naked DNA into a cell or introduction of DNA into a cell using a viral vector. The reduction can be a reduction of at least 10%, 20%, 30%, 40%, 50%, 60%, 70%, 80%, 90%, 100% or any percentage in between these percentages. In some embodiments, off-target effects of integration are reduced as compared to off-target integration after introduction of naked DNA into a cell or introduction of DNA into a cell using a viral vector. The reduction can be a reduction of at least 10%, 20%, 30%, 40%, 50%, 60%, 70%, 80%, 90%, 100% or any percentage in between these percentages.

In some cases, the methods described herein provide for high cell viability of cells to which the RNP and nucleic acid (e.g., DNA template) has been introduced. In some cases, the viability of the cells to which the RNP and nucleic acid (e.g., DNA template) has been introduced is at least about 20%, 25%, 30%, 35%, 40%, 45%, 50%, 55%, 60%, 65%, 70%, 75%, 80%, 85%, 90%, 95%, 97.5%, 99%, 99.5%, 99%, or higher. In some cases, the viability of the cells to which the RNP and nucleic acid (e.g., DNA template) has been introduced is from about 20% to about 99%, from about 30% to about 90%, from about 35% to about 85% or 90% or higher, from about 40% to about 85% or 90% or higher, from about 50% to about 85% or 90% or higher, from about 50% to about 85% or 90% or higher, from about 60% to about 85% or 90% or higher, or from about 70% to about 85% or 90% or higher.

In the methods provided herein, the molar ratio of RNP to nucleic acid (e.g., DNA template) can be from about 3:1 to about 100:1. For example, the molar ratio can be from about 3:1 to 10:1, from about 3:1 to about 15:1, 3:1 to about 20:1; 3:1 to about 25:1; from about 3:1 to 50:1, from about 3:1 to 75:1, from about 3:1 to 100:1; from about 5:1 to 10:1, from about 5:1 to about 15:1, 5:1 to about 20:1; 5:1 to about 25:1; from about 5:1 to 50:1, from about 5:1 to 75:1, from about 5:1 to 100:1; from about 8:1 to about 12:1; from about 8:1 to about 15:1, from about 8:1 to about 20:1, from about 8:1 to about 25:1, from about 8:1 to 50:1, from about 8:1 to 75:1, from about 8:1 to 100:1; from about 10:1 to about 15:1, 10:1 to about 20:1, 10:1 to about 25:1; from about 10:1 to 50:1, from about 10:1 to 75:1, or from about 10:1 to 100:1.

In some embodiments, the nucleic acid (e.g., DNA template) is at a concentration of about 2.5 pM to about 25 pM. For example, the concentration of nucleic acid (e.g., DNA template) can be about 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25 pM or any concentration in between these concentrations.

In some embodiments, the size or length of the nucleic acid (e.g., DNA template) is greater than about 4.5 kb, 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, 7.0 kb, 7.1 kb, 7.2 kb, 7.3 kb, 7.4 kb, 7.5 kb, 7.6 kb, 7.7 kb, 7.8 kb, 7.9 kb, 8.0 kb, 8.1 kb, 8.2 kb, 8.3 kb, 8.4 kb, 8.5 kb, 8.6 kb, 8.7 kb, 8.8 kb, 8.9 kb, 9.0 kb, 9.1 kb, 9.2 kb, 9.3 kb, 9.4 kb, 9.5 kb, 9.6 kb, 9.7 kb, 9.8 kb, 9.9 kb, 10 kb, 11 kb, 12 kb, 13 kb, 14 kb, 15 kb, or 16 kb or any size of nucleic acid (e.g., DNA template) in between these sizes. For example, the size of the DNA template can be about 4.5 kb to about 15 kb, about 4.5 kb to about 14 kb, about 4.5 kb to about 10 kb, about 5 kb to about 15 kb, about 5 kb to about 14 kb, about 5 kb to about 10 kb, about 5 kb to about 9 kb, about 5 kb to about 8 kb, about 5 kb to about 7 kb, about 5 kb to about 6 kb, about kb 6 to about 15 kb, about kb 6 to about 14 kb, about kb 6 to about 10 kb, about 6 kb to about 9 kb, about 6 kb to about 8 kb, about 6 kb to about 7 kb, about 7 kb to about 15 kb, about 7 kb to about 14 kb, about 7 kb to about 10 kb, about 7 kb to about 9 kb, about 7 kb to about 8 kb, about 8 kb to about 15 kb, about 8 kb to about 14 kb, about 8 kb to about 10 kb, about 8 kb to about 9 kb, about 9 kb to about 15 kb, about 9 kb to about 14 kb, about 9 kb to about 13 kb, about 9 kb to about 12 kb, about 9 kb to about 11 kb, about 9 kb to about 10 kb, about 10 kb to about 15 kb, about 10 kb to about 14 kb, about 10 kb to about 13 kb, about 10 kb to about 12 kb, or about 10 kb to about 11 kb.

In some embodiments, the amount of nucleic acid (e.g., DNA template) is about 1 µg to about 10 µg. For example, the amount of nucleic acid (e.g., DNA template) can be about 1 µg to about 2 µg, about 1 µg to about 3 µg, about 1 µg to about 4 µg, about 1 µg to about 5 µg, about 1 µg to about 6 µg, about 1 µg to about 7 µg, about 1 µg to about 8 µg, about 1 µg to about 9 µg, about 1 µg to about 10 µg. In some embodiments the amount of DNA template is about 2 µg to about 3 µg, about 2 µg to about 4 µg, about 2 µg to about 5 µg, about 2 µg to about 6 µg, about 2 µg to about 7 µg, about 2 µg to about 8 µg, about 2 µg to about 9 µg, or 2 µg to about 10 µg. In some embodiments the amount of nucleic acid (e.g., DNA template) is about 3 µg to about 4 µg, about 3 µg to about 5 µg, about 3 µg to about 6 µg, about 3 µg to about 7 µg, about 3 µg to about 8 µg, about 3 µg to about 9 µg, or about 3 µg to about 10 µg. In some embodiments, the amount of nucleic acid (e.g., DNA template) is about 4 µg to about 5 µg, about 4 µg to about 6 µg, about 4 µg to about 7 µg, about 4 µg to about 8 µg, about 4 µg to about 9 µg, or about 4 µg to about 10 µg. In some embodiments, the amount of DNA template is about 5 µg to about 6 µg, about 5 µg to about 7 µg, about 5 µg to about 8 µg, about 5 µg to about 9 µg, or about 5 µg to about 10 µg. In some embodiments, the amount of DNA template is about 6 µg to about 7 µg, about 6 µg to about 8 µg, about 6 µg to about 9 µg, or about 6 µg to about 10 µg. In some embodiments, the amount of nucleic acid (e.g., DNA template) is about 7 µg to about 8 µg, about 7 µg to about 9 µg, or about 7 µg to about 10 µg. In some embodiments, the amount of DNA template is about 8 µg to about 9 µg, or about 8 µg to about 10 µg. In some embodiments, the amount of DNA template is about 9 µg to about 10 µg.

In some cases, the size of the nucleic acid (e.g., DNA template) is large enough and in sufficient quantity to be lethal as naked DNA. In some embodiments, the DNA template encodes a heterologous protein or a fragment thereof. In some embodiments, the nucleic acid (e.g., DNA template) encodes at least one gene. In some embodiments, the DNA template encodes at least two genes. In some embodiments, the nucleic acid (e.g., DNA template) encodes one, two, three, four, five, six, seven, eight, nine, ten, or more genes.

In some embodiments, the nucleic acid (e.g., DNA template) includes regulatory sequences, for example, a promoter sequence and/or an enhancer sequence to regulate expression of the heterologous protein or fragment thereof after insertion into the genome of a cell. In some embodiments, the promoter is an inducible promoter. In some embodiments, the inducible promoter comprises one or more HNF1α enhancer elements. In some embodiments, the inducible promoter comprises a YB-TATA promoter element. In some embodiments, the inducible promoter comprises a sequence as set forth in SEQ ID NO: 256. In some embodiments, the promoter is an constitutive promoter. In some embodiments, the constitutive promoter is an EF1α promoter. In some embodiments, the constitutive promoter comprises the sequence of SEQ ID NO: 179.

In some cases, the nucleic acid (e.g., DNA template) is a linear DNA template. In some cases, the nucleic acid (e.g., DNA template) is a single-stranded DNA template. In some cases, the single-stranded DNA template is a pure single-stranded DNA template. As used herein, by "pure single-stranded DNA" is meant single-stranded DNA that substantially lacks the other or opposite strand of DNA. By "substantially lacks" is meant that the pure single-stranded DNA lacks at least 100-fold more of one strand than another strand of DNA.

In some cases, an RNP and nucleic acid (e.g., DNA template) complex is formed by incubating the RNP with the nucleic acid (e.g., DNA template) for less than about one minute to about thirty minutes, at a temperature of about 20° C. to about 25° C. For example, the RNP can be incubated with the DNA template for about 5 seconds, 10 seconds, 15 seconds, 20 seconds, 25 seconds, 30 seconds, 35 seconds, 40 seconds, 45 seconds, 50 seconds, 55 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes or 30 minutes or any amount of time in between these times, at a temperature of about 20° C., 21° C., 22° C., 23° C., 24° C., or 25° C. In another example, the RNP can be incubated with the nucleic acid (e.g., DNA template) for less than about one minute to about one minute, for less than about one minute to about 5 minutes, for less than about 1 minute to about 10 minutes, for about 5 minutes to 10 minutes, for about 5 minutes to 15 minutes, for about 10 to about 15 minutes, for about 10 minutes to about 20 minutes, or for about 10 minutes to about 30 minutes, at a temperature of about 20° C. to about 25° C. In some embodiments, the RNP-DNA template complex and the cell are mixed prior to introducing the RNP-DNA template complex into the cell. In some embodiments, the RNP and nucleic acid (e.g., DNA template) and the cell are mixed prior to introducing the RNP and nucleic acid (e.g., DNA template) into the cell.

In some embodiments introducing the RNP complex and nucleic acid (e.g., DNA template) comprises electroporation. Methods, compositions, and devices for electroporating cells to introduce a RNP and nucleic acid (e.g., DNA template) can include those described in the examples herein. Additional or alternative methods, compositions, and devices for electroporating cells to introduce a RNP and nucleic acid (e.g., DNA template) can include those described in WO/2006/001614 or Kim, J. A. et al. Biosens. Bioelectron. 23, 1353-1360 (2008). Additional or alternative methods, compositions, and devices for electroporating cells to introduce a RNP and nucleic acid (e.g., DNA template) can include those described in U.S. Patent Appl. Pub. Nos. 2006/0094095; 2005/0064596; or 2006/0087522. Additional or alternative methods, compositions, and devices for electroporating cells to introduce a RNP-DNA template complex can include those described in Li, L. H. et al. Cancer Res. Treat. 1, 341-350 (2002); U.S. Pat. Nos. 6,773,669; 7,186,559; 7,771,984; 7,991,559; 6,485,961; 7,029,916; and U.S. Patent Appl. Pub. Nos: 2014/0017213; and 2012/0088842, all of which are hereby incorporated by reference. Additional or alternative methods, compositions, and devices for electroporating cells to introduce a RNP and nucleic acid (e.g., DNA template) can include those described in Geng, T. et al. J. Control Release 144, 91-100 (2010); and Wang, J., et al. Lab. Chip 10, 2057-2061 (2010), all of which are hereby incorporated by reference.

In some embodiments, the Cas9 protein can be in an active endonuclease form, such that when bound to target nucleic acid as part of a complex with a guide RNA or part of a complex with a nucleic acid (e.g., DNA template), a double strand break is introduced into the target nucleic acid. The double strand break can be repaired by NHEJ to introduce random mutations, or HDR to introduce specific mutations. Various Cas9 nucleases can be utilized in the methods described herein. For example, a Cas9 nuclease that requires an NGG protospacer adjacent motif (PAM) immediately 3' of the region targeted by the guide RNA can be utilized. Such Cas9 nucleases can be targeted to any region of a genome that contains an NGG sequence. As another example, Cas9 proteins with orthogonal PAM motif requirements can be utilized to target sequences that do not have an adjacent NGG PAM sequence. Exemplary Cas9 proteins with orthogonal PAM sequence specificities include, but are not limited to, CFP1, those described in Nature Methods 10, 1116-1121 (2013), and those described in Zetsche et al., Cell, Volume 163, Issue 3, p759-771, 22 Oct. 2015, both of which are hereby incorporated by reference.

In some cases, the Cas9 protein is a nickase, such that when bound to target nucleic acid as part of a complex with a guide RNA, a single strand break or nick is introduced into the target nucleic acid. A pair of Cas9 nickases, each bound to a structurally different guide RNA, can be targeted to two proximal sites of a target genomic region and thus introduce a pair of proximal single stranded breaks into the target genomic region. Nickase pairs can provide enhanced specificity because off-target effects are likely to result in single nicks, which are generally repaired without lesion by base-excision repair mechanisms. Exemplary Cas9 nickases include Cas9 nucleases having a D10A or H840A mutation.

In some embodiments, the RNP comprises a Cas9 nuclease. In some embodiments, the RNP comprises a Cas9 nickase. In some embodiments, the RNP-DNA template complex comprises at least two structurally different RNP complexes. In some embodiments, the at least two structurally different RNP complexes contain structurally different Cas9 nuclease domains In some embodiments, the at least two structurally different RNP complexes contain structurally different guide RNAs. In some embodiments, wherein the at least two structurally different RNP complexes contain structurally different guide RNAs, each of the structurally different RNP complexes comprises a Cas9 nickase, and the structurally different guide RNAs hybridize to opposite strands of the target region.

In some cases, a plurality of RNP and nucleic acids (e.g., DNA templates) comprising structurally different ribonucleoprotein complexes is introduced into the cell. For example a Cas9 protein can be complexed with a plurality (e.g., 2, 3, 4, 5, or more, e.g., 2-10, 5-100, 20-100) of structurally different guide RNAs to target insertion of a nucleic acid (e.g., DNA template) at a plurality of structurally different target genomic regions.

In the methods and compositions provided herein, cells include, but are not limited to, eukaryotic cells, prokaryotic cells, animal cells, plant cells, fungal cells and the like. Optionally, the cell is a mammalian cell, for example, a human cell. The cell can be in vitro, ex vivo or in vivo. The cell can also be a primary cell, a germ cell, a stem cell or a precursor cell. The precursor cell can be, for example, a pluripotent stem cell, or a hematopoietic stem cell. In some embodiments, the cell is a primary hematopoietic cell or a primary hematopoietic stem cell. In some embodiments, the primary hematopoietic cell is an immune cell. In some embodiments, the immune cell is a T cell. In some embodiments, the T cell is a regulatory T cell, an effector T cell, or a naïve T cell. In some embodiments, the T cell is a $CD4^+$ T cell. In some embodiments, the T cell is a $CD8^+$ T cell. In some embodiments, the T cell is a $CD4^+CD8^+$ T cell. In some embodiments, the T cell is a $CD4^-CD8^-$ T cell. Populations of any of the cells modified by any of the methods described herein are also provided. In some embodiments, the methods further comprise expanding the population of modified cells.

In some cases, the cells are removed from a subject, modified using any of the methods described herein and administered to the patient. In other cases, any of the constructs described herein is delivered to the patient in vivo. See, for example, U.S. Pat. No. 9,737,604 and Zhang et al. "Lipid nanoparticle-mediated efficient delivery of CRISPR/Cas9 for tumor therapy," *NPG Asia Materials* Volume 9, page e441 (2017), both of which are hereby incorporated by reference.

In some embodiments, the RNP and nucleic acid (e.g., DNA template) is introduced into about $1\times10^5$ to about $2\times10^6$ cells. For example, the RNP-DNA template complex can be introduced into about $1\times10^5$ to about $5\times10^5$ cells, about $1\times10^5$ to about $1\times10^6$, $1\times10^1$ to about $1.5\times10^6$, $1\times10^1$ to about $2\times10^6$, about $1\times10^6$ to about $1.5\times10^6$ cells or about $1\times10^6$ to about $2\times10^6$.

In some cases, the methods and compositions described herein can be used for generation, modification, use, or control of recombinant T cells, such as chimeric antigen receptor T cells (CAR T cells). Such CAR T cells can be used to treat or prevent cancer, an infectious disease, or autoimmune disease in a subject. For example, in some embodiments, one or more gene products are inserted or knocked-in to a T cell to express a heterologous protein (e.g., a chimeric antigen receptor (CAR) or a priming receptor).

Insertion Sites

Methods for editing the genome of a T cell, specifically, include a method of editing the genome of a human T cell comprise inserting a nucleic acid sequence or construct into a target region in exon 1 of the TCR-α subunit (TRAC) gene in the human T cell. In some embodiments, the target region is in exon 1 of the constant domain of TRAC gene. In other embodiments, the target region is in exon 1, exon 2 or exon 3, prior to the start of the sequence encoding the TCR-α transmembrane domain.

Methods for editing the genome of a T cell also include a method of editing the genome of a human T cell comprise inserting a nucleic acid sequence or construct into a target region in exon 1 of a TCR-β subunit (TRBC) gene in the human T cell. In some embodiments, the target region is in exon 1 of the TRBC1 or TRBC2 gene.

Methods for editing the genome of a T cell, specifically, include a method of editing the genome of a human T cell comprise inserting a nucleic acid sequence or construct into a target region of a genomic safe harbor (GSH).

Gene editing therapies include, for example, vector integration and site specific integration. Site-specific integration is a promising alternative to random integration of viral vectors, as it mitigates the risks of insertional mutagenesis or insertional oncogenesis (Kolb et al. Trends Biotechnol. 2005 23:399-406; Porteus et al. Nat Biotechnol. 2005 23:967-973; Paques et al. Curr Gen Ther. 2007 7:49-66). However, site specific integration continues to face challenges such as poor knock-in efficiency, risk of insertional oncogenesis, unstable and/or anomalous expression of adjacent genes or the transgene, low accessibility (e.g. within 20 kB of adjacent genes), etc. These challenges can be addressed, in part, through the identification and use of safe harbor loci or safe harbor sites (SHS), which are sites in which genes or genetic elements can be incorporated without disruption to expression or regulation of adjacent genes.

The most widely used of the putative human safe harbor sites is the AAVS1 site on chromosome 19q, which was initially identified as a site for recurrent adenoassociated virus insertion. Other potential SHS have been identified on the basis of homology, with sites first identified in other species (e.g., the human homolog of the permissive murine Rosa26 locus) or among the growing number of human genes that appear non-essential under some circumstances. One putative SHS of this type is the CCR5 chemokine receptor gene, which, when disrupted, confers resistance to human immunodeficiency virus infection. Additional potential genomic SHS have been identified in human and other cell types on the basis of viral integration site mapping or gene-trap analyses, as was the original murine Rosa26 locus. The three top SHS, AAVS1, CCR5, and Rosa26, are in close proximity to many protein coding genes and regulatory elements. (See Sadelain, M., et al. (2012). Safe harbours for the integration of new DNA in the human genome. Nature reviews Cancer, 12(1), 51-58, the relevant disclosures of which are herein incorporated by reference in their entirety).

The AAVS1 (also known as the PPP1R12C locus) on human chromosome 19 is a known SHS for hosting transgenes (e.g. DNA transgenes) with expected function. It is at position 19q13.42. It has an open chromatin structure and is transcription-competent. The canonical SHS locus for AAVS1 is chr19: 55,625,241-55,629,351. See Pellenz et al. "New Human Chromosomal Sites with "Safe Harbor" Potential for Targeted Transgene Insertion." Human gene therapy vol. 30, 7 (2019): 814-828, the relevant disclosures of which are herein incorporated by reference. An exemplary AAVS1 target gRNA and target sequence are provided below:

```
AAVS1-gRNA sequence:
                                       (SEQ ID NO: 268)
ggggccactagggacaggatGTTTTAGAGCTAGAAATAGCAAGTTAAAAT

AAGGCTAGTCCGTTATCAACTTGAAAAAGTGGCACCGAGTCGGTGCTTTT

TTT

AAVS1 target sequence:
                                       (SEQ ID NO: 269)
ggggccactagggacaggat
```

CCR5, which is located on chromosome 3 at position 3p21.31, encodes the major co-receptor for HIV-1. Disruption at this site in the CCR5 gene has been beneficial in HIV/AIDS therapy and prompted the development of zinc-finger nucleases that target its third exon. The canonical SHS locus for CCR5 is chr3: 46,414,443-46,414,942. See Pellenz et al. "New Human Chromosomal Sites with "Safe Harbor" Potential for Targeted Transgene Insertion." Human gene therapy vol. 30, 7 (2019): 814-828, the relevant disclosures of which are herein incorporated by reference.

The mouse Rosa26 locus is particularly useful for genetic modification as it can be targeted with high efficiency and is expressed in most cell types tested. Irion et al. 2007 ("Identification and targeting of the ROSA26 locus in human embryonic stem cells." Nature biotechnology 25.12 (2007): 1477-1482, the relevant disclosure of which are herein incorporated by reference) identified the human homolog, human ROSA26, in chromosome 3 (position 3p25.3). The canonical SHS locus for human Rosa26 (hRosa26) is chr3: 9,415,082-9,414,043. See Pellenz et al. "New Human Chromosomal Sites with "Safe Harbor" Potential for Targeted Transgene Insertion." Human gene therapy vol. 30, 7 (2019): 814-828, the relevant disclosures of which are herein incorporated by reference.

Additional examples of safe harbor sites are provided in Pellenz et al. "New Human Chromosomal Sites with "Safe Harbor" Potential for Targeted Transgene Insertion." Human gene therapy vol. 30, 7 (2019): 814-828, the relevant disclosures of which are herein incorporated by reference. Examples of additional integration sites are provided in Table D.

In some embodiments, the safe harbor sites allow for high transgene expression (sufficient to allow for transgene functionality or treatment of a disease of interest) and stable expression of the transgene over several days, weeks or months. In some embodiments, knockout of the gene at the safe harbor locus confers benefit to the function of the cell, or the gene at the safe harbor locus has no known function within the cell. In some embodiments the safe harbor locus results in stable transgene expression in vitro with or without CD3/CD28 stimulation, negligible off-target cleavage as detected by iGuide-Seq or CRISPR-Seq, less off-target cleavage relative to other loci as detected by iGuide-Seq or CRISPR-Seq, negligible transgene-independent cytotoxicity, negligible transgene-independent cytokine expression, negligible transgene-independent chimeric antigen receptor expression, negligible deregulation or silencing of nearby genes, and positioned outside of a cancer-related gene.

As used, a "nearby gene" can refer to a gene that is within about 100 kB, about 125 kB, about 150 kB, about 175 kB, about 200 kB, about 225 kB, about 250 kB, about 275 kB, about 300 kB, about 325 kB, about 350 kB, about 375 kB, about 400 kB, about 425 kB, about 450 kB, about 475 kB, about 500 kB, about 525 kB, about 550 kB away from the safe harbor locus (integration site).

In some embodiments, the present disclosure contemplates inserts that comprise one or more transgenes. The transgene can encode a therapeutic protein, an antibody, a peptide, or any other gene of interest. The transgene integration can result in, for example, enhanced therapeutic properties. These enhanced therapeutic properties, as used herein, refer to an enhanced therapeutic property of a cell when compared to a typical immune cell of the same normal cell type. For example, a T cell having "enhanced therapeutic properties" has an enhanced, improved, and/or increased treatment outcome when compared to a typical, unmodified and/or naturally occurring T cell. The therapeutic properties of immune cells can include, but are not limited to, cell transplantation, transport, homing, viability, self-renewal, persistence, immune response control and regulation, survival, and cytotoxicity. The therapeutic properties of immune cells are also manifested by: antigen-targeted receptor expression; HLA presentation or lack thereof; tolerance to the intratumoral microenvironment; induction of bystander immune cells and immune regulation; improved target specificity with reduction; resistance to treatments such as chemotherapy.

As used herein, the term "insert size" refers to the length of the nucleotide sequence being integrated (inserted) at the target locus or safe harbor site. In some embodiments, the insert size comprises at least about 4.5 kilobasepairs (kb) to about 10 kilobasepairs (kb). In some embodiments, the insert size comprises about 5000 nucleotides or more basepairs. In some embodiments, the insert size comprises up to 4.5, 4.8, 5, 6, 7, 8, 9, 10, 11, 12, 13, 14, 15, 16, 17, 18, 19, 20 kbp (kilo basepairs) or the sizes in between. In some embodiments, the insert size is greater than 4.5, 4.8, 5, 6, 7, 8, 9, 10, 11, 12, 13, 14, 15, 16, 17, 18, 19, 20 kbp or the sizes in between. In some embodiments, the insert size is within the range of 4.5-15 kbp or is any number in that range. In some embodiments, the insert size is within the range of 4.8-8.3 kbp or is any number in that range. In some embodiments, the insert size is within the range of 5-8.3 kbp or is any number in that range. In some embodiments, the insert size is within the range of 5-15 kbp or is any number in that range. In some embodiments, the insert size is within the range of 4.5-20 kbp or is any number in that range. In some embodiments, the insert size is 5-10 kbp. In some embodiments, the insert size is 4.5-10, 5-10, 6-10, 7-10, 8-10, 9-10 kbp. In some embodiments, the insert size is 4.5-11, 6-11, 7-11, 8-11, 9-11, or 10-11 kbp. In some embodiments, the insert size is 4.5-12, 6-12, 7-12, 8-12, 9-12, 10-12, or 11-12 kbp. In some embodiments, the insert size is 4.5-13, 6-13, 7-13, 8-13, 9-13, 10-13, 11-13, or 12-13 kbp. In some embodiments, the insert size is 4.5-14, 6-14, 7-14, 8-14, 9-14, 10-14, 11-14, 12-14 or 13-14 kbp. In some embodiments, the insert size is 4.5-15, 6-15, 7-15, 8-15, 9-15, 10-15, 11-15, 12-15, 13-15, or 14-15 kbp. In some embodiments, the insert size is 4.5-16, 6-16, 7-16, 8-16, 9-16, 10-16, 11-16, 12-16, 13-16, 14-16 or 15-16 kbp. In some embodiments, the insert size is 4.5-17, 6-17, 7-17, 8-17, 9-17, 10-17, 11-17, 12-17, 13-17, or 14-17, 15-17 or 16-17 kbp. In some embodiments, the insert size is 4.5-18, 6-18, 7-18, 8-18, 9-18, 10-18, 11-18, 12-18, 13-18, 14-18, 15-18, 16-18 or 17-18 kbp. In some embodiments, the insert size is 4.5-19, 6-19, 7-19, 8-19, 9-19, 10-19, 11-19, 12-19, 13-19, 14-19, 15-19, 16-19, 17-19, or 18-19 kbp. In some embodiments, the insert size is 4.5-20, 6-20, 7-20, 8-20, 9-20, 10-20, 11-20, 12-20, 13-20, 14-20, 15-20, 16-20, 17-20, 18-20, or 19-20 kbp.

The inserts of the present disclosure refer to nucleic acid molecules or polynucleotide inserted at a target locus or safe harbor site. In some embodiments, the nucleotide sequence is a DNA molecule, e.g., genomic DNA, or comprises deoxy-ribonucleotides. In some embodiments, the insert comprises a smaller fragment of DNA, such as a plastid DNA, mitochondrial DNA, or DNA isolated in the form of a plasmid, a fosmid, a cosmid, a bacterial artificial chromosome (BAC), a yeast artificial chromosome (YAC), and/or any other sub-genome segment of DNA. In some embodiments, the insert is an RNA molecule or comprises ribonucleotides. The nucleotides in the insert are contemplated as naturally occurring nucleotides, non-naturally occurring, and modified nucleotides. Nucleotides may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications. The polynucleotides can be in any topological conformation, including single-stranded, double-stranded, partially duplexed, triplexed, hairpinned, circular conformations, and other three-dimension conformations contemplated in the art.

The inserts can have coding and/or non-coding regions. The insert can comprises a non-coding sequence (e.g., control elements, e.g., a promoter sequence). In some embodiments, the insert encodes transcription factors. In some embodiments, the insert encodes an antigen binding receptors such as single receptors, T-cell receptors (TCRs), priming receptors, CARs, mAbs, etc. In some embodiments, the the insert is a human sequence. In some embodiments, the insert is chimeric. In some embodiments, the insert is a multi-gene/multi-module therapeutic cassette. A multi-gene/multi-module therapeutic cassette refers to an insert or cassette having one or more than one receptor (e.g., synthetic receptors such as a CAR or a priming receptor), other exogenous protein coding sequences, non-coding RNAs, transcriptional regulatory elements, and/or insulator sequences, etc.

In some embodiments, the nucleic acid sequence is inserted into the genome of the cell such as an immune cell or T cell via non-viral delivery. In non-viral delivery methods, the nucleic acid can be naked DNA, or in a non-viral plasmid or vector. Non-viral delivery techniques can be site-specific integration techniques, as described herein or known to those of ordinary skill in the art. Examples of site-specific techniques for integration into the safe harbor loci include, without limitation, homology-dependent engineering using nucleases and homology independent targeted insertion using Cas9 or other CRISPR endonucleases.

In some embodiments, the insert is integrated at a safe harbor site by introducing into the engineered cell, (a) a targeted nuclease that cleaves a target region in the safe harbor site to create the insertion site; and (b) the nucleic acid sequence (insert), wherein the insert is incorporated at the insertion site by, e.g., HDR. Examples of non-viral delivery techniques that can be used in the methods of the present disclosure are provided in U.S. Pat. No. 11,033,584B2 and 11,814,624B2, the relevant disclosures of which are herein incorporated by reference in their entirety.

Examples of integration sites contemplated are provided in Table D.

TABLE D

| sgRNA sequences | | | | | |
|---|---|---|---|---|---|
| sgRNAID | SEQ ID NO: | sgRNA Sequence | sgRNA start coor GRCH38 | sgRNA Target Loci | Integration Site | Median (% Modified), summarized from 2 donors, 2 primersets |
| sgRNA270_1 | 1 | GCACCTGAATACCACGCCTG | chr16:88811818 | APRT | APRT | 79.28 |
| sgRNA271_2 | 2 | CGCCTGCGATGTAGTCGATG | chr16:88811551 | APRT | APRT | 78.60 |
| sgRNA272_3 | 3 | CAGGACGGGCGAGATGTCCC | chr16:88811640 | APRT | APRT | 85.25 |
| sgRNA273_4 | 4 | CTGAATCTTTGGAGTACCTG | chr15:44715425 | B2M | B2M | 78.51 |
| sgRNA274_5 | 5 | GGCCACGGAGCGAGACATCT | chr15:44711550 | B2M | B2M | 94.75 |
| sgRNA275_6 | 6 | AAGTCAACTTCAATGTCGGA | chr15:44715515 | B2M | B2M | 70.97 |
| sgRNA276_7 | 7 | GCTTGGAGGCCTGATCAGCG | chr19:36141111 | CAPNS1 | CAPNS1 | 89.34 |
| sgRNA277_8 | 8 | CTTATCTCTTCGCAGCGAGG | chr19:36142301 | CAPNS1 | CAPNS1 | 91.09 |
| sgRNA278_9 | 9 | CACACATTACTCCAACATTG | chr19:36142676 | CAPNS1 | CAPNS1 | 71.98 |
| sgRNA279_10 | 10 | TTCCGCAAAATAGAGCCCCA | chr3:105746019 | CBLB | CBLB | 91.55 |
| sgRNA280_11 | 11 | TGCACAGAACTATCGTACCA | chr3:105751622 | CBLB | CBLB | 91.43 |
| sgRNA281_12 | 12 | GCAATAAGACTCTTTAAAGA | chr3:105853470 | CBLB | CBLB | 76.18 |
| sgRNA282_13 | 13 | CAAAGAGATTACGAATGCCT | chr1:116754658 | CD2 | CD2 | 89.80 |
| sgRNA283_14 | 14 | CAAGGCACCCCAGGTTTCCA | chr1:116754663 | CD2 | CD2 | 92.70 |
| sgRNA284_15 | 15 | TTACGAATGCCTTGGAAACC | chr1:116754666 | CD2 | CD2 | 92.82 |
| sgRNA285_16 | 16 | CAGAGACGCATCTGACCCTC | chr11:118315540 | CD3E | CD3E | 90.96 |
| sgRNA286_17 | 17 | CATGCAGTTCTCACACACTG | chr11:118313715 | CD3E | CD3E | 87.47 |
| sgRNA287_18 | 18 | GTGTGAGAACTGCATGGAGA | chr11:118313715 | CD3E | CD3E | 86.65 |
| sgRNA288_19 | 19 | TCTCATTTCAGGAAACCACT | chr11:118349748 | CD3G | CD3G | 87.24 |
| sgRNA289_20 | 20 | AGTCATACACCTTAACCAAG | chr11:118349754 | CD3G | CD3G | 87.99 |
| sgRNA290_21 | 21 | TTCAAGGAAACCAGTTGAGG | chr11:118352458 | CD3G | CD3G | 86.55 |

TABLE D-continued sgRNA sequences

| sgRNA ID | SEQ ID NO: | sgRNA Sequence | sgRNA start coor GRCH38 | sgRNA Target Loci | Integration Site | Median (% Modified), summarized from 2 donors, 2 primersets |
|---|---|---|---|---|---|---|
| sgRNA291 | 22 | GAGCCTTGCCTGGAAATCTG | chr11:61118177 | CD5 | CD5 | 84.03 |
| sgRNA292 | 23 | AAGCGTCAAAAGTCTGCCAG | chr11:61118324 | CD5 | CD5 | 89.19 |
| sgRNA293 | 24 | CGTTCCAACTCGAAGTGCCA | chr11:61118121 | CD5 | CD5 | 83.11 |
| sgRNA294 | 25 | GAGCGACTGGGACACGGTGA | chr9:136866246 | EDF1 | EDF1 | 88.84 |
| sgRNA295 | 26 | GCTGCGCAAGAAGGGCCCTA | chr9:136866211 | EDF1 | EDF1 | 91.04 |
| sgRNA296 | 27 | TTGTTCTGGCCAGCAGCCCC | chr9:136863433 | EDF1 | EDF1 | 85.98 |
| sgRNA297 | 28 | CTTCCAGAGCCACATCATCG | chr19:48965791 | FTL | FTL | 93.10 |
| sgRNA298 | 29 | GGGACTCACCAGAGAGAGGT | chr19:48965601 | FTL | FTL | 88.86 |
| sgRNA299 | 30 | CGGTCGAAATAGAAGCCCTA | chr19:48965770 | FTL | FTL | 93.14 |
| sgRNA300 | 31 | AAAAGGATATTGTGCAACTG | chr10:87933015 | PTEN | PTEN | 92.37 |
| sgRNA301 | 32 | TGTGCATATTTATTACATCG | chr10:87933183 | PTEN | PTEN | 90.64 |
| sgRNA302 | 33 | TTTGTGAAGATCTTGACCAA | chr10:87933087 | PTEN | PTEN | 85.36 |
| sgRNA303 | 34 | TGTCATGCTGAACCGCATTG | chr18:12830972 | PTPN2 | PTPN2 | 87.94 |
| sgRNA304 | 35 | CCACTCTATGAGGATAGTCA | chr18:12859219 | PTPN2 | PTPN2 | 92.45 |
| sgRNA305 | 36 | TTGACATAGAAGAGGCACAA | chr18:12836828 | PTPN2 | PTPN2 | 93.96 |
| sgRNA306 | 37 | GAGTACTACACTCAGCAGCA | chr12:6952098 | PTPN6 | PTPN6 | 89.61 |
| sgRNA307 | 38 | TCACGCACAAGAAACGTCCA | chr12:6954872 | PTPN6 | PTPN6 | 82.74 |
| sgRNA308 | 39 | AGGTCTCGGTGAAACCACCT | chr12:6951610 | PTPN6 | PTPN6 | 91.27 |
| sgRNA309 | 40 | AGCATTATCCAAAGAGTCCG | chr1:198696873 | PTPRC | PTPRC | 88.88 |
| sgRNA310 | 41 | ATATTAATTCTTACCAGTGG | chr1:198692370 | PTPRC | PTPRC | 88.95 |
| sgRNA311 | 42 | AGCTTTAAATCAAGGTTCAT | chr1:198756176 | PTPRC | PTPRC | 96.89 |
| sgRNA312 | 43 | ATCCCGAGCCCTAAGGTGCA | chr11:67436325 | PTPRCAP | PTPRCAP | 84.08 |
| sgRNA313 | 44 | GGCAGCGCGGAGGACAGCGT | chr11:67436285 | PTPRCAP | PTPRCAP | 97.74 |
| sgRNA314 | 45 | CTCAGGGGCTACTACCACC | chr11:67436170 | PTPRCAP | PTPRCAP | 91.50 |

TABLE D-continued sgRNA sequences

| sgRNA ID | SEQ ID NO: | sgRNA Sequence | sgRNA start coor GRCH38 | sgRNA Target Loci | Integration Site | Median (% Modified), summarized from 2 donors, 2 primersets |
|---|---|---|---|---|---|---|
| sgRNA315_46 | 315 | GTCACCGACGAGACCAGAAG | chr5:82277810 | RPS23 | RPS23 | 79.40 |
| sgRNA316_47 | 316 | GTCGTGGACTTCGTACTGCT | chr5:82277843 | RPS23 | RPS23 | 83.07 |
| sgRNA317_48 | 317 | TAATTTTTAGGCAAGTGTCG | chr5:82277860 | RPS23 | RPS23 | 61.94 |
| sgRNA318_49 | 318 | TTAGCTGTTAGACTTGAATA | chr14:51993810 | RTRAF | RTRAF | 85.50 |
| sgRNA319_50 | 319 | CGAGAGCCGTCAACTTGCGT | chr14:51989652 | RTRAF | RTRAF | 85.64 |
| sgRNA320_51 | 320 | CGGCTTCAACTGCAAAGGTG | chr14:51989700 | RTRAF | RTRAF | 88.77 |
| sgRNA321_52 | 321 | TATGAAAAGCAGAGCGACT | chr15:43793025 | SERF2 | SERF2 | 89.61 |
| sgRNA322_53 | 322 | TCTGGCGGGCGAGCTCACGC | chr15:43792989 | SERF2 | SERF2 | 86.73 |
| sgRNA323_54 | 323 | CTCACGCTGGTTACCGCCTA | chr15:43792977 | SERF2 | SERF2 | 80.57 |
| sgRNA324_55 | 324 | AAAGATTACGAACTTCCCTG | chr12:46207559 | SLC38A1 | SLC38A1 | 92.24 |
| sgRNA325_56 | 325 | GTTAAAAACAGACATGCCTA | chr12:46229232 | SLC38A1 | SLC38A1 | 91.51 |
| sgRNA326_57 | 326 | ATGCCTAAGGAGGTTGTACC | chr12:46229246 | SLC38A1 | SLC38A1 | 79.48 |
| sgRNA327_58 | 327 | CTCCAGGTATCCCATCGAAA | chr18:47869418 | SMAD2 | SMAD2 | 79.53 |
| sgRNA328_59 | 328 | CACCAAATACGATAGATCAG | chr18:47870532 | SMAD2 | SMAD2 | 86.61 |
| sgRNA329_60 | 329 | TGGCGGCGTGAATGGCAAGA | chr18:47896729 | SMAD2 | SMAD2 | 82.91 |
| sgRNA330_61 | 330 | TAGGATGGTAGCACACAACC | chr16:11255478 | SOCS1 | SOCS1 | 92.25 |
| sgRNA331_62 | 331 | CAGCAGCAGAGCCCCGACGG | chr16:11255432 | SOCS1 | SOCS1 | 83.79 |
| sgRNA332_63 | 332 | CGGCGTGCGAACGGAATGTG | chr16:11255296 | SOCS1 | SOCS1 | 84.24 |
| sgRNA333_64 | 333 | TATAGACGCTGCCCGACGTC | chr15:40038895 | SRP14 | SRP14 | 95.12 |
| sgRNA334_65 | 334 | TCCAAAGAAGGGTACTGTGG | chr15:40038368 | SRP14 | SRP14 | 92.14 |
| sgRNA335_66 | 335 | ACAGTACCCTTCTTTGGAAT | chr15:40038358 | SRP14 | SRP14 | 65.82 |
| sgRNA336_67 | 336 | GCGACGGGCGCATCTACGTG | chr12:120469572 | SRSF9 | SRSF9 | 83.68 |
| sgRNA337_68 | 337 | CCCGACCTCCATAAGTCCTG | chr12:120465700 | SRSF9 | SRSF9 | 92.56 |

TABLE D-continued sgRNA sequences

| sgRNAID | SEQ ID NO: | sgRNA Sequence | sgRNA start coor GRCH38 | sgRNA Target Loci | Integration Site | Median (% Modified), summarized from 2 donors, 2 primersets |
|---|---|---|---|---|---|---|
| sgRNA338 | _69 | GGGGTCCTCGAAGCGCACGA | chr12:12046926 | SRSF9 | SRSF9 | 89.94 |
| sgRNA339 | _70 | TGCTCTGTTTAGAAGATGAC | chr5:32591641 | SUB1 | SUB1 | 79.36 |
| sgRNA340 | _71 | ATATTCTTTTCTAGTTAAAG | chr5:32591566 | SUB1 | SUB1 | 70.93 |
| sgRNA341 | _72 | CCTGTAAAGAAACAAAAGAC | chr5:32591614 | SUB1 | SUB1 | 93.66 |
| sgRNA342 | _73 | TGGAGAAAGACGTAACTTCG | chr4:105234315 | TET2 | TET2 | 83.53 |
| sgRNA343 | _74 | TCTGCCCTGAGGTATGCGAT | chr4:105234747 | TET2 | TET2 | 90.97 |
| sgRNA344 | _75 | ATTCCGCTTGGTGAAAACGA | chr4:105235656 | TET2 | TET2 | 89.62 |
| sgRNA345 | _76 | CAGGCACAATAGAAACAACG | chr3:114295571 | TIGIT | TIGIT | 92.65 |
| sgRNA346 | _77 | CCATTTGTAATGCTGACTTG | chr3:114295700 | TIGIT | TIGIT | 60.75 |
| sgRNA347 | _78 | CTGGGTCACTTGTGCCGTGG | chr3:114295634 | TIGIT | TIGIT | 87.99 |
| sgRNA348 | _79 | GTCAGGGTTCTGGATATCTG | chr14:22547508 | TRAC | TRAC | 98.20 |
| sgRNA349 | _80 | TGGATTTAGAGTCTCTCAGC | chr14:22547541 | TRAC | TRAC | 88.15 |
| sgRNA350 | _81 | CTGCGGCTGTGGTCCAGCTG | chr14:22550661 | TRAC | TRAC | 94.77 |
| sgRNA351 | _82 | ACAAAACTGTGCTAGACATG | chr14:22547658 | TRAC | TRAC | 87.86 |
| sgRNA352 | _83 | TTCTTCCCCAGCCCAGGTAA | chr14:22547778 | TRAC | TRAC | 89.85 |
| sgRNA353 | _84 | CGTCATGAGCAGATTAAACC | chr14:22550625 | TRAC | TRAC | 95.81 |
| sgRNA354 | _85 | GAGAGCGCCTGCGACCCGAG | chr19:58544980 | TRIM28 | TRIM28 | 89.44 |
| sgRNA355 | _86 | CCAGCGGGTGAAGTACACCA | chr19:58544869 | TRIM28 | TRIM28 | 94.79 |
| sgRNA356 | _87 | GGAGCGCTTTTCGCCGCCAG | chr19:58544839 | TRIM28 | TRIM28 | 91.81 |
| sgRNA357 | _88 | TGAGGCCTGGACCTTATGCA | chr10:33134193 | chr10:33130000-33140000 | desert_1 (GS88) | 69.44 |
| sgRNA358 | _89 | CCTGGTGGAGTGAACCATGA | chr10:33132917 | chr10:33130000-33140000 | desert_1 (GS89) | 95.25 |
| sgRNA359 | _90 | CAAGCACTTAGGTTCCCCTG | chr10:33134633 | chr10:33130000-33140000 | desert_1 (GS90) | 91.13 |
| sgRNA360 | _91 | GGTCTCCCTACAATTCAGCG | chr10:72294568 | chr10:72290000-72300000 | desert_2 (GS91) | 92.02 |

TABLE D-continued sgRNA sequences

| sgRNAID | SEQ ID NO: | sgRNA Sequence | sgRNA start coor GRCH38 | sgRNA Target Loci | Integration Site | Median (% Modified), summarized from 2 donors, 2 primersets |
|---|---|---|---|---|---|---|
| sgRNA361_92 | 92 | CACAGCGCGTGACTGCAATG | chr10:72298268 | chr10:72290000-72300000 | desert_2 (GS92) | 90.22 |
| sgRNA362_93 | 93 | TCTGGGGCACCAATTCTAGG | chr10:72292786 | chr10:72290000-72300000 | desert_2 (GS93) | 86.35 |
| sgRNA363_94 | 94 | GAGCCATGCTTGGCTTACGA | chr11:128342576 | chr11:128340000-128350000 | desert_3 (GS94) | 91.24 |
| sgRNA364_95 | 95 | GTACAAGTACTTATCTCATG | chr11:128343592 | chr11:128340000-128350000 | desert_3 (GS95) | 89.02 |
| sgRNA365_96 | 96 | GAGATAACAACATAACAACA | chr11:128347170 | chr11:128340000-128350000 | desert_3 (GS96) | 96.47 |
| sgRNA366_97 | 97 | CATATTCCATAGTCTTTGGG | chr11:65425000 | chr11:65425000-65427000 | desert_4 (GS97) (NEAT1) | 88.54 |
| sgRNA367_98 | 98 | CTGCCCCTTAGCAACTTAGG | chr11:65425507 | chr11:65425000-65427000 | desert_4 (GS98) (NEAT1) | 92.76 |
| sgRNA368_99 | 99 | TGTTTAAAAATATGTTGACA | chr11:65426264 | chr11:65425000-65427000 | desert_4 (GS99) (NEAT1) | 90.76 |
| sgRNA369_100 | 100 | CCAGGAATGGAAACTCACGC | chr15:92830315 | chr15:92830000-92840000 | desert_5 (GS100) | 87.84 |
| sgRNA370_101 | 101 | GAGGCCGCTGAATTAACCCG | chr15:92831850 | chr15:92830000-92840000 | desert_5 (GS101) | 85.32 |
| sgRNA371_102 | 102 | ATACACGCACACTTGCAGAA | chr15:92831131 | chr15:92830000-92840000 | desert_5 (GS102) | 99.92 |
| sgRNA372_103 | 103 | GAGCAGACAGAAACCCAGGG | chr16:11225670 | chr16:11220000-11230000 | desert_6 (GS103) | 87.92 |
| sgRNA373_104 | 104 | TGAGTCTCCAAACAGAACAG | chr16:11226284 | chr16:11220000-11230000 | desert_6 (GS104) | 88.53 |
| sgRNA374_105 | 105 | TAATATCACTGACTTCACGG | chr16:11225029 | chr16:11220000-11230000 | desert_6 (GS105) | 87.65 |
| sgRNA375_106 | 106 | TACACACAATGTAAGCAGCA | chr2:87467461 | chr2:87460000-87470000 | desert_7 (GS106) | 71.79 |
| sgRNA376_107 | 107 | GGGAGCTCAATTCGAAACCA | chr2:87468809 | chr2:87460000-87470000 | desert_7 (GS107) | 65.89 |
| sgRNA377_108 | 108 | TTGGACAGGTGAGACAGTCG | chr2:87467001 | chr2:87460000-87470000 | desert_7 (GS108) | 72.64 |
| sgRNA378_109 | 109 | AAGCTCACTCAGATAGTGTG | chr3:186511316 | chr3:186510000-186520000 | desert_8 (GS109) | 76.89 |
| sgRNA379_110 | 110 | CAGGAGAACCACCTTACACG | chr3:186515260 | chr3:186510000-186520000 | desert_8 (GS110) | 86.31 |
| sgRNA380_111 | 111 | GGACAGACCCTGATTCACAA | chr3:186519655 | chr3:186510000-186520000 | desert_8 (GS111) | 85.47 |
| sgRNA381_112 | 112 | ACATGGCAGTCTATGAACAG | chr3:59451154 | chr3:59450000-59460000 | desert_9 (GS112) | 87.77 |
| sgRNA382_113 | 113 | CCTATAGAGAGTACTACTTG | chr3:59456416 | chr3:59450000-59460000 | desert_9 (GS113) | 79.33 |

TABLE D-continued sgRNA sequences

| sgRNAID | SEQ ID NO: | sgRNA Sequence | sgRNA start coor GRCH38 | sgRNA Target Loci | Integration Site | Median (% Modified), summarized from 2 donors, 2 primersets |
|---|---|---|---|---|---|---|
| sgRNA383_114 | 114 | CCAACCGGGTCTTCATTACG | chr3:59457029 | chr3:59450000-59460000 | desert_9 (GS114) | 92.21 |
| sgRNA384_115 | 115 | TCAAGCGTAGAGTTCCGAGT | chr8:127993006 | chr8:127980000-128000000 | desert_10 (GS115) | 93.07 |
| sgRNA385_116 | 116 | TCATGCAATTATGGACCCAG | chr8:127994663 | chr8:127980000-128000000 | desert_10 (GS116) | 89.40 |
| sgRNA386_117 | 117 | CGGGAAAGTGACTGGCCATG | chr8:127996766 | chr8:127980000-128000000 | desert_10 (GS117) | 87.45 |
| sgRNA387_118 | 118 | TGAGATTGAAATCAAATCGG | chr9:7974159 | chr9:7970000-7980000 | desert_11 (GS118) | 84.84 |
| sgRNA388_119 | 119 | TATGCAATATTCATCACGCG | chr9:7977914 | chr9:7970000-7980000 | desert_11 (GS119) | 85.44 |
| sgRNA389_120 | 120 | AATGTGTTAAATCAAATGCA | chr9:7976895 | chr9:7970000-7980000 | desert_11 (GS120) | 83.48 |

CRISPR-Cas Editing

One effective example of gene editing is the CRISPR-Cas approach (e.g. CRISPR-Cas9). This approach incorporates the use of a guide polynucleotide (e.g. guide ribonucleic acid or gRNA) and a cas endonuclease (e.g. Cas9 endonuclease).

As used herein, a polypeptide referred to as a "Cas endonuclease" or having "Cas endonuclease activity" refers to a CRISPR-related (Cas) polypeptide encoded by a Cas gene, wherein a Cas polypeptide is a target DNA sequence that can be cleaved when operably linked to one or more guide polynucleotides (see, e.g., U.S. Pat. No. 8,697,359). Also included in this definition are variants of Cas endonuclease that retain guide polynucleotide-dependent endonuclease activity. The Cas endonuclease used in the donor DNA insertion method detailed herein is an endonuclease that introduces double-strand breaks into DNA at the target site (e.g., within the target locus or at the safe harbor site).

As used herein, the term "guide polynucleotide" relates to a polynucleotide sequence capable of complexing with a Cas endonuclease and allowing the Cas endonuclease to recognize and cleave a DNA target site. The guide polynucleotide can be a single molecule or a double molecule. The guide polynucleotide sequence can be an RNA sequence, a DNA sequence, or a combination thereof (RNA-DNA combination sequence). A guide polynucleotide comprising only ribonucleic acid is also referred to as "guide RNA". In some embodiments, a polynucleotide donor construct is inserted at a safe harbor locus using a guide RNA (gRNA) in combination with a nuclease such as a cas endonuclease (e.g. Cas9 endonuclease).

The guide polynucleotide includes a first nucleotide sequence domain (also referred to as a variable targeting domain or VT domain) that is complementary to a nucleotide sequence in the target DNA, and a second nucleotide sequence that interacts with a Cas endonuclease polypeptide. It can be a double molecule (also referred to as a double-stranded guide polynucleotide) comprising a sequence domain (referred to as a Cas endonuclease recognition domain or CER domain). The CER domain of this double molecule guide polynucleotide comprises two separate molecules that hybridize along the complementary region. The two separate molecules can be RNA sequences, DNA sequences and/or RNA-DNA combination sequences.

Genome editing using CRISPR-Cas approaches relies on the repair of site-specific DNA double-strand breaks (DSBs) induced by the RNA-guided Cas endonuclease (e.g. Cas 9 endonuclease). Homology-directed repair (HDR) of these DSBs enables precise editing of the genome by introducing defined genomic changes, including base substitutions, sequence insertions, and deletions. Conventional HDR-based CRISPR/Cas9 genome-editing involves transfecting cells with Cas9, gRNA and donor DNA containing homologous arms matching the genomic locus of interest.

HITI (homology independent targeted insertion) uses a non-homologous end joining (NHEJ)-based homology-independent strategy and the method can be more efficient than HDR. Guide RNAs (gRNAs) target the insertion site. For HITI, donor plasmids lack homology arms and DSB repair does not occur through the HDR pathway. The donor polynucleotide construct can be engineered to include Cas9 cleavage site(s) flanking the gene or sequence to be inserted. This results in Cas9 cleavage at both the donor plasmid and the genomic target sequence. Both target and donor have blunt ends and the linearized donor DNA plasmid is used by the NHEJ pathway resulting integration into the genomic DSB site. (See, for example, Suzuki, K., et al. (2016). In vivo genome editing via CRISPR/Cas9 mediated homology-independent targeted integration. Nature, 540(7631), 144-149, the relevant disclosures of which are herein incorporated in their entirety).

Methods for conducting gene editing using CRISPR-Cas approaches are known to those of ordinary skill in the art. (See, for example, US application Nos. U.S. Ser. No. 16/312,676, U.S. Ser. No. 15/303,722, and U.S. Ser. No. 15/628,533, the disclosures of which are herein incorporated by reference in their entirety). Additionally, uses of endonucleases for inserting transgenes into safe harbor loci are described, for example, in U.S. application Ser. No. 13/036,343, the disclosures of which are herein incorporated by reference in their entirety.

The guide RNAs and/or mRNA (or DNA) encoding an endonuclease can be chemically linked to one or more moieties or conjugates that enhance the activity, cellular distribution, or cellular uptake of the oligonucleotide. Non-limiting examples of such moieties include lipid moieties such as a cholesterol moiety, cholic acid, a thioether, a thiocholesterol, an aliphatic chain (e.g., dodecandiol or undecyl residues), a phospholipid, e.g., di-hexadecyl-rac-glycerol or triethylammonium 1,2-di-O-hexadecyl-rac-glycero-3-H-phosphonate, a polyamine or a polyethylene glycol chain, adamantane acetic acid, a palmityl moiety and an octadecylamine or hexylamino-carbonyl-t oxycholesterol moiety. See for example US Patent Publication No. 20180127786, the disclosure of which is herein incorporated by reference in its entirety.

Therapeutic Applications

For therapeutic applications, the engineered cells, populations thereof, or compositions thereof are administered to a subject, generally a mammal, generally a human, in an effective amount. The engineered cells may be administered to a subject by infusion (e.g., continuous infusion over a period of time) or other modes of administration known to those of ordinary skill in the art.

The engineered cells provided herein not only find use in gene therapy but also in non-pharmaceutical uses such as, e.g., production of animal models and production of recombinant cell lines expressing a protein of interest.

The engineered cells of the present disclosure can be any cell, generally a mammalian cell, generally a human cell that has been modified by integrating a transgene at a safe harbor locus described herein. Exemplary cells are provided in the Recombinant Cells section.

The engineered cells, compositions and methods of the present disclosure are useful for therapeutic applications such as CAR T cell therapy and TCR T cell therapy. In some embodiments, the insertion of a sequence encoding a transgene within a safe harbor locus maintains the TCR expression relative to instances when there is no insertion and enables transgene expression while maintaining TCR function.

In some embodiments, the present disclosure provides methods of treating a subject in need of treatment by administering to the subject a composition comprising any of the engineered cells described herein. In some embodiments, administration of the engineered cell composition results in a desired pharmacological and/or physiological effect. That effect can be partial or complete cure of the disease and/or adverse effects resulting from the disease. In some embodiments, treatment encompasses any treatment of a disease in a subject (e.g., mammal, e.g., human). Further, treatment may stabilize or reduce undesirable clinical symptoms in subjects (e.g., patients). The cells provided herein populations thereof, or compositions thereof may be administered during or after the occurrence of the disease.

In certain embodiments, the subject has a disease, condition, and/or injury that can be treated and/or ameliorated by cell therapy. In some embodiments, the subject in need of cell therapy is a subject having an injury, disease, or condition, thereby causing cell therapy (e.g., therapy in which cellular material is administered to the subject). However, it is contemplated that it is possible to treat, ameliorate and/or reduce the severity of at least one symptom associated with the injury, disease or condition.

Method of Administration

An effective amount of the immune cell comprising the system may be administered for the treatment of cancer. The appropriate dosage of the immune cell comprising the system may be determined based on the type of cancer to be treated, the type of the immune cell comprising the system, the severity and course of the cancer, the clinical condition of the individual, the individual's clinical history and response to the treatment, and the discretion of the attending physician.

Determining Expression of PSMA and/or CA9

Also provided herein are methods of treating a cancer in a subject in need thereof comprising: determining or having determined the expression of PSMA in the subject; determining or having determined the expression of CA9 in the subject; and administering or having administered to the subject a system comprising a priming receptor comprising a first extracellular antigen-binding domain that specifically binds to PSMA, a chimeric antigen receptor comprising a second extracellular antigen-binding domain that specifically binds to CA9.

Also provided herein are methods of treating a cancer in a subject in need thereof comprising: determining or having determined the expression of PSMA in the subject; determining or having determined the expression of CA9 in the subject; and administering or having administered to the subject a cell comprising a priming receptor comprising a first extracellular antigen-binding domain that specifically binds to PSMA, a chimeric antigen receptor comprising a second extracellular antigen-binding domain that specifically binds to CA9, and optionally a synthetic pathway activator inserted into a target region of the genome of the cell. In some embodiments, the cell is an immune cell. In some embodiments, the immune cell is a primary immune cell.

In some embodiments, the method further comprises determining or having determined the expression level of PSMA and/or CA9 in a biological sample from the individual. In some embodiments the biological sample includes, but is not limited to a body fluid, a tissue sample, an organ sample, urine, feces, blood, saliva, CSF and any combination thereof. In some embodiments the biological sample is derived from a tumor tissue. In some embodiments, the expression level of PSMA and/or CA9 comprises the mRNA expression level of PSMA and/or CA9. In some embodiments, the expression level of PSMA and/or CA9 comprises the protein expression level of PSMA and/or CA9. In some embodiments the expression level of PSMA and/or CA9 is detected in the sample using a method selected from the group consisting of FACS, Western blot, ELISA, immunoprecipitation, immunohistochemistry, monoplex immunohistochemistry, multiplex immunohistochemistry, immunofluorescence, radioimmunoassay, dot blotting, immunodetection methods, HPLC, surface plasmon resonance, optical spectroscopy, mass spectrometry, qPCR, RT-qPCR, multiplex qPCR or RT-qPCR, RNA-seq, microarray analysis, SAGE, MassARRAY technique, Luminex, MSD, and FISH, and combinations thereof.

In some aspects, provided herein are methods of determining an expression level of PSMA and/or CA9 protein in a sample from a subject comprising contacting the sample with an anti-PSMA and/or CA9 antibody and performing an immunohistochemistry assay. In some embodiments, the anti-PSMA antibody comprises the PSMA 1 antibody as set forth in SEQ ID NOs: 117-125. In some embodiments, the anti-PSMA antibody comprises the PSMA 2 antibody as set forth in SEQ ID NOs: 129-137. In some embodiments, the anti-PSMA antibody comprises the Clone 3E6 antibody. In some embodiments, the anti-CA9 antibody comprises the CA9 1 antibody as set forth in SEQ ID NOs: 99-106. In some embodiments, the anti-CA9 antibody comprises the CA9 2 antibody as set forth in SEQ ID NOs: 110-113. In some embodiments, the anti-CA9 antibody comprises the Clone M75 antibody.

In another aspect, the present invention provides methods for identifying an individual who may respond to immunotherapy (e.g. with the PSMA and/or CA9 protein system or a cell comprising a PSMA and/or CA9 protein system described herein) for the treatment of an immune-related condition (e.g. cancer) comprising: detecting the expression level of PSMA in a biological sample from the individual; detecting the expression level of CA9 in a biological sample from the individual; and determining based on the expression level of PSMA and/or CA9, whether the individual may respond immunotherapy, wherein co-expression of PSMA and CA9 in a tumor sample from the individual indicates that the individual may respond to immunotherapy. In some embodiments, the PSMA and/or CA9 expression in the individual has already been determined. In some embodiments, the expression level of PSMA and/or CA9 comprises the mRNA expression level of PSMA and/or CA9. In other embodiments, the expression level of PSMA and/or CA9 comprises the protein expression level of PSMA and/or CA9.

In some embodiments the expression level of PSMA and/or CA9 is detected in the sample using a nucleic acid or protein assay. Exemplary a nucleic acid or protein assays include, but are not limited to, FACS, Western blot, ELISA, immunoprecipitation, immunohistochemistry, monoplex immunohistochemistry, multiplex immunohistochemistry, immunofluorescence, radioimmunoassay, dot blotting, immunodetection methods, HPLC, surface plasmon resonance, optical spectroscopy, mass spectrometry, qPCR, RT-qPCR, multiplex qPCR or RT-qPCR, RNA-seq, microarray analysis, SAGE, MassARRAY technique, Luminex, MSD, and FISH, and combinations thereof. In these embodiments, the anti-PSMA and/or CA9 antibody binds to the PSMA and/or CA9 protein, but does not necessarily have to effect a biological response, such as ADCC. In some embodiments the biological sample is derived from a tumor tissue. In some embodiments the biological sample includes, but is not limited to a body fluid, a tissue sample, an organ sample, urine, feces, blood, saliva, CSF and any combination thereof.

In some embodiments, the assay is an immunohistochemistry assay and the anti-PSMA antibody comprises the PSMA 1 antibody as set forth in SEQ ID NOs: 117-125; the anti-PSMA antibody comprises the PSMA 2 antibody as set forth in SEQ ID NOs: 129-137; or anti-PSMA antibody comprises the Clone 3E6 antibody. In some embodiments, the assay is an immunohistochemistry assay and the anti-CA9 antibody comprises the CA9 1 antibody as set forth in SEQ ID NOs: 99-106; the CA9 2 antibody as set forth in SEQ ID NOs: 110-113; or the anti-CA9 antibody comprises the Clone M75 antibody.

Pharmaceutical Compositions

The engineered recombinant cells provided herein can be administered as part of a pharmaceutical compositions. These compositions can comprise, in addition to one or more of the recombinant cells, a pharmaceutically acceptable excipient, carrier, buffer, stabiliser or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes. The pharmaceutical composition may comprise one or more pharmaceutical excipients. Any suitable pharmaceutical excipient may be used, and one of ordinary skill in the art is capable of selecting suitable pharmaceutical excipients. Accordingly, the pharmaceutical excipients provided below are intended to be illustrative, and not limiting. Additional pharmaceutical excipients include, for example, those described in the *Handbook of Pharmaceutical Excipients*, Rowe et al. (Eds.) 6th Ed. (2009), incorporated by reference in its entirety.

Various modes of administering the additional therapeutic agents are contemplated herein. In some embodiments, the additional therapeutic agent is administered by any suitable mode of administration.

A composition can be administered alone or in combination with other treatments, either simultaneously or sequentially dependent upon the condition to be treated.

Kits and Articles of Manufacture

The present application provides kits comprising any one or more of the system or cell compositions described herein along with instructions for use. The instructions for use can be present in the kits as a package insert, in the labeling of the container of the kit or components thereof, or can be in digital form (e.g. on a CD-ROM, via a link on the internet). A kit can include one or more of a genome-targeting nucleic acid, a polynucleotide encoding a genome-targeting nucleic acid, a site-directed polypeptide, and/or a polynucleotide encoding a site-directed polypeptide. Additional components within the kits are also contemplated, for example, buffer (such as reconstituting buffer, stabilizing buffer, diluting buffer), and/or one or more control vectors.

In some embodiments, the kits further contain a component selected from any of secondary antibodies, reagents for immunohistochemistry analysis, pharmaceutically acceptable excipient and instruction manual and any combination thereof. In one specific embodiment, the kit comprises a pharmaceutical composition comprising any one or more of the antibody compositions described herein, with one or more pharmaceutically acceptable excipients.

The present application also provides articles of manufacture comprising any one of the antibody compositions or kits described herein. Examples of an article of manufacture include vials (including sealed vials).

Additional Embodiments

Embodiment 1 At least one polypeptide comprising at least one of:
 a first antigen-binding domain that specifically binds Prostate-Specific Membrane Antigen (PSMA) (SEQ ID NO: 2) wherein the first antigen-binding domain comprises a first variable heavy (VH) chain sequence comprising three heavy chain CDR sequences, CDR-H1, CDR-H2, and CDR-H3, of the VH sequence set forth in SEQ ID NO: 118 or 130, and a first variable light (VL) chain sequence comprising three light chain CDR sequences, CDR-L1, CDR-L2, and CDR-L3, of the VL sequence set forth in SEQ ID NOs: 119 or 131; and/or a second antigen-binding domain that specifically binds to Carbonic Anhydrase IX (CA9) (SEQ ID NO: 1) wherein the second antigen-binding domain comprises a second variable heavy (VH) chain sequence comprising three heavy chain CDR sequences, CDR-H1, CDR-H2, and CDR-H3, of the VH sequence set forth in SEQ ID NOs: 99 or 110, and, optionally, a second variable light (VL) chain sequence comprising three light chain CDR sequences, CDR-L1, CDR-L2, and CDR-L3, of the VL sequence set forth in SEQ ID NO: 100).

Embodiment 2 The at least one polypeptide of embodiment 1, wherein:
a. the first variable heavy (VH) chain sequence comprises:
 i. a CDR-H1 comprising the sequence set forth in SEQ ID NO: 120, a CDR-H2 comprising the sequence set forth in SEQ ID NO: 121, and a CDR-H3 comprising the sequence set forth in SEQ ID NO: 122, and the first variable light (VL) chain sequence comprises a CDR-L1 comprising the sequence set forth in SEQ ID NO: 123, a CDR-L2 comprises the sequence set forth in SEQ ID NO: 124, and a CDR-L3 comprising the sequence set forth in SEQ ID NO: 125; or
 ii. a CDR-H1 comprising the sequence set forth in SEQ ID NO: 132, a CDR-H2 comprising the sequence set forth in SEQ ID NO: 133, and a CDR-H3 comprising the sequence set forth in SEQ ID NO: 134, and the first variable light (VL) chain sequence comprises a CDR-L1 comprising the sequence set forth in SEQ ID NO: 135, a CDR-L2 comprises the sequence set forth in SEQ ID NO: 136, and a CDR-L3 comprising the sequence set forth in SEQ ID NO: 137 and/or
b. the second variable heavy (VH) chain sequence comprises:
 i. a CDR-H1 comprising the sequence set forth in SEQ ID NO: 101, a CDR-H2 comprising the sequence set forth in SEQ ID NO: 102, and a CDR-H3 comprising the sequence set forth in SEQ ID NO: 103, and the second variable light (VL) chain sequence comprises a CDR-L1 comprising the sequence set forth in SEQ ID NO: 104, a CDR-L2 comprises the sequence set forth in SEQ ID NO: 105, and a CDR-L3 comprising the sequence set forth in SEQ ID NO: 106; or
 ii. a CDR-H1 comprising the sequence set forth in SEQ ID NO: 111, a CDR-H2 comprising the sequence set forth in SEQ ID NO: 112, and a CDR-H3 comprising the sequence set forth in SEQ ID NO: 113.

Embodiment 3 The at least one polypeptide of embodiment 1, wherein the first VH chain sequence comprises the sequence set forth in SEQ ID NOs: 118 or 130, and the first VL chain sequence comprises the sequence set forth in SEQ ID NOs: 119 or 131.

Embodiment 4 The at least one polypeptide of embodiments 1-3, wherein the second VH comprises the sequence as set forth in SEQ ID NOs: 99 or 110, and, optionally wherein the second VL comprises the sequence set forth in SEQ ID NO: 100.

Embodiment 5 A system comprising:
a first chimeric polypeptide comprising a priming receptor comprising the first antigen-binding domain that specifically binds PSMA (SEQ ID NO: 2); and
a second chimeric polypeptide comprising a chimeric antigen receptor (CAR) comprising the second antigen-binding domain that specifically binds to CA9 (SEQ ID NO: 1).

Embodiment 6 The system of embodiment 5, wherein:
the first antigen-binding domain comprises a first variable heavy (VH) chain sequence comprising three heavy chain CDR sequences, CDR-H1, CDR-H2, and CDR-H3, of the VH sequence set forth in SEQ ID NOs: 118 or 130, and a first variable light (VL) chain sequence comprising three light chain CDR sequences, CDR-L1, CDR-L2, and CDR-L3, of the VL sequence set forth in SEQ ID NOs: 119 or 131; and/or
the second antigen-binding domain comprises a second variable heavy (VH) chain sequence comprising three heavy chain CDR sequences, CDR-H1, CDR-H2, and CDR-H3, of the VH sequence set forth in SEQ ID NOs: 99 or 110, and, optionally, a second variable light (VL) chain sequence comprising three light chain CDR sequences, CDR-L1, CDR-L2, and CDR-L3, of the VL sequence set forth in SEQ ID NO: 100.

Embodiment 7 The system of embodiment 6, wherein:
a. the first variable heavy (VH) chain sequence comprises:
 i. a CDR-H1 comprising the sequence set forth in SEQ ID NO: 120, a CDR-H2 comprising the sequence set forth in SEQ ID NO: 121, and a CDR-H3 comprising the sequence set forth in SEQ ID NO: 122, and the first variable light (VL) chain sequence comprises a CDR-L1 comprising the sequence set forth in SEQ ID NO: 123, a CDR-L2 comprises the sequence set forth in SEQ ID NO: 124, and a CDR-L3 comprising the sequence set forth in SEQ ID NO: 125; or
 ii. a CDR-H1 comprising the sequence set forth in SEQ ID NO: 132, a CDR-H2 comprising the sequence set forth in SEQ ID NO: 133, and a CDR-H3 comprising the sequence set forth in SEQ ID NO: 134, and the first variable light (VL) chain sequence comprises a CDR-L1 comprising the sequence set forth in SEQ ID NO: 135, a CDR-L2 comprises the sequence set forth in SEQ ID NO: 136, and a CDR-L3 comprising the sequence set forth in SEQ ID NO: 137 and/or
b. the second variable heavy (VH) chain sequence comprises:
 i. a CDR-H1 comprising the sequence set forth in SEQ ID NO: 101, a CDR-H2 comprising the sequence set forth in SEQ ID NO: 102, and a CDR-H3 comprising the sequence set forth in SEQ ID NO: 103, and the second variable light (VL) chain sequence comprises a CDR-L1 comprising the sequence set forth in SEQ ID NO: 104, a CDR-L2 comprises the sequence set forth in SEQ ID NO: 105, and a CDR-L3 comprising the sequence set forth in SEQ ID NO: 106 or
 ii. a CDR-H1 comprising the sequence set forth in SEQ ID NO: 111, a CDR-H2 comprising the sequence set forth in SEQ ID NO: 112, and a CDR-H3 comprising the sequence set forth in SEQ ID NO: 113.

Embodiment 8 The system of embodiments 6 or 7, wherein the first VH chain sequence comprises the sequence set forth in SEQ ID NO: 118 or 130 and the first VL chain sequence comprises the sequence set forth in SEQ ID NO: 119 or 131.

Embodiment 9 The system of embodiments 6-8, wherein the second VH comprises the sequence as set forth in SEQ ID NO: 99 or 110 and wherein the second VL comprises the sequence set forth in SEQ ID NO: 100.

Embodiment 10 The system of embodiments 5-9, wherein the priming receptor comprises from N-terminus to C-terminus:
the first antigen-binding domain;
a transmembrane domain comprising one or more ligand-inducible proteolytic cleavage sites; and
an intracellular domain comprising a transcriptional effector, wherein binding of PSMA by the first antigen-binding domain results in cleavage at the one or more ligand-inducible proteolytic cleavage sites.

Embodiment 11 The system of embodiments 5-10, wherein the priming receptor comprises a sequence as set forth in SEQ ID NO: 127, 252, 138, or 253.

Embodiment 12 The system of embodiments 5-11, wherein the CAR comprises, from N-terminus to C-terminus:
the antigen-binding domain;
a transmembrane domain;
an optional intracellular co-stimulatory domain; and
an intracellular activation domain.

Embodiment 13 The system of embodiments 5-12, wherein the CAR comprises a sequence as set forth in SEQ ID NOs: 108, 250, 115, or 251.

Embodiment 14 The system of embodiments 5-13, further comprising a third polypeptide comprising a SPA comprising the sequence as set forth in SEQ ID NOs: 108, 250, 115, or 251.

Embodiment 15 The system of embodiments 5-14, wherein the system is encoded by a nucleic acid comprising a sequence with at least 80%, 85%, 90%, 91%, 92%, 93%, 94%, 95%, 96%, 97%, 98%, 99%, or 100% identity to a sequence as set forth in SEQ ID NOs: 143, 144, 145, or 146.

Embodiment 16 A system comprising the at least one polypeptide of embodiments 1-4 and further comprising at least one or more nucleic acids comprising a nucleic acid sequence at least 15 nucleotides in length complementary to at least one of:
a nucleic acid sequence encoding human Fas Cell Surface Death Receptor (FAS) comprising the sequence set forth in SEQ ID NO: 3; and
a nucleic acid sequence encoding human transforming growth factor (TGF)-β Receptor 2 (TGFBR2) comprising the sequence set forth in SEQ ID NO: 4.

Embodiment 17 The system of embodiment 16, wherein the nucleic acid sequence complementary to human FAS comprises a sequence selected from the group consisting of the sequences set forth in SEQ ID NOs: 6-20.

Embodiment 18 The system of embodiments 16-17, wherein the nucleic acid sequence complementary to human TGFBR2 comprises a sequence selected from the group consisting of the sequences set forth in SEQ ID NOs: 34-82.

Embodiment 19 One or more nucleic acid(s) comprising a nucleotide sequence encoding the at least one polypeptide of embodiments 1-4.

Embodiment 20 The one or more nucleic acid(s) of embodiment 19, further comprising at least one or more nucleic acids comprising a nucleic acid sequence at least 15 nucleotides in length complementary to at least one of:
a. a nucleic acid sequence encoding human Fas Cell Surface Death Receptor (FAS) comprising the sequence set forth in SEQ ID NO: 3; and
b. a nucleic acid sequence encoding human transforming growth factor (TGF)-β Receptor 2 (TGFBR2) comprising the sequence set forth in SEQ ID NO: 4.

Embodiment 21 One or more nucleic acid(s) comprising a nucleotide sequence encoding the system of embodiments 5-18.

Embodiment 22 The one or more nucleic acid(s) of embodiment 21, further comprising at least one or more nucleic acids comprising a nucleic acid sequence at least 15 nucleotides in length complementary to at least one of:
a. a nucleic acid sequence encoding human Fas Cell Surface Death Receptor (FAS) comprising the sequence set forth in SEQ ID NO: 3; and
b. a nucleic acid sequence encoding human transforming growth factor (TGF)-β Receptor 2 (TGFBR2) comprising the sequence set forth in SEQ ID NO: 4.

Embodiment 23 One or more vector(s) comprising the one or more nucleic acid(s) of embodiments 19-22.

Embodiment 24 A cell comprising the at least one polypeptide of embodiments 1-6.

Embodiment 25 The cell of embodiment 24, wherein the cell is a primary human immune cell.

Embodiment 26 A pharmaceutical composition comprising the cell of embodiment 24 or 25, and a pharmaceutically acceptable excipient.

Embodiment 27 A cell comprising the system of embodiments 7-21, optionally wherein the cell is a primary human immune cell.

Embodiment 28 A method of editing an immune cell, comprising:
a. providing a ribonucleoprotein complex (RNP) and a nucleic acid, wherein the RNP comprises a nuclease domain and a guide RNA, wherein the nucleic acid comprises the nucleic acid of embodiment 19, and wherein the 5' and 3' ends of the nucleic acid comprise nucleotide sequences that are homologous to genomic sequences flanking an insertion site in the genome of the immune cell;
b. non-virally introducing the RNP complex and nucleic acid into the immune cell, wherein the guide RNA specifically hybridizes to a target region of the genome of the primary immune cell, and wherein the nuclease domain cleaves the target region to create the insertion site in the genome of the immune cell; and
c. editing the immune cell via insertion of the nucleic acid into the insertion site in the genome of the immune cell.

Embodiment 29 A method of treating a disease or increasing an immune response in a subject comprising administering to the subject a cell comprising at least one polypeptide comprising at least one of:
a first antigen-binding domain that specifically binds Prostate-Specific Membrane Antigen (PSMA) (SEQ ID NO: 2); and/or
a second antigen-binding domain that specifically binds to Carbonic Anhydrase IX (CA9) (SEQ ID NO: 1, optionally wherein the disease is cancer.

Embodiment 30 The method of embodiment 29, wherein the target cell is a cancer cell, optionally wherein the cancer cell is a cancer cell of kidney cancer, clear cell renal cell carcinoma (ccRcc), colorectal cancer, or lung cancer.

EXAMPLES

Below are examples of specific embodiments for carrying out the present disclosure.

The examples are offered for illustrative purposes only, and are not intended to limit the scope of the present disclosure in any way. Efforts have been made to ensure accuracy with respect to numbers used (e.g., amounts, temperatures, etc.), but some experimental error and deviation should, of course, be allowed for.

The practice of the present disclosure will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pennsylvania: Mack Publishing Company, 1990); Carey and Sundberg *Advanced Organic Chemistry* $3^{rd}$ Ed. (Plenum Press) Vols A and B(1992).

Example 1: CA9 Binder Generation and Synthesis

The CA9 1 binder is a fully human antibody, generated following an immunization and screening campaign with humanized transgenic mice. A total of 12 mice were immunized with recombinant human CA9 protein and serum titers evaluated on day 49 for anti-CA9 binding. The draining lymph nodes were harvested from the top 6 responding mice, with selection based on sera-reactivity to recombinant human CA9 by ELISA and human CA9-engineered HEK293 cells by flow cytometry. Single Cell Technology, Inc., performed all single cell screening work utilizing their AbTheneum™ platform. The draining lymph nodes were harvested from the top 6 responding mice, with selection based on sera-reactivity to recombinant human CA9 by ELISA and human CA9-engineered HEK293 cells by flow cytometry. CD138 positive plasma cells were isolated from lymph nodes and subsequently single cells were deposited into microwells of a slide. Secreted IgG from the single cells was screened for binding to recombinant human CA9 antigen. The plasma cell-secreted antibody was separated from cells, captured and screened for binding to fluorescently-labeled target antigen, with binding events captured through imaging. Single cell mRNA was recovered and cDNA was sequenced by NGS to retrieve antibody VH and VL sequences. Antibody binding and sequence data were paired for further analysis.

Fully-human VH and VL sequences were recovered from monoclonal plasma cells via next-generation sequencing (NGS) and paired with single cell screening data to identify binder sequences of interest. The VH sequence of CA9 1 is provided in SEQ ID NO: 99. The VL sequence of CA9 1 is provided in SEQ ID NO: 100. An scFv of CA9 1 was also generated, provided in SEQ ID NO: 98.

The CA9 2 binder is a human, single-domain, anti-CA9 VH-only antibody fragment isolated from a proprietary phage display library. Three iterative rounds of phage selection were performed against HEK293 cells engineered to overexpress human CA9. Monoclonal phage were prepared, screened for binding to recombinant human CA9 by ELISA and ELISA-positive hits sequenced by NGS. The VH sequence of CA9 2 is provided in SEQ ID NO: 110.

To further characterize the sequences, VH and VL pairs or VH single domains were cloned into mammalian expression vectors containing mouse IgG2a constant domains. The resulting chimeric CA9 1-mIgG2a and CA9 2-mIgG2a antibodies were transiently expressed from CHO cultures and purified via affinity chromatography.

Binding of recombinant CA9 1-mIgG2a and CA9 2-mIgG2a to CA9 was assessed by cell binding dose curves on parental HEK293T cells and HEK293T-CA9 expressing cell lines. Briefly, HEK293T parental and HEK293T-CA9 engineered cells were first blocked with human Fc blocker for 10 min at room temperature, stained for 30 min on ice with recombinant antibodies in an 8-point serial dilution, and washed 3 times with BD Stain Buffer. Subsequently, cells were stained for 30 min on ice with anti-mouse IgG2a-PE secondary antibody. Cell surface binding was measured on an Attune flow cytometer, with geometric mean fluorescence intensity (gMFI) data analyzed in FlowJo and plotted using GraphPad Prism. The dose-response curves and EC50 value were analyzed and obtained using the nonlinear fit model of (agonist) versus response (three parameters).

Figure 2A:
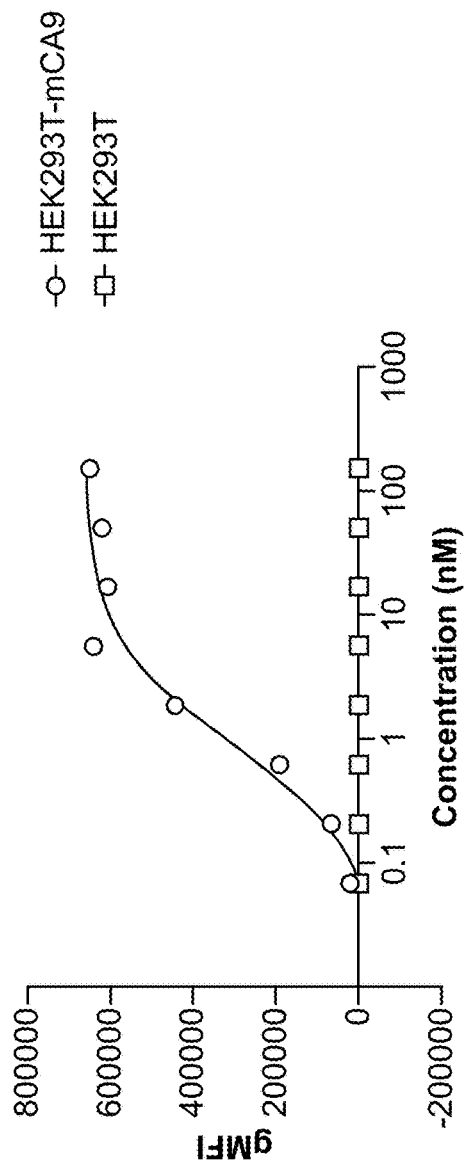
FIG. 2A shows binding of the CA9 1 antigen biding fragment to HEK293T-CA9 cells (expressing human CA9) but not to HEK293T parental cells.

As shown in FIG. 2A, CA9 1-mIgG2a bound in a dose-dependent manner to HEK293T-CA9, with an EC50 value of 0.92 nM. There was no binding to parental HEK293T cells.

The binding affinity of recombinant CA9 antibodies to human CA9 target antigen and cross-reactivity to mouse homologs was measured on the Octet R8. Briefly, recombinant antibody was loaded onto anti-mouse capture (AMC) Octet biosensors. Biosensors were then dipped into different concentrations of recombinant target antigen (analyte) solution, and the rate of protein-protein complex formation (association) measured. Protein-protein dissociation rates were measured when the biosensors were dipped into kinetic buffer alone. The Octet Analysis Studio 13.0 software calculated the response in equilibrium (Req) using the association and dissociation signal. The KD value and other kinetics parameters were determined by the values of Req for each analyte concentration (Table 1).

CA9 1-mIgG2a bound recombinant human CA9 with high affinity, resulting in a $K_D$ value of 0.15 nM. There was no detectable binding to recombinant mouse CA9.

TABLE 1

Binding kinetics of CA9 1

| Ligand | Analyte | $K_D$ | $k_{association}$ | $k_{dissociation}$ |
|---|---|---|---|---|
| CA9 1_mIgG2a | Human CA9 | 0.15 nM | $3.246 \times 10^5$ $M^{-1}s^{-1}$ | $4.90 \times 10^{-5}$ $s^{-1}$ |

To assess cross-reactivity of CA9 1 to mouse CA9 and further confirm the binding kinetics to human CA9, HEK293T-mCA9 cells were stained with increasing concentrations of CA9 1-mIgG2a then analyzed by flow cytometry. Recombinant CA9 1-mIgG2a protein was titrated against parental and engineered HEK293T cell lines expressing mouse CA9. Target cells were also stained with positive control antibodies to confirm expression of mouse CA9 on the engineered HEK293T cells. Following primary staining, the cells were washed, stained with secondary antibody, and subsequently analyzed by flow cytometry. Data were analyzed using FlowJo. Target cells were also stained using an anti-mouse CA9 positive control antibody to confirm expression of mouse CA9 on the HEK293T-mCA9 cells.

Figure 2B:
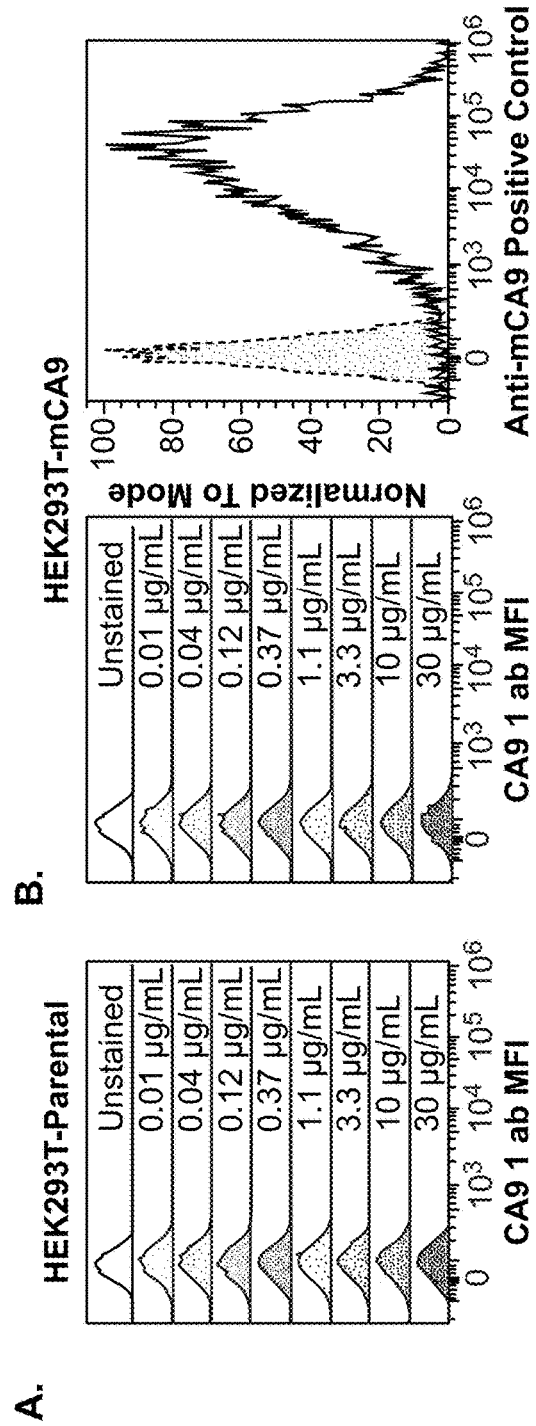
FIG. 2B shows that the CA9 1 antigen biding fragment did not bind to HEK293T-mCA9 cells (expressing mouse CA9).

No cross-reactivity of CA9 1 mouse CA9 was observed as evidenced by a lack of increase in MFI relative to the HEK293T parental cell line and unstained controls (FIG. 2B). Staining of HEK293T-mCA9 with positive control antibodies confirmed target CA9 antigen expression on the cell line. Thus, CA9 1 was not cross react with mouse CA9 (FIG. 2B).

CA9 1 and CA9 2 were specific to the CA9-expressing cell line and did not bind to the CA9-negative parental cells (FIG. 2B and data not shown). CA9 1 and CA9 2 also exhibited potent anti-CA9 activity in CAR T cells that contain the CA9 1 or CA9 2 binding domains as well as the compatibility of the CA9 1 or CA9 2 CAR T cells with a logic gate with a PSMA priming receptor (primeR) (data not shown).

Cell microarray technology was used to screen for specific off-target binding interactions for the antibodies CA9 1 and CA9 2. CA9 1 and CA9 2 were screened for binding against fixed human HEK293 cells, individually expressing 5861 full-length human plasma membrane proteins and cell surface-tethered human secreted proteins plus a further 371 human heterodimers. CA9 1 showed specific interactions with CA9, the primary target, on both fixed and live microarrays (data not shown). Although classed as non-specific due to the binding of controls, CA9 1 also showed an interaction with ASGR1 but only on fixed cells. CA9 2 showed specific interactions with CA9, the primary target, on both fixed and live microarrays. CA9 2 showed no non-specific binding above controls. (data not shown)

To further validate the interactions with ASGR1 observed with the above results, flow cytometry was used to determine whether CA9 1 shows any binding with HEK293T cell lines overexpressing ASGR1, with CA9-engineered K562 cells acting as a positive control. FIG. 2C shows that CA9 1 has no interaction with HEK293T-ASGR1+ cells across a range of concentration up to 5 ug/mL, while bindings were detected on engineered K562 expressing CA9. Taken together, CA9 1 demonstrated specific interactions with CA9 but not ASGR1 expressing cell lines.

HEK293T cell lines were generated to express CA9 isoforms with an R131 W single nucleotide polymorphism (SNP), a Q326R SNP or a 91-96 deletion (91-96del). CA9 1 and CA9 2 scFvs were used to stain the CA9-91-96del, CA9-R131 W, and CA9-Q326R cell lines followed by a secondary mouse anti human IgG2 stain. As shown in FIG. 2D, all three cell lines expressing the CA9 isoforms showed very strong positive staining with both CA9 1 and CA9 2. Thus, both CA9 1 and CA9 2 could bind to various isoforms of CA9.

In sum, immunization and screening of transgenic mice were successful in isolating anti-CA9 binding domains that are specific to human CA9, with an EC50 value of 0.92 nM binding to HEK293T cells expressing human CA9, and with no cross-reactivity detected against the murine homologs.

Example 2: PSMA Binder Generation and Synthesis

Two binders for PSMA, PSMA 1 and PSMA 2, were generated following an immunization and screening campaign with humanized transgenic mice. A total of 12 mice were immunized with recombinant human PSMA protein and serum titers evaluated on day 35 for anti-PSMA binding. Single Cell Technology, Inc., performed all single cell screening work utilizing their AbTheneum™ platform. The draining lymph nodes were harvested from the top 6 responding mice, with selection based on sera-reactivity to recombinant human PSMA by ELISA and human PSMA-engineered HEK293 cells by flow cytometry. CD138 positive plasma cells were isolated from lymph nodes and subsequently single cells were deposited into microwells of a slide. Secreted IgG from the single cells was screened for binding to recombinant human PSMA antigen. The plasma cell-secreted antibody was separated from cells, captured and screened for binding to fluorescently-labeled target antigen, with binding events captured through imaging. Single cell mRNA was recovered and cDNA was sequenced by NGS to retrieve antibody VH and VL sequences. Antibody binding and sequence data were paired for further analysis.

Fully-human VH and VL sequences were recovered from monoclonal plasma cells via next-generation sequencing (NGS) and paired with single cell screening data to identify binder sequences of interest. The VH sequence of PSMA 1 is provided in SEQ ID NO: 118. The VL sequence of PSMA 1 is provided in SEQ ID NO: 119. The VH sequence of PSMA 2 is provided in SEQ ID NO: 130. The VL sequence of PSMA 2 is provided in SEQ ID NO: 131.

To further characterize the sequences, identified VH and VL pairs were cloned into mammalian expression vectors containing mouse IgG2a constant domains. The resulting chimeric PSMA 1-mIgG2a and PSMA 2-mIgG2a constructs were transiently expressed from CHO cultures and purified via affinity chromatography.

PSMA expressing HEK293T cell lines were used to assess the binding of recombinant antibodies to cell surface expressed PSMA. Briefly, HEK293T parental and HEK293T-PSMA engineered cells were first blocked with human Fc blocker for 10 min at room temperature, stained for 30 min on ice with recombinant antibodies in an 8-point serial dilution, and washed 3 times with BD Stain Buffer. Subsequently, cells were stained for 30 min on ice with anti-mouse IgG2a-PE secondary antibody. Cell surface binding was measured on an Attune flow cytometer, with geometric mean fluorescence intensity (gMFI) data analyzed in FlowJo and plotted using GraphPad Prism. The dose-response curves and EC50 value were analyzed and obtained using the nonlinear fit model of (agonist) versus response (three parameters).

As shown in FIG. 3A, PSMA 1-mIgG2a bound in a dose-dependent manner to HEK293T-PSMA, with an EC50 value of 1.86 nM (Table 2). There was no binding to parental HEK293T cells.

The binding affinity of recombinant antibodies to human PSMA target antigen and cross-reactivity to mouse homologs was measured on the Octet R8 instrument. Briefly, recombinant antibody was loaded onto anti-mouse capture (AMC) Octet biosensors. Biosensors were then dipped into different concentrations of recombinant target antigen (analyte) solution, and the rate of protein-protein complex formation (association) measured. Protein-protein dissociation rates were measured when the biosensors were dipped into kinetic buffer alone. The Octet Analysis Studio 13.0 software calculated the response in equilibrium (Req) using the association and dissociation signal. The $K_D$ value and other kinetics parameters were determined by the values of Req for each analyte concentration (Table 2).

PSMA 1-mIgG2a bound recombinant human PSMA with high affinity, resulting in a $K_D$ value of 0.30 nM. There was no detectable binding to recombinant mouse PSMA.

TABLE 2

Binding kinetics of PSMA 1

| Ligand | Analyte | $K_D$ | $k_{association}$ | $k_{dissociation}$ |
|---|---|---|---|---|
| PSMA 1-mIgG2a | Human PSMA | 0.30 nM | $6.326 \times 10^4$ M$^{-1}$s$^{-1}$ | $1.887 \times 10^{-5}$ s$^{-1}$ |

Cross-reactivity of PSMA 1 to mouse PSMA was evaluated using flow cytometry. In brief, HEK293T cells expressing mouse PSMA (HEK293T-mPSMA) were stained for 30 min on ice with increasing concentrations of PSMA 1-mIgG2a. Target cells were also stained with positive control antibodies to confirm expression of mouse PSMA on the engineered HEK293T cells. Following primary staining, the cells were washed, stained with secondary antibody, and subsequently analyzed by flow cytometry. Data were analyzed using FlowJo.

No cross-reactivity of PSMA 1 to mouse PSMA (FIG. 3B) was observed as evidenced by a lack of increase in MFI relative to the HEK293T parental cell line. Staining of HEK293T-mPSMA with positive control antibodies confirmed target PSMA antigen expression on the cell line. Thus, PSMA 1 was not cross react with mouse PSMA (FIG. 3B).

Binding of PSMA 1-mIgG2a or PSMA 2-mIgG2a to PSMA was assessed by cell binding dose curves on parental HEK293T cells and HEK293T-PSMA expressing cell lines. PSMA 1 and PSMA 2 were both specific to the PSMA-expressing cell line and did not bind to the PSMA-negative parental cells. (data not shown) PSMA 1 and PSMA 2 also exhibited specific and strong anti-PSMA induction of the CA9 CAR when incorporated into a logic gate. (data not shown)

Specific off-target binding interactions for the recombinant binding proteins, PSMA 1 and PSMA 2, was assessed via cell microarray technology. PSMA 1 was screened for binding against fixed human HEK293 cells, individually expressing 5861 full-length human plasma membrane proteins and cell surface-tethered human secreted proteins plus a further 371 human heterodimers. PSMA 1 showed specific interactions with PSMA, the primary target, on both fixed and live microarrays. No other target was detected from the screen. (data not shown)

PSMA 2 was screened for binding against fixed human HEK293 cells, individually expressing 5861 full-length human plasma membrane proteins and cell surface-tethered human secreted proteins plus a further 371 human heterodimers. PSMA 2 showed specific interactions with PSMA, the primary target, on both fixed and live microarrays. CD70 was identified as an off target but only on fixed cells; when fresh CD70+ HEKs were stained with AVD2157, no binding was detected. (data not shown)

Figure 3C:
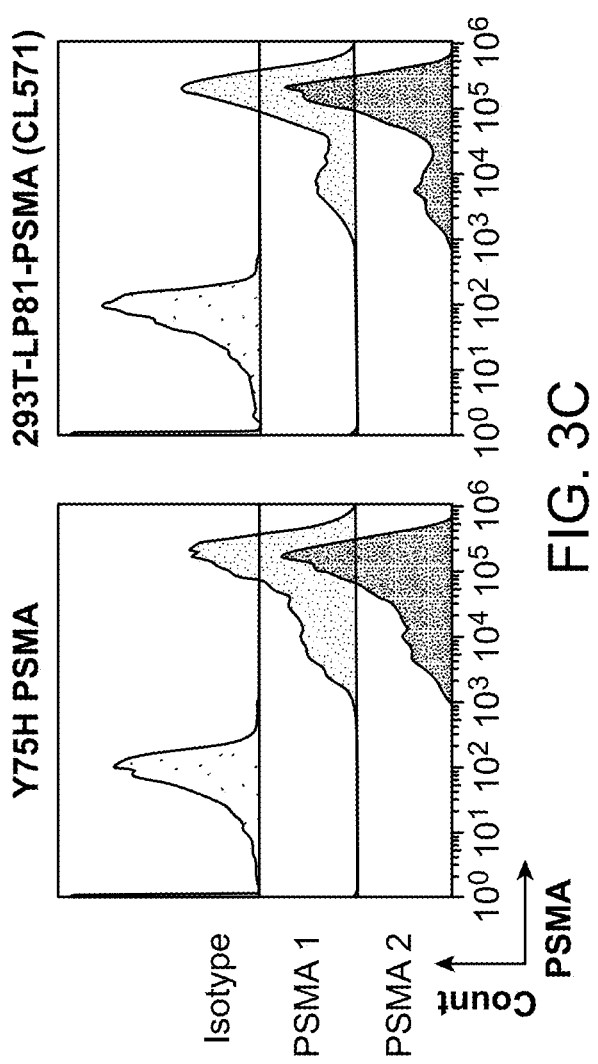
FIG. 3C shows that both PSMA 1 and PSMA 2 scFvs bound to cells expressing the PSMA isoform SNP Y75H and wt PSMA-expressing cells (293T-LP81-PSMA).

HEK293T cell lines were generated to express PSMA with a Y75H single nucleotide polymorphism (SNP). PSMA 1 and PSMA 2 scFvs were used to stain the PSMA-Y75H cell line followed by a secondary mouse anti human IgG2 stain. As shown in FIG. 3C, both PSMA 1 and PSMA 2 scFvs bound to cells expressing the protein with the PSMA SNP Y75H. Thus, both PSMA 1 and PSMA 2 could bind to various isoforms of PSMA.

In sum, immunization and screening of transgenic mice were successful in isolating anti-PSMA binding domains that are specific to human PSMA, with an EC50 value of 1.86 nM binding to HEK293T cells expressing human PSMA, and with no cross-reactivity detected against the murine homologs.

Example 3: Logic Gate Synthesis and In Vitro Characterization

Materials and Methods

Logic Gate Screening

Hundreds of novel scFv and VH/VHH binders targeting PSMA (as a priming target) and CA9 (as a cytolytic target) were generated via two parallel de novo binder discovery efforts: 1) transgenic mice immunizations and 2) phage display panning campaigns. Two independent arrayed screens with 500 PSMA prime receptors (PrimeR) and 750 CA9 CARs were conducted to find PrimeRs with high inducibility and CARs with strong on-target potency. Characterization of the top PSMA and CA9 binding proteins are provided in Examples 1 and 2.

From these screens, the top 25 PSMA PrimeRs and 20 CA9 CARs were combined with an exemplary shRNA cassette for targeted knockdowns along with two variations of a synthetic pathway activator (SPA). A fully-automated workcell was used to perform end-to-end arrayed screening of the resulting 1,000 member library in T cells engineered from four human donors. Non-viral editing techniques were used to electroporate primary CD4/CD8 cells and robotic handlers were used to set up co-cultures. Circuit specificity and potency were assessed by flow cytometry and cytokine secretion and resistance to exhaustion was assessed in a seven day killing assay. Although the library was built from components that functioned well independently, it was found that when combined, many of the circuits displayed suboptimal function. (data not shown) Integrated screening identified 20 variants that each far exceeded the performance of a small set of initial prototypes built from "best-guess" selections of individual components.

The final logic gate candidates were significantly superior to constitutive CAR-T cells in a long term killing assay, show potent cytotoxicity of low expressing antigen lines, and display background levels of cytotoxicity against single antigen targets. (data not shown) Engineering multiple features into T cell products can be limited by unpredictable negative interactions between components. This high-throughput screening generated development-ready candidates for ccRCC with finely tuned desirability criteria in less than 18 months.

ICT Construct Expression in T Cells

Integrated circuit T (ICT) cells were generated through site directed CRISPR mediated knock in (KI). T cells were activated for two days using CD3-CD28 beads. At day 2, beads were removed followed by the delivery of the ICT transgene to the GS94 site in the genome of the T cells. Transgene integration was performed using a CRISPR-based process and electroporation step that combined activated T cells, CRISPR/Cas9 RNP targeting the GS94 non-coding autosomal integration site, and plasmid DNA constituting a repair template to effect insertion of the transgene cassette via cellular DNA repair machinery.

The GS94 CRISPR/Cas9 RNP used was generated by complexing single guide RNA (sgRNA) with recombinant *Streptococcus pyogenes* Cas9 (SpCas9). The sgRNA contained a protospacer sequence directing the CRISPR/Cas9 RNP to the GS94-transgene integration site. The plasmid DNA repair template contained the ICT transgene cassette, flanked by 450 base pair (bp) sequences homologous to the regions flanking the integration site to effect repair-mediated insertion.

Figure 1B:
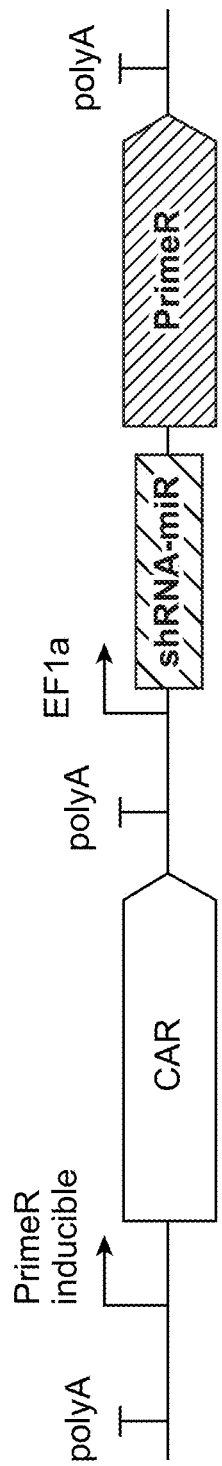
FIG. 1B shows an exemplary insertion cassette encoding a logic gate (priming receptor (primeR) and CAR) and an shRNA module.

A diagram of the various ICT transgene cassettes generated is provided in FIG. 1A FIG. 1B provides a schematic including the inducible and constitutive promoters and polyA sequences. The ICT constructs 1, 2, 3, and 4 comprised a constitutively expressed PSMA priming receptor, an inducible CA9 CAR (forming a Logic Gate or "LG"), constitutively expressed shRNAs targeting FAS and TGFBR2, and a synthetic pathway activator (SPA). One ICT also included an shRNA targeting PTPN2 and LNGFR in place of the SPA (LG 5 IC).

The sequence of the PSMA priming receptor 1 (primeR 1) is provided in SEQ ID NO: 127 and 252. The PSMA 1 primeR sequence provided in SEQ ID NO: 127 includes the leader sequence, while the PSMA 1 primeR sequence provided in SEQ ID NO: 252 excludes the leader sequence. The sequence of the PSMA priming receptor 2 (primeR 2) is provided in SEQ ID NO: 138 and 253. The PSMA 2 primeR sequence provided in SEQ ID NO: 138 includes the leader sequence, while the PSMA 2 primeR sequence provided in SEQ ID NO: 253 excludes the leader sequence.

The sequence of the CA9 1 CAR (CAR 1) is provided in SEQ ID NO: 108 and 250. The CA9 1 CAR sequence provided in SEQ ID NO: 108 includes the leader sequence, while the CA9 1 CAR sequence provided in SEQ ID NO: 250 excludes the leader sequence. The sequence of the CA9 2 CAR (CAR 2) is provided in SEQ ID NO: 115 and 251. The CA9 2 CAR sequence provided in SEQ ID NO: 115 includes the leader sequence, while the CA9 2 CAR sequence provided in SEQ ID NO: 251 excludes the leader sequence. The sequence of the SPA is provided in SEQ ID NO: 141 and 254. The SPA sequence provided in SEQ ID NO: 141 includes the leader sequence, while the SPA sequence provided in SEQ ID NO: 254 excludes the leader sequence. The sequence of LNGFR is provided in SEQ ID NO: 142 and 255. The LNGFR sequence provided in SEQ ID NO: 142 includes the leader sequence, while the LNGFR sequence provided in SEQ ID NO: 255 excludes the leader sequence.

The sequence of the FAS and dual TGFBR2 shRNA cassette is provided in SEQ ID NO: 83, while the sequence of the FAS/PTPN2/dual TGFBR2 shRNA cassette is provided in SEQ ID NO: 84. The full transgene cassettes comprising a logic gate with the shRNA and optional SPA are termed Logic Gate 1 integrated circuit ("IC" or LG 1 IC) (SEQ ID NO: 143), Logic Gate 2 IC (LG 2 IC) (SEQ ID NO: 144), Logic Gate 3 IC (LG 3 IC) (SEQ ID NO: 145), Logic Gate 4 IC (LG 4 IC) (SEQ ID NO: 146), or Logic Gate 5 IC (LG 5 IC) (SEQ ID NO: 147).

Following electroporation, cells were recovered and expanded in T cell media for 7 days. When indicated, negative control T cells were generated using a mock electroporation process that edited T cells with ribonucleoprotein (RNP) in the absence of donor plasmid and are referred to as "RNP control".

ICT cells were assessed for transgene KI and the expression of the PrimeR and CAR using flow based staining. Constructs contained tags myc and flag on the distal extracellular portion of the PrimeR and CAR respectively following the signal peptide. ICT cells at day 7 post activation were stained with myc, flag and CD3 antibodies for 30 min at 4c. Following activation, cells were washed in FACs buffer and run by flow cytometry. ICTs were analyzed for PrimeR and CAR expression following gating each sample for live CD3+ cells.

ICT Induction of CARs

ICTs were generated as described above from the T cells of 2 donors. On day 11 post activation, ICTs were measured for CAR and PrimeR expression by Flag and Myc staining. % KI was quantify by summing the % of T cells in a sample that were PrimeR+ or CAR+. Before co-culture setup, ICTs were normalized to the same % KI using the addition of donor matched RNP only cell. $1\times10^7$ ICTs were co-cultured with $1\times10^7$ target cells or media for 72 hours and stained to calculate the % of CAR+ cells using flag staining. Basal CAR expression was measured during assay set up.

shRNA Knockdown

ICT cells contain a constitutive shRNA module targeting knockdown of FAS and TGFBR2, whereas cells without a transgene KI (PrimeR negative cells) have normal expression of FAS and TGFBR2 and can be used as an internal control. Multicolor flow cytometry was performed on four productions of ICT cells to characterize transgene expression and assess shRNA-miR knockdown of FAS and TGFBR2. Antibodies against CD4, CD8, CD95 (FAS) and TGFBR2 were used in the flow cytometry. The panel also included rhPSMA for PrimeR detection and rhCA9 for CAR detection as well as Zombi NIR for live vs dead cell staining.

Surface protein knockdown of FAS and TGFBR2 in ICT cells was determined using flow cytometry. Cells were stained with anti-FAS and anti-TGFBR2 antibodies, and geometric mean fluorescence intensity (gMFI) was measured for both PrimeR-positive and PrimeR-negative subsets of ICT cells. Data are representative of 4 donors. The formula used to calculate % KD (percent knockdown) =100%(1−(MFI PrimeR+)/(MFI PrimeR−)).

Synthetic Pathway Activators

Synthetic Pathway Activators (SPAs) constitutively drive STAT signaling without the need for external cytokine input. SPAs can be designed to engage activity of multiple STAT family transcription factors at variable levels through rational design. Exemplary Class I SPAs primarily increase pSTAT3 activity and exemplary Class II SPAs primarily increase pSTAT5 activity.

A synthetic pathway activator (SPA) based on gp130 was constructed. The SPA comprises the transmembrane region and intracellular domain of gp130 linked to an ectodomain derived from the cell adhesion protein CD34. An unpaired cysteine residue was introduced into the receptor ectodomain to permit formation of a covalent bond and subsequent dimerization of individual synthetic gp130 monomers. The SPA drives constitutive recruitment and phosphorylation of STAT1 and STAT3 transcription factors. (data not shown)

To demonstrate the ability of the SPA module to drive constitutive STAT3 phosphorylation, ICTs expressing the SPA module under non-stimulated conditions were fixed, permeabilized, and stained for pSTAT3 and the PrimeR protein using rhPSMA protein to distinguish between edited and non-edited cells.

Cytotoxicity, Engineered K562 Cells

ICT cells expressing the integrated circuits comprising Logic Gate 1 IC (SEQ ID NO: 143), Logic Gate 2 IC (SEQ ID NO:144), Logic Gate 3 IC (SEQ ID NO:145), Logic Gate 4 IC (SEQ ID NO:146), or Logic Gate 5 IC (SEQ ID NO: 147) with shRNA and optionally a SPA were co-cultured with K562_EFG, K562_EFG_CA9, K562_EFG_PSMA, or K562_EFG_CA9_PSMA at varying E:T ratios for 72 hours at 37° C. Following incubation, cytotoxicity was measured using a luciferase reporter assay. Data are presented as the mean±standard deviation of 4 donors.

Cytokine Secretion

To further assess the specificity and function of ICT cells expressing Logic Gate 1-5 ICs, supernatants were collected from K562 target cytotoxicity co-cultures (Effector:Target ratio of 1:1, 72 hour co-culture). Following incubation, supernatants were collected at endpoint and cytokine release levels were measured using a Luminex assay. Data from 4 donors are shown.

Cytotoxicity in A498 Cells

ICT cells expressing LG 1-5 ICs were co-cultured with A498_PSMA cells (A498 cells endogenously expresses CA9 and engineered to express PSMA) at varying E:T ratios for 72 hours at 37° C. Following incubation, cytotoxicity was measured using a luciferase reporter assay. Data are presented as the mean±standard deviation of 4 donors. Prior to luciferase readout described above, supernatants were collected at endpoint and cytokines (B) IFN-γ, (C) TNFα, (D) GM-CSF and (E) IL-2 were measured using a Luminex assay. Data from 4 donors are shown.

Mixed Co-Culture Cytotoxicity

ICT cells expressing Logic Gates 1-5 were co-cultured with PSMA+/CA9− HUVEC and luciferase expressing PSMA−/CA9+ cells (K562-EFG-CA9) at varying E:T ratios for 72 hours at 37° C. Following incubation, cytotoxicity was measured using a luciferase reporter assay. Data are from one normal donor. ICT-mediated CA9+ target cell killing was evaluated relative to an RNP-electroporated negative control using a luciferase reporter assay.

Soluble CA9 and PSMA

ICT cells expressing Logic Gates 1-5 were co-cultured with luciferase expressing 786-O-PSMA-CA9 cells at a 1:1 effector: target ratio with titrating levels of (A) soluble rhCA9 or (B) soluble rhPSMA for 72 hours at 37° C. Following incubation, cytotoxicity was measured using a luciferase reporter assay. Data are presented as one representative donor of 2 tested.

Transwell Assay

On Day −3 HUVEC+-PSMA endothelial cells were plated to form a monolayer on the upper layer of the transwell plate insert and K562-CA9 tumor cells were plated on the lower layer of the transwell insert below the cell permeable membrane. Monolayers were confirmed to be impermeable to 70 KDa FITC-dextran on day 0. On Day 0, ICT cells expressing Logic Gate 1, the shRNA, and SPA were added to the transwell plate. Total cells at the bottom of the well were counted 3 days after addition of the ICT cells. LG 1 ICT cells were co-cultured were co-cultured with 5K PSMA+ HUVEC cells and 15K K562-CA9 tumor cells for 72 hours at 37° C. Following incubation, cytotoxicity of K562-EFG-CA9 was measured by luciferase reporter assay. Data presented in triplicate from one healthy donor.

Results

Figure 4A:
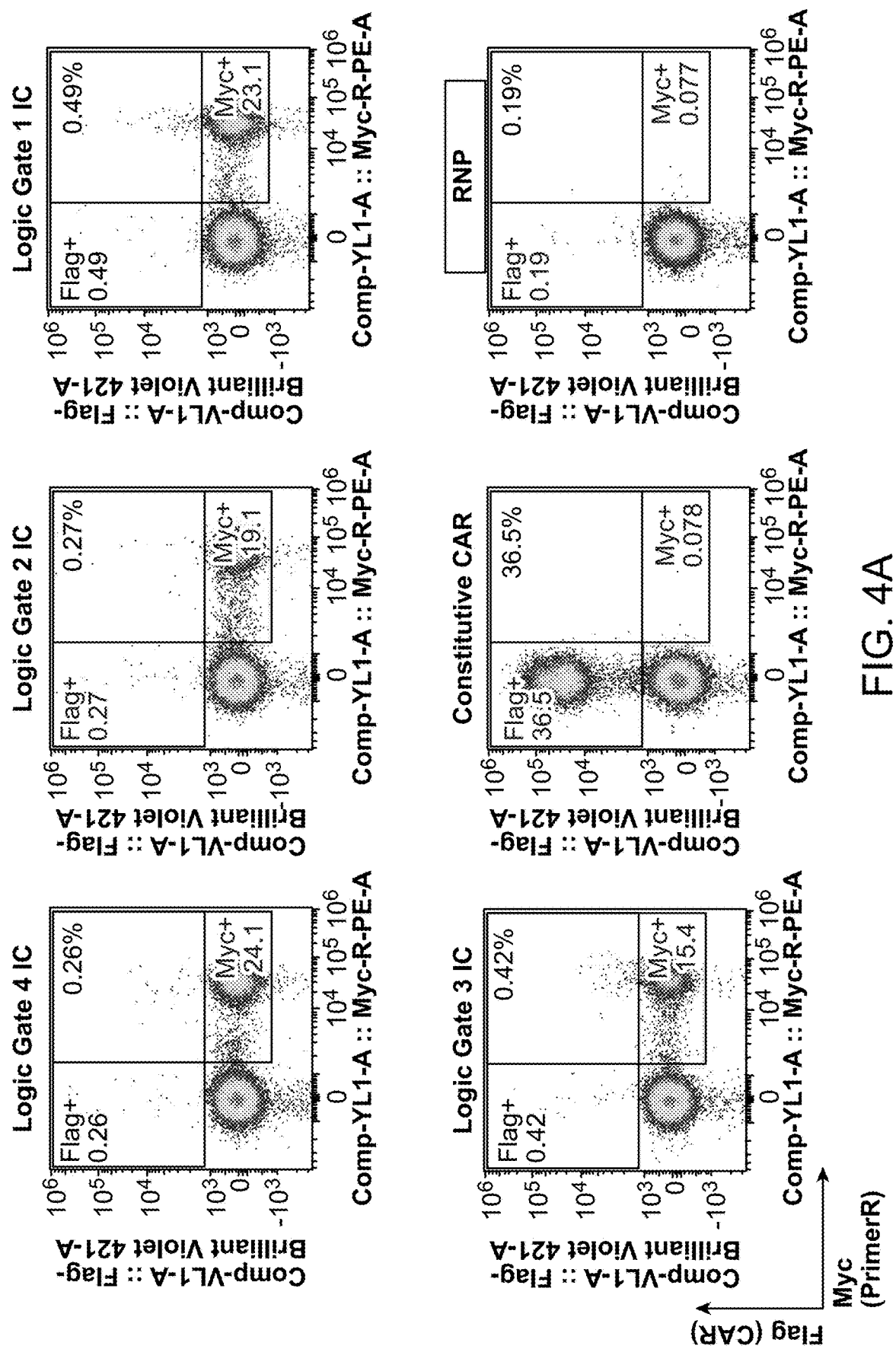
FIG. 4A shows that all ICT cells constitutively expressed the priming receptor (PrimeR) construct.

All ICT cells constitutively expressed the PrimeR construct as shown by myc expression (FIG. 4A). The inducible CAR was not expressed at basal state in the ICT cells, as indicated by the lack of FLAG expression (FIG. 4A), indicating that the priming receptor had not induced expression of the CAR.

Figure 4B:
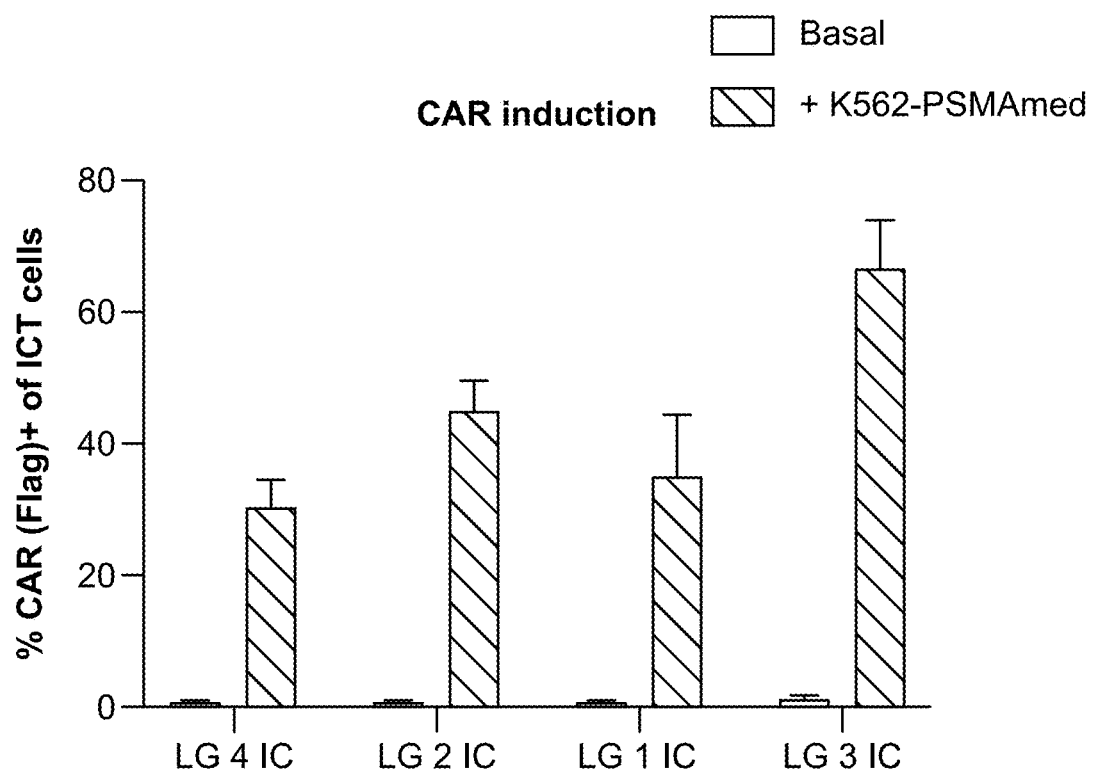
FIG. 4B shows that the ICT cells induced CA9 CAR expression when co-cultured with PSMA expressing cell lines.

As shown in FIG. 4B, the ICT cells induced CA9 CAR expression when co-cultured with PSMA expressing cell lines. Numbers shown in FIG. 4B are the (% CAR)/(% KI normalized to at the start of the assay)*100. Thus, the logic gate circuit functioned correctly by not expressing the CA9 CAR in the absence of binding of the primeR to PSMA (FIG. 4A) and induction of expression of the CA9 CAR upon binding of the PSMA primeR to its cognate ligand on a target cell (FIG. 4B).

Figure 5:
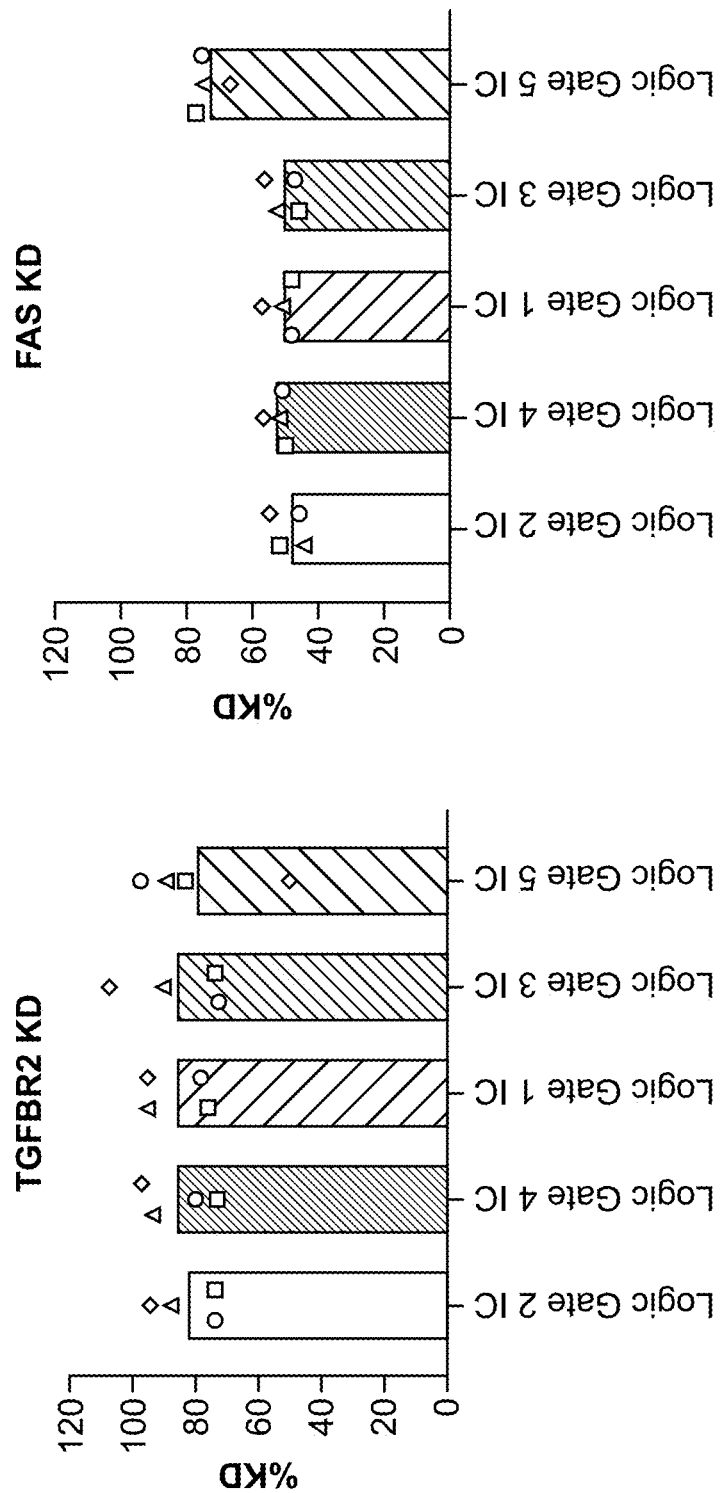
FIG. 5 shows that inclusion of the shRNA module in ICT cells resulted in lower MFI for both FAS and TGFBR2 in ICT cells expressing the priming receptor-CAR logic gate (PrimeR+) normalized to non-edited cells (PrimeR−).

Inclusion of the shRNA module in ICT cells showed lower MFI for both FAS and TGFBR2 in ICT cells expressing the priming receptor-CAR logic gate (PrimeR+) normalized to non-edited cells (PrimeR−), indicating knockdown of both FAS and TGFBR2 in ICT PrimeR+ cells (FIG. 5).

Figure 6:
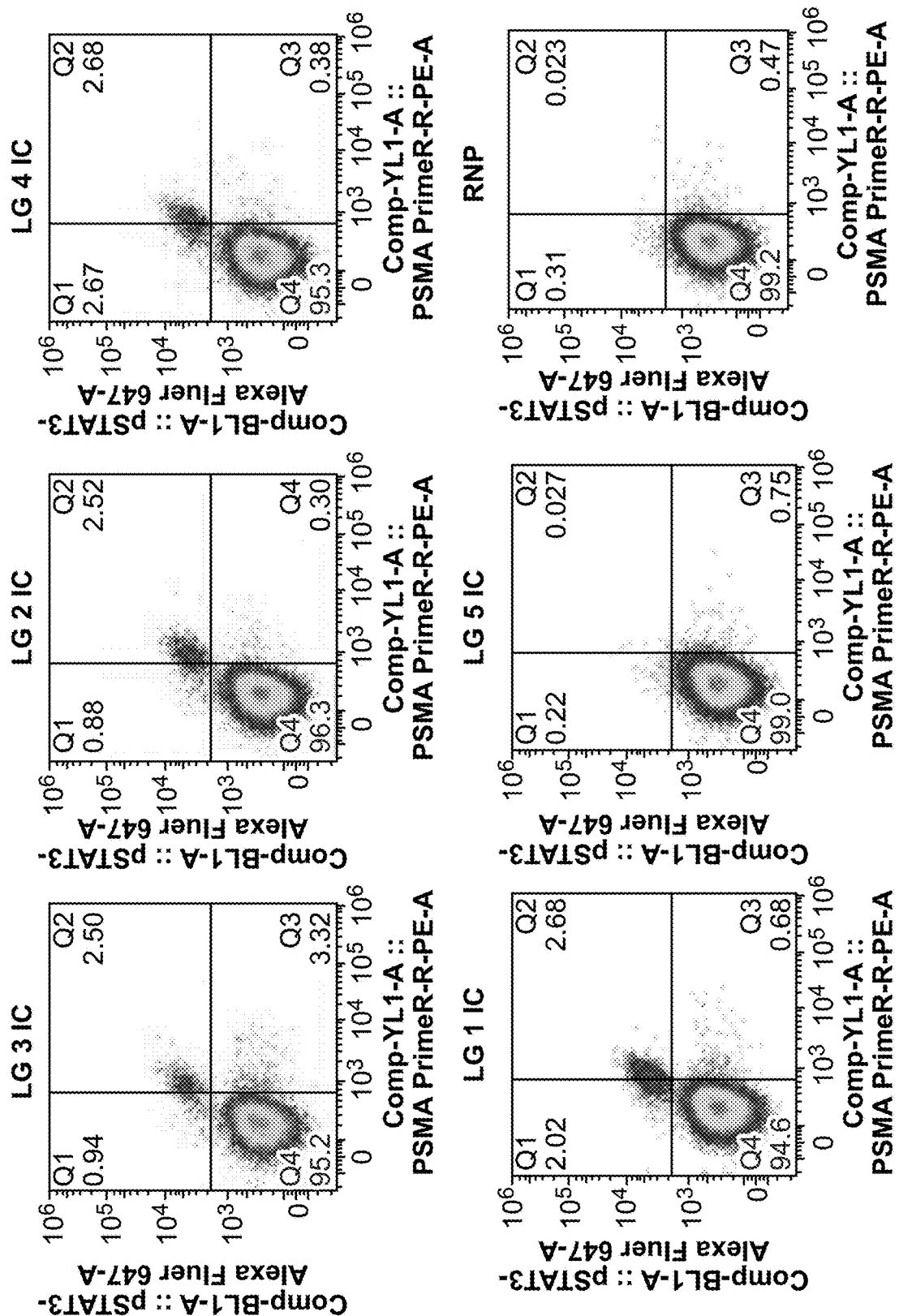
FIG. 6 shows that ICT cells expressing the SPA exhibit approximately two logs higher pSTAT3 expression when compared to the PrimeR− cells lacking a SPA (EGFRt).

As shown in FIG. 6, flow cytometry analysis revealed that ICT cells expressing the SPA (LG 1-4 ICs) exhibit approximately two logs higher pSTAT3 expression when compared to the PrimeR− cells (RNP). In contrast, edited T cells with a EGFRt (non-signaling) module in the place of a SPA (LG 5 IC) does not exhibit increased pSTAT3 staining when compared to PrimeR− cells. Overall, the results indicate that ICTs expressing the SPA module exhibit increased STAT3 phosphorylation.

ICTs expressing LG 1-5 ICs demonstrated cytotoxicity against only dual CA9 and PSMA expressing cells as compared to unedited control cells (RNP). FIG. 7A shows cytotoxicity against parental K562 cells expressing neither CA9 or PSMA, FIG. 7B shows cytotoxicity against K562 cells expressing only CA9, FIG. 7C shows cytotoxicity against K562 cells expressing only PSMA, and FIG. 7D shows cytotoxicity against K562 cells expressing both PSMA and CA9. As shown in FIG. 7D, the ICTs exhibited cytotoxicity against only cells expressing both PSMA and CA9 as compared to unedited cells (RNP).

Figure 8:
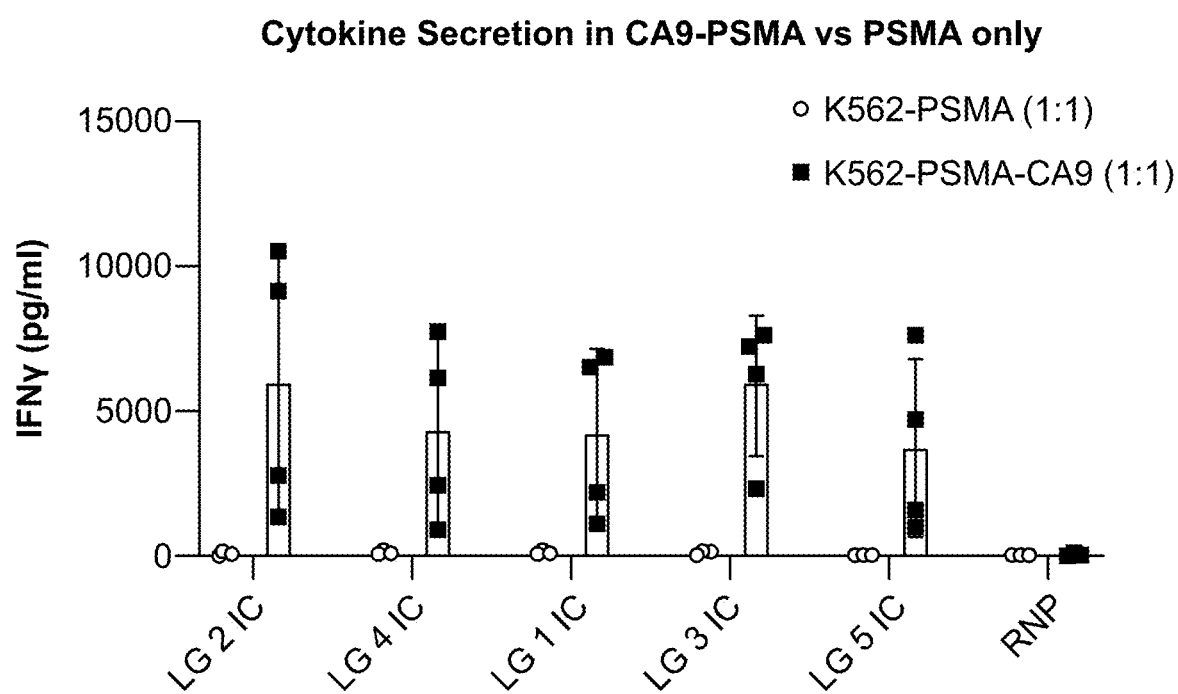
FIG. 8 shows IFN-γ production from ICTs expressing Logic Gates 1-5 only in supernatants taken from co-cultures where the target cells expressed either PSMA only (left bar) and target cells with PSMA and CA9 (right bar).

IFN-γ production from ICTs expressing LG 1-5 ICs was observed only in supernatants taken from co-cultures where the target cells expressed both PSMA and CA9 (FIG. 8). Results from the cytokine analysis were consistent with the cytotoxicity data. Together, these data further demonstrate that ICT activity is driven by co-expression of PSMA and CA9.

Figure 9A:
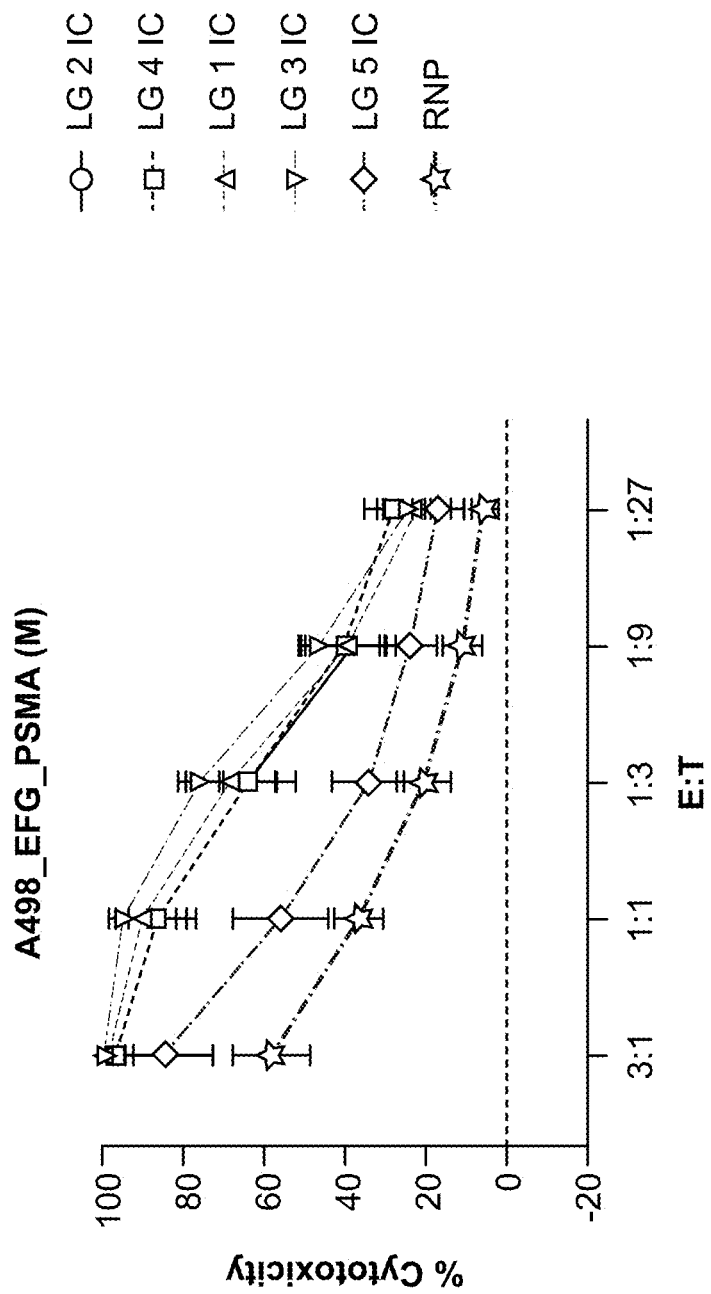
FIG. 9A shows that ICTs expressing Logic Gates 1-5 demonstrated in vitro cytotoxicity against the A498-PSMA-med cell line expressing endogenous CA9 antigen
Figure 9B:
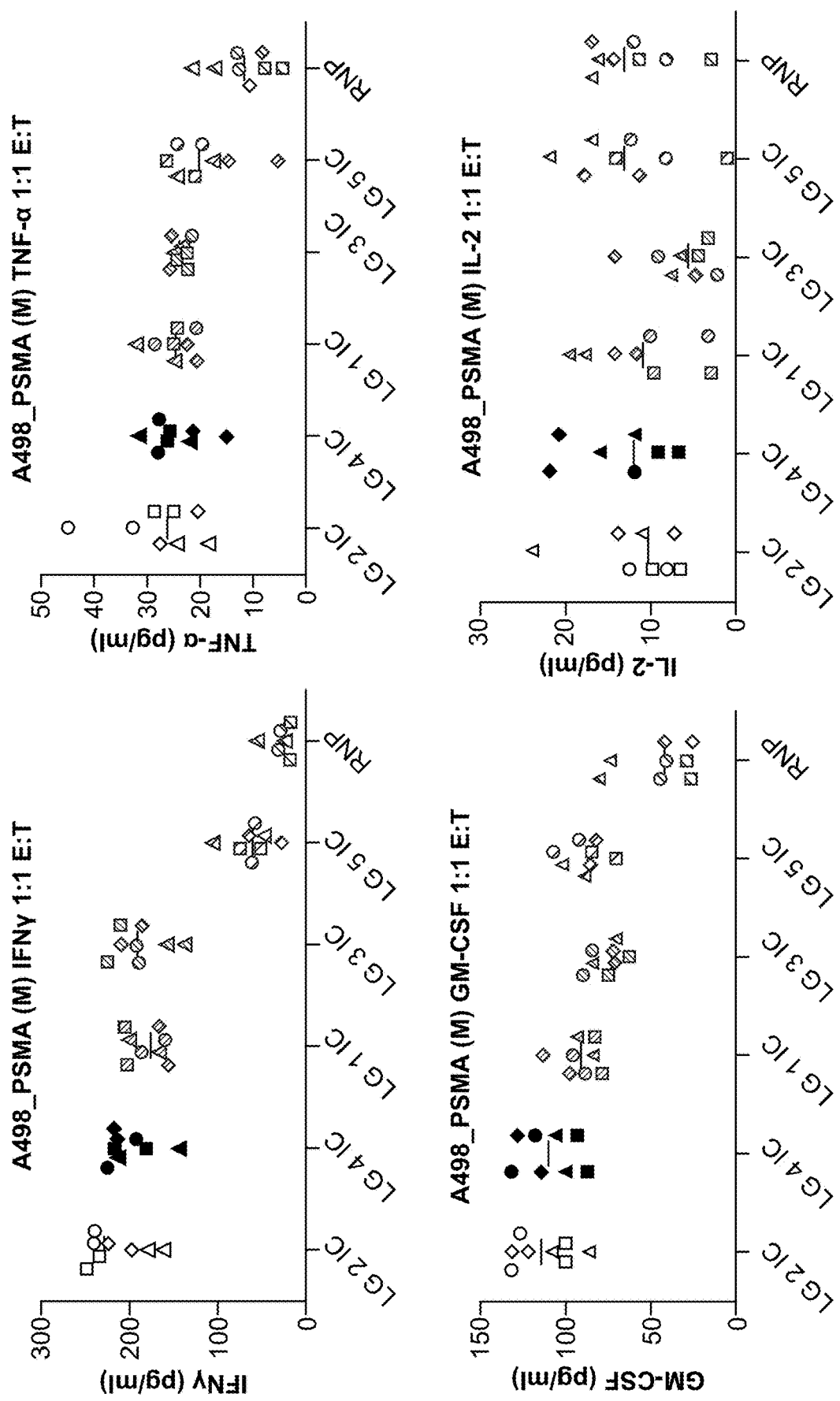
FIG. 9B shows IFNγ, TNFα, GM-CSF, and IL-2 secretion by ICT cells after co-culture with A498-PSMA cells.

ICTs expressing LG 1-5 ICs demonstrated in vitro cytotoxicity against the A498-PSMAmed cell line expressing endogenous CA9 antigen (FIG. 9A). ICTs also secrete cytokines after A498-PSMA co-culture. FIG. 9B shows IFNγ, TNFα, GM-CSF, and IL-2 secretion by ICT cells after co-culture with A498-PSMA cells. Thus, ICTs expressing LG 1-5 ICs secreted cytokines and killed ccRCC cell lines that express endogenous CA9 antigen in the presence of PSMA.

Figure 10:
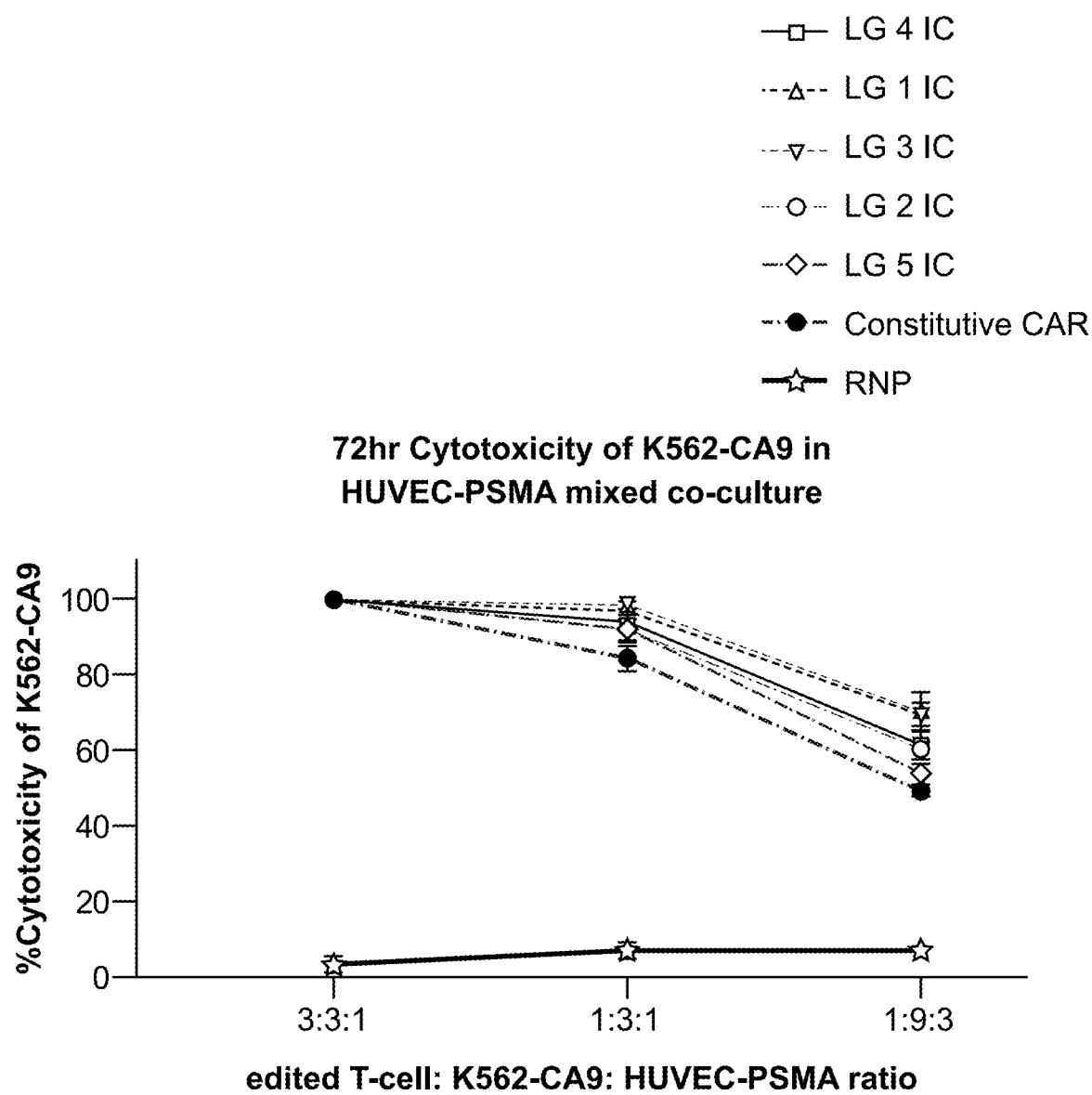
FIG. 10 shows that co-culture with HUVEC-PSMA induced expression of the CAR protein on ICT cells and specific killing of CA9+ cells.

Co-culture with HUVEC-PSMA induced expression of the CAR protein on ICT cells and specific killing of CA9+ cells was confirmed (FIG. 10). Thus, ICTs expressing LG 1-5 ICs were capable of inducing CAR expression through interaction with PSMA+ endothelial cells and subsequently specifically engaging and killing CA9+ tumor cells. Therefore, without wishing to be bound by theory, ICTs can be primed by binding to endothelial cells expressing PSMA in order to express the CAR and then kill CA9+ target tumor cells.

ICT cytotoxicity was not affected by soluble PSMA (FIG. 11B) or soluble CA9 (FIG. 11A).

Thus, logic gated ICT cells that utilize the presence of two antigens to trigger tumor cell killing to improve the therapeutic index of CA9 CAR T cells were developed, thereby enhancing tumor specificity. Induction of the CA9 CAR was gated on the expression of PSMA found on the tumor neovasculature of ccRCC. PSMA and CA9 are not known to be co-expressed in normal tissues. When the anti-PSMA priming receptor (PrimeR) binds PSMA, PrimeR engagement triggers proteolytic release of a transcription factor that induces expression of a CA9 CAR.

Figure 17A:
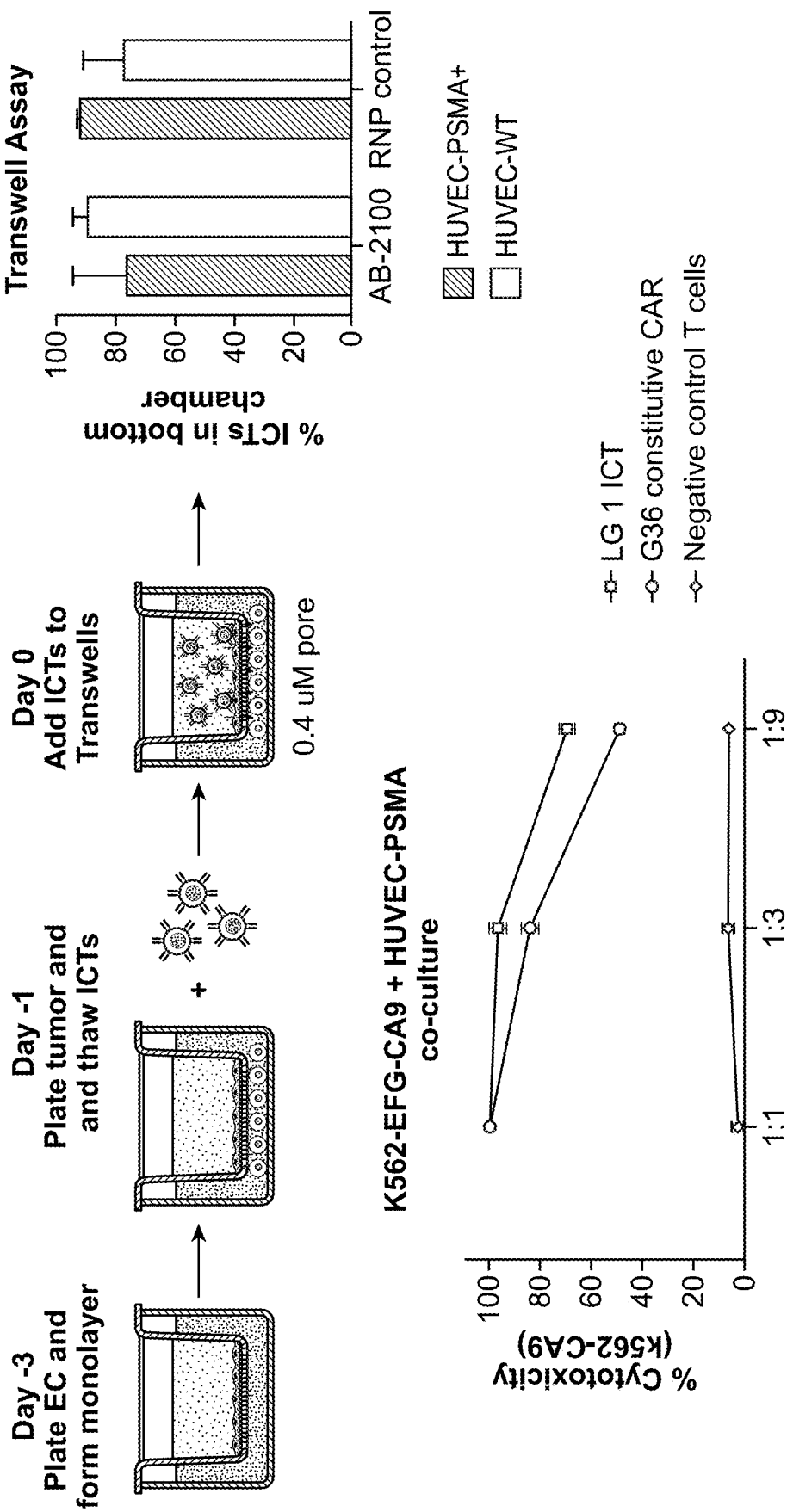
FIG. 17A shows that ICT cells can be primed during transmigration and can kill CA9+ tumor cells.
Figure 17B:
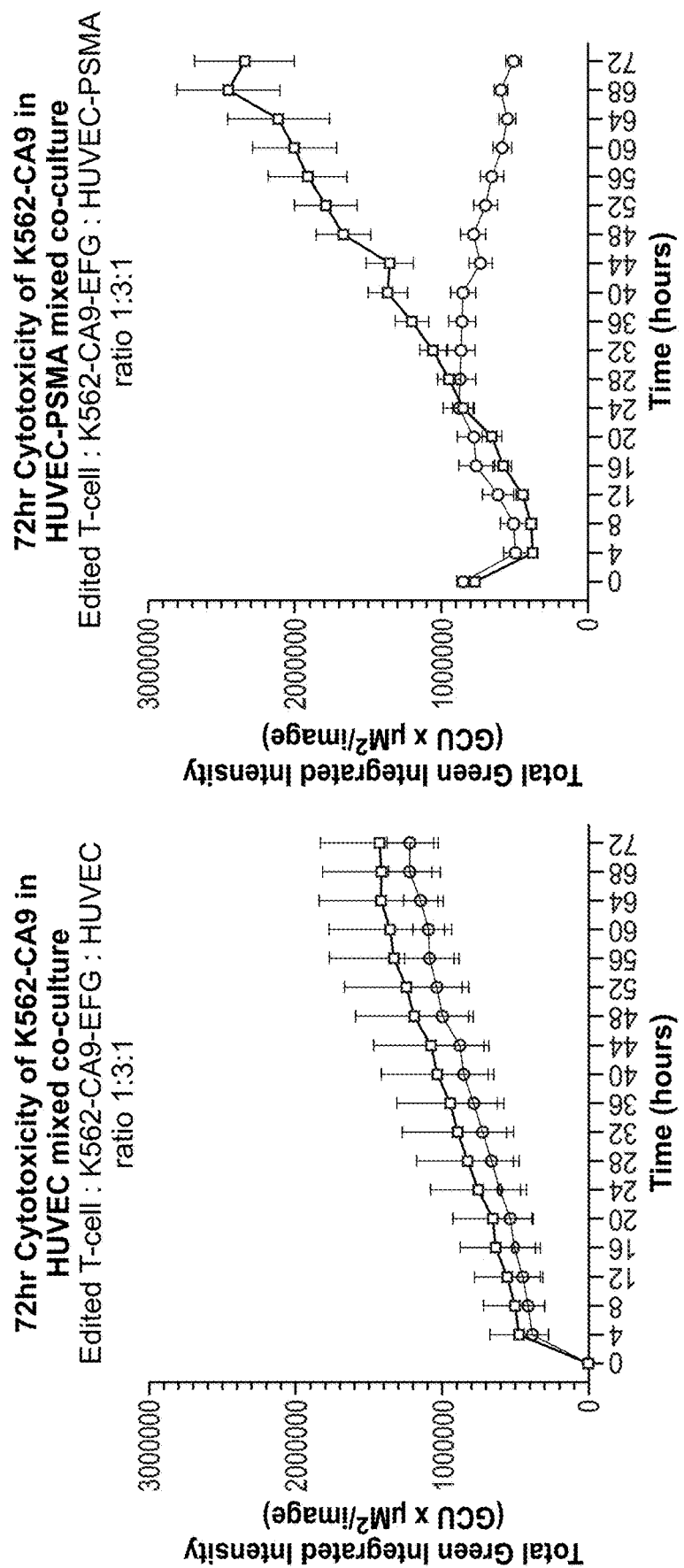
FIG. 17B shows that T cells can be primed during transmigration and can kill CA9+ tumor cells while unprimed ICT cells demonstrated no cytotoxicity

The feasibility of vascular priming was confirmed using a transwell assay where ICTs expressing LG 1 IC were primed by a PSMA expressing endothelial cell line and then migrated across a transwell membrane to kill CA9 expressing RCC cells (FIGS. 17A and 17B). As shown in FIG. 17A, T cells expressing a PSMA/CA9 logic gate can be primed during transmigration and can kill CA9+ tumor cells. As shown in FIG. 17B, the LG 1 ICT cells co-cultured with the HUVEC cells did not result in cytotoxicity of the K562-CA9 cells as the K562-CA9 cells continued to grow during the assay time course. In contrast, co-culturing the LG 1 ICT cells with HUVEC-PSMA cells did result in cytotoxicity of the K562-CA9 cells during the assay.

When constitutively expressed in the ICT cells, the SPA resulted in significant enhancements in T-cell potency and expansion. Repetitive stimulation assays, wherein T cells were challenged with tumor cells every 2 days, show that Class I SPAs result in 6-log or higher improved tumor cell clearance over a 2-week assay period. (data not shown) Across various mouse xenograft models (FIGS. 12A, 12D, 13B, and data not shown), SPA-expressing ICTs reach at least 6-fold improved tumor growth inhibition. RNAseq and ATACseq analysis indicate changes to gene expression profiles in T cells expressing Class I SPAs, with maintenance of T cell stem-like phenotypes, and restricted accessibility of various exhaustion marker genes (data not shown). Importantly, despite significantly increased levels of expansion, ICTs equipped with SPAs are not immortalized, showing no signs of cytokine-independent outgrowth. (data not shown) In addition, SPA-expressing ICT cells rapidly contract following tumor clearance in-vivo (FIG. 12B, 12C, 12E, 12F).

To further increase the potency and persistence of the ICT cells, an shRNA cassette targeting both FAS and TGFBR2, a receptor used for TGFB signaling in T cells, was inserted into the ICTs. Addition of FAS/TGFBR2 shRNAs enhanced antitumor activity of PSMAxCA9 logic gate expressing T cells during in vitro chronic stimulation assays conducted in the presence of exogenous TGFb (data not shown). Furthermore, FAS/TGFBR shRNA containing ICTs demonstrated enhanced antitumor activity in multiple xenograft RCC models (Example 4). Collectively, these results demonstrate that PSMAxCA9 ICT cells can (i) selectively target antigens that cannot generally be safely targeted by conventional CARs; and (ii) overcome multiple suppressive mechanisms in the tumor microenvironment.

Example 4: In Vivo Efficacy of PSMA primeR and CA9 CAR Logic Gate T Cells

Materials and Methods

A498 RCC Efficacy Model

Human ccRCC A498 cells express endogenous levels of CA-9 and were engineered to express physiological levels of PSMA antigen. $2\times10^6$ A498 PSMA cells were inoculated into the right dorsal flank of five-six weeks old, female NSG MHC I/II DKO mice. Day 35 post tumor inoculation, mean tumor volume of 150 mm$^3$ was reached and tumor-bearing animals were randomized into various treatment groups such that mean tumor volume per group was within 10% of the overall mean. Seven mice/group were injected intravenously with a single dose of $0.15\times10^6$ of PrimeR+ ICT cells expressing one of the five LG ICTs described in Example 3 (LG 1 IC, LG 2 IC, LG 3 IC, LG 4 IC, or LG 5 IC), RNP or PBS. The study was repeated with ICTs generated from two different normal donors. Tumor volumes and body weight were recorded bi-weekly. Tumor volume was calculated as per formula $\frac{1}{2}*L*W^2$, where L is tumor length and W is tumor width.

Blood pharmacokinetics demonstrated the expansion of ICTs on day 14 followed by complete contraction by day 42 post T cell injection. PrimeR+ ICTs in mouse blood were quantified to track expansion of ICTs using flow cytometry with count bright beads for T cell quantification/volume. Mean and SEM plotted.

Dual Flank Model

Human ccRCC 786-O cells were engineered to express either CA9 and PSMA or CA9 only. $2\times10^6$ 786-O-CA9+ and 786-O-CA9+-PSMA+ cells were inoculated into the left and right dorsal flank respectively of five-six weeks old, female NSG MHC I/II DKO mice. Day 35 post tumor inoculation, mean tumor volume of 150-200 mm$^3$ was reached on each flank and tumor-bearing animals were randomized into various treatment groups such that mean tumor volume per group on the right flank was within 10% of the overall mean. Seven mice/group were injected intravenously with a single dose of $0.25\times10^6$ or $1\times10^6$ of PrimeR+ ICT cells, constitutive CAR T cells, RNP or PBS control. Tumor volumes and body weight were recorded bi-weekly. Tumor volume was calculated as per formula $\frac{1}{2}*L*W^2$, where L is tumor length and W is tumor width. (B) tumor volumes on the 786-O CA9 only flank (left), and (C) tumor volumes on the 786-O-CA9+ PSMA+ flank (right). Data represents a single donor study with 7 mice per group, mean and SEM plotted.

Results

A498 RCC Efficacy Model

Figure 12A:
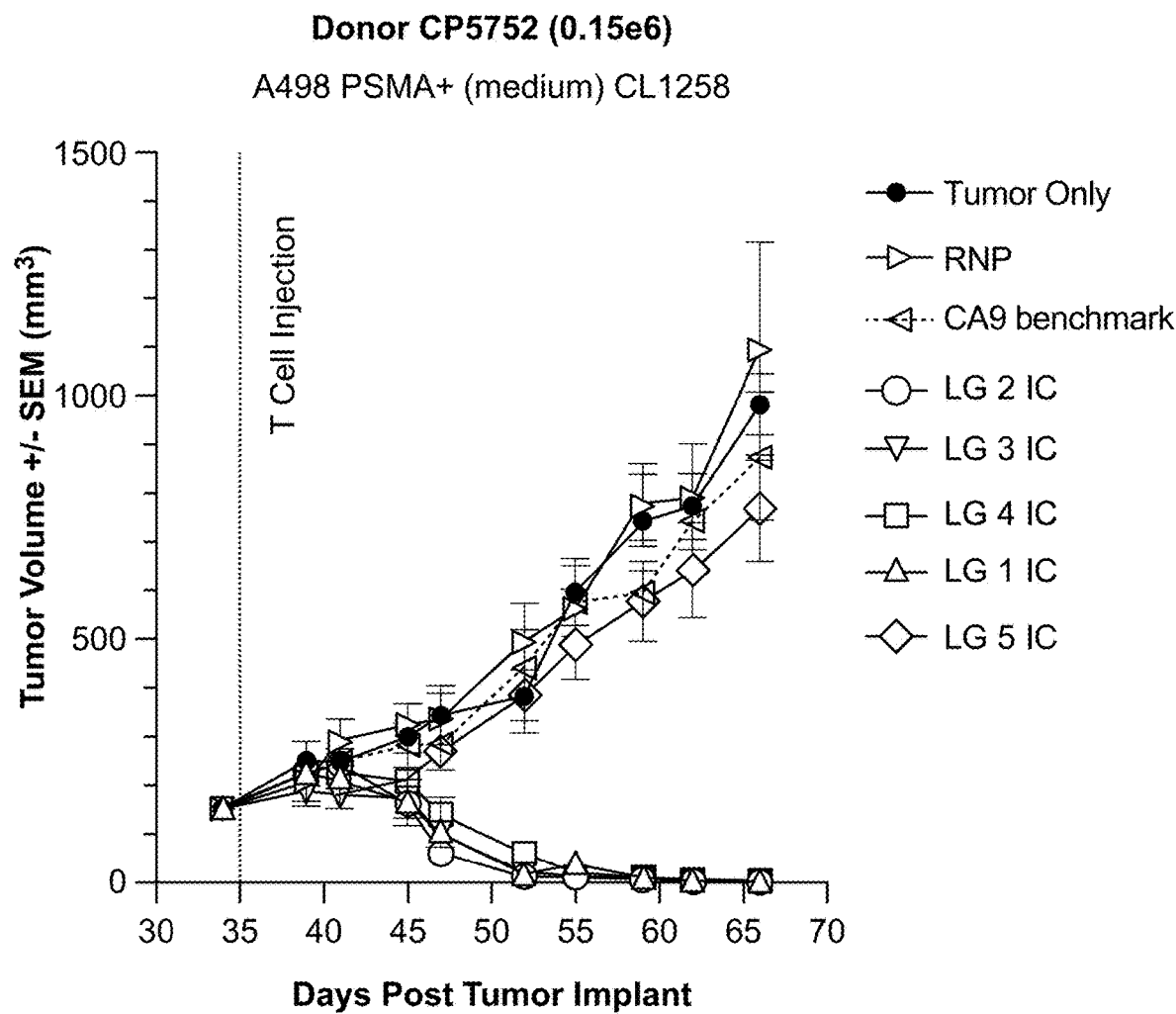
FIG. 12A shows the tumor volume post tumor implant in mice treated with ICTs expressing Logic Gates 1-5, RNP or PBS generated from donor 1.
Figure 12B:
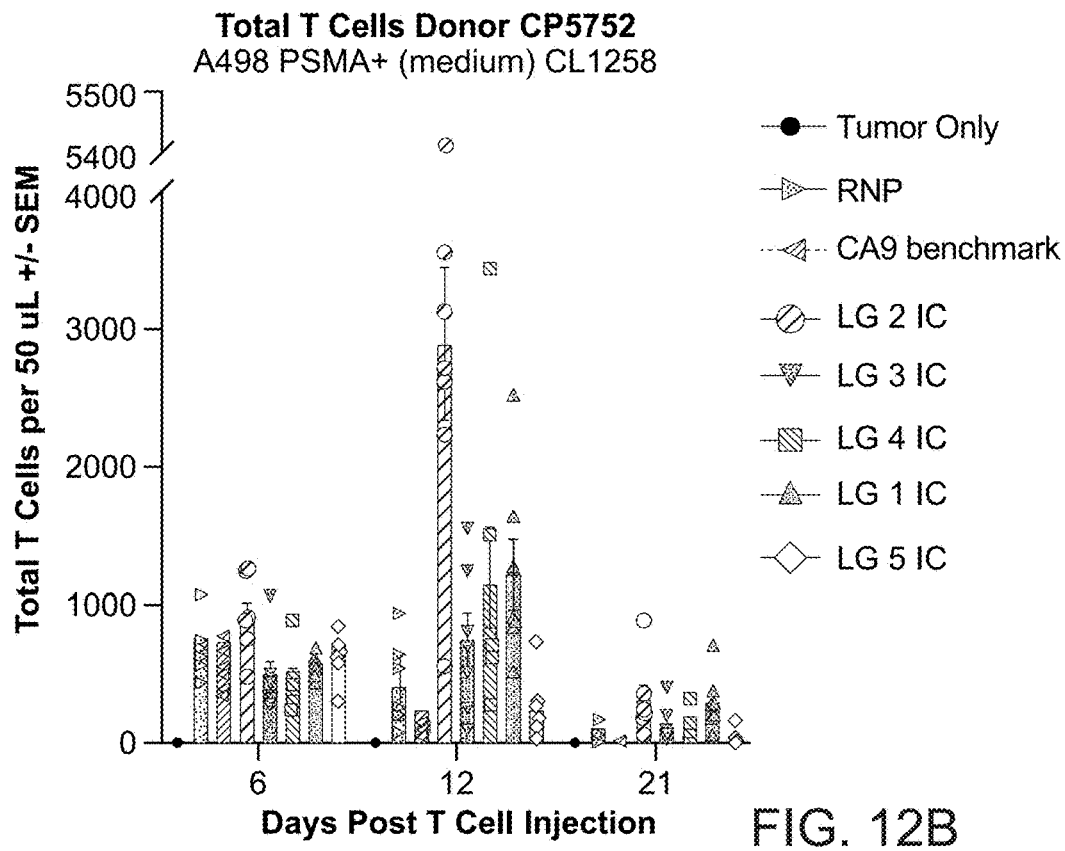
FIG. 12B shows the total T cells and expansion of the ICTs on day 12 post inoculation followed by contraction by day 21.
Figure 12C:
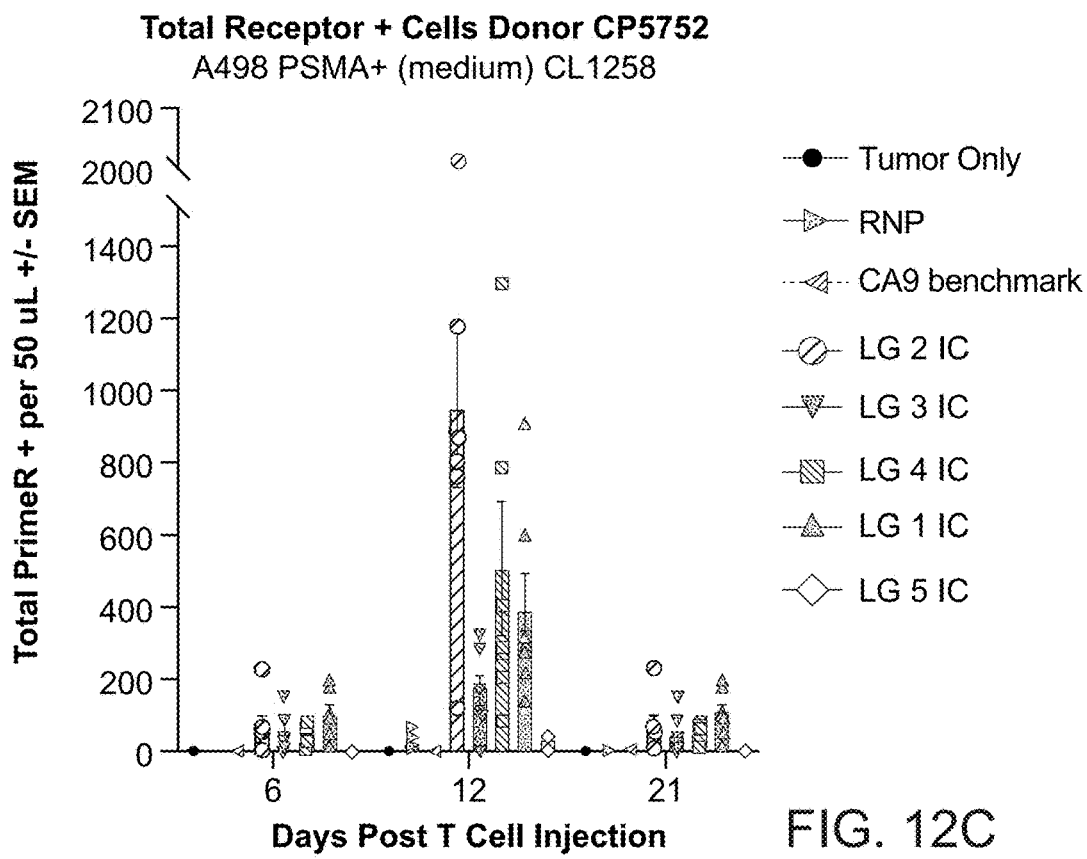
FIG. 12C shows total T cells expressing the priming receptor on days 12 and 21.
Figure 12D:
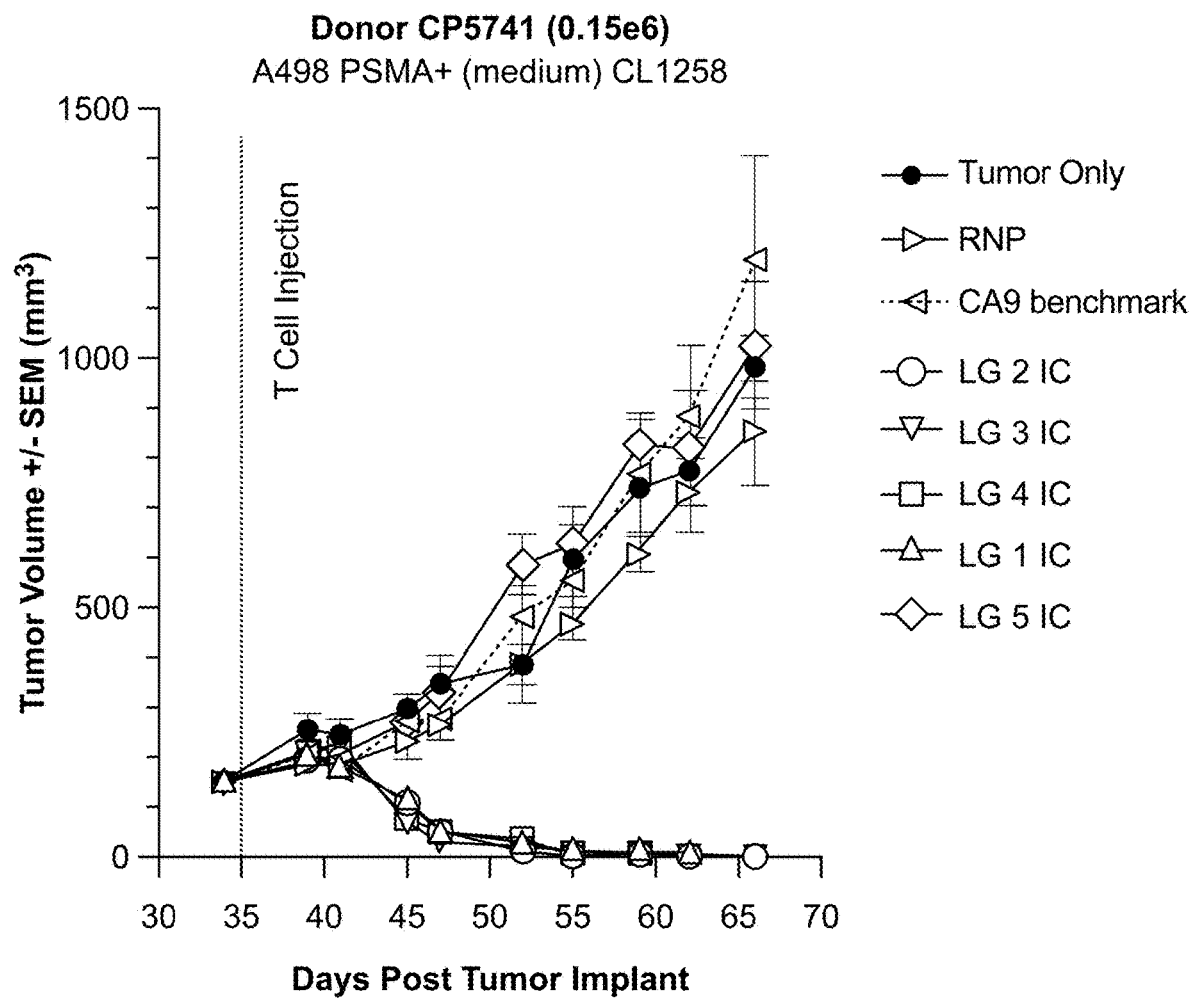
FIG. 12D show the tumor volume post tumor implant in mice treated with ICTs expressing Logic Gates 1-5, RNP or PBS generated from donor 2.
Figure 12E:
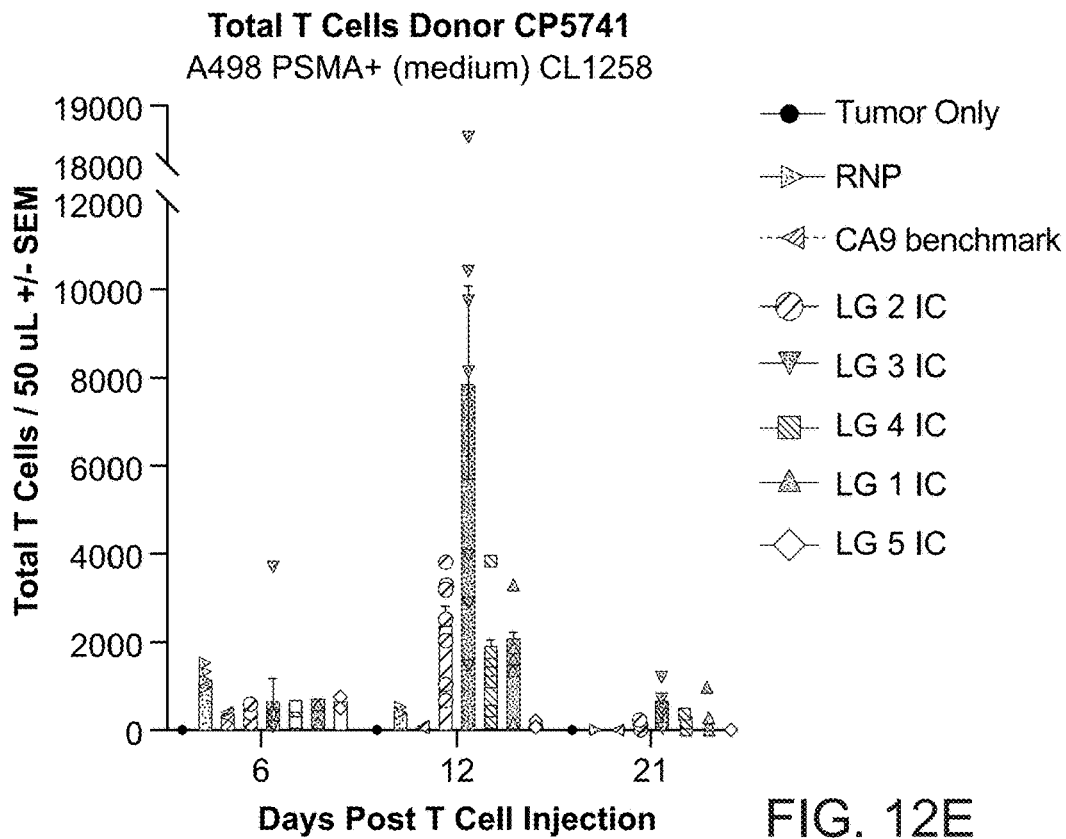
FIG. 12E shows the total T cells and expansion of the ICTs on day 12 post inoculation followed by contraction by day 21.
Figure 12F:
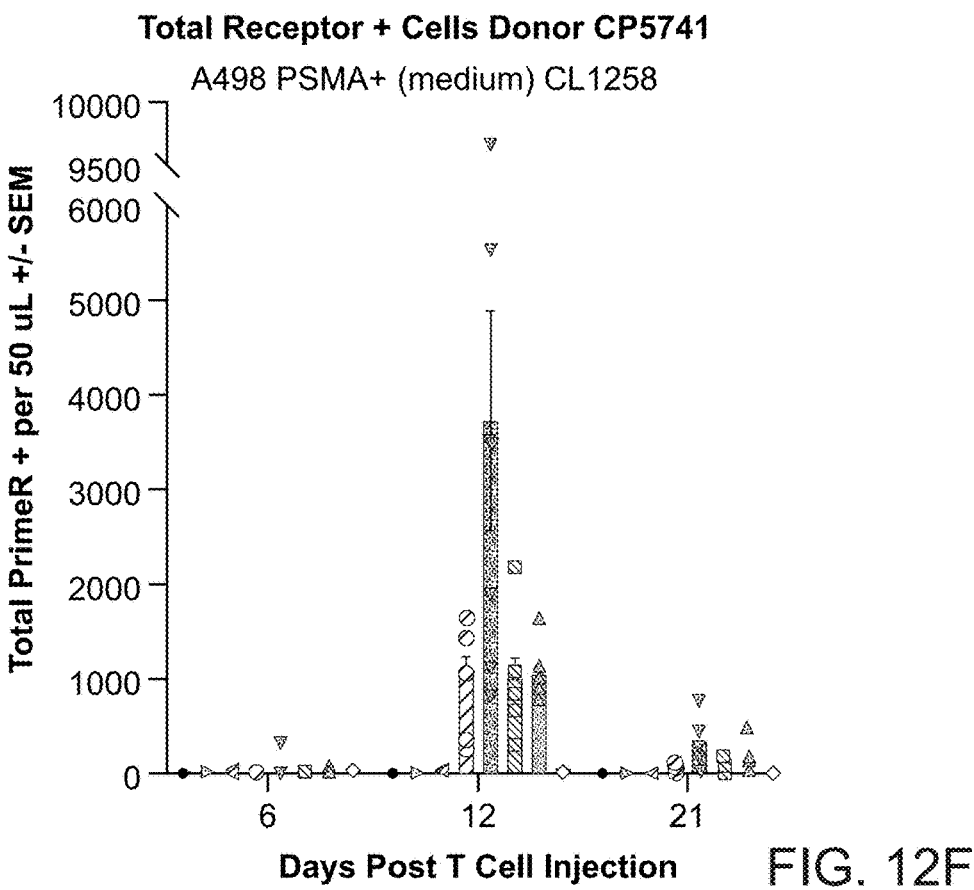
FIG. 12F shows total T cells expressing the priming receptor on days 12 and 21.

ICTs expressing LG 1-5 ICs showed tumor elimination in a ccRCC model. FIGS. 12A and 12D show the tumor volume post tumor implant in mice treated with ICTs expressing Logic Gates 1-5, RNP or PBS generated from T cells from either donor 1 (FIGS. 12A-C) or donor 2 (FIGS. 12D-F). FIGS. 12B and 12E show the total T cells and expansion of the ICTs on day 12 post inoculation followed by contraction by day 21. FIGS. 12C and 12F show total T cells expressing the priming receptor on days 12 and 21. In both replicates, the ICT cells demonstrated significant tumor-growth inhibition in mice (P<0.05).

Dual Flank Model

Figures 13A, 13B:
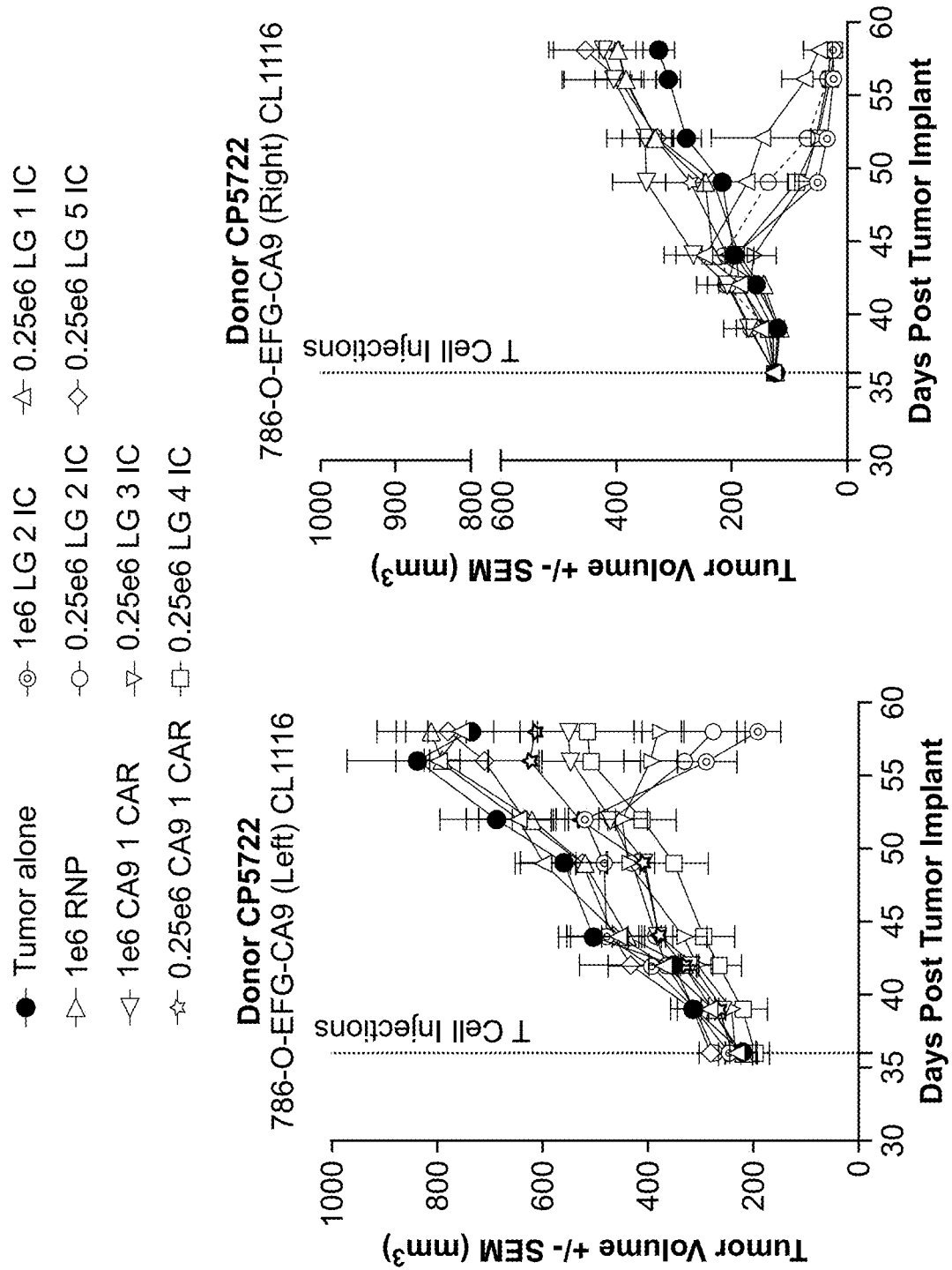
FIG. 13A shows tumor growth inhibition (TGI) in the single positive CA9-only flank.
FIG. 13B shows tumor growth inhibition (TGI) in the dual positive PSMA-CA9 flank.

The ICTs expressing LG 1-5 ICs showed specificity in a dual flank model (FIG. 13A-B). Greater tumor growth inhibition (TGI) was observed in the dual positive PSMA-CA9 flank (FIG. 13B) than the single positive CA9-only flank (FIG. 13A). Thus, the dual flank xenograft model shows that logic gated circuits (ICTs) more selectively killed tumors that express both CA9 and PSMA, and not tumors that express CA9 alone.

Figure 14:
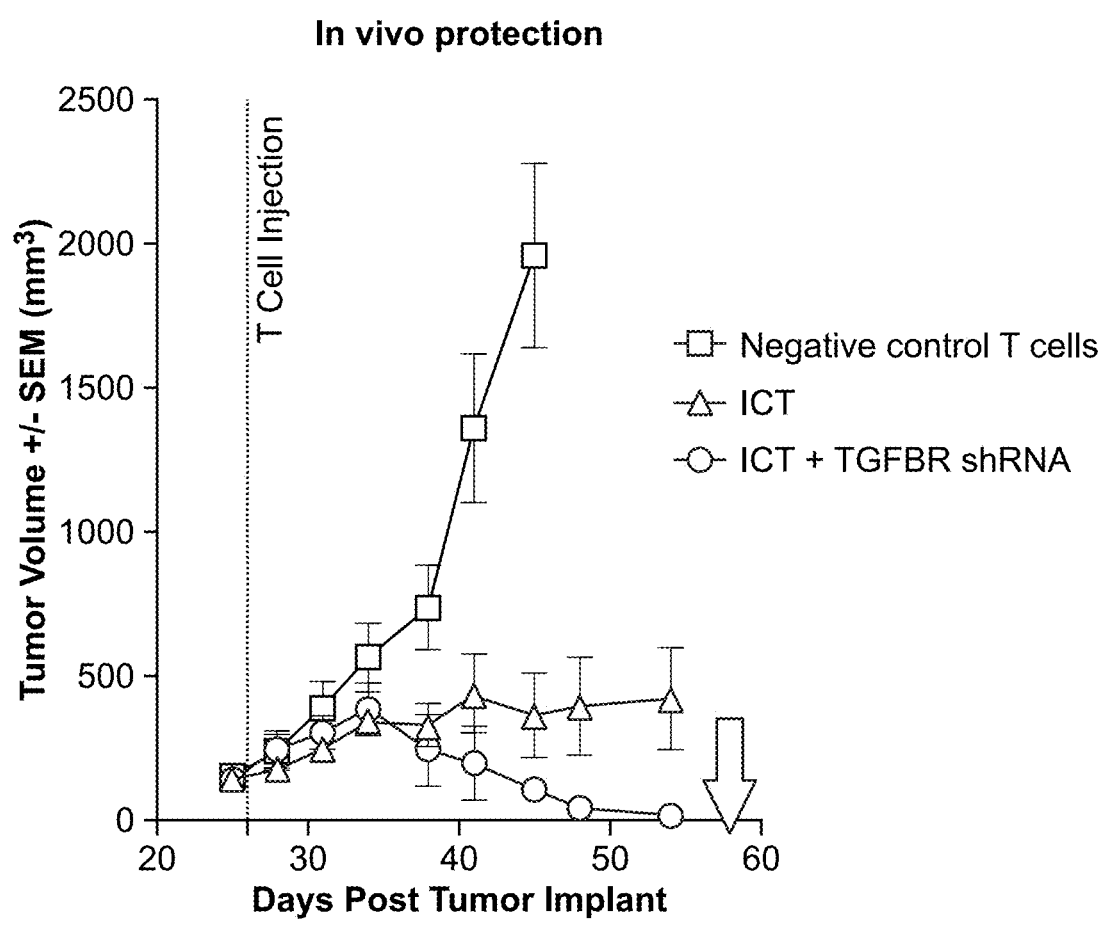
FIG. 14 shows that TGFBR knockdown protects ICT cells against TGFβ-mediated inhibition.
Figure 15:
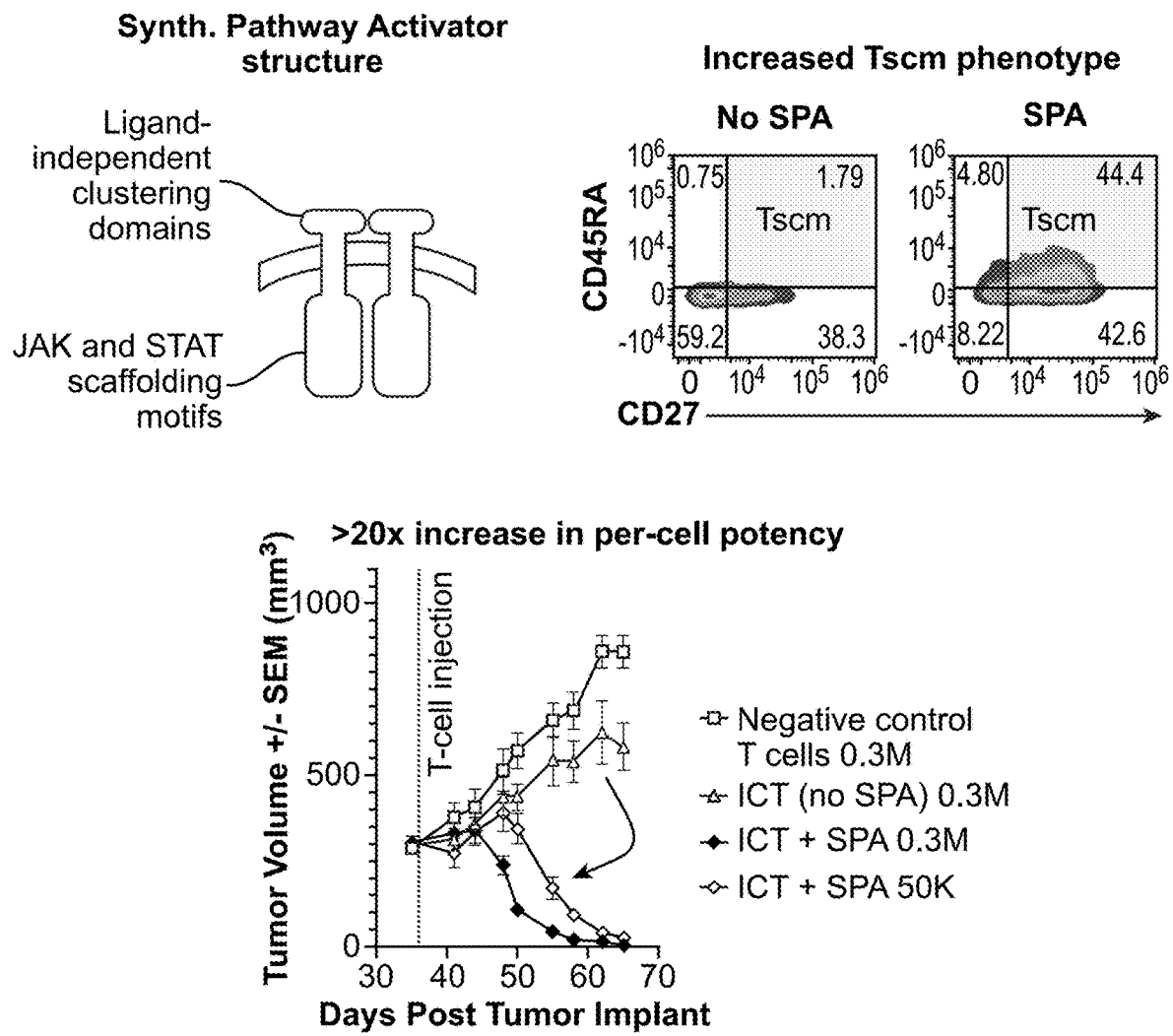
FIG. 15 shows an exemplary synthetic pathway activator and that synthetic pathway activators increase potency and T stem memory phenotype.
Figure 16:
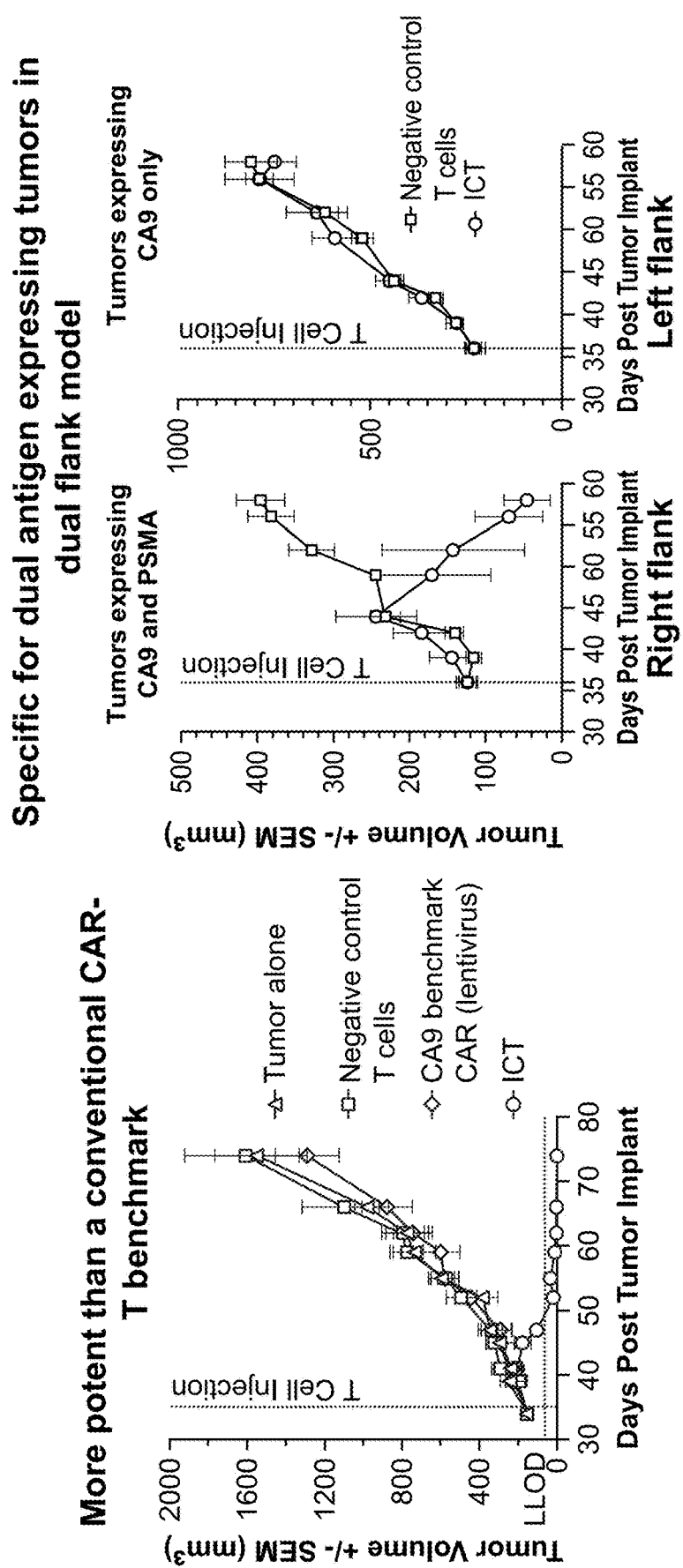
FIG. 16 shows that the ICT was more potent than a conventional CAR-T benchmark.

Example 5: Synthesis and Characterization of PSMA primeR and CA9 CAR Logic Gate T Cells with TGFBR Knockdown or a Synthetic Pathway Activator T cells expressing the PSMA and CA9 logic gate (also called integrated circuit T cells (ICTs)) as well as a synthetic pathway activator (SPA) and/or FAS and/or TGFBR shRNA were constructed and characterized. The results are provided in FIGS. 14, 15, and 16. FIG. 14 shows that TGFBR knockdown protected ICT cells against TGFβ-mediated inhibition in vitro. FIG. 15 shows the structure of an exemplary synthetic pathway activator and that synthetic pathway activators can increase cell anti-tumor potency and T stem cell memory phenotype. FIG. 16 shows that ICT cells are a potent and specific cell therapy in a Renal Cell Carcinoma model in vivo. ICT cells expressing a CA9 and PSMA logic gate demonstrated significant and specific tumor reduction against tumor cells expressing both CA9 and PSMA in a dual flank model as described in Example 4.

The ICT cells were also more potent than a conventional CA9 CAR T cell used as a benchmark.

Example 6: PSMA and CA9 Expression in Renal Carcinoma (ccRCC)

Materials and Methods

PSMA IHC Staining

Fixed human tumor tissue microarray (TMA) slides KD20811a, KD20812a, KD603, and KD951a ccRCC tumor samples were commercially purchased from Tissue Array LLC (TissueArray.com LLC, Derwood, MD). Briefly, TMA and control slides were baked at 60° C. for 1 hour in an oven. The slides were deparaffinized and rehydrated using standard methods. Antigen retrieval was performed using the Diva Decloaker buffer in a pressure cooker at 110° C. for 15 minutes. The slides were then placed inside an Biocare IntelliPATH FLX autostainer for staining. Briefly, the slides were subject to IntelliPATH Peroxidase Blocking Reagent, IntelliPATH Background Punisher, anti-PSMA antibody (Clone 3E6 or negative control), DAB chromogen, and lastly hematoxylin. The slides were then dehydrated, and the coverslips were applied onto the slides.

CA9 IHC Staining

The ccRCC tumor samples as described above were deparaffinized and rehydrated using standard methods. Antigen retrieval was performed using the Borg Decloaker buffer in a pressure cooker at 110° C. for 15 minutes. The slides were then placed inside an Biocare IntelliPATH FLX autostainer for staining. Briefly, the slides were subject to IntelliPATH Peroxidase Blocking Reagent, IntelliPATH Background Punisher, anti-CA9 antibody (Clone M75) or negative control), DAB chromogen, and lastly hematoxylin. The slides were then dehydrated, and the coverslips were applied onto the slides.

IHC Scoring

IHC scoring was manually conducted using brightfield microscopy. Positive CA9 staining was defined by either ≥50 or ≥80% of the evaluable tumor cells exhibiting 1+ or greater staining intensity on plasma membrane. Positive PSMA staining was defined by 1+ or greater staining of PSMA in ≥1% of endothelial cell staining in tumor cores. H-scores on tumors were calculated by standard methods.

Results

Figure 18:
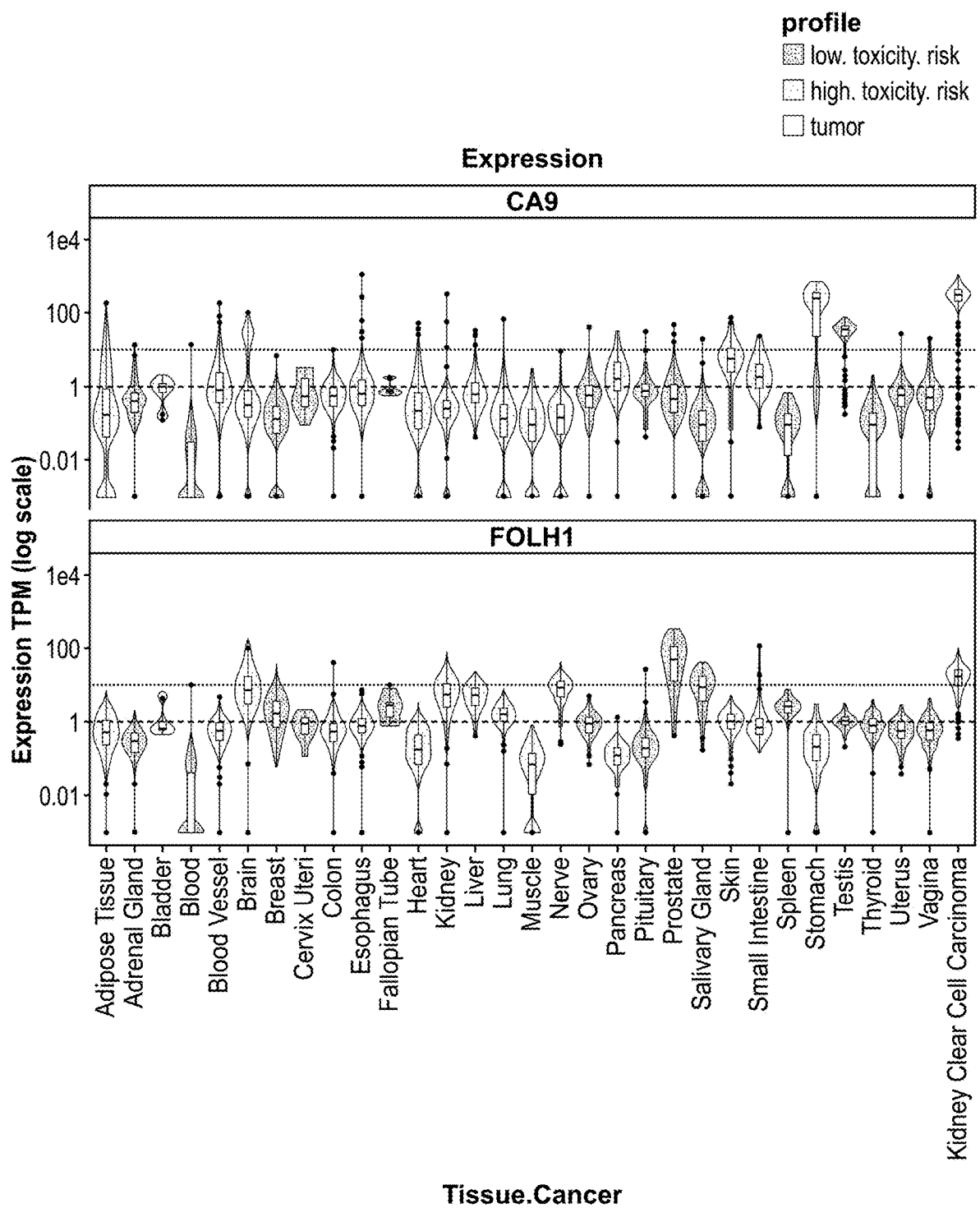
FIG. 18 shows the co-expression of PSMA and CA9 mRNA in ccRCC with limited overlapping expression in normal tissues
Figure 18:
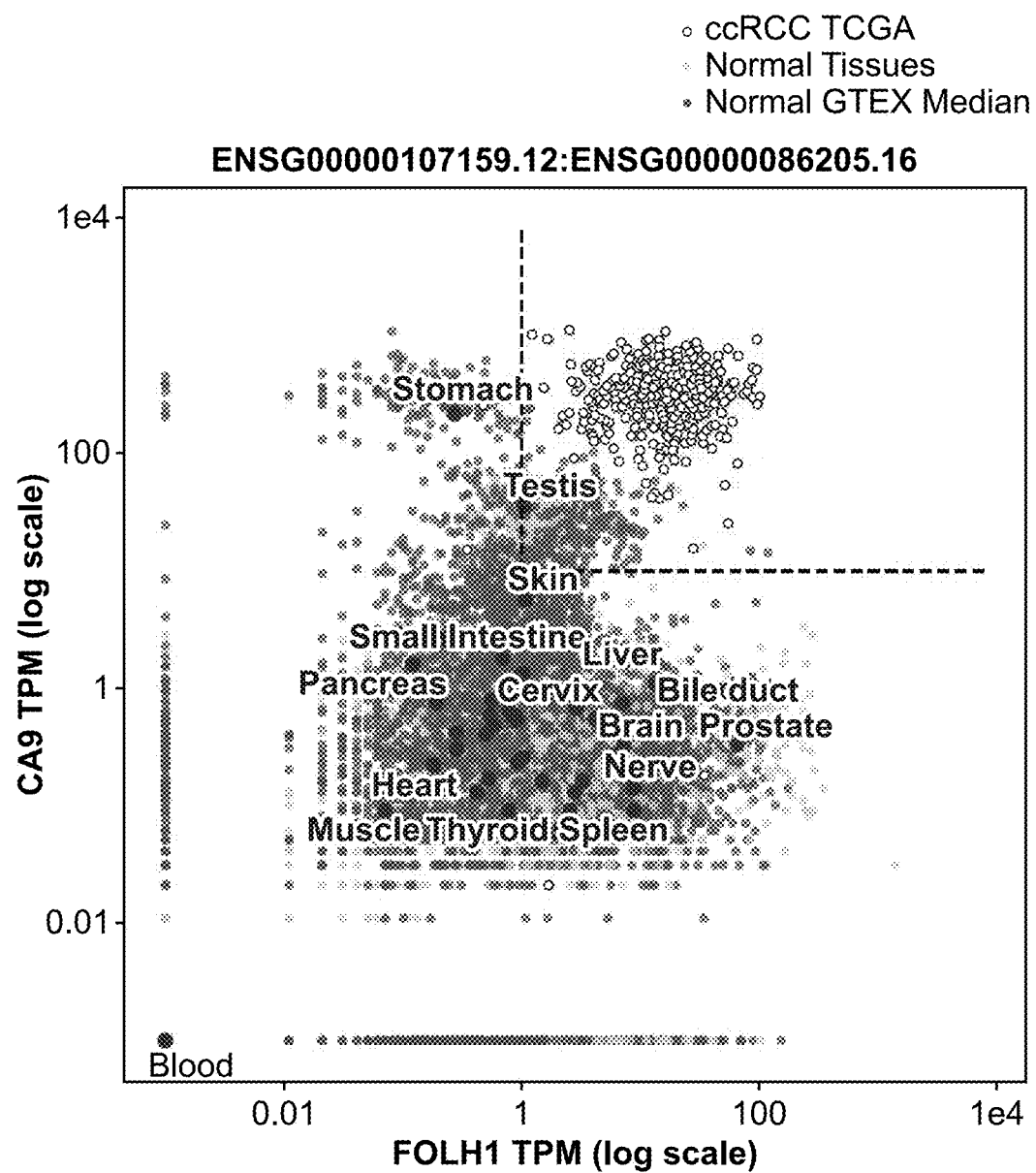

More than 2000 cytoplasmic membrane proteins and more than 4,00,000 potential antigens combinations were identified and compared to a tumor and primary sample bulk RNAseq database with more than 20,000 samples. Cytolytic targets had high expression in tumors with limited expression in normal tissues. Priming targets were expressed in tumors and not expressed in normal tissues with cytolytic targets. Exemplary target pairs had cytolytic and priming targets exclusively co-expressed in tumors. Out of this identification strategy, PSMA and CA9 were identified due to the co-expression of PSMA and CA9 mRNA in ccRCC with limited overlapping expression in normal tissues (FIG. 18).

Figure 19:
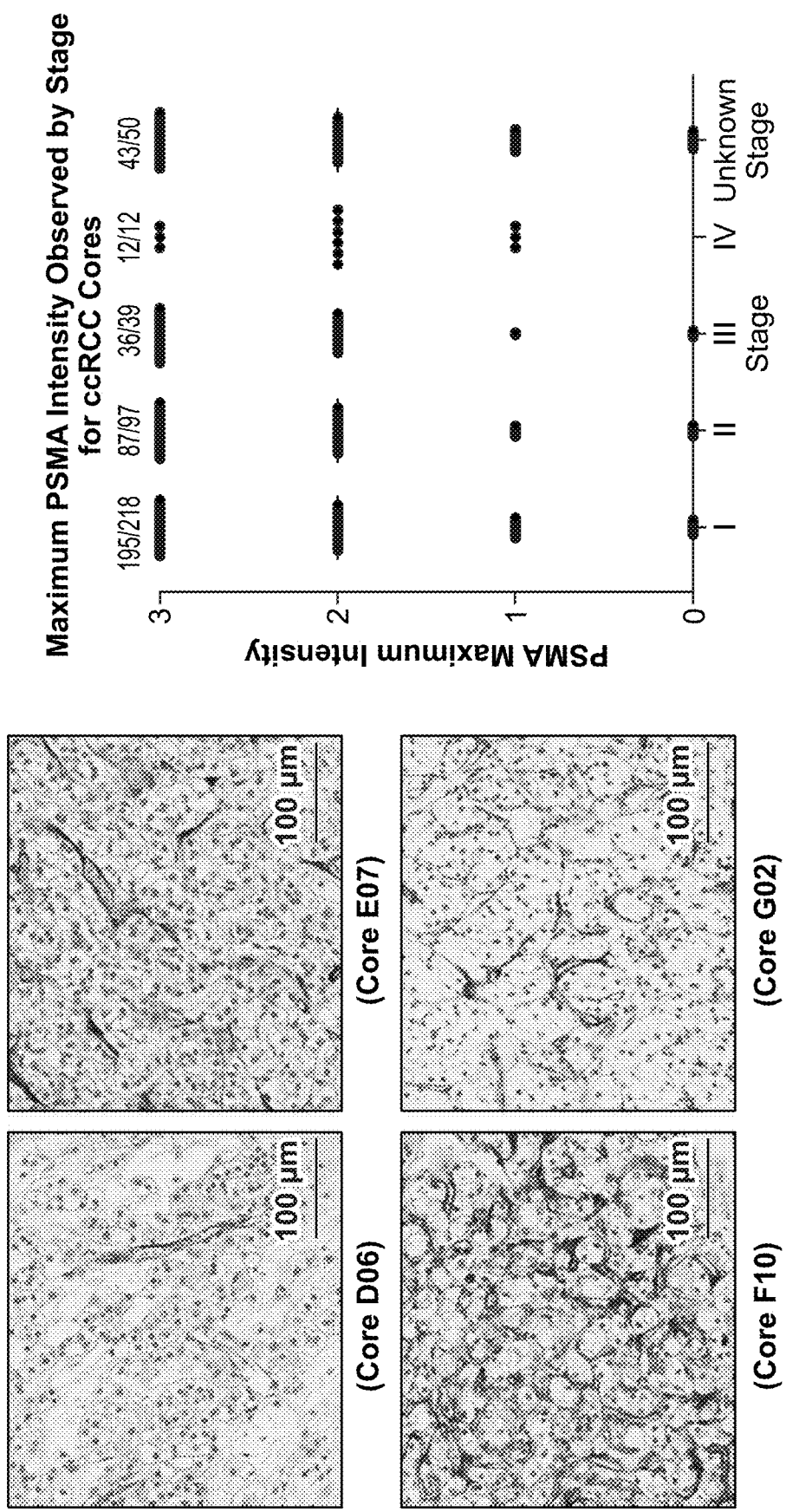
FIG. 19 shows representative images of endothelial cells in ccRCC tumor samples stained with anti-PSMA at different staining intensities with 40× magnification and maximum PSMA intensity according to different ccRCC disease stages.

IHC staining of endothelial cells in ccRCC tumor samples with anti-PSMA clone 3E6 (Agilent Technologies, Inc., Santa Clara, CA) showed that ccRCC vasculature is PSMA-positive (PSMA+). Representative images at different staining intensities with 40× magnification are provided in FIG. 19. PSMA IHC intensity was scored on ccRCC tumor microarrays KD20811a, KD20812a, KD603, and KD951a and binned by AJCC disease stage (FIG. 19). As shown in FIG. 19, PSMA expression was observed on cells in all stages of ccRCC.

Figure 20:
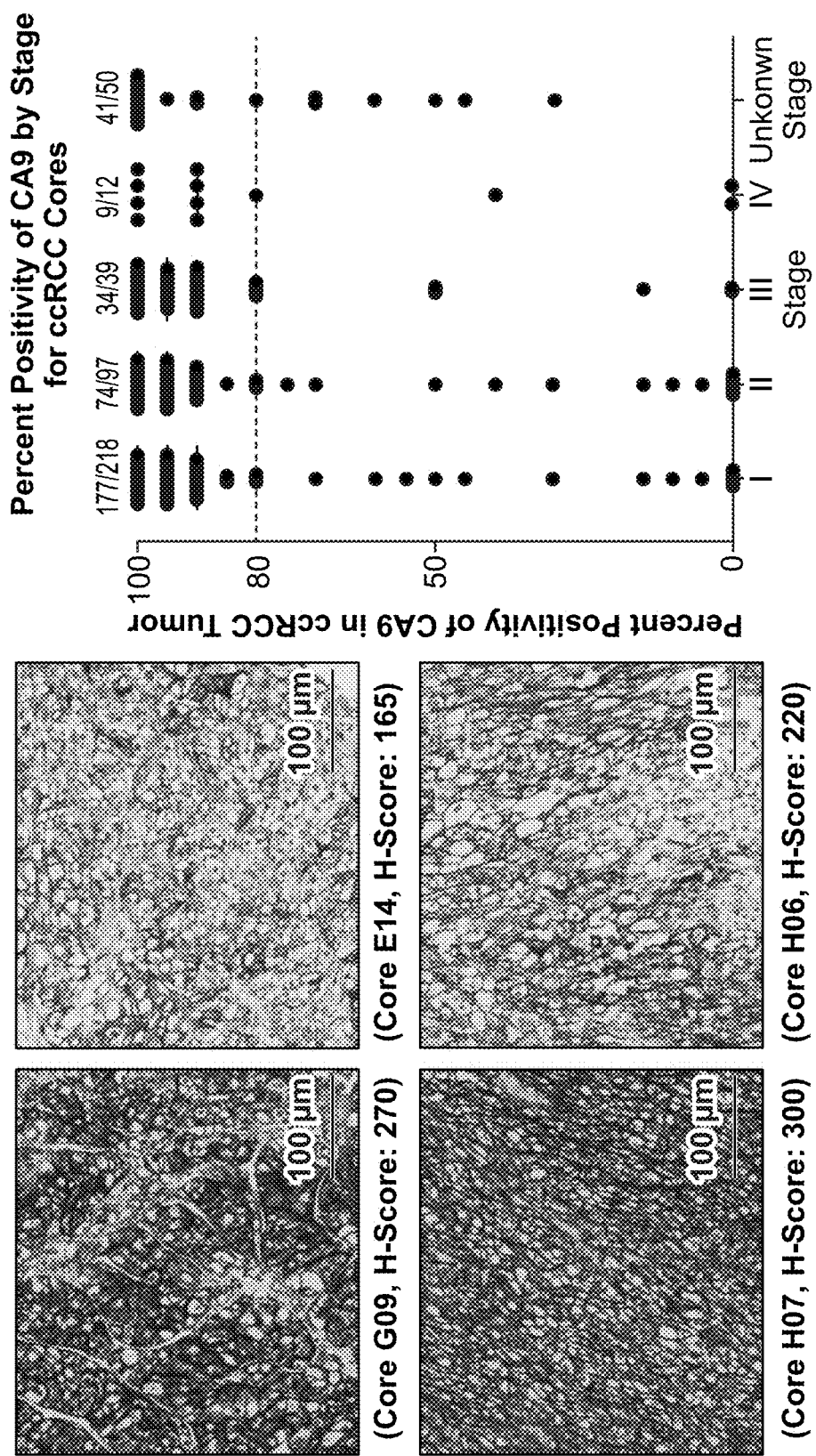
FIG. 20 shows representative images of endothelial cells in ccRCC tumor samples stained with anti-CA9 at different staining intensities with 40× magnification and percent positivity of CA9 in ccRCC tumor samples according to different ccRCC disease stages.

IHC staining of endothelial cells in ccRCC tumor samples with anti-CA9 clone M75 (Creative Biolabs, Shirley, NY) showed that ccRCC tumors are CA9-positive (CA9+). Representative images at different staining intensities with 40× magnification are provided in FIG. 20. CA9 IHC intensity was scored on ccRCC tumor microarrays KD20811a, KD20812a, KD603, and KD951a and binned by AJCC disease stage (FIG. 20). As shown in FIG. 20, CA9 expression was observed on ccRCC cells in all stages of ccRCC.

Figure 21A:
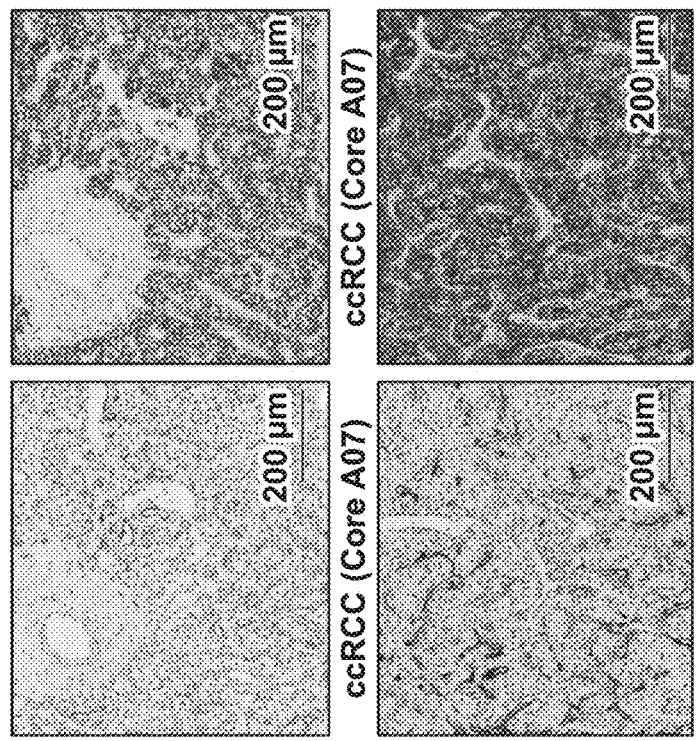
FIG. 21A provides representative images of ccRCC tumor samples co-stained for PSMA and CA9 with 20× magnification.
Figure 21B:
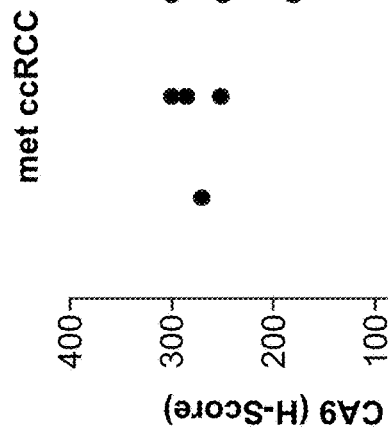
FIG. 21B shows co-expression of PSMA and CA9 in ccRCC via IHC (n=416).
Figure 21C:
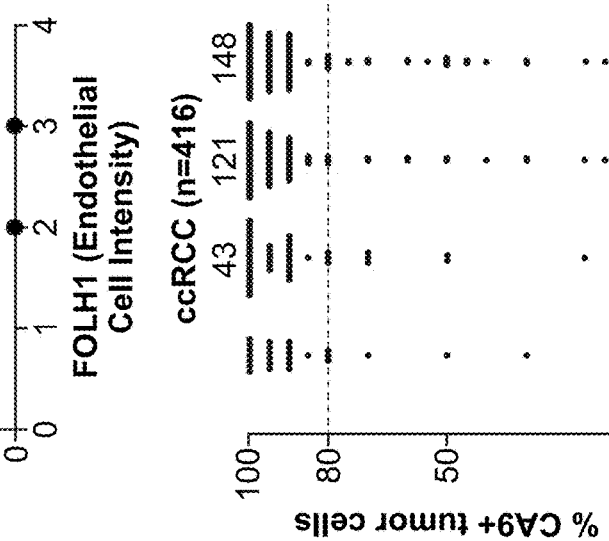
FIG. 21C provides co-positivity measurement of PSMA and CA9 in metastatic specimens.

PSMA and CA9 were commonly co-positive in ccRCC. Representative images of ccRCC tumor samples co-stained for PSMA and CA9 with 20× magnification are provided in FIG. 21A. Co-expression of PSMA and CA9 in ccRCC via IHC (n=416) is provided in FIG. 21B. Positivity of PSMA was defined at 1+ or greater intensity of IHC signal observed in ccRCC endothelial compartment. Positivity of CA9 was set as 80% of the tumor expressing 1+ or greater intensity of IHC signal. Using these relative cutoff criteria for PSMA and CA9 positivity, co-positivity of PSMA and CA9 was 75% (312/416) in ccRCC by IHC. FIG. 21C provides co-positivity measurement of PSMA and CA9 in metastatic specimens according to the previous cutoff criteria. In these samples, co-positivity was 73% (8/11).

Figure 22:
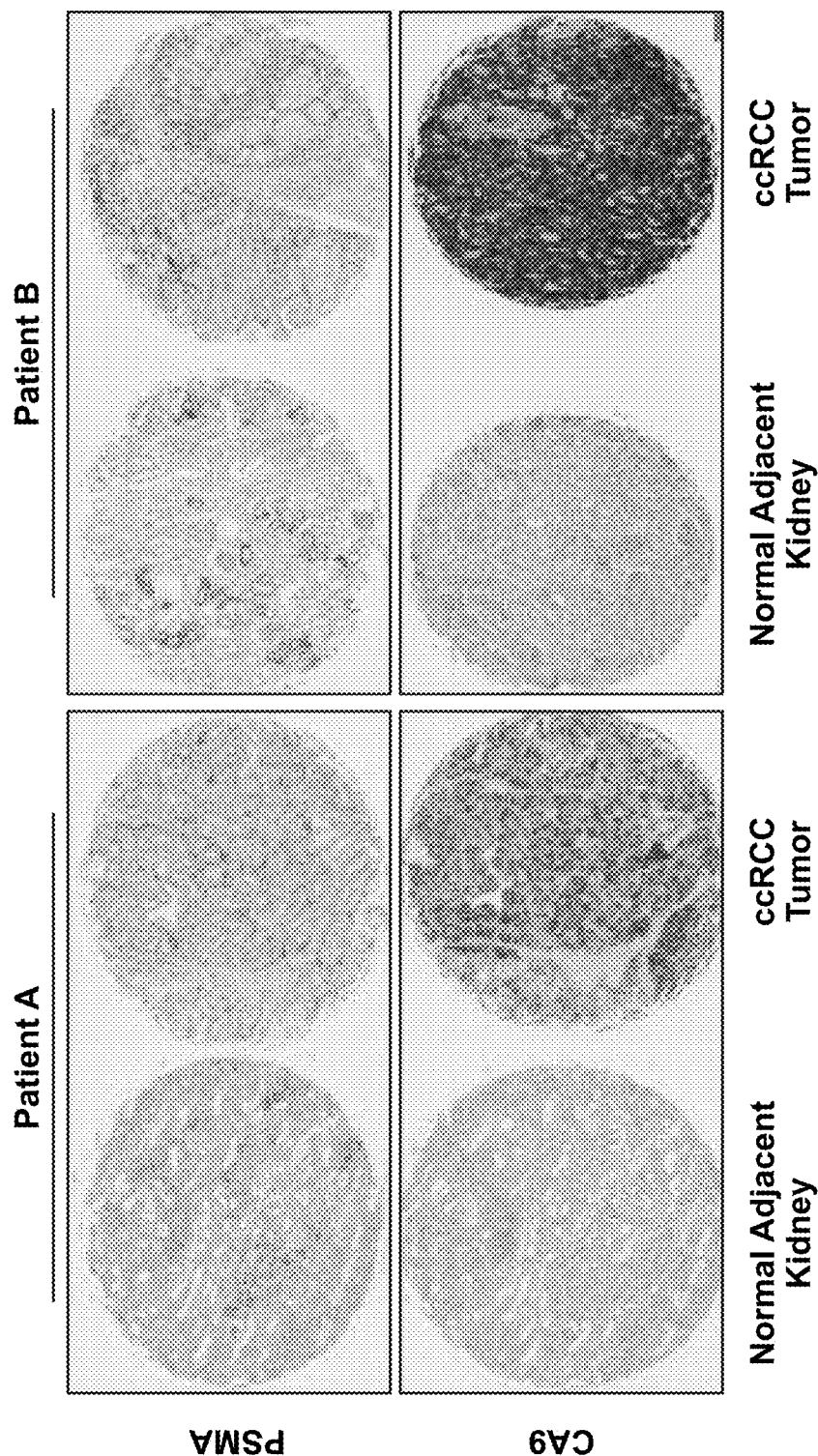
FIG. 22 provides images of CA9 and PSMA IHC staining in ccRCC samples versus normal adjacent kidney samples.

Normal adjacent kidney tissue was negative for CA9 staining, indicating that CA9 positivity is associated with ccRCC tumors. FIG. 22 provides images of CA9 and PSMA IHC in ccRCC samples versus normal adjacent kidney samples. Representative images of patient-matched ccRCC and normal adjacent kidney specimens were stained with PSMA and CA-9 antibodies as described above. Stained sections may not be sequential. PSMA staining was observed in both normal adjacent kidney samples and tumor samples, while CA9 expression was limited to tumor samples only.

PSMA and CA9 were identified as priming and cytolytic antigen targets, respectively, in clear cell renal cell carcinoma (ccRCC). Using a bioinformatic discovery path, PSMA and CA9 mRNA are co-expressed in 94% of ccRCC tumors (n=530, TCGA). Immunohistochemical (IHC) assessments further reveal robust membranous PSMA and CA9 protein co-expression in 80% of ccRCC (n=416). Expression of CA9 and PSMA was evaluated across disease stage and co-expression was confirmed throughout disease progression. Distant metastases similarly showed evidence of common expression. In contrast, IHC assessment of normal tissues revealed limited membranous co-expression of PSMA and CA9 in normal high-risk toxicity tissues. Without wishing to be bound by theory, these findings collectively support the utility of PSMA and CA9 as target antigens for AND-logic-gated therapeutics for the treatment of ccRCC.

Example 7: PSMA and CA9 Expression in Colorectal Cancer (CRC)

Materials and Methods

PSMA IHC Staining

Fixed human tumor tissue microarray (TMA) slides (CO1922) were commercially purchased from US Biomax. Briefly, TMA and control slides were baked at 60° C. for 1 hour in an oven. The slides were deparaffinized and rehydrated using standard methods. Antigen retrieval was performed using the Diva Decloaker buffer in a pressure cooker at 110° C. for 15 minutes. The slides were then placed inside an Biocare IntelliPATH FLX autostainer for staining. Briefly, the slides were subject to IntelliPATH Peroxidase Blocking Reagent, IntelliPATH Background Punisher, anti-PSMA antibody (Clone 3E6 (Agilent Technologies, Inc., Santa Clara, CA) or negative control), DAB chromogen, and lastly hematoxylin. The slides were then dehydrated, and the coverslips were applied onto the slides.

CA9 IHC Staining

Fixed human tumor tissue microarray (TMA) slides (described above) were deparaffinized and rehydrated using standard methods. Antigen retrieval was performed using the Borg Decloaker buffer in a pressure cooker at 110° C. for 15 minutes. The slides were then placed inside an Biocare IntelliPATH FLX autostainer for staining. Briefly, the slides were subject to IntelliPATH Peroxidase Blocking Reagent, IntelliPATH Background Punisher, anti-CA9 antibody (Clone M75 (Creative Biolabs, Shirley, NY)) or negative control), DAB chromogen, and lastly hematoxylin. The slides were then dehydrated, and the coverslips were applied onto the slides.

IHC Scoring

IHC scoring was manually conducted using brightfield microscopy. Positive CA9 staining was defined by either ≥50 or ≥80% of the evaluable tumor cells exhibiting 1+ or greater staining intensity on plasma membrane. Positive PSMA staining was defined by 1+ or greater staining of PSMA in ≥1% of endothelial cell staining in tumor cores. H-scores on tumors were calculated by standard methods.

Results

Figure 23:
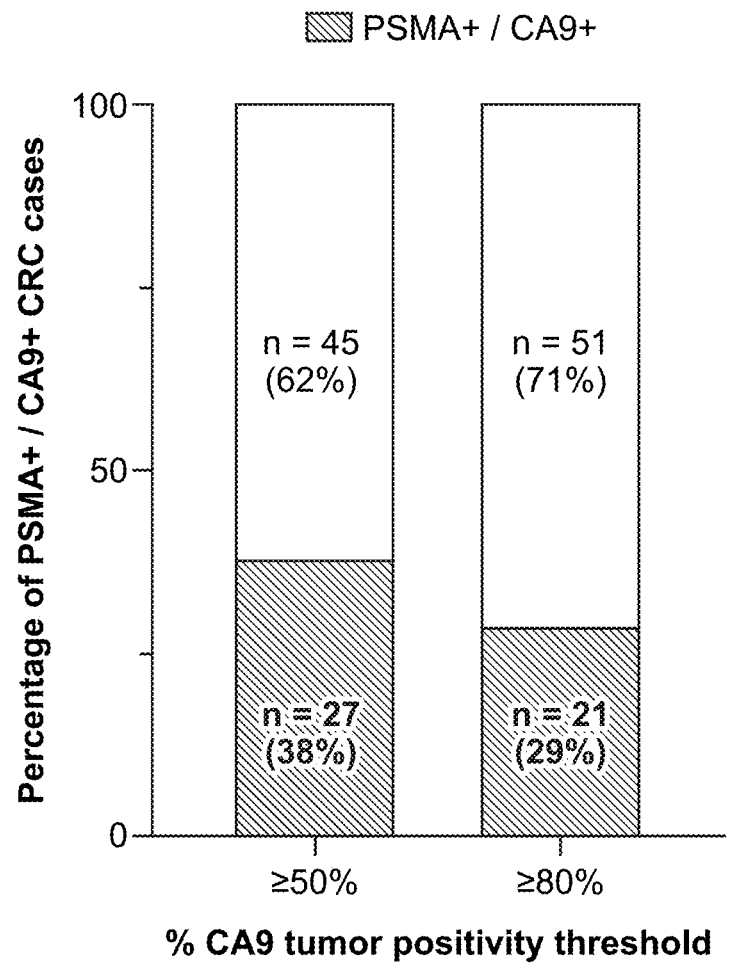
FIG. 23 shows the percentage of colorectal cancer patient samples, based on the CO1922 tissue microarray (TMA), that exhibited expression of both PSMA and CA9.

38% of colorectal cancer (CRC) tumor samples exhibited co-positivity of both PSMA and CA9 after applying a >50% tumor positivity IHC threshold. Increasing the IHC positivity threshold to 80% resulted in 29% of the CRC tumor samples exhibiting co-positivity of both PSMA and CA9 (FIG. 23). FIG. 23 shows the percentage of colorectal cancer patient samples, based on the CO1922 tissue microarray (TMA), that exhibited expression of both PSMA and CA9. The number of patient specimens exhibiting positivity for both PSMA and CA9 is listed as n, with the percentage (%) underneath.

Example 8: PSMA and CA9 Expression in Lung Cancer

Materials and Methods

PSMA IHC Staining

Fixed human tumor tissue microarray (TMA) slides for lung adenocarcinoma (LU-AD) and lung squamous cell carcinoma (LU-SSC) (tissue array LC819a) were commercially purchased from Tissue Array LLC (Tissue Array.com LLC, Derwood, MD). PSMA staining was performed as described in Examples 6 and 7. Lung adenocarcinoma (LU-AD) and lung squamous cell carcinoma (LU-SSC) samples were purchased from.

CA9 IHC Staining

Fixed human tumor tissue microarray (TMA) slides for lung adenocarcinoma (LU-AD) and lung squamous cell carcinoma (LU-SSC) (tissue array LC819a) were commercially purchased from Tissue Array LLC (Tissue Array.com LLC, Derwood, MD). CA9 staining was performed as described in Examples 6 and 7.

IHC Scoring

IHC scoring was manually conducted using brightfield microscopy. Positive CA9 staining was defined by either ≥50 or ≥80% of the evaluable tumor cells exhibiting 1+ or greater staining intensity on plasma membrane. Positive PSMA staining was defined by 1+ or greater staining of PSMA in ≥1% of endothelial cell staining in tumor cores. H-scores on tumors were calculated by standard methods.

Results

Figure 24:
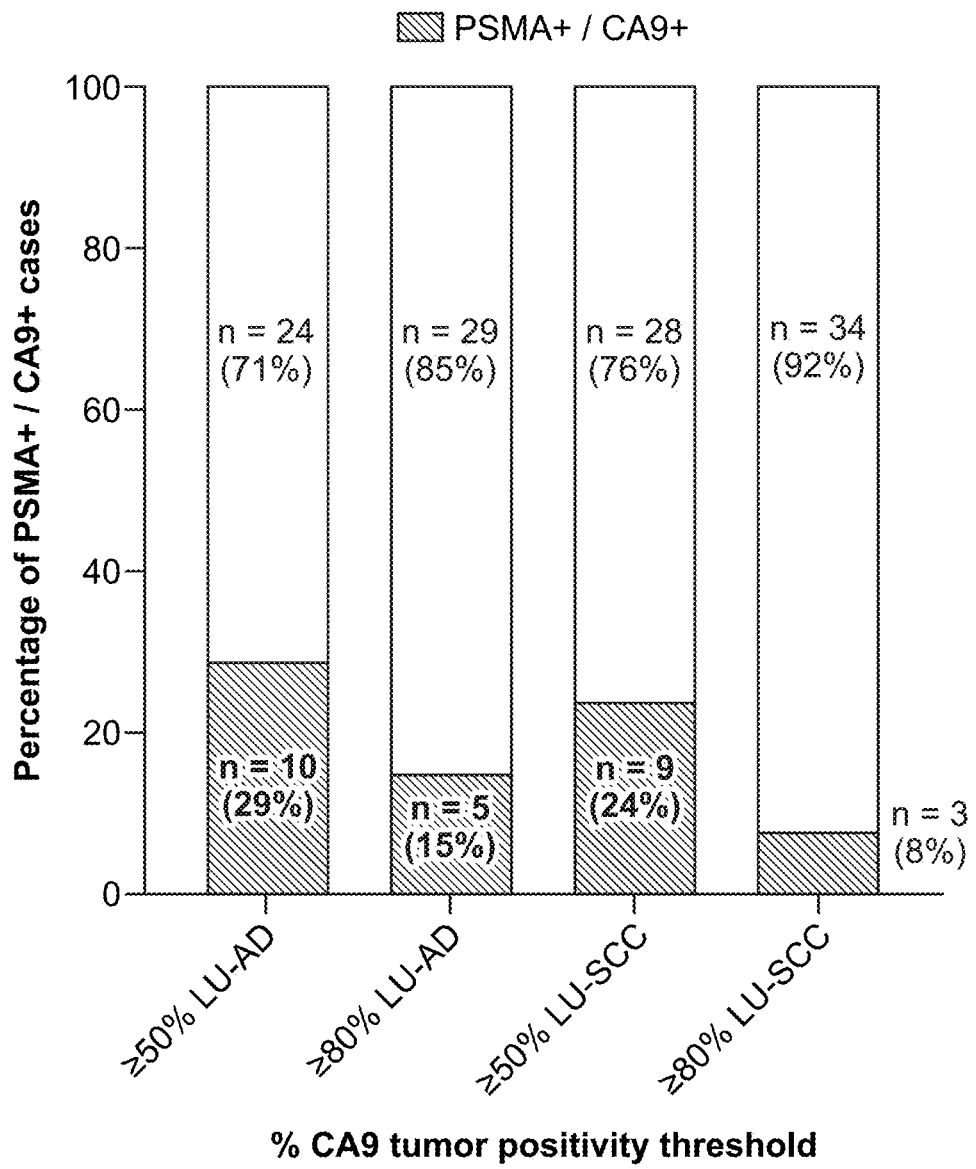
FIG. 24 shows the percentage of lung cancer patients, based on the LC819a TMA, that exhibited expression of both PSMA and CA9. The number of patient specimens exhibiting positivity for both PSMA and CA9 is listed as n, with the percentage (%) underneath.

The prevalence of PSMA and CA9 expression in lung adenocarcinoma (LU-AD) and lung squamous cell carcinoma (LU-SSC), subtypes that account for approximately 70% of all lung cancer, was analyzed via immunohistochemistry (IHC) (FIG. 24). FIG. 24 shows the percentage of lung cancer patients, based on the LC819a TMA, that exhibited expression of both PSMA and CA9. The number of patient specimens exhibiting positivity for both PSMA and CA9 is listed as n, with the percentage (%) underneath.

29% of LU-AD patient samples exhibited co-positivity of both PSMA and CA9 after applying a >50% tumor positivity IHC threshold. Increasing the IHC positivity threshold to 80% resulted in 15% of the LU-AD patient samples exhibiting co-positivity of both PSMA and CA9 (FIG. 24).

24% of LU-SCC patient samples exhibited co-positivity of both PSMA and CA9 after applying a >50% tumor positivity IHC threshold. Increasing the IHC positivity threshold to 80% resulted in 8% of the LU-SCC patient samples exhibiting co-positivity of both PSMA and CA9 (FIG. 24).

Figure 25:
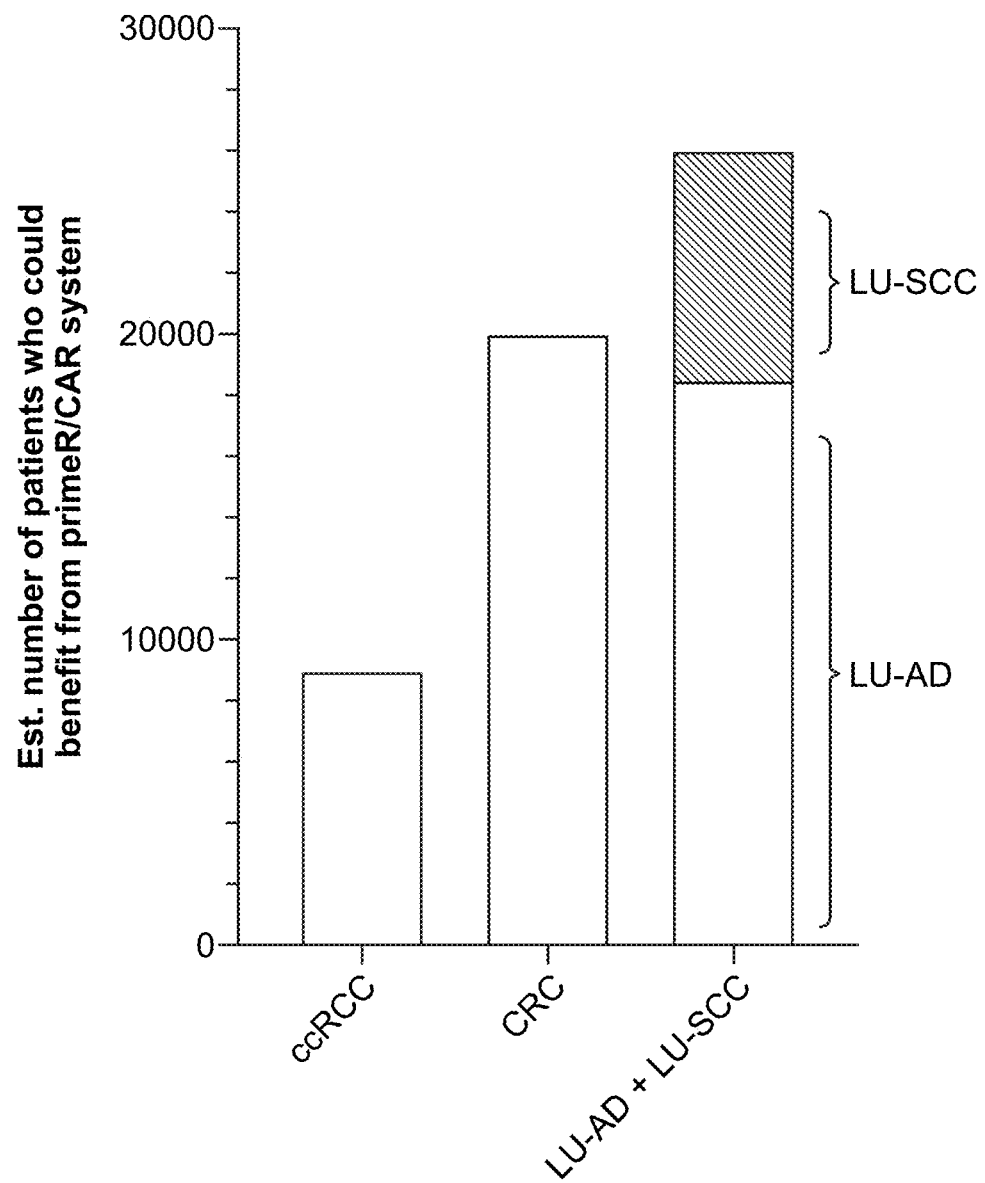
FIG. 25 provides an estimated number of patients that may benefit from treatment with a PSMA primeR/CA9 CAR Logic Gate T cell described herein. The numbers are calculated based on estimated new deaths from the indicated cancer types in 2023 from the American Cancer Society.

To assess the number of ccRcc, colorectal and lung cancer patients who may benefit from PSMA primeR and CA9 CAR Logic Gate T cells described in Examples 1 to 5, an analysis based on the estimated new deaths for each indication in 2023 and percentage of patients that express PSMA and CA9 was conducted. Based on this calculation, approximately 9,000, 20,000, 64,000 and 32,000 ccRcc, CRC, LU-AD and LU-SCC patients, respectively, may benefit from the PSMA primeR and CA9 CAR Logic Gate T cells disclosed herein (FIG. 25).

Example 9: Human Clinical Trial Study Design

Materials and Methods

Patients will be enrolled into a phase ½ open label, multicenter study for safety and efficacy of the LG T cells (PrimeR$^+$ cells) described in Examples 1 to 5 to treat advanced/metastatic clear cell renal cell carcinoma (ccRCC). The targeted patient population will be patients with advanced/metastatic clear cell renal cell carcinoma (ccRCC) after immune checkpoint inhibitor and VEGF-targeted therapy. No initial selection for PSMA and CA9 expression will be performed.

The study will consist of phase 1 for safety/escalation dosing and phase 2 for efficacy. The Phase 1 study design is a First-in-Human (FIH) escalation with patient backfill in a 3+3 design. There will be approximately 60 patients in the phase 1 cohort. The phase 1 backfill cohorts can be up to 12 patients/cohort. There will be up to 70 patients in the phase 2 cohort.

Figure 26:
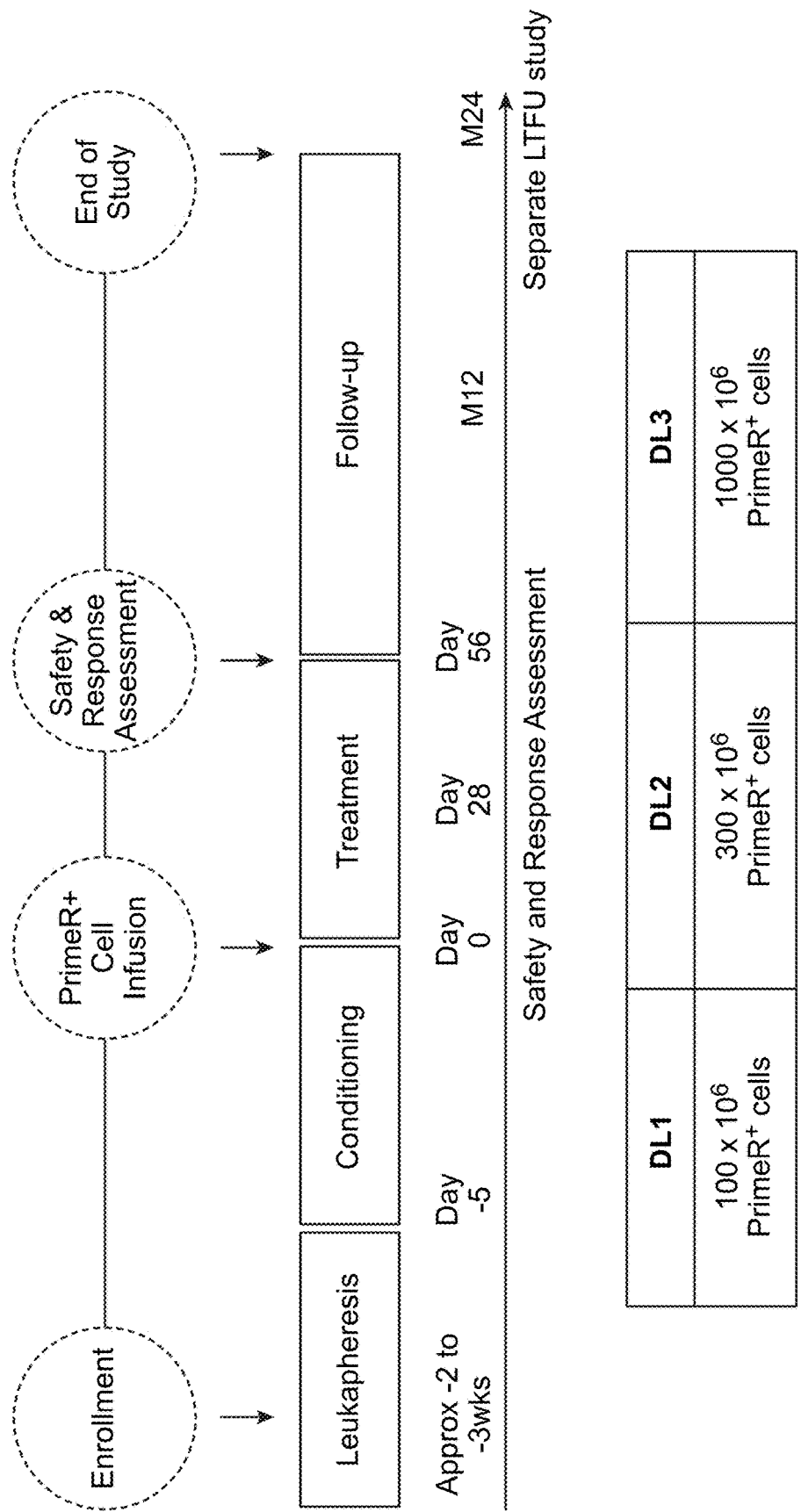
FIG. 26 provides a phase 1 study design.

The phase 1 study design is provided in FIG. 26. Patients will be enrolled and undergo leukapheresis for T cell collection. This stage will take about 2-3 weeks.

In the phase 1 study, patients will be conditioned prior to LG T cell infusion. On Days −5, −4, and −3 patients will be conditioned with 30 mg/m$^2$ fludarabine and 300 mg/m$^2$ cyclophosphamide. Dosing of the LG T cells in the phase 1 study without the conditioning may also be performed.

LG T cells (PrimeR$^+$ cells) will be infused on Day 0 and treatment will run until Day 56. LG T cells (PrimeR$^+$ cells) will be dosed at $100\times10^6$, $300\times10^6$ or $1000\times10^6$ cells. Safety and response assessments will be taken on Day 56 as well as through the study. Post-treatment follow up appointments will be done at month 12 and month 24 post Day 0. A separate Long term follow up (LTFU) study will also be performed.

While the disclosure has been particularly shown and described with reference to a preferred embodiment and various alternate embodiments, it will be understood by persons skilled in the relevant art that various changes in form and details can be made therein without departing from the spirit and scope of the disclosure.

All references, issued patents and patent applications cited within the body of the instant specification are hereby incorporated by reference in their entirety, for all purposes.

The invention claimed is:

1. One or more nucleic acid(s) encoding a system comprising:
   a. a first chimeric polypeptide comprising a priming receptor comprising a first extracellular antigen-binding domain that specifically binds Prostate-Specific Membrane Antigen (PSMA), wherein the first antigen-binding domain comprises a first variable heavy (VH) chain sequence comprising three heavy chain CDR sequences, CDR-H1, CDR-H2, and CDR-H3, of the VH sequence set forth in SEQ ID NO: 118, and a first variable light (VL) chain sequence comprising three light chain CDR sequences, CDR-L1, CDR-L2, and CDR-L3, of the VL sequence set forth in SEQ ID NO: 119; and
   b. a second chimeric polypeptide comprising a chimeric antigen receptor (CAR) comprising a second extracellular antigen-binding domain that specifically binds to Carbonic Anhydrase IX (CA9), wherein the second antigen-binding domain comprises a second variable heavy (VH) chain sequence comprising three heavy chain CDR sequences, CDR-H1, CDR-H2, and CDR-H3, of the VH sequence set forth in SEQ ID NO: 99, and a second variable light (VL) chain sequence comprising three light chain CDR sequences, CDR-L1, CDR-L2, and CDR-L3, of the VL sequence set forth in SEQ ID NO: 100.

2. One or more vector(s) comprising the one or more nucleic acid(s) of claim 1.

3. The one or more nucleic acid(s) of claim 1, wherein
   a. the first variable heavy (VH) chain sequence comprises a CDR-H1 comprising the sequence set forth in SEQ ID NO: 120, a CDR-H2 comprising the sequence set forth in SEQ ID NO: 121, and a CDR-H3 comprising the sequence set forth in SEQ ID NO: 122, and the first variable light (VL) chain sequence comprises a CDR-L1 comprising the sequence set forth in SEQ ID NO: 123, a CDR-L2 comprising the sequence set forth in SEQ ID NO: 124, and a CDR-L3 comprising the sequence set forth in SEQ ID NO: 125; and b. the second variable heavy (VH) chain sequence comprises a CDR-H1 comprising the sequence set forth in SEQ ID NO: 101, a CDR-H2 comprising the sequence set forth in SEQ ID NO: 102, and a CDR-H3 comprising the sequence set forth in SEQ ID NO: 103, and the second variable light (VL) chain sequence comprises a CDR-L1 comprising the sequence set forth in SEQ ID NO: 104, a CDR-L2 comprising the sequence set forth in SEQ ID NO: 105, and a CDR-L3 comprising the sequence set forth in SEQ ID NO: 106.

4. The one or more nucleic acid(s) of claim 1, wherein the first VH chain sequence comprises the sequence set forth in SEQ ID NO: 118, and the first VL chain sequence comprises the sequence set forth in SEQ ID NOs: 119.

5. The one or more nucleic acid(s) of claim 1, wherein the first extracellular antigen-binding domain comprises the sequence set forth in SEQ ID NO: 117.

6. The one or more nucleic acid(s) of claim 1, wherein the second VH chain sequence comprises the sequence as set forth in SEQ ID NO: 99, and the second VL chain sequence comprises the sequence set forth in SEQ ID NO: 100.

7. The one or more nucleic acid(s) of claim 1, wherein the second extracellular antigen-binding domain comprises the sequence set forth in SEQ ID NO: 98.

8. The one or more nucleic acid(s) of claim 1, wherein the priming receptor comprises from N-terminus to C-terminus:
   a. the first extracellular antigen-binding domain;
   b. a first transmembrane domain comprising one or more ligand-inducible proteolytic cleavage sites; and
   c. an intracellular domain comprising a transcriptional effector, wherein binding of PSMA by the first antigen-binding domain results in cleavage at the one or more ligand-inducible proteolytic cleavage sites.

9. The one or more nucleic acid(s) of claim 8, wherein the priming receptor further comprises a first hinge domain positioned between the first extracellular antigen-binding domain and the first transmembrane domain and wherein the hinge comprises the sequence as set forth in SEQ ID NO: 85.

10. The one or more nucleic acid(s) of claim 8, wherein the first transmembrane domain comprises the sequence as set forth in SEQ ID NO: 86.

11. The one or more nucleic acid(s) of claim 8, wherein the intracellular domain comprises the sequence as set forth in SEQ ID NO: 90.

12. The one or more nucleic acid(s) of claim 8, wherein the priming receptor further comprises a stop-transfer-sequence between the first transmembrane domain and the intracellular domain and wherein the stop-transfer-sequence comprises the sequence as set forth in SEQ ID NO: 87.

13. The one or more nucleic acid(s) of claim 8, wherein the priming receptor further comprises a first hinge domain positioned between the first extracellular antigen-binding domain and the first transmembrane domain, wherein the first hinge domain comprises a CD8a hinge domain.

14. The one or more nucleic acid(s) of claim 8, wherein the first transmembrane domain comprises a Notch1 transmembrane domain.

15. The one or more nucleic acid(s) of claim 8, wherein the intracellular domain comprises an HNF1α/p65 domain.

16. The one or more nucleic acid(s) of claim 1, wherein the priming receptor comprises the sequence as set forth in SEQ ID NO: 252 or 127.

17. The one or more nucleic acid(s) of claim 1, wherein the CAR comprises, from N-terminus to C-terminus,
   a. the second extracellular antigen-binding domain;
   b. a second transmembrane domain;
   c. an intracellular co-stimulatory domain; and
   d. an intracellular activation domain.

18. The one or more nucleic acid(s) of claim 17, wherein the second transmembrane domain comprises a CD28 transmembrane domain.

19. The one or more nucleic acid(s) of claim 17, wherein the second transmembrane domain comprises the sequence as set forth in SEQ ID NO: 95.

20. The one or more nucleic acid(s) of claim 17, wherein the intracellular co-stimulatory domain comprises a 4-1BB domain comprising the sequence as set forth in SEQ ID NO: 96.

21. The one or more nucleic acid(s) of claim 17, wherein the intracellular activation domain comprises a CD33 domain comprising the sequence as set forth in SEQ ID NO: 97.

22. The one or more nucleic acid(s) of claim 17, wherein the CAR further comprises a hinge domain from CD8a or CD28.

23. The one or more nucleic acid(s) of claim 22, wherein the hinge domain comprises a CD28 hinge comprising the sequence as set forth in SEQ ID NO: 94.

24. The one or more nucleic acid(s) of claim 1, wherein the CAR comprises the sequence as set forth in SEQ ID NO: 250 or 108.

25. The one or more nucleic acid(s) of claim 1, wherein the one or more nucleic acid(s) further comprises an inducible promoter operably linked to the nucleotide sequence encoding the chimeric antigen receptor and a constitutive promoter operably linked to the nucleotide sequence encoding the priming receptor.

26. The one or more nucleic acid(s) of claim 25, wherein the inducible promoter comprises one or more Hepatocyte Nuclear Factor 1α (HNF1α) enhancer element(s) and a YB-TATA promoter sequence.

27. The one or more nucleic acid(s) of claim 26, wherein the inducible promoter comprises the sequence as set forth in SEQ ID NO: 256.

28. The one or more nucleic acid(s) of claim 25, wherein the constitutive promoter is an EF1α promoter comprising the sequence as set forth in SEQ ID NO: 179.

29. The one or more nucleic acid(s) of claim 1, wherein the nucleic acid(s) further comprises a 5' homology directed repair arm and a 3' homology directed repair arm complementary to an insertion site in a host cell chromosome.

30. An ex vivo cell comprising the one or more nucleic acids of claim 1.

31. The ex vivo cell of claim 30, wherein the cell is an immune cell, a primary cell, a primary immune cell, a primary human immune cell, a T cell, a CD8+ T cell, a CD4+ T cell, a primary T cell, a T cell progenitor cell, or a natural killer (NK) cell.

32. A pharmaceutical composition comprising the ex vivo cell of claim 30 and a pharmaceutically acceptable excipient.

33. The ex vivo cell of claim 30, wherein the cell is a primary human T cell that is a CD8+ T cell or a CD4+ T cell.

34. A population of cells comprising the ex vivo cell of claim 30, wherein the population comprises CD8+ T cells and CD4+ T cells.

35. A pharmaceutical composition comprising the population of cells of claim 34, and a pharmaceutically acceptable excipient.

36. The one or more nucleic acid(s) of claim 1, wherein the one or more nucleic acid(s) further comprises an inducible promoter operably linked to the nucleotide sequence encoding the chimeric antigen receptor.

37. The one or more nucleic acid(s) of claim 1, wherein the one or more nucleic acid(s) further comprises a constitutive promoter operably linked to the nucleotide sequence encoding the priming receptor.

38. The one or more nucleic acid(s) of claim 1, wherein the priming receptor comprises the sequence as set forth in SEQ ID NO: 252 or 127 and the CAR comprises the sequence as set forth in SEQ ID NO: 250 or 108.

39. One or more vector(s) comprising the one or more nucleic acid(s) of claim 38.

40. The one or more nucleic acid(s) of claim 1, wherein the priming receptor is encoded by the sequence as set forth in SEQ ID NO: 128.

41. The one or more nucleic acid(s) of claim 1, wherein the CAR is encoded by the sequence as set forth in SEQ ID NO: 109.

42. One or more nucleic acid(s) encoding a system comprising:
  i. a first chimeric polypeptide comprising a priming receptor comprising a first extracellular antigen-binding domain that specifically binds Prostate-Specific Membrane Antigen (PSMA), wherein the priming receptor comprises the sequence as set forth in SEQ ID NO: 252 or 127; and
  ii. a second chimeric polypeptide comprising a chimeric antigen receptor (CAR) comprising a second extracellular antigen-binding domain that specifically binds to Carbonic Anhydrase IX (CA9), wherein the CAR comprises the sequence as set forth in SEQ ID NO: 250 or 108;
  wherein the one or more nucleic acid(s) further comprise a constitutive EF1α promoter comprising the sequence as set forth in SEQ ID NO: 179 operably linked to the nucleotide sequence encoding the priming receptor and an inducible promoter comprising the sequence as set forth in SEQ ID NO: 256 operably linked to the nucleotide sequence encoding the chimeric antigen receptor.

43. One or more vector(s) comprising the one or more nucleic acid(s) of claim 42.

44. An ex vivo cell comprising the one or more nucleic acids of claim 42.

45. The ex vivo cell of claim 44, wherein the cell is an immune cell, a primary cell, a primary immune cell, a primary human immune cell, a T cell, a CD8+ T cell, a CD4+ T cell, a primary T cell, a T cell progenitor cell, or a natural killer (NK) cell.

46. A pharmaceutical composition comprising the ex vivo cell of claim 44 and a pharmaceutically acceptable excipient.

47. The ex vivo cell of claim 44, wherein the cell is a primary human T cell that is a CD8+ T cell or a CD4+ T cell.

48. A population of cells comprising the ex vivo cell of claim 44, wherein the population comprises CD8+ T cells and CD4+ T cells.

49. A pharmaceutical composition comprising the population of cells of claim 48, and a pharmaceutically acceptable excipient.

50. The one or more nucleic acid(s) of claim 42, wherein the one or more nucleic acid(s) further comprises a 5' homology directed repair arm and a 3' homology directed repair arm complementary to an insertion site in a host cell chromosome.

51. The one or more nucleic acid(s) of claim 42, wherein the priming receptor is encoded by the sequence as set forth in SEQ ID NO: 128.

52. The one or more nucleic acid(s) of claim 42, wherein the CAR is encoded by the sequence as set forth in SEQ ID NO: 109.

53. An ex vivo primary human T cell comprising one or more nucleic acid(s) encoding a system comprising:
  a. a first chimeric polypeptide comprising a priming receptor comprising a first extracellular antigen-binding domain that specifically binds Prostate-Specific Membrane Antigen (PSMA), wherein the priming receptor comprises the sequence as set forth in SEQ ID NO: 252 or 127 and
  b. a second chimeric polypeptide comprising a chimeric antigen receptor (CAR) comprising a second extracellular antigen-binding domain that specifically binds to Carbonic Anhydrase IX (CA9), wherein the CAR comprises the sequence as set forth in SEQ ID NO: 250 or 108;
  wherein the one or more nucleic acid(s) further comprise a constitutive EF1α promoter comprising the sequence as set forth in SEQ ID NO: 179 operably linked to the nucleotide sequence encoding the priming receptor and an inducible promoter comprising the sequence as set forth in SEQ ID NO: 256 operably linked to the nucleotide sequence encoding the chimeric antigen receptor.

54. The ex vivo primary human T cell of claim 53, wherein the one or more nucleic acids are non-virally inserted into an insertion site in the genome of the cell.

55. A pharmaceutical composition comprising the ex vivo cell of claim 53 and a pharmaceutically acceptable excipient.

56. The ex vivo primary human T cell of claim 53, wherein the one or more nucleic acid(s) further comprises a 5' homology directed repair arm and a 3' homology directed repair arm complementary to an insertion site in a host cell chromosome.

57. The ex vivo cell of claim 53, wherein the cell is a primary human T cell that is a CD8+ T cell or a CD4+ T cell.

58. A population of cells comprising the ex vivo cell of claim 53, wherein the population comprises CD8+ T cells and CD4+ T cells.

59. A pharmaceutical composition comprising the population of cells of claim 58, and a pharmaceutically acceptable excipient.

60. The ex vivo cell of claim 53, wherein the priming receptor is encoded by the sequence as set forth in SEQ ID NO: 128.

61. The ex vivo cell of claim 53, wherein the CAR is encoded by the sequence as set forth in SEQ ID NO: 109.

* * * * *